(12) United States Patent
Kyrychenko et al.

(10) Patent No.: US 11,473,060 B2
(45) Date of Patent: Oct. 18, 2022

(54) COMPOSITIONS AND METHODS FOR DIFFERENTIATING STEM CELLS INTO NK CELLS

(71) Applicant: CRISPR THERAPEUTICS AG, Zug (CH)

(72) Inventors: Viktoriia Kyrychenko, Cambridge, MA (US); Wai Lun Leung, Cambridge, MA (US); Patrick Claudio Ovando Roche, Cambridge, MA (US)

(73) Assignee: CRISPR Therapeutics AG, Zug (CH)

( * ) Notice: Subject to any disclaimer, the term of this patent is extended or adjusted under 35 U.S.C. 154(b) by 0 days.

(21) Appl. No.: 17/538,719

(22) Filed: Nov. 30, 2021

(65) Prior Publication Data
US 2022/0204934 A1 Jun. 30, 2022

Related U.S. Application Data

(60) Provisional application No. 63/132,230, filed on Dec. 30, 2020, provisional application No. 63/250,037, filed on Sep. 29, 2021.

(51) Int. Cl.
*C12N 5/0783* (2010.01)
*C12N 5/0789* (2010.01)

(52) U.S. Cl.
CPC ......... *C12N 5/0646* (2013.01); *C12N 5/0647* (2013.01); *C12N 2500/22* (2013.01); *C12N 2500/34* (2013.01); *C12N 2501/115* (2013.01); *C12N 2501/125* (2013.01); *C12N 2501/145* (2013.01); *C12N 2501/155* (2013.01); *C12N 2501/16* (2013.01); *C12N 2501/165* (2013.01); *C12N 2501/2303* (2013.01); *C12N 2501/2307* (2013.01); *C12N 2501/2315* (2013.01); *C12N 2501/26* (2013.01); *C12N 2501/415* (2013.01); *C12N 2501/727* (2013.01); *C12N 2506/02* (2013.01); *C12N 2506/03* (2013.01); *C12N 2506/45* (2013.01); *C12N 2527/00* (2013.01)

(58) Field of Classification Search
CPC .............. C12N 5/0646; C12N 2506/03; C12N 2506/45
See application file for complete search history.

(56) References Cited

U.S. PATENT DOCUMENTS

| 7,387,776 | B2 | 6/2008 | Keler et al. |
|---|---|---|---|
| 8,652,845 | B2 | 2/2014 | Niwa et al. |
| 9,121,011 | B2 | 9/2015 | Osafune et al. |
| 9,260,696 | B2 | 2/2016 | Kaufman et al. |
| 9,629,877 | B2 | 4/2017 | Cooper et al. |
| 9,765,330 | B1 | 9/2017 | Niazi et al. |
| 9,834,754 | B2 | 12/2017 | Keller et al. |
| 9,890,357 | B2 | 2/2018 | Osafune et al. |
| 9,931,377 | B2 | 4/2018 | Pavlakis et al. |
| 9,938,499 | B2 | 4/2018 | Slukvin et al. |
| 10,166,255 | B2 | 1/2019 | Moriarity et al. |
| 10,428,305 | B2 | 10/2019 | Campana et al. |
| 10,501,543 | B2 | 12/2019 | Bemett et al. |
| 10,626,372 | B1 | 4/2020 | Valamehr et al. |
| 10,815,301 | B2 | 10/2020 | Kochenderfer |
| 10,894,944 | B2 | 1/2021 | Elefanty et al. |
| 11,136,547 | B2 | 10/2021 | Eto et al. |
| 2013/0287751 | A1 | 10/2013 | Kaufman et al. |
| 2016/0097035 | A1 | 4/2016 | Yonemitsu et al. |
| 2018/0008637 | A1 | 1/2018 | Murphy et al. |
| 2018/0021378 | A1 | 1/2018 | Kang et al. |
| 2018/0044636 | A1 | 2/2018 | Spanholtz et al. |
| 2018/0072992 | A1 | 3/2018 | Valamehr et al. |
| 2018/0298101 | A1 | 10/2018 | Huntington et al. |
| 2018/0305664 | A1 | 10/2018 | Vodyanyk et al. |
| 2018/0346877 | A1 | 12/2018 | Zhang et al. |
| 2019/0062735 | A1 | 2/2019 | Welstead et al. |
| 2019/0144828 | A1 | 5/2019 | Ng et al. |
| 2019/0153389 | A1 | 5/2019 | Ffischkoff et al. |
| 2019/0271005 | A1 | 9/2019 | Valamehr et al. |
| 2019/0309259 | A1 | 10/2019 | Meissner et al. |
| 2019/0330592 | A1 | 10/2019 | Hariri et al. |
| 2019/0365876 | A1 | 12/2019 | Russell et al. |
| 2019/0381154 | A1 | 12/2019 | Russell et al. |
| 2020/0080059 | A1 | 3/2020 | Thomson et al. |
| 2020/0095544 | A1 | 3/2020 | Boehm et al. |
| 2020/0123501 | A1 | 4/2020 | Vodyanyk et al. |
| 2020/0131475 | A1 | 4/2020 | Kimbrel et al. |
| 2020/0157503 | A1 | 5/2020 | Lanza et al. |

(Continued)

FOREIGN PATENT DOCUMENTS

| CN | 111235105 A | 6/2020 |
|---|---|---|
| EP | 3875578 A1 | 9/2021 |

(Continued)

OTHER PUBLICATIONS

Yuan et al., Indian J Med Res. 2013;138(1):104-110 (Year: 2013).*
Abel et al., "Natural Killer Cells: Development, Maturation, and Clinical Utilization", Frontiers in Immunology, Aug. 2018, pp. 1-23, vol. 9, No. 1869.
Bhardwaj et al., "Sonic hedgehog induces the proliferation of primitive human hematopoietic cells via BMP regulation", Nature Immunology, Feb. 2001, pp. 172-180, vol. 2, No. 2.
Bhatia et al., "Bone Morphogenetic Proteins Regulate the Developmental Program of Human Hematopoietic Stem Dells", Journal of Experimental Medicine, Apr. 5, 1999, pp. 1139-1147, vol. 189, No. 7.
Cao et al., "Differentiation and Functional Comparison of Monocytes and Macrophages from hiPSCs with Peripheral Blood Derivatives", Stem Cell Reports, Jun. 11, 2019, pp. 1282-1297, vol. 12.

(Continued)

*Primary Examiner* — Daniel C Gamett
(74) *Attorney, Agent, or Firm* — Polsinelli PC

(57) ABSTRACT

The disclosure features methods and compositions for differentiating stem cells into hematopoietic stem and progenitor cells (HSPC) and/or Natural Killer (NK) cells. The methods and compositions described herein are used to differentiate stem or progenitor cells having at least one gene-edit that is maintained in the differentiated cell. Also provided are differentiated cells produced using the methods and compositions described herein for therapeutic applications.

29 Claims, 43 Drawing Sheets

(56) References Cited

U.S. PATENT DOCUMENTS

| | | | |
|---|---|---|---|
| 2020/0354673 | A1 | 11/2020 | Schrepfer et al. |
| 2021/0017494 | A1 | 1/2021 | Vodyanyk et al. |
| 2021/0024897 | A1 | 1/2021 | Matsuo et al. |
| 2021/0040449 | A1 | 2/2021 | Gschweng et al. |
| 2021/0062151 | A1 | 3/2021 | Valamehr et al. |
| 2021/0130785 | A1 | 5/2021 | Akashi et al. |
| 2021/0161971 | A1 | 6/2021 | Nagy et al. |
| 2021/0284965 | A1 | 9/2021 | Germeroth |
| 2021/0395684 | A1 | 12/2021 | Feng et al. |

FOREIGN PATENT DOCUMENTS

| | | |
|---|---|---|
| WO | 2010/099539 A1 | 9/2010 |
| WO | 2016/183041 A2 | 11/2016 |
| WO | 2016/209021 A1 | 12/2016 |
| WO | 2017/078807 A1 | 5/2017 |
| WO | 2017/079673 A1 | 5/2017 |
| WO | 2017/100861 A1 | 6/2017 |
| WO | 2017/152015 A1 | 9/2017 |
| WO | 2017/193177 A1 | 11/2017 |
| WO | 2018/227286 A1 | 12/2018 |
| WO | 2019/068099 A1 | 4/2019 |
| WO | 2019/112899 A2 | 6/2019 |
| WO | 2019/118516 A1 | 6/2019 |
| WO | 2019/143292 A1 | 7/2019 |
| WO | 2019/209991 A1 | 10/2019 |
| WO | 2019/213610 A1 | 11/2019 |
| WO | 2019/217956 A1 | 11/2019 |
| WO | 2019/229109 A1 | 12/2019 |
| WO | 2020/086889 A1 | 4/2020 |
| WO | 2020/113029 A2 | 6/2020 |
| WO | 2020/113182 A1 | 6/2020 |
| WO | 2020/150534 A2 | 7/2020 |
| WO | 2020/154412 A1 | 7/2020 |
| WO | 2020/168300 A1 | 8/2020 |
| WO | 2021/015615 A1 | 1/2021 |
| WO | 2021/022223 A1 | 2/2021 |
| WO | 2021/032851 A1 | 2/2021 |
| WO | 2021/032855 A1 | 2/2021 |
| WO | 2021/041316 A1 | 3/2021 |
| WO | 2021/051088 A1 | 3/2021 |
| WO | 2021/085462 A1 | 5/2021 |
| WO | 2021/097346 A1 | 5/2021 |
| WO | 2021/173458 A1 | 9/2021 |
| WO | 2021/174004 A1 | 9/2021 |

OTHER PUBLICATIONS

Ceccaldi et al., "Homologous recombination-deficient tumors are hyper-dependent on Polθ-mediated repair", Nature, Feb. 2015, pp. 258-262, vol. 518.
Chadwick et al., "Cytokines and BMP-4 promote hematopoietic differentiation of human embryonic stem cells", Blood, Aug. 1, 2003, pp. 906-915, vol. 102, No. 3.
Chang et al., "A Chimeric Receptor with NKG2D Specificity Enhances Natural Killer Cell Activation and Killing of Tumor Cells", Cancer Research, Mar. 15, 2013, pp. 1777-1786, vol. 73, No. 6.
Chen et al., "Small molecule-mediated disruption of Wnt-dependent signaling in tissue regeneration and cancer", Nat Chem Biol., Feb. 2009, pp. 100-107, vol. 5, No. 2.
Chen et al., "Pharmacological inhibition of porcupine induces regression of experimental skin fibrosis by targeting Wnt signalling", Ann Rheum Dis., Feb. 2017, pp. 773-778, vol. 76, No. 4.
Cho et al., "DNA repair: Familiar ends with alternative endings", Nature, Feb. 2015, pp. 174-176, vol. 518.
Cichocki et al., "iPSC-derived NK cells maintain high cytotoxicity and enhance in vivo tumor control in concert with T cells and anti-PD-1 therapy", Sci Transl Med., Nov. 2020, 30 pgs., vol. 12.
Cox et al., "Therapeutic Genome Editing: Prospects and Challenges", Nature Medicine, Feb. 2015, pp. 121-131, vol. 21, No. 2.

Davidson et al., "Turning Mesoderm into Blood: The Formation of Hematopoietic Stem Cells during Embryogenesis", Current Topics in Developmental Biology, 2000, pp. 45-60, vol. 50.
Delconte et al., "CIS is a potent checkpoint in NK cell-mediated tumor immunity", Nature Immunology, Jul. 2016, pp. 816-824, vol. 17, No. 7.
Deng et al., "Transcription Factor Foxo1 is a Negative Regulator of Natural Killer Cell Maturation and Function", Immunity, Mar. 17, 2015, pp. 457-470, vol. 42.
Dodge et al., "Diverse Chemical Scaffolds Support Direct Inhibition of the Membrane-Bound O-Acyltransferase Porcupine", Journal of Biological Chemistry, Jun. 29, 2012, pp. 23246-23254, vol. 287, No. 27.
Drexler et al., "FLT3: Receptor and Ligand", Growth Factors, Jun. 2004, pp. 71-73, vol. 22, No. 2.
Duraiswamy et al., "Discovery and Optimization of a Porcupine Inhibitor", Journal of Medicinal Chemistry, 2015, 11 pgs., vol. 58.
Enblad et al., "CAR T-Cell Therapy: The Role of Physical Barriers and Immunosuppression in Lymphoma", Human Gene Therapy, 2015, pp. 498-505, vol. 26, No. 8.
Gornalusse et al., "HLA-E-expressing pluripotent stem cells escape allogeneic responses and lysis by NK cells", Nature Biotechnology, 2017, pp. 765-773, vol. 35.
Guo et al., "Immunobiology of the IL-15/IL-15Rα complex as an antitumor and antiviral agent", Cytokine and Growth Factor Reviews, 2017, pp. 10-21, vol. 38.
Guo et al., "Structure-based rational design of a novel chimeric PD1-NKG2D receptor for natural killer cells", Molecular Immunology, 2019, pp. 108-113, vol. 114.
Hagn et al., "A Colorimetric Assay that Specifically Measures Granzyme B Proteolytic Activity: Hydrolysis of Boc-Ala-Ala-Asp-S-Bzl", Journal of Visualized Experiments, Nov. 2014, e52419, pp. 1-9, vol. 93.
Han et al., "Generation of hypoimmunogenic human pluripotent stem cells", PNAS, May 2019, pp. 10441-10446, vol. 116, No. 21.
Huber et al., "Cooperative Effects of Growth Factors Involved in the Induction of Hematopoietic Mesoderm", Blood, Dec. 1, 1998, pp. 4128-4137, vol. 92, No. 11.
Hurton et al., "Tethered IL-15 augments antitumor activity and promotes a stem-cell memory subset in tumorspecific T cells", PNAS, Nov. 14, 2016, pp. E7788-E7797, vol. 113, No. 48.
Imai et al., "Genetic modification of primary natural killer cells overcomes inhibitory signals and induces specific killing of leukemic cells". Blood, Jul. 2005, pp. 376-383, vol. 106, No. 1.
Jackson et al., "Differentiating Embryonic Stem Cells Pass through 'Temporal Windows' That Mark Responsiveness to Exogenous and Paracrine Mesendoderm Inducing Signals", PLoS One, May 2010, e10706, pp. 1-12, vol. 5, No. 5.
Jiang et al., "Inactivating mutations of RNF43 confer Wnt dependency in pancreatic ductal adenocarcinoma", PNAS, Jul. 2013, pp. 12649-12654, vol. 110, No. 31.
Kakarla et al., "CAR T cells for solid tumors: armed and ready to go?". Cancer Journal, 2014, pp. 151-155, vol. 20.
Kent et al., "Mechanism of Microhomology-Mediated End-Joining Promoted by Human DNA Polymerase θ", Mature Structural and Molecular Biology, Mar. 2015, pp. 230-237, vol. 22.
Kiselyov et al., "Structural Basis for a Direct Interaction between FGFR1 and NCAM and Evidence fora Regulatory Role of ATP", Structure, Jun. 2003, pp. 691-701, vol. 11.
Kitajima et al., "GSK3β inhibition activates the CDX/HOX pathway and promotes hemogenic endothelial progenitor iifferentiation from human pluripotent stem cells". Experimental Hematology, 2016, pp. 68-74, vol. 44.
Lin et al., "Synthetic peptide F2A4-K-NS mimics fibroblast growth factor-2 in vitro and is angiogenic in vivo", International Journal of Molecular Medicine, 2006, pp. 833-839, vol. 17.
Liu et al., "Targeting Wnt-driven cancer through the inhibition of Porcupine by LGK974", PNAS, Dec. 2013, pp. 20224-20229, vol. 110, No. 50.
Ludwig et al., "Derivation of human embryonic stem cells in defined conditions", Nature Biotechnology, Feb. 2006, pp. 185-187, vol. 24, No. 2.

(56) References Cited

OTHER PUBLICATIONS

Madan et al., "Wnt addiction of genetically defined cancers reversed by PORCN inhibition", Oncogene, 2016, pp. 2197-2207, vol. 35.
Marshall et al., "Polarized expression of bone morphogenetic protein-4 in the human aorta-gonad-mesonephros region", Blood, Aug. 2000, pp. 1591-1593, vol. 96, No. 4.
Mateos-Gomez et al., "Mammalian Polymerase θ Promotes Alternative-NHEJ and Suppresses Recombination", Nature, Feb. 2015, pp. 254-257, vol. 518.
Matsubara et al., "Induction of human pluripotent stem cell-derived natural killer cells for immunotherapy under chemically defined conditions", Biochemical and Biophysical Research Communications, 2019, pp. 1-8, vol. 515.
Maude et al., "CD19-targeted chimeric antigen receptor T-cell therapy for acute lymphoblastic leukemia", Blood, Jun. 2015, pp. 4017-4023, vol. 125, No. 26.
Mishra et al., "Anti-ADAM17 monoclonal antibody MEDI3622 increases IFNγ production by human NK cells in the presence of antibody-bound tumor cells", Cancer Immunol Immunother., Sep. 2018, pp. 1407-1416, vol. 67.
Ng et al., "A protocol describing the use of a recombinant protein-based, animal product-free medium (APEL) for human embryonic stem cell differentiation as spin embryoid bodies", Nature Protocols, 2008, pp. 768-776, vol. 3, No. 5.
Poulsen et al., "A Pharmacophore Model for Wnt/Porcupine Inhibitors and its Use for Drug Design", Journal of Chemical Information and Modeling, 2015, pp. 1-49, vol. 55.
Proffitt et al., "Pharmacological Inhibition of the Wnt Acyltransferase PORCN Prevents Growth of WNT-Driven Mammary Cancer", Cancer Research, Jan. 2013, pp. 502-507, vol. 73.
Ratajczak et al., "Effect of basic (FGF-2) and acidic (FGF-1) fibroblast growth factors on early haemopoietic cell development", British Journal of Haematology, 1996, pp. 772-782, vol. 93.
Rautela et al., "Therapeutic blockade of Activin—A improves NK cell function and anti-tumor immunity", Sci Signal., 2019, pp. 1-54, vol. 12.
Savoldo et al., "CD28 costimulation improves expansion and persistence of chimeric antigen receptor-modified T cells in lymphoma patients", The Journal of Clinical Investigation, May 2011, pp. 1822-1826, vol. 121, No. 5.
Uenishi et al., "Tenascin C.Promotes Hematoendothelial Development and T Lymphoid Commitment from Human Pluripotent Stem Cells in Chemically Defined Conditions", Stem Cell Reports, Dec. 2014, pp. 1073-1084, vol. 3.
van der Stegen et al., "The pharmacology of second-generation chimeric antigen receptors", Nature Reviews, Drug Discovery, Jul. 2015, pp. 499-509, vol. 14.
Wang et al., "The Developrhent of Highly Potent Inhibitors for Porcupine", J Med Chem., Mar. 2013, pp. 2700-2704, vol. 56.
Wu et al., "Role of ADAM17 as a regulatory checkpoint of CD16A in NK cells and as a potential target for cancer immunotherapy", Journal of Leukocyte Biology, 2019, pp. 1297-1303, vol. 105.
Xie et al., "CAR-NK cells: A promising cellular immunotherapy for cancer", EBioMedicine, 2020,102975, pp. 1-10, vol. 59.
Zhu et al., "An Improved Method to Produce Clinical-Scale Natural Killer Cells from Human Pluripotent Stem Cells", Methods in Molecular Biology, 2019, pp. 107-119, vol. 2048.
Zhu et al., "Metabolic reprograming via deletion of CISH in human iPSC-derived NK cells promotes in vivo persistence and enhances anti-tumor activity", Cell Stem Cell, Aug. 2020, pp. 224-237, vol. 27.
International Search Report and Written Opinion relating to International Application No. PCT/IB2021/061148, dated Feb. 22, 2022; 17 pgs.
International Search Report and Written Opinion relating to International Application No. PCT/IB2021/061150, dated Mar. 7, 2022; 17 pgs.
Harding et al., "Induction of long-term allogeneic cell acceptance and formation of immune privileged tissue in immunocompetent hosts", Jul. 30, 2019, pp. 1-34; XP055718117, DOI: 10.1101/716571. Retrieved from the Internet: URL:https://www.biorxiv.org/content/10.1101/716571v1.full.pdf (retrieved Jul. 27, 2020).
Lanza et al., "Engineering universal cells that evade immune detection", Nature Reviews/ Immunology, 2019, pp. 723-733, vol. 19.
Zhao et al., "Strategies for Genetically Engineering Hypoimmunogenic Universal Pluripotent Stem Cells", iScience, Jun. 2020, 101162, pp. 1-9, vol. 23.

* cited by examiner

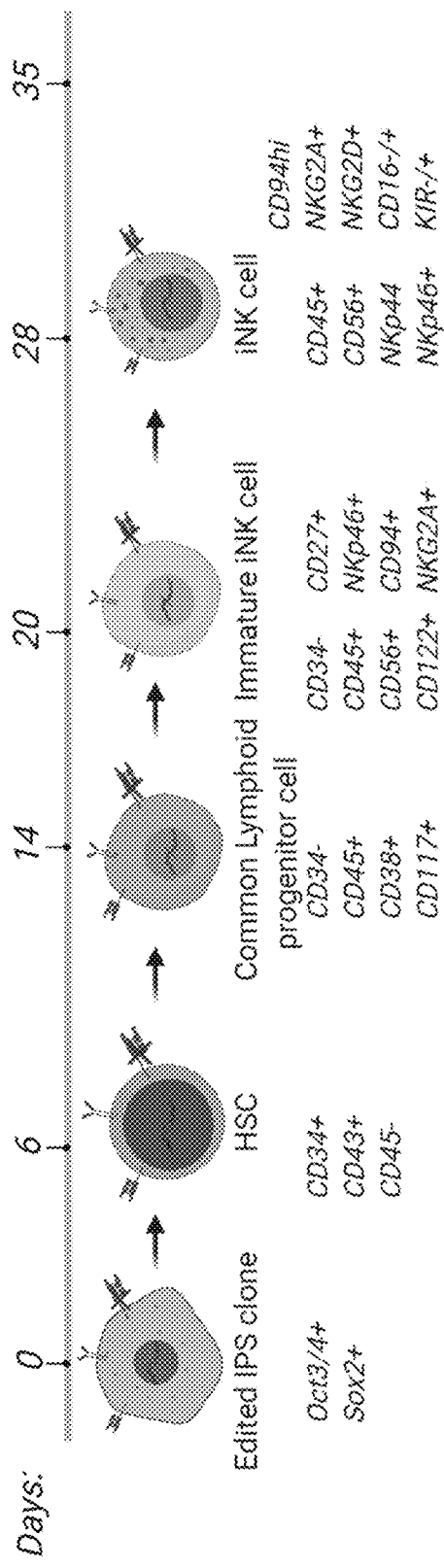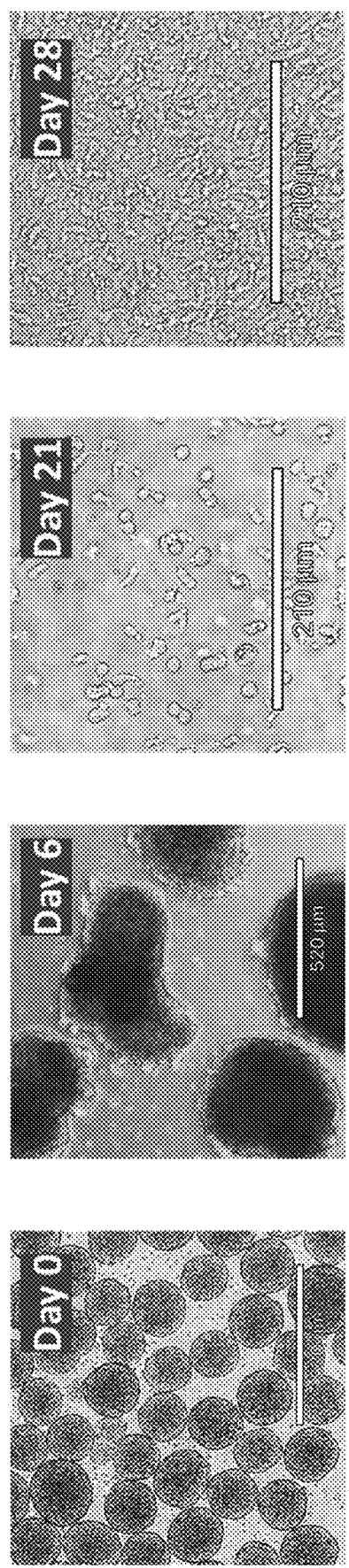
FIG. 2A

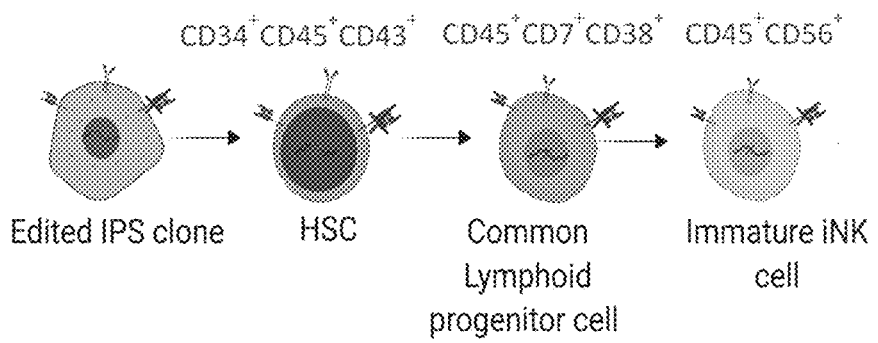
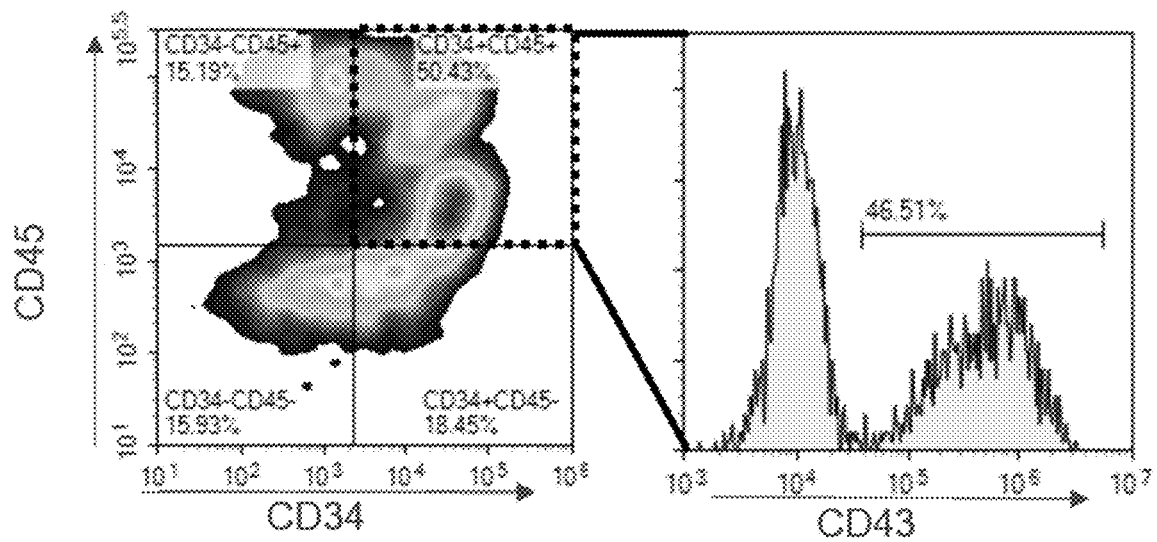
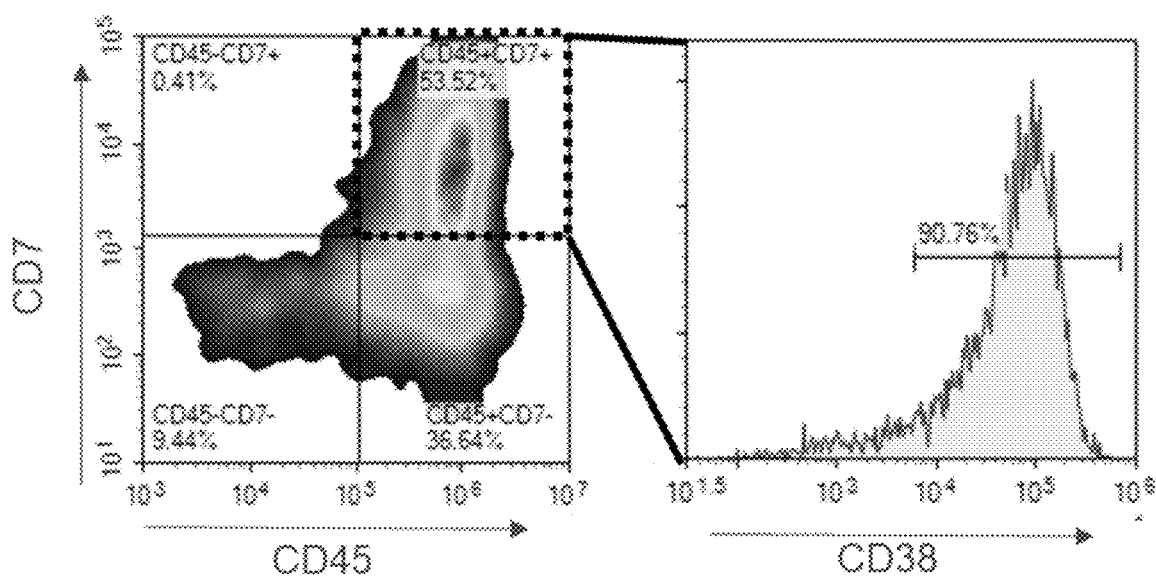
FIG. 2B

| Exp No | Exp Name | Run Order | Incl/Excl | Zinc, uM | 2-Mercaptoethanol, uM | Human Serum Albumin, % | Glucose, mM | Yield (total cells, at 4mL) | CD34+CD45+, % | Yield (CD34+CD45+) | CD45+, % | Yield (CD45+) |
|---|---|---|---|---|---|---|---|---|---|---|---|---|
| 1 | N1 | 9 | Incl | 1.7 | 0 | 2 | 8 | 9.95E+05 | 41.1% | 4.09E+05 | 91.9% | 9.15E+05 |
| 2 | N2 | 2 | Incl | 20 | 0 | 2 | 8 | 1.29E+06 | 40.4% | 5.21E+05 | 92.2% | 1.19E+06 |
| 3 | N3 | 13 | Incl | 1.7 | 50 | 2 | 8 | 4.22E+05 | 0.12% | 2.24E+01 | 0.12% | 5.07E+02 |
| 4 | N4 | 4 | Incl | 20 | 50 | 2 | 8 | 2.10E+05 | 0% | 0.00E+00 | 0.12% | 2.52E+02 |
| 5 | N5 | 5 | Incl | 1.7 | 0 | 20 | 8 | 5.22E+06 | 47.3% | 2.47E+06 | 93.8% | 4.89E+06 |
| 6 | N6 | 6 | Incl | 20 | 0 | 20 | 8 | 6.17E+06 | 48.0% | 2.96E+06 | 94.4% | 5.83E+06 |
| 7 | N7 | 15 | Incl | 1.7 | 50 | 20 | 8 | 1.92E+04 | 0.42% | 8.04E+01 | 0.82% | 1.57E+02 |
| 8 | N8 | 10 | Incl | 20 | 50 | 20 | 8 | 1.38E+04 | 0.10% | 1.38E+01 | 0.31% | 4.27E+01 |
| 9 | N9 | 11 | Incl | 1.7 | 0 | 2 | 20 | 3.46E+06 | 58.4% | 2.02E+06 | 94.2% | 3.26E+06 |
| 10 | N10 | 19 | Incl | 20 | 0 | 2 | 20 | 2.08E+06 | 37.0% | 7.69E+05 | 92.8% | 1.93E+06 |
| 11 | N11 | 3 | Incl | 1.7 | 50 | 2 | 20 | 3.51E+05 | 0.042% | 1.47E+02 | 0.22% | 7.72E+02 |
| 12 | N12 | 8 | Incl | 20 | 50 | 2 | 20 | 3.62E+05 | 0.023% | 8.33E+01 | 0.091% | 3.30E+02 |
| 13 | N13 | 17 | Incl | 1.7 | 0 | 20 | 20 | 5.62E+06 | 51.8% | 2.96E+06 | 95.4% | 5.36E+06 |
| 14 | N14 | 12 | Incl | 20 | 0 | 20 | 20 | 6.22E+06 | 45.9% | 2.85E+06 | 94.1% | 5.85E+06 |
| 15 | N15 | 14 | Incl | 1.7 | 50 | 20 | 20 | 2.66E+03 | 0.50% | 1.33E+01 | 0.92% | 2.45E+01 |
| 16 | N16 | 1 | Incl | 20 | 50 | 20 | 20 | 1.80E+04 | 0.050% | 9.00E+00 | 0.10% | 1.80E+01 |
| 17 | N17 | 16 | Incl | 10.85 | 25 | 11 | 14 | 8.40E+03 | 0.22% | 1.85E+01 | 0.76% | 6.38E+01 |
| 18 | N18 | 18 | Incl | 10.85 | 25 | 11 | 14 | 2.45E+04 | 0.13% | 3.19E+01 | 0.26% | 6.38E+01 |
| 19 | N19 | 7 | Incl | 10.85 | 25 | 11 | 14 | 2.76E+04 | 0% | 0.00E+00 | 0.10% | 2.76E+01 |
| | Stempro34 control | | | | | | | 9.86E+06 | 3.4% | 3.38E+05 | 70.0% | 6.90E+06 |

FIG. 15

| Exp No | Exp Name | Run Order | Incl/Excl | Zinc, uM | 2-Mercaptoethanol, uM | HSA, % | Glucose, mM | Yield (total, 4mL) | CD56+/CD45+ % | CD45+, % | CD56+/CD16+ (activated NK) % |
|---|---|---|---|---|---|---|---|---|---|---|---|
| 1 | N1 | 5 | incl | 25 | 0 | 20 | 25 | 5.02E+06 | 92.77% | 99.27% | 26.58% |
| 2 | N2 | 13 | incl | 40 | 0 | 20 | 25 | 4.53E+06 | 93.83% | 99.39% | 22.96% |
| 3 | N3 | 19 | incl | 25 | 7.5 | 20 | 25 | 4.34E+06 | 94.66% | 99.54% | 20.07% |
| 4 | N4 | 16 | incl | 40 | 7.5 | 20 | 25 | 4.29E+06 | 94.00% | 99.40% | 19.63% |
| 5 | N5 | 10 | incl | 25 | 0 | 40 | 25 | 1.12E+06 | 89.83% | 98.65% | 28.44% |
| 6 | N6 | 7 | incl | 40 | 0 | 40 | 25 | 1.12E+06 | 93.09% | 99.27% | 29.83% |
| 7 | N7 | 3 | incl | 25 | 7.5 | 40 | 25 | 8.72E+05 | 92.72% | 99.33% | 26.19% |
| 8 | N8 | 14 | incl | 40 | 7.5 | 40 | 25 | 1.54E+06 | 92.61% | 99.28% | 27.12% |
| 9 | N9 | 11 | incl | 25 | 0 | 20 | 40 | 4.54E+06 | 94.64% | 99.73% | 19.83% |
| 10 | N10 | 8 | incl | 40 | 0 | 20 | 40 | 4.04E+06 | 93.89% | 99.37% | 24.81% |
| 11 | N11 | 12 | incl | 25 | 7.5 | 20 | 40 | 5.48E+06 | 95.03% | 99.27% | 23.28% |
| 12 | N12 | 4 | incl | 40 | 7.5 | 20 | 40 | 5.26E+06 | 93.85% | 99.15% | 24.21% |
| 13 | N13 | 2 | incl | 25 | 0 | 40 | 40 | 1.70E+06 | 93.22% | 99.25% | 24.72% |
| 14 | N14 | 9 | incl | 40 | 0 | 40 | 40 | 1.04E+06 | 94.34% | 99.41% | 24.60% |
| 15 | N15 | 18 | incl | 25 | 7.5 | 40 | 40 | 1.64E+06 | 93.49% | 99.01% | 24.15% |
| 16 | N16 | 6 | incl | 40 | 7.5 | 40 | 40 | 1.32E+06 | 93.01% | 98.84% | 26.08% |
| 17 | N17 | 1 | incl | 32.5 | 3.75 | 30 | 32.5 | 2.29E+06 | 93.63% | 99.04% | 29.03% |
| 18 | N18 | 15 | incl | 32.5 | 3.75 | 30 | 32.5 | 2.16E+06 | 93.71% | 99.07% | 30.80% |
| 19 | N19 | 17 | incl | 32.5 | 3.75 | 30 | 32.5 | 2.83E+06 | 94.68% | 99.30% | 32.71% |

FIG. 16

| Exp No | Ascorbic acid, mg/L | 2-Mercaptoethanol, uM | Human Serum Albumin, % | Glucose mM | Yield (total cells, in 10 mL) | CD56+CD45+, % | Yield (CD56+CD45+) | CD56+CD16+, % | Yield (CD56+CD16+) |
|---|---|---|---|---|---|---|---|---|---|
| 1 | 2 | 0 | 2 | 8 | 1.65E+07 | 11.97% | 1.98E+06 | 0.39% | 6.45E+04 |
| 2 | 30 | 0 | 2 | 8 | 1.85E+07 | 18.22% | 3.37E+06 | 0.40% | 7.30E+04 |
| 3 | 2 | 50 | 2 | 8 | 1.37E+07 | 13.35% | 1.82E+06 | 0.39% | 5.26E+04 |
| 4 | 30 | 50 | 2 | 8 | 1.21E+07 | 14.97% | 1.81E+06 | 0.36% | 4.30E+04 |
| 5 | 2 | 0 | 20 | 8 | 3.98E+07 | 14.99% | 5.97E+06 | 0.91% | 3.60E+05 |
| 6 | 30 | 0 | 20 | 8 | 1.63E+07 | 27.36% | 4.46E+06 | 1.61% | 2.62E+05 |
| 7 | 2 | 50 | 20 | 8 | 2.44E+07 | 24.29% | 5.92E+06 | 2.20% | 5.36E+05 |
| 8 | 30 | 50 | 20 | 8 | 2.13E+07 | 45.28% | 9.66E+06 | 3.00% | 6.40E+05 |
| 9 | 2 | 0 | 2 | 20 | 1.40E+07 | 12.63% | 1.77E+06 | 0.26% | 3.57E+04 |
| 10 | 30 | 0 | 2 | 20 | 1.59E+07 | 10.74% | 1.70E+06 | 0.19% | 2.93E+04 |
| 11 | 2 | 50 | 2 | 20 | 1.03E+07 | 10.45% | 1.07E+06 | 0.15% | 1.54E+04 |
| 12 | 30 | 50 | 2 | 20 | 6.99E+06 | 13.07% | 9.13E+05 | 0.20% | 1.40E+04 |
| 13 | 2 | 0 | 20 | 20 | 3.05E+07 | 32.87% | 1.00E+07 | 1.97% | 6.01E+05 |
| 14 | 30 | 0 | 20 | 20 | 2.15E+07 | 48.11% | 1.04E+07 | 3.26% | 7.01E+05 |
| 15 | 2 | 50 | 20 | 20 | 2.79E+07 | 26.24% | 7.31E+06 | 1.63% | 4.53E+05 |
| 16 | 30 | 50 | 20 | 20 | 2.19E+07 | 47.34% | 1.04E+07 | 3.17% | 6.95E+05 |
| 17 | 16 | 25 | 11 | 14 | 2.57E+07 | 32.81% | 8.44E+06 | 2.61% | 6.70E+05 |
| 18 | 16 | 25 | 11 | 14 | 3.05E+07 | 32.20% | 9.82E+06 | 2.74% | 8.34E+05 |
| 19 | 16 | 25 | 11 | 14 | 2.60E+07 | 42.67% | 1.11E+07 | 3.16% | 8.22E+05 |

FIG. 22

| Exp No | B-Me uM | NAM mM | Glucose mM | Human Serum % | Novocyte | | | | | | Other |
|---|---|---|---|---|---|---|---|---|---|---|---|
| | | | | | Cell conc. | CD56+/CD4 5+ | CD56+/CD16+ | TRAIL | PD1 | KIR3DL2 | Total Yield |
| 1 | 0 | 0 | 20 | 5 | 7.64E+05 | 99.43% | 6.68% | 81.09% | 1.94% | 2.17% | 1.91E+07 |
| 2 | 24 | 0 | 20 | 30 | 6.15E+05 | 99.22% | 6.74% | 81.35% | 2.05% | 3.01% | 1.54E+07 |
| 3 | 0 | 20 | 20 | 30 | 1.39E+05 | 99.72% | 2.88% | 1.61% | 2.73% | 3.42% | 3.48E+06 |
| 4 | 24 | 20 | 20 | 5 | 4.78E+04 | 99.68% | 1.36% | 1.29% | 4.58% | 2.26% | 1.20E+06 |
| 5 | 0 | 0 | 60 | 30 | 3.66E+05 | 99.29% | 6.41% | 80.21% | 2.84% | 1.46% | 9.16E+06 |
| 6 | 24 | 0 | 60 | 5 | 2.86E+05 | 98.84% | 3.93% | 83.62% | 4.43% | 1.94% | 7.14E+06 |
| 7 | 0 | 20 | 60 | 5 | 4.30E+04 | 99.44% | 1.32% | 1.04% | 1.28% | 1.66% | 1.08E+06 |
| 8 | 24 | 20 | 60 | 30 | 5.82E+04 | 99.58% | 1.90% | 1.24% | 1.49% | 1.36% | 1.45E+06 |
| 9 | 12 | 10 | 40 | 17.5 | 1.82E+06 | 99.62% | 18.24% | 10.03% | 1.09% | 15.28% | 4.55E+07 |
| 10 | 12 | 10 | 40 | 17.5 | 2.08E+06 | 99.42% | 18.14% | 8.69% | 1.11% | 15.45% | 5.20E+07 |
| 11 | 12 | 10 | 40 | 17.5 | 2.02E+06 | 99.19% | 16.95% | 7.36% | 1.77% | 12.97% | 5.05E+07 |
| 12 | 12 | 10 | 40 | 17.5 | 1.41E+06 | 99.09% | 13.98% | 2.91% | 2.53% | 8.18% | 3.53E+07 |

FIG. 23

COMPOSITIONS AND METHODS FOR DIFFERENTIATING STEM CELLS INTO NK CELLS

CROSS-REFERENCE TO RELATED APPLICATIONS

This application claims priority from U.S. Provisional Application No. 63/132,230 filed Dec. 30, 2020 and U.S. Provisional Application No. 63/250,037, filed Sep. 29, 2021, the entire contents of which are hereby incorporated by reference.

FIELD

The invention relates to methods and compositions for differentiating stem cells into hematopoietic stem and progenitor cells (HSPC) and/or Natural Killer (NK) cells.

BACKGROUND

Natural Killer (NK) cells are lymphocytes involved in the innate immune response. Due to their function, NK cells are becoming cells of interest for use in the treatment of different diseases such as cancer. Recent success in editing immune cells (e.g. CART cells) for enhanced therapeutic ability prompts the use of NK cells in further therapy discoveries. Unfortunately, differentiating natural killer cells is typically a low output 5 to 6-week process. Additionally, current methods require feeder cells and cell sorting which adds additional time and cost for generating the cells. Accordingly, methods of differentiation are needed that reduce the cost, increase cell output, and reduce the time needed to generate NK cells. Improving upon these methods will allow for efficient output of NK cells and NK cell therapy for use in treating disease.

SUMMARY OF THE INVENTION

In some aspects, the disclosure provides a method for generating Natural Killer (NK) cells from stem cells, the method comprising: (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; and (g) culturing the cell population in a seventh medium comprising IL-7, FLT3L, IL-15 and SCF for a time sufficient to generate NK cells.

In some aspects, the disclosure provides a method for generating Natural Killer (NK) cells from stem cells, the method comprising: (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; and (g) culturing the cell population in a seventh medium comprising IL-7, FLT3L, IL-15 and SCF; and (h) culturing the cell population in an eighth medium comprising IL-7, FLT3L, IL-15, SCF and nicotinamide for a time sufficient to generate NK cells.

In some aspects, the disclosure provides a method for generating Natural Killer (NK) cells from stem cells, the method comprising: (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; and (g) culturing the cell population in a seventh medium comprising IL-7, FLT3L, IL-15 and SCF; and (h) culturing the cell population in an eighth medium comprising IL-7, FLT3L, IL-15, and SCF for a time sufficient to generate NK cells.

In some aspects, culturing the cell population in the fifth medium in step (e) results in the cell population comprising at least about 25% of HSPCs, optionally comprising about 25% to about 55% of HSPCs. In some aspects, culturing the cell population in the fifth medium in step (e) results in the cell population comprising about 29% to about 50% of HSPCs. In some aspects, culturing the cell population in the fifth medium in step (e) results in the cell population comprising about 36% of HSPCs or about 50% of HSPCs.

In some aspects, culturing the cell population in the sixth medium in step (f) results in the formation of progenitor cell population comprising common lymphoid progenitor (CLP) cells. In some aspects, the progenitor cell population comprises at least about 15% of CLP cells, optionally wherein the CLP cells express CD7 and CD45⁻. In some aspects, the progenitor cell population comprises about 15% to about 50% of CLP cells, optionally about 19% to about 45%. In some aspects, the progenitor cell population comprises about 35% of CLP cells.

In some aspects, culturing the cell population in the seventh medium in step (g) results in the cell population comprising at least about 70% of NK cells. In some aspects, culturing the cell population in the seventh medium in step (g) results in the cell population comprising at least about 95% of NK cells.

In some aspects, culturing the cell population in the eighth medium in step (h) results in the cell population comprising at least about 70% of NK cells. In some aspects, culturing the cell population in the eighth medium in step (h) results in the cell population comprising at least about 95% of NK cells.

In some aspects, the second medium further comprises a ROCK inhibitor. In some aspects, the ROCK inhibitor is thiazovivin. In some aspects, the ROCK inhibitor is Y27632.

In some aspects, the WNT pathway activator is CHIR-99021. In some aspects, the activin/nodal inhibitor is SB-431542.

In some aspects, step (a) comprises culturing for 12-48 hours. In some aspects, step (b) comprises culturing for up to 24 hours. In some aspects, step (c) comprises culturing for 1-3 days. In some aspects, step (d) comprises culturing for 1-3 days. In some aspects, step (e) comprises culturing for 1-3 days. In some aspects, step (f) comprises culturing for at least 6 days and up to 8 days. In some aspects, step (g) comprises culturing for at least 6 days and up to 21-28 days total. In some aspects, step (g) comprises culturing for up to 6 days and step (h) comprises culturing for at least 6 days and up to 10-16 days total.

In any of the foregoing or related aspects, step (a) comprises culturing for 16-20 hours; step (b) comprises culturing for 6-10 hours; step (c) comprises culturing for 2 days; step (d) comprises culturing for 2 days; step (e) comprises culturing for 2 days; step (f) comprises culturing for 6-8 days; and step (g) comprises culturing for 6-28 days.

In any of the foregoing or related aspects, step (a) comprises culturing for 16-20 hours; step (b) comprises culturing for 6-10 hours; step (c) comprises culturing for 2 days; step (d) comprises culturing for 2 days; step (e) comprises culturing for 2 days; step (f) comprises culturing for 6-8 days; step (g) comprises culturing for 6 days; and step (h) comprises culturing for 6-16 days.

In some aspects, steps (a)-(g) occurs between 20-42 days. In some aspects, steps (a)-(g) occurs in less than 20 days. In some aspects, NK cells are generated in about 20 days. In some aspects, steps (a)-(g) occurs in about 20 days and culturing the cell population in the seventh medium in step (g) results in the cell population comprising at least about 70% NK cells or 95% NK cells.

In some aspects, steps (a)-(h) occurs between 19-33 days. In some aspects, steps (a)-(h) occurs in less than 20 days. In some aspects, NK cells are generated in about 20 days. In some aspects, NK cells are generated in about 16 days. In some aspects, NK cells are generated in about 23 to 40 days. In some aspects, steps (a)-(h) occurs in about 23-40 days. In some aspects, NK cells are generated in about 23 to 30 days. In some aspects, steps (a)-(h) occurs in about 23-30 days. In some aspects, steps (a)-(h) occurs in about 28-30 days. In some aspects, culturing the cell population in the eighth medium in step (h) results in the cell population comprising at least about 70% NK cells or 95% NK cells. In some aspects, steps (a)-(h) occurs in about 30 days and culturing the cell population in the eighth medium in step (h) results in the cell population comprising at least about 70% NK cells or 95% NK cells.

In any of the foregoing or related aspects, the method is carried out under suspension agitation. In some aspects, suspension agitation comprises rotation, optionally wherein the rotation speed is at least about 35 RPM to about 100 RPM.

In any of the foregoing or related aspects, the first and second media comprise StemFlex medium. In any of the foregoing or related aspects, the first media comprises StemFlex medium or StemBrew medium. In some aspects, the third, fourth and fifth media comprise APEL medium. In some aspects, the second, third, fourth and fifth media comprise APEL medium. In some aspects, the sixth and seventh media comprise DMEM/F12 medium. In some aspects, the sixth and seventh media comprise DMEM (high glucose)/F12 medium.

In any of the foregoing or related aspects, the sixth and seventh media comprise human serum, zinc sulfate, ethanolamine, β-mercaptoethanol, glucose, or any combination thereof. In some aspects, the concentration of human serum is about 5%-40%, the concentration of zinc sulfate is about 1.7-40 the concentration of ethanolamine is about 20-60 the concentration of β-mercaptoethanol is about 0.5-45 and the concentration of glucose is about 8-40 mM. In some aspects, the concentration of human serum is about 15%, the concentration of zinc sulfate is about 37 the concentration of ethanolamine is about 50 the concentration of β-mercaptoethanol is about 1 and the concentration of glucose is about 27 mM. In some aspects, the concentration of human serum is about 20%, the concentration of zinc sulfate is about 36.2 the concentration of ethanolamine is about 50 and the concentration of glucose is about 20 mM. In some aspects, the sixth and seventh media do not comprise β-mercaptoethanol.

In any of the foregoing or related aspects, the sixth and seventh media comprises DMEM/F12 medium and a supplement of human serum, zinc sulfate, ethanolamine, β-mercaptoethanol, glucose, or any combination thereof. In any of the foregoing or related aspects, the sixth and seventh media comprises DMEM (high glucose)/F12 medium and a supplement of human serum, zinc sulfate, ethanolamine, β-mercaptoethanol, glucose, or any combination thereof. In some aspects, the supplement provides an additional concentration of human serum of about 5%-40%, an additional concentration of zinc sulfate of about 1.7-40 an additional concentration of ethanolamine of about 20-60 an additional concentration of β-mercaptoethanol of about 0.5-45 and an additional concentration of glucose of about 2-40 mM. In some aspects, the additional concentration of human serum is about 15%, the additional concentration of zinc sulfate is about 37 the additional concentration of ethanolamine is about 50 the additional concentration of β-mercaptoethanol is about 1 and the additional concentration of glucose is about 27 mM. In some aspects, the additional concentration of human serum is about 15%, the additional concentration of zinc sulfate is about 37 μM, the additional concentration of ethanolamine is about 50 μM, the additional concentration of β-mercaptoethanol is about 1 μM, and the additional concentration of glucose is about 10.25 mM. In some aspects, the additional concentration of human serum is about 20%, the additional concentration of zinc sulfate is about 36.2 μM, the additional concentration of ethanolamine is about 50 μM, and the additional concentration of glucose is about 20 mM. In some aspects, the additional concentration of human serum is about 20%, the additional concentration of zinc sulfate is about 36.2 μM, the additional concentration of ethanolamine is about 50 μM, and the additional concentration of glucose is about 4.66 mM. In some aspects, the sixth and seventh media do not comprise a supplement comprising β-mercaptoethanol.

In any of the foregoing or related aspects, the eighth media comprises DMEM/F12 or DMEM (high glucose)/F12 medium and a supplement of human serum, zinc sulfate, ethanolamine, glucose, or any combination thereof. In some aspects, the supplement provides an additional concentration of human serum of about 5%-40%, an additional concentration of zinc sulfate of about 1.7-40 μM, an additional concentration of ethanolamine of about 20-60 μM, and an additional concentration of glucose of about 2-40 mM. In some aspects, the additional concentration of human serum is about 10%, the additional concentration of zinc sulfate is about 37 μM, the additional concentration of ethanolamine is about 50 μM, and the additional concentration of glucose is about 2.3 mM.

In some aspects, the first medium comprises 10 μM of the ROCK inhibitor. In some aspects, the second medium comprises 30 ng/mL BMP-4. In some aspects, the second medium further comprises 10 μM of a ROCK inhibitor. In some aspects, the second medium comprises 30 ng/mL BMP-4 and 10 µM of a ROCK inhibitor. In some aspects, the third medium comprises 30 ng/mL BMP-4, 100 ng/mL FGF2, 3-10 µM CHIR-99021, optionally 6 µM CHIR-99021 or 7 µM CHIR-99021, and 2.5-5.0 ng/mL Activin A. In some aspects, the third medium is added to the second medium at a 1:1 ratio. In some aspects, the fourth and fifth media comprise 20 ng/mL FGF, 20 ng/mL VEGF, 20 ng/mL TPO, 100 ng/mL SCF, 40 ng/mL IL-3, and 10-20 ng/mL FLT3L. In some aspects, the fourth medium further comprises 5 µM SB-431542. In some aspects, the fourth medium further comprises 0.5-5 µM WNT C-59. In some aspects, the sixth and seventh media comprises 20 ng/mL IL-7, 10-20 ng/mL FLT3L, 10-20 ng/mL IL-15, and 20 ng/mL SCF. In some aspects, the sixth medium comprises 5 ng/mL IL-3.

In any of the foregoing or related aspects, the eighth medium can comprise IL-7, FLT3L, IL-15, SCF and nicotinamide. In various aspects, the eighth medium can comprise 10-20 ng/mL IL-7, 5-20 ng/mL FLT3L, 10-30 ng/mL IL-15, 20-40 ng/mL SCF, and 1-15 mM nicotinamide. In various aspects, the eighth medium comprises 10 ng/mL IL-7, 7.5 ng/mL FLT3L, 15 ng/mL IL-15, 20 ng/mL SCF and 6.5 mM nicotinamide.

In any of the foregoing or related aspects, the eighth medium can comprise IL-7, FLT3L, IL-15, and SCF. In various aspects, the eighth medium can comprise 10-20 ng/mL IL-7, 5-20 ng/mL FLT3L, 10-30 ng/mL IL-15, and about 20-40 ng/mL SCF. In various aspects, the eighth medium comprises about 10 ng/mL IL-7, about 7.5 ng/mL FLT3L, about 15 ng/mL IL-15, and about 20 ng/mL SCF. In various aspects, the eighth medium does not comprise nicotinamide.

In any of the foregoing or related aspects, the HSPCs of (d) express CD34 and/or CD45−. In some aspects, the NK cells express CD56 and/or CD45−. In some aspects, the NK cells express at least one activating receptor. In some aspects, the at least one activating receptor is selected from the group of NKp44, NKp46, NKG2D, CD16, KIR2DL4, NKp30, and any combination thereof. In some aspects, the NK cells express at least one inhibitory receptor. In some aspects, the at least one inhibitory receptor is selected from the group of NKG2A, KIR3DL2, and any combination thereof. In some aspects, the NK cells express at least one co-receptor. In some aspects, the at least one co-receptor is CD94. In some aspects, the NK cells comprise at least one function associated with endogenous NK cells. In some aspects, the at least one function comprises the ability to induce cell lysis and cell death of a target cell. In some aspects, the at least one function comprises degranulation. In some aspects, degranulation comprises release of perforin and granzyme B. In some aspects, degranulation comprises expression of CD107a on the cell surface of an NK cell.

In some aspects, the NK cells are generated without sorting CD34+ cells from the cell population.

In some aspects, the population of stem cells is a population of engineered cells. In some aspects, the stem cells are genetically modified by an RNA-guided endonuclease system. In some aspects, the RNA-guided endonuclease system is a CRISPR system comprising a CRISPR nuclease and a guide RNA.

In any of the foregoing or related aspects, the stem cells are induced pluripotent stem cells (iPSC), pluripotent stem cells (PSC), embryonic stem cells (ESC), or adult stem cells (ASC). In some aspects, the stem cell is a mammalian cell, optionally wherein the cell is a human cell.

In some aspects, the disclosure provides a population of stem cells differentiated by or obtainable by a method described herein. In some aspects, the disclosure provides a population of hematopoietic stem and progenitor cells differentiated by or obtainable by at least one step in a method described herein. In other aspects, the disclosure provides a plurality of NK cells generated by or obtainable by a method described herein.

In some aspects, the disclosure provides a composition comprising a plurality of NK cells generated by or obtainable by a method described herein, for use as a medicament. In other aspects, the disclosure provides a composition comprising a population of stem cells (e.g., hematopoietic stem and progenitor cells) differentiated by or obtainable by a method described herein, for use as a medicament. In some aspects, the composition may be a pharmaceutical composition.

In some aspects, the population of cells and/or the composition provided herein is provided for the use of treating a subject in need thereof (e.g., treating a condition in a subject in need thereof). In some aspects, the plurality of NK cells, the population of stem cells (e.g., hematopoietic stem and progenitor cells) and/or the composition provided herein is provided for the use of treating a subject in need thereof (e.g., treating a condition in a subject in need thereof). In some aspects, the disclosure provides a plurality of NK cells for use in treating a subject in need thereof. In some aspects, the disclosure provides a population of hematopoietic stem and progenitor cells for use in treating a subject in need thereof. In some aspects, the subject is a human who has, is suspected of having, or is at risk for a cancer. In some aspects, the subject is a human who has, is suspected of having, or is at risk for an infectious disease or an autoimmune disease. In some aspects, the plurality of NK cells, the population of stem cells (e.g., hematopoietic stem and progenitor cells) and/or the composition provided herein is provided for the use for treating cancer. In some aspects, the plurality of NK cells, the population of stem cells (e.g., hematopoietic stem and progenitor cells) and/or the composition provided herein is provided for the use for treating an infectious disease or an autoimmune disease.

In other aspects, the disclosure provides a method comprising administering to a subject a plurality of NK cells described herein or a pharmaceutical composition comprising the plurality of NK cells described herein. In some aspects, the plurality of NK cells is administered as a pharmaceutical composition. In other aspects, the disclosure provides a method comprising administering to a subject a population of hematopoietic stem and progenitor cells described herein. In some aspects, the population of hematopoietic stem and progenitor cells is administered as a pharmaceutical composition. In some aspects, the subject is a human who has, is suspected of having, or is at risk for a cancer. In some aspects, the subject is a human who has, is suspected of having, or is at risk for an infectious disease or an autoimmune disease.

BRIEF DESCRIPTION OF THE DRAWINGS

FIG. 2A provides a schematic timeline and cell stages of iNK differentiation, the characteristic cell markers at each stage, and images of cells during iNK differentiation at day 0, day 6, day 21, and day 28.

FIG. 2B provides a schematic of the various cell stages during the iNK differentiation process and flow cytometry analysis of CD45, CD34, and CD43 expressing cells at Day 10 and flow cytometry analysis of CD7, CD45 and CD38 expressing cells at Day 14.

FIG. 15 shows DoE I medium formulation test and yield results.

FIG. 16 shows DoE II medium formulation test and yield results.

FIG. 22 shows DoE IV medium formulation test and yield results.

FIG. 23 shows DoE V medium formulation test and yield results.

DETAILED DESCRIPTION OF THE INVENTION

Figure 1:
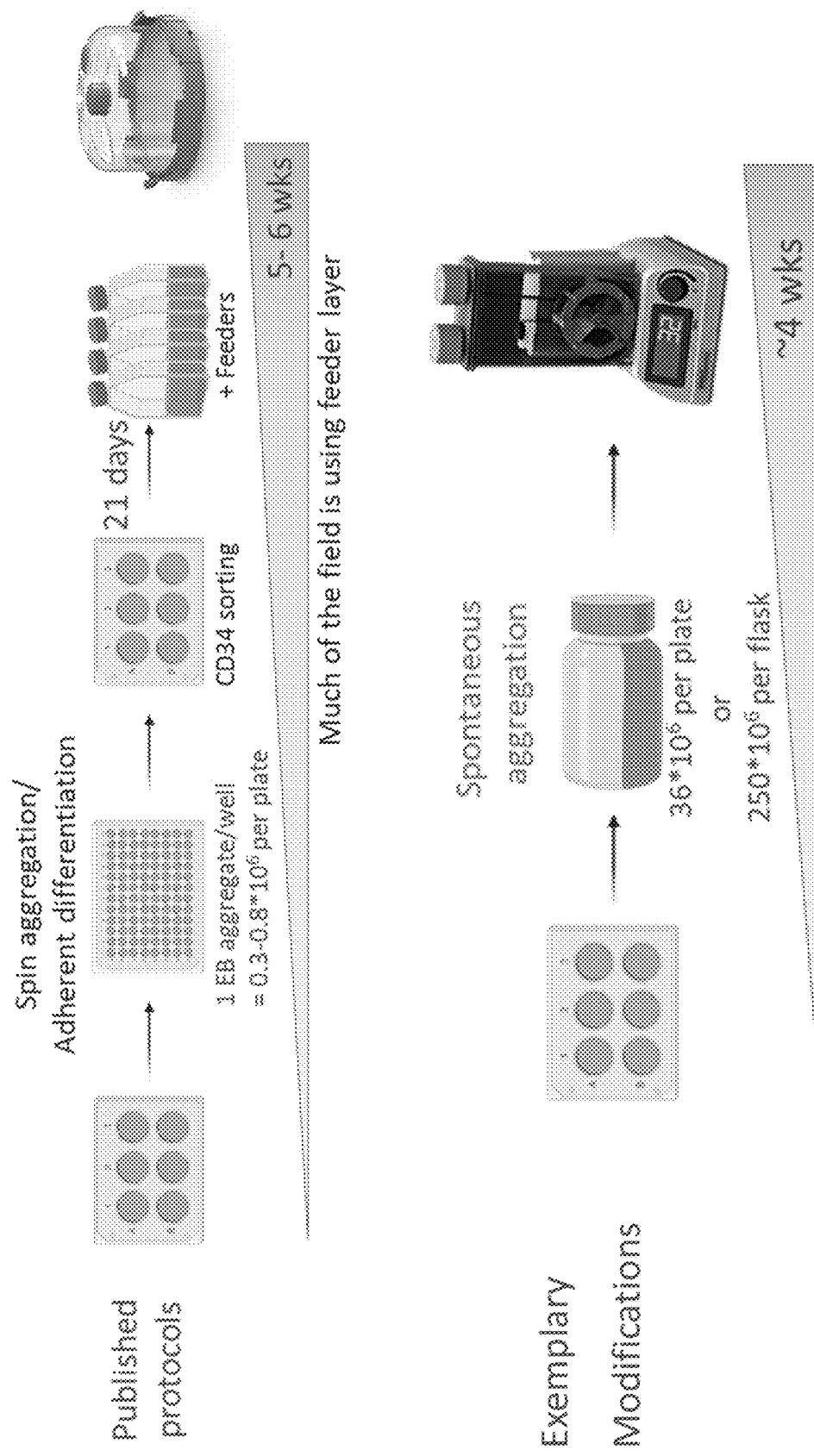
FIG. 1 provides a schematic comparison of a published iNK (NK cells differentiated from iPSC) differentiation protocol and an exemplary modified iNK differentiation protocol described herein.

The present disclosure is based, at least in part, on the discovery of a differentiation protocol for NK cells that provides a shortened differentiation period relative to known differentiation protocols. Specifically, current differentiation protocols require 5-6 weeks to generate NK cells, and typically utilize spin aggregation, adherent differentiation with feeder layers, and require cell sorting. As shown herein, a series of differentiation steps comprising various growth factors, cytokines, and protein inhibitors and activators, contributes to a shortened differentiation protocol that does not require feeder cells or cell sorting. Without wishing to be bound by theory, the methods described herein provide means to differentiate cells that is more amenable to scale-up and/or manufacturing as the methods utilize controlled aggregation, do not require feeder layers or cell sorting, and has a shorter timeline, e.g., NK cells start developing at 14 days and reach 70%-90% within 3-4 weeks.

Further, the disclosure provides methods for differentiating stem and/or progenitor cells comprising at least one gene-edit. Gene editing NK cells for therapeutic application is difficult due to their resistance to gene delivery and editing. Without wishing to be bound by theory, differentiating a stem and/or progenitor cells comprising a gene-edit allows for successful gene editing of NK cells by using the differentiation and gene editing methods described herein, such that the gene-edit is maintained in the differentiated cell.

Accordingly, the disclosure provides methods, compositions and kits for differentiating the cells described herein.

Methods of Differentiation

In some aspects, the disclosure provides methods and compositions for differentiating stem or progenitor cells into HSPCs and/or NK cells. In some embodiments, HSPCs differentiated from stem or progenitor cells using the methods and compositions described herein are further differentiated into any cell in the hematopoietic lineage.

In some embodiments, stem or progenitor cells are differentiated into NK cells using any of the methods described herein. In some embodiments, stem or progenitor cells are differentiated into HSPCs using any of the methods described herein. In some embodiments, mesodermal cells are differentiated into NK cells. In some embodiments, hemogenic endothelium is differentiated into NK cells. In some embodiments, HSPCs are differentiated into NK cells. In some embodiments, common lymphoid progenitor cells are differentiated into NK progenitors. In some embodiments, common lymphoid progenitor cells are differentiated into NK cells. In some embodiments, NK progenitors are differentiated into NK cells. In some embodiments, common lymphoid progenitors or NK progenitors are differentiated into innate lymphoid cells. In some embodiments, immature NK cells are differentiated into NK cells. In some embodiments, NK cells are further matured and differentiated to express terminal and/or exhaustion markers. In some embodiments, induced pluripotent stem cells (iPSCs) are differentiated into HSPCs. In some embodiments, iPSCs are differentiated into HSPCs which are differentiated into NK cells. It is noted that any of the differentiation methods provided herein may be performed in vitro or ex vivo. Accordingly, in some embodiments, the methods for differentiating NK cells or intermediary stem cells do not comprise a method for treatment of the human or animal body by therapy. Likewise, in some embodiments, the methods for differentiating NK cells or intermediate stem cells (e.g., HSPCs) do not comprise methods for modifying the germ line genetic identity of human beings.

Stage I: Differentiation of Stem Cells into HSPCs

In some embodiments, the disclosure provides compositions and methods for differentiating stem cells or progenitor cells into HSPCs.

In some embodiments, stem cells are differentiated into a cell population comprising HSPCs using the following method:

(a) culturing a population of stem cells in a medium comprising an amount of a ROCK inhibitor under conditions sufficient to form a population comprising cell aggregates;

(b) culturing the population comprising cell aggregates in a medium comprising BMP-4;

(c) culturing the population comprising cell aggregates in a medium comprising BMP-4, FGF2, a WNT pathway activator, and Activin A;

(d) culturing the population comprising cell aggregates in a medium comprising FGF2, VEGF, TPO, SCF, IL-3, FLT3L, WNT C-59 and an activin/nodal inhibitor to form a cell population comprising hematopoietic stem and progenitor cells (HSPCs). In some embodiments, the medium of (b) comprises BMP-4 and a ROCK inhibitor.

In some embodiments, step (a) comprises culturing the population of stem cells for about 12-48 hours. In some embodiments, step (a) comprises culturing the population of stem cells for about 12-24 hours. In some embodiments, step (a) comprises culturing the population of stem cells for about 16-20 hours. In some embodiments, step (b) comprises culturing the population comprising cell aggregates for up to 24 hours. In some embodiments, step (b) comprises culturing the population comprising cell aggregates for about 4-24 hours. In some embodiments, step (b) comprises culturing the population comprising cell aggregates for about 4-12 hours. In some embodiments, step (b) comprises culturing the population comprising cell aggregates for about 6-10 hours. In some embodiments, step (c) comprises culturing the population comprising cell aggregates for about 1-3 days. In some embodiments, step (c) comprises culturing the population comprising cell aggregates for about 2 days. In some embodiments, step (d) comprising culturing the population comprising cell aggregates for about 1-3 days. In some embodiments, step (d) comprising culturing the population comprising cell aggregates for about 2 days.

In some embodiments, step (a) comprises culturing the population of stem cells for about 12-48 hours; step (b) comprises culturing the population comprising cell aggregates for up to about 24 hours; step (c) comprises culturing the population comprising cell aggregates for about 1-3 days; and step (d) comprises culturing the population comprising cell aggregates for about 1-3 days. In some embodiments, step (a) comprises culturing the population of stem cells for about 16-20 hours; step (b) comprises culturing the population comprising cell aggregates for about 6-10 hours; step (c) comprises culturing the population comprising cell aggregates for about 2 days; and step (d) comprises culturing the population comprising cell aggregates for about 2 days.

In some embodiments, the time to generate aggregates in step (a) is about 12 hours, about 18 hours, about 24 hours, about 30 hours, about 36 hours, about 42 hours, or about 48 hours. In some embodiments, the time to generate aggregates in step (a) is about 16 hours, about 17 hours, about 18 hours, about 19 hours, or about 20 hours.

In some embodiments, differentiating a population of stem cells into a cell population comprising HSPCs takes about 4-9 days. In some embodiments, differentiating a population of stem cells into a cell population comprising HSPCs takes about 5-7 days.

In some embodiments, steps (a)-(d) form a cell population comprising HSPCs that are then differentiated into NK cells using the methods described herein. In some embodiments, steps (a)-(d) form a cell population comprising HSPCs that are then differentiated into any cell within the hematopoietic lineage using methods known to those of skill in the art.

Stem and Progenitor Cells

In some embodiments, stem or progenitor cells are differentiated into natural killer (NK) cells. In some embodiments, stem or progenitor cells are differentiated into HSPCs. In some embodiments, the stem or progenitor cell is a mammalian cell. In some embodiments, the stem or progenitor cell is a human cell. In some embodiments, the stem or progenitor cell is a pluripotent stem cell (PSC). In some embodiments, the stem or progenitor cell is an embryonic stem cell (ESC), an adult stem cell (ASC), an induced pluripotent stem cell (iPSC), or a hematopoietic stem or progenitor cell (HSPC). In some embodiments, the stem or progenitor cell is an iPSC.

In some embodiments, the stem cells described herein (e.g., iPSCs) are gene-edited and then differentiated into a cell type of interest, e.g., HSPC or NK cell. In some embodiments, the differentiated cell retains the gene-edits of the cell from which it is derived.

Stem cells are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In some embodiments, the term "progenitor" or "stem cell" refers to a generalized mother cell whose descendants (progeny) specialize, often in different directions, by differentiation, e.g., by acquiring completely individual characteristics, as occurs in progressive diversification of embryonic cells and tissues. Cellular differentiation is a complex process typically occurring through many cell divisions. A differentiated cell may derive from a multipotent cell that itself is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

A "differentiated cell" is a cell that has progressed further down the developmental pathway than the cell to which it is being compared. Thus, stem cells can differentiate into lineage-restricted precursor cells (such as a hematopoietic stem and progenitor cell (HSPC)), which in turn can differentiate into other types of precursor cells further down the pathway (such as a common lymphoid progenitor cell), and then to an end-stage differentiated cell, such as a natural killer cell, which plays a characteristic role in a certain tissue type, and may or may not retain the capacity to proliferate further.

Embryonic Stem Cells

In some embodiments, HSPCs and/or NK cells are differentiated from embryonic stem cells (ESCs). ESCs are derived from blastocytes of mammalian embryos and are able differentiate into any cell type and propagate rapidly. ESCs are also believed to have a normal karyotype, maintaining high telomerase activity, and exhibiting remarkable long-term proliferative potential, making these cells excellent candidates for use as gene-edited stem cells. In some embodiments, HSPCs are differentiated from ESCs. In some embodiments, NK cells are differentiated from ESCs. In some embodiments, ESCs are differentiated into HSPCs and/or NK cells using any method described herein. In some embodiments, ESCs are gene-edited before differentiation into HSPCs and/or NK cells.

Adult Stem Cells

In some embodiments, HSPCs and/or NK cells are differentiated from adult stem cells (ASCs). ASCs are undifferentiated cells that may be found in mammals, e.g., humans. ASCs are defined by their ability to self-renew, e.g., be passaged through several rounds of cell replication while maintaining their undifferentiated state, and ability to differentiate into several distinct cell types, e.g., glial cells. Adult stem cells are a broad class of stem cells that may encompass hematopoietic stem cells, mammary stem cells, intestinal stem cells, mesenchymal stem cells, endothelial stem cells, neural stem cells, olfactory adult stem cells, neural crest stem cells, and testicular cells. In some embodiments, HSPCs are differentiated from ASCs. In some embodiments, NK cells are differentiated from ASCs. In some embodiments, ASCs are differentiated into HSPCs and/or NK cells using any method described herein. In some embodiments, ASCs are gene-edited before differentiation into HSPCs and/or NK cells.

Induced Pluripotent Stem Cells

In some embodiments, HSPCs and/or NK cells are differentiated from pluripotent stem cells (iPSCs). An iPSC may be generated directly from an adult human cell by introducing genes that encode critical transcription factors involved in pluripotency, e.g., Oct4, Sox2, cMyc, and Klf4. An iPSC may be derived from the same subject to which subsequent progenitor cells are to be administered. That is, a somatic cell can be obtained from a subject, reprogrammed to an induced pluripotent stem cell, and then re-differentiated into a progenitor cell to be administered to the subject (e.g., autologous cells). However, in the case of autologous cells, a risk of immune response and poor viability post-engraftment remain. In some embodiments, iPSC are generated from adult somatic cells using genetic reprogramming methods known in the art. In some embodiments, the iPSCs are derived from a commercial source. In some embodiments, HSPCs are differentiated from iPSCs. In some embodiments, NK cells are differentiated from iPSCs. In some embodiments, iPSCs are differentiated into HSPCs and/or NK cells using any method described herein. In some embodiments, iPSCs are gene-edited before differentiation into HSPCs and/or NK cells.

Mesoderm

In some embodiments, mesodermal cells are produced using the differentiation methods described herein. In some embodiments, mesodermal cells are an intermediate cell type between a stem cell and an HSPC. A mesodermal cell type is one of the three germinal layers in embryonic development. The mesoderm eventually differentiates in to, but is not limited to muscle, connective tissue, bone, red blood cells, white blood cells, and microglia. In some embodiments, mesodermal cells are derived from any of the stem cells described herein. In some embodiments, mesodermal cells are derived from iPSC. In some embodiments, mesodermal cells have any of the gene-edits described herein. In some embodiments, mesodermal cells are differentiated into HSPCs. In some embodiments, mesodermal cells are differentiated into NK cells. In some embodiments, mesodermal cells are differentiated into HSPCs and/or NK cells using any method described herein. In some embodiments, mesodermal cells are gene-edited before differentiation into HSPCs and/or NK cells.

Hemogenic Endothelium

In some embodiments, hemogenic endothelium (HE) cells are produced using the differentiation methods described herein. In some embodiments, HE cells are an intermediate cell type between a stem cell and an HSPC. This cell type is an intermediate precursor of hematopoietic progenitors. In some embodiments, HE cells are derived from any of the stem cells described herein. In some embodiments, HE cells are derived from iPSC. In some embodiments, the HE cells have any of the gene-edits described herein. In some embodiments, the HE cells are differentiated into HSPCs. In some embodiments, the HE cells are differentiated into NK cells. In some embodiments, HE cells are differentiated into HSPCs and/or NK cells using any method described herein. In some embodiments, HE cells are gene-edited before differentiation into HSPCs and/or NK cells.

Human Hematopoietic Stem and Progenitor Cells

In some embodiments, hematopoietic stem and progenitor cells (hHSPCs) are produced using the differentiation methods described herein. This stem cell lineage gives rise to all blood cell types, including erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells). Blood cells are produced by the proliferation and differentiation of a very small population of pluripotent hematopoietic stem cells (HSCs) that also have the ability to replenish themselves by self-renewal. During differentiation, the progeny of HSCs progress through various intermediate maturational stages, generating multi-potential and lineage-committed progenitor cells prior to reaching maturity. Bone marrow (BM) is the major site of hematopoiesis in humans and, under normal conditions, only small numbers of hematopoietic stem and progenitor cells (HSPCs) can be found in the peripheral blood (PB). Treatment with cytokines, some myelosuppressive drugs used in cancer treatment, and compounds that disrupt the interaction between hematopoietic and BM stromal cells can rapidly mobilize large numbers of stem and progenitors into the circulation. In some embodiments, HSPCs are derived from any of the stem cells described herein. In some embodiments, HSPCs are derived from iPSCs. In some embodiments, the HSPCs have any of the gene-edits described herein. In some embodiments, the HSPCs cells are differentiated into NK cells. In some embodiments, HSPCs are differentiated into NK cells using any method described herein. In some embodiments, HSPCs are gene-edited before differentiation into NK cells.

Stage I Cell Phenotypes

In some embodiments, cell aggregates are maintained through differentiation from stem cell to HSPC. In some embodiments, single cells form during differentiation into HSPCs.

In some embodiments, the stem or progenitor cells are Oct3/4+ and Sox2+. In some embodiments, Oct3/4 and Sox2 expression is reduced as cells differentiate into HSPCs. In some embodiments, the differentiating cells are $CD34^+$/$CD43^-$. In some embodiments, CD43 expression increases throughout the differentiation process. In some embodiments, the population of cells comprising HSPCs formed in step (d) of Stage I comprises $CD34^+/CD43^+/CD45^-$ cells. In some embodiments, the population of cells comprising HSPCs formed in step (d) of Stage I comprise $CD34^+/CD43^+/CD45^+$ cells. In some embodiments, the population of cells comprising HSPCs formed in step (d) of Stage I comprise $CD34^+CD43^-CD45^+$ cells. In some embodiments, the cells in steps (a)-(d) are $CD56^-$.

Stage II: Differentiation of HSPCs into NK Cells

In some embodiments, the disclosure provides compositions and methods for differentiating HSPCs into NK cells.

In some embodiments, a cell population comprising HSPCs is differentiated into a cell population comprising NK cells using the following method:

(a) culturing the cell population in a medium comprising FGF2, VEGF, TPO, SCF, IL-3 and FLT3L;

(b) culturing the cell population in a medium comprising IL-3, IL-7, FLT3L, IL-15 and SCF;

(c) culturing the cell population in a medium comprising IL-7, FLT3L, IL-15 and SCF for a time sufficient to generate NK cells.

In some embodiments, step (a) comprises culturing the cell population for about 1-3 days. In some embodiments, step (a) comprises culturing the cell population for about 2 days. In some embodiments, step (b) comprises culturing the cell population for up to 8 days. In some embodiments, step (b) comprises culturing the cell population for about 6-8 days. In some embodiments, step (c) comprises culturing the cell population for at least 6 days. In some embodiments, step (c) comprises culturing the cell population for at least 6 days and up to 21-28 days total. In some embodiments, step (c) comprises culturing the cell population for about 6-28 days. In some embodiments, step (a) comprises culturing cell population for about 1-3 days; step (b) comprises culturing the cell population for up to about 8 days; and step (c) comprises culturing the for at least 6 days. In some embodiments, step (a) comprises culturing the cell population for about 2 days; step (b) comprises culturing the cell population for about 6-8 days; and step (c) comprises culturing the cell population for about 6-28 days.

In some embodiments, differentiating a cell population comprising HSPCs into a cell population comprising NK cells takes about 14-40 days. In some embodiments, differentiating a cell population comprising HSPCs into a cell population comprising NK cells takes about 14-17 days.

In some embodiments, a time sufficient to generate a first NK cell in step (c) is about 6 days, about 7 days, about 8 days, about 9 days, about 10 days, about 11 days, about 12 days, about 13 days, about 14 days, or about 15 days. In some embodiments, a time sufficient to generate a cell population comprising at least about 70% NK cells is about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days. In some embodiments, a time sufficient to generate a cell population comprising at least about 80% NK cells is about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days. In some embodiments, a time sufficient to generate a cell population comprising at least about 90% NK cells is about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days. In some embodiments, a time sufficient to generate a cell population comprising at least about 95% NK cells is about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days. In some embodiments, a time sufficient to generate a cell population comprising at least about 99% NK cells is about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some embodiments, a cell population comprising HSPCs is differentiated into a cell population comprising NK cells using the following method:
  (a) culturing the cell population in a medium comprising FGF2, VEGF, TPO, SCF, IL-3 and FLT3L;
  (b) culturing the cell population in a medium comprising IL-3, IL-7, FLT3L, IL-15 and SCF;
  (c) culturing the cell population in a medium comprising IL-7, FLT3L, IL-15 and SCF;
  (d) culturing the cell population in a medium comprising IL-7, FLT3L, IL-15, SCF, and nicotinamide for a time sufficient to generate NK cells.

In some embodiments, a cell population comprising HSPCs is differentiated into a cell population comprising NK cells using the following method:
  (a) culturing the cell population in a medium comprising FGF2, VEGF, TPO, SCF, IL-3 and FLT3L;
  (b) culturing the cell population in a medium comprising IL-3, IL-7, FLT3L, IL-15 and SCF;
  (c) culturing the cell population in a medium comprising IL-7, FLT3L, IL-15 and SCF;
  (d) culturing the cell population in a medium comprising IL-7, FLT3L, IL-15, and SCF for a time sufficient to generate NK cells.

In some embodiments, step (a) comprises culturing the cell population for about 1-3 days. In some embodiments, step (a) comprises culturing the cell population for about 2 days. In some embodiments, step (b) comprises culturing the cell population for up to 8 days. In some embodiments, step (b) comprises culturing the cell population for about 6-8 days. In some embodiments, step (c) comprises culturing the cell population for up to 6 days. In some embodiments, step (c) comprises culturing the cell population for about 6 days. In some embodiments, step (d) comprises culturing the cell population for at least 6 days and up to 10-16 days total. In some embodiments, step (d) comprises culturing the cell population for about 8 to 16 days. In some embodiments, step (a) comprises culturing the cell population for about 1-3 days; step (b) comprises culturing the cell population for up to about 8 days; step (c) comprises culturing the cell population for up to 6 days; and step (d) comprises culturing the cell population for at least 6 days and up to 10-16 days total. In some embodiments, step (a) comprises culturing the cell population for about 2 days; step (b) comprises culturing the cell population for about 6-8 days; step (c) comprises culturing the cell population for about 6 days, and step (d) comprises culturing the cell population for about 8 to 16 days.

In some embodiments, differentiating a cell population comprising HSPCs into a cell population comprising NK cells takes about 14-40 days. In some embodiments, differentiating a cell population comprising HSPCs into a cell population comprising NK cells takes about 14-19 days.

In some embodiments, a time sufficient to generate a first NK cell in step (d) is about 6 days, about 7 days, about 8 days, about 9 days, about 10 days, about 11 days, about 12 days, about 13 days, about 14 days, about 15 days, or about 16 days. In some embodiments, a time sufficient to generate a cell population comprising at least about 70% NK cells in step (d) is about 6 days, about 7 days, about 8 days, about 9 days, about 10 days, about 11 days, about 12 days, about 13 days, about 14 days, about 15 days, or about 16 days. In some embodiments, a time sufficient to generate a cell population comprising at least about 80% NK cells in step (d) about 6 days, about 7 days, about 8 days, about 9 days, about 10 days, about 11 days, about 12 days, about 13 days, about 14 days, about 15 days, or about 16 days. In some embodiments, a time sufficient to generate a cell population comprising at least about 90% NK cells in step (d) is about 6 days, about 7 days, about 8 days, about 9 days, about 10 days, about 11 days, about 12 days, about 13 days, about 14 days, about 15 days, or about 16 days. In some embodiments, a time sufficient to generate a cell population comprising at least about 95% NK cells in step (d) is about 6 days, about 7 days, about 8 days, about 9 days, about 10 days, about 11 days, about 12 days, about 13 days, about 14 days, about 15 days, or about 16 days. In some embodiments, a time sufficient to generate a cell population comprising at least about 99% NK cells in step (d) is about 6 days, about 7 days, about 8 days, about 9 days, about 10 days, about 11 days, about 12 days, about 13 days, about 14 days, about 15 days, or about 16 days.

Common Lymphoid Progenitor

In some embodiments, HSPCs are differentiated into CLPs. In some embodiments, CLPs are an intermediate cell type generated while differentiating a stem or progenitor cell into NK cells. In some embodiments, CLPs are an intermediate cell type generated while differentiating HSPCs to NK cells. CLPs are descendants of HSPCs. These cells differentiate into the lymphoid lineage of blood cells. Further differentiation yields B-cell progenitor cells, Natural Killer cells, and thymocytes. In some embodiments, CLP cells are derived from iPSCs. In some embodiments, CLP cells are differentiated from HSPCs. In some embodiments, the CLP cells have any of the gene-edits described herein. In some embodiments, the CLP cells are differentiated into NK cells. In some embodiments, CLP cells are differentiated into NK cells using any method described herein. In some embodiments, CLP cells are gene-edited before differentiation into NK cells.

NK Progenitor Cells

In some embodiments, HSPCs are differentiated into NK progenitor cells (NKP) and immature NK cells. In some embodiments, CLPs differentiate into a bipotent NK/T progenitor that can develop exclusively into T and/or NK cells. In some embodiments, the transition from NK/T progenitor to NKP is marked by the acquisition of the IL-2/15Rb subunit (CD122 receptor). Expression of CD122 turns NKPs into IL-2/IL-15 responsive cells that are committed to the NK cell lineage. NKP cells are capable of differentiating into immature NK cells. In some embodiments, expression of growth factor receptors, such as FLT3 and IL-7Ra, decrease as cells proceed from NKP to immature NK cells, whereas the expression of IL-2Rb, CD2 and 2B4 (CD244) increases. As described herein, maturation of immature NK cells involves the acquisition of activation and inhibitory markers.

Innate Lymphoid Cells (ILCs)

In some embodiments, the methods described herein produce innate lymphoid cells (ILCs). ILCs are a growing family of immune cells that mirror the phenotypes and functions of T cells. NK cells can be considered the innate counterparts of cytotoxic $CD8^+$ T cells, whereas ILC1s, ILC2s, and ILC3s may represent the innate counterparts of $CD4^+$ T helper 1 (TH1), TH2, and TH17 cells. However, in contrast to T cells, ILCs do not express antigen receptors or undergo clonal selection and expansion when stimulated. Instead, ILCs react promptly to signals from infected or injured tissues and produce an array of secreted cytokines, that direct the developing immune response into one that is adapted to the original insult. ILCs develop from CLPs.

In some embodiments, NK cells are generally included in the ILC family because their phenotypic, developmental and functional properties overlap considerably with those of ILC1s. In some embodiments, both human ILCs and human NK cells express CD56 and NKp46. Accordingly, in some embodiments, ILCs are differentiated from stem cells using the methods described herein.

Stage II Cell Phenotypes

In some embodiments, the cell population comprises cell aggregates and single cells. In some embodiments, the cell aggregates dissociate into single cells. In some embodiments, the cell population comprises a majority of single cells.

In some embodiments, the HSPC cells are $CD34^+/CD43^+/CD45^-$. In some embodiments, the HSPCs are differentiated to common lymphoid progenitors. In some embodiments, the CLPs are $CD34^-/CD45^+/CD38^+/CD117^+/CD7^+$. In some embodiments, CLPs are CD34+. In some embodiments, CLPs are CD38−. In some embodiments, CLPs are $CD117^-$. In some embodiments, CD56 expression increases in differentiating cells. In some embodiments, differentiating cells are $CD45^+/CD56^+$. In some embodiments, differentiating cells are $CD34-/CD45^+/CD56^+/NKp46^+/CD94^+/NKG2A^+$. In some embodiments, NK cells formed in step (c) or step (d) of Stage II are $CD45^+/CD56^+/NKp44^+/NKp46^+/CD94^+/NKG2A^+/NKG2D^+/CD16^{-/+}/KIR^{-/+}$. In some embodiments, NK cells formed in step (c) or step (d) of Stage II are $CD45^+/CD56^+/NKp44^+/NKp46^+/CD94^+/NKG2A^+/NKG2D^+/CD16^+/KIR^+$. In some embodiments, NK cells formed in step (c) or step (d) of Stage II are $CD45^+/CD56^+/NKp44^+/NKp46^+/CD94^+/NKG2A^+/NKG2D^+/CD16^+/KIR^+$. In some embodiments, NK cells formed in step (c) or step (d) of Stage II are $CD45^+/CD56^+/NKp44^+/NKp46^+/CD94^+/NKG2A^+/NKG2D^+/CD16^-/KIR^+$. In some embodiments, NK cells formed in step (c) or step (d) of Stage II are $CD45^+/CD56^+/NKp44+/NKp46/CD94^+/NKG2A^+/NKG2D^+/CD16^+/KIR^+$. In some embodiments, the NK cells formed in step (c) or step (d) of Stage II do not express CD3.

In some embodiments, the NK cells formed in step (c) or step (d) are $CD45^+/CD56^+$.

In some embodiments, the NK cells formed in step (c) or step (d) of Stage II comprise at least one function of endogenous NK cells as described herein.

Stage III. Expansion of NK Cells

In some embodiments, the disclosure provides compositions and methods for expanding differentiated NK cells.

In some embodiments, one iPSC generates about 200 to about 340 NK cells during differentiation. In some embodiments, one iPSC generates about 200 to about 340 NK cells in 28 days. In some embodiments, one iPSC generates about 200 to about 340 NK cells in 34 days.

In some embodiments, NK cells are expanded without feeder cells. In some embodiments, NK cells are expanded with feeder cells. In some embodiments, culturing NK cells with K562 feeder cells enhances NK cell expansion.

In some embodiments, NK cells are expanded in static cell culture conditions. In some embodiments, NK cells are expanded in spinner cultures.

In some embodiments, NK cells are cultured for cell expansion in a medium comprising IL-15, IL-7, SCF, FLT3L, or any combination thereof. In some embodiments, NK cells are cultured for cell expansion in a medium comprising IL-15, IL-7, SCF and FLT3L. In some embodiments, NK cells are cultured for cell expansion in a medium comprising 15 ng/mL IL-15, 20 ng/mL TL-7, 20 ng/mL SCF, and 15 ng/mL FLT3L.

In some embodiments, fresh media is added two days after the start of expansion culture. In some embodiments, fresh media is added on the second day, and again on the third day after the start of expansion culture. In some embodiments, cells are cultured at $0.3\times10^6$ cells/mL, $0.5\times10^6$ cells/mL, $1\times10^6$ cells/mL, $1.1\times10^6$ cells/mL, $1.2\times10^6$ cells/mL, $1.3\times10^6$ cells/mL, $1.4\times10^6$ cells/mL, $1.5\times10^6$ cells/mL, $1.6\times10^6$ cells/mL, $1.7\times10^6$ cells/mL, $1.8\times10^6$ cells/mL, $1.9\times10^6$ cells/mL, or $2.0\times10^6$ cells/mL for NK cell expansion. In some embodiments, cell density does not exceed $3.0\times10^6$ cells/mL. In some embodiments, culture media is replaced during expansion if the lactate concentration in the media is above 13-16 mmol/L.

Cell Culture Conditions

In some embodiments, cells are washed in phosphate buffered saline between culture in different mediums. In some embodiments, cells are cultured in suspension culture. In some embodiments, cells are collected by centrifugation after washing with PBS.

In some embodiments, cells are seeded at $3\times10^5$, $4.0\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, or $9\times10^7$ cells per culture dish. One of skill in the art will know what cell density is appropriate depending on the size of the culture dish.

In some embodiments the cells are cultured using a suspension agitation method. Methods for suspension agitation cell culture are known to those of skill in the art. In some embodiments, the suspension agitation comprises rotation. In some embodiments the culture is under a 38 rotation per minute (rpm) agitation condition. In some embodiments the culture is under a 39 rpm agitation condition. In some embodiments, the culture is under a 35 rpm agitation condition, In some embodiments, the culture is under a 45 rpm condition. In some embodiments the culture is under a 50 rpm agitation condition. In some embodiments, the culture is under a 65 rpm agitation condition. In some embodiments, the culture is under a 75 rpm agitation condition. In some embodiments, the culture is under a 98 rpm agitation. In some embodiments, the culture is under a 110 rpm agitation condition.

In some embodiments, the culture is under an agitation condition between about 30 and 115 rpm, between about 30 and 110 rpm, between about 30 and 105 rpm, between about 30 and 100 rpm, between about 30 and 95 rpm, between about 30 and 90 rpm, between about 30 and 85 rpm, between about 30 and 80 rpm, between about 30 and 75 rpm, between about 30 and 70 rpm, between about 30 and 65 rpm, between about 30 and 60 rpm, between about 30 and 55 rpm, between about 30 and 50 rpm, between about 30 and 45 rpm, or between about 30 and 40 rpm. In some embodiments, the culture is under an agitation condition between about 35 and 115 rpm, between about 35 and 110 rpm, between about 35 and 105 rpm, between about 35 and 100 rpm, between about 35 and 95 rpm, between about 35 and 90 rpm, between about 35 and 85 rpm, between about 35 and 80 rpm, between about 35 and 75 rpm, between about 35 and 70 rpm, between about 35 and 65 rpm, between about 35 and 60 rpm, between about 35 and 55 rpm, between about 35 and 50 rpm, between about 35 and 45 rpm, or between about 35 and 40 rpm.

In some embodiments, the culture is under an agitation condition between about 40 and 115 rpm, between about 40 and 110 rpm, between about 40 and 105 rpm, between about 40 and 100 rpm, between about 40 and 95 rpm, between about 40 and 90 rpm, between about 40 and 85 rpm, between about 40 and 80 rpm, between about 40 and 75 rpm, between about 40 and 70 rpm, between about 40 and 65 rpm, between about 40 and 60 rpm, between about 40 and 55 rpm, between about 40 and 50 rpm, or between about 40 and 45 rpm. In some embodiments, the culture is under an agitation condition between about 45 and 115 rpm, between about 45 and 110 rpm, between about 45 and 105 rpm, between about 45 and 100 rpm, between about 45 and 95 rpm, between about 45 and 90 rpm, between about 45 and 85 rpm, between about 45 and 80 rpm, between about 45 and 75 rpm, between about 45 and 70 rpm, between about 45 and 65 rpm, between about 45 and 60 rpm, between about 45 and 55 rpm, or between about 45 and 50 rpm. In some embodiments, the culture is under an agitation condition between about 50 and 115 rpm, between about 50 and 110 rpm, between about 50 and 105 rpm, between about 50 and 100 rpm, between about 50 and 95 rpm, between about 50 and 90 rpm, between about 50 and 85 rpm, between about 50 and 80 rpm, between about 50 and 75 rpm, between about 50 and 70 rpm, between about 50 and 65 rpm, between about 50 and 60 rpm, or between about 50 and 55 rpm. In some embodiments, the culture is under an agitation condition between about 55 and 115 rpm, between about 55 and 110 rpm, between about 55 and 105 rpm, between about 55 and 100 rpm, between about 55 and 95 rpm, between about 55 and 90 rpm, between about 55 and 85 rpm, between about 55 and 80 rpm, between about 55 and 75 rpm, between about 55 and 70 rpm, between about 55 and 65 rpm, or between about 55 and 60 rpm.

In some embodiments, the culture is under an agitation condition between about 60 and 115 rpm, between about 60 and 110 rpm, between about 60 and 105 rpm, between about 60 and 100 rpm, between about 60 and 95 rpm, between about 60 and 90 rpm, between about 60 and 85 rpm, between about 60 and 80 rpm, between about 60 and 75 rpm, between about 60 and 70 rpm, or between about 60 and 65 rpm. In some embodiments, the culture is under an agitation condition between about 65 and 115 rpm, between about 65 and 110 rpm, between about 65 and 105 rpm, between about 65 and 100 rpm, between about 65 and 95 rpm, between about 65 and 90 rpm, between about 65 and 85 rpm, between about 65 and 80 rpm, between about 65 and 75 rpm, or between about 65 and 70 rpm. In some embodiments, the culture is under an agitation condition between about 70 and 120 rpm, between about 70 and 115 rpm, between about 70 and 110 rpm, between about 70 and 105 rpm, between about 70 and 100 rpm, between about 70 and 95 rpm, between about 70 and 90 rpm, between about 70 and 85 rpm, between about 70 and 80 rpm, or between about 70 and 75 rpm. In some embodiments, the culture is under an agitation condition between about 75 and 120 rpm, between about 75 and 115 rpm, between about 75 and 110 rpm, between about 75 and 105 rpm, between about 75 and 100 rpm, between about 75 and 95 rpm, between about 75 and 90 rpm, between about 75 and 85 rpm, or between about 75 and 80 rpm agitation condition.

In some embodiments, the culture is under an agitation condition between about 80 and 120 rpm, between about 80 and 115 rpm, between about 80 and 110 rpm, between about 80 and 105 rpm, between about 80 and 100 rpm, between about 80 and 95 rpm, between about 80 and 90 rpm, or between about 80 and 85 rpm. In some embodiments, the culture is under an agitation condition between about 85 and 120 rpm, between about 85 and 115 rpm, between about 85 and 110 rpm, between about 85 and 105 rpm, between about 85 and 100 rpm, between about 85 and 95 rpm, or between about 85 and 90 rpm. In some embodiments, the culture is under an agitation condition between about 90 and 120 rpm, between about 90 and 115 rpm, between about 90 and 110 rpm, between about 90 and 105 rpm, between about 90 and 100 rpm, or between about 90 and 95 rpm. In some embodiments, the culture is under an agitation condition between about 95 and 120 rpm, between about 95 and 115 rpm, between about 95 and 110 rpm, between about 95 and 105 rpm, or between about 95 and 100 rpm. In some embodiments, the culture is under an agitation condition between about 100 and 120 rpm, between about 100 and 115 rpm, between about 100 and 110 rpm, or between about 100 and 105 rpm. In some embodiments, the culture is under an agitation condition between about 105 and 120 rpm, between about 105 and 115 rpm, or between about 105 and 110 rpm.

In various embodiments, the culture is under an agitation condition of about 30 to 40 rpm. For example, in some embodiments, the culture may under about 35 rpm agitation condition. In various embodiments, the culture is under an agitation condition of about 40 to 50 rpm. For example, the culture may be under about 45 rpm agitation condition. In various embodiments, the culture may be under an agitation condition about 60 and 70 rpm. For example, the culture may be about 65 rpm agitation condition.

In some embodiments, suspension agitation occurs in 6 well plates. In some embodiments, suspension agitation occurs in roller bottles. In some embodiments, suspension agitation occurs in PBS spinner bottles.

Differentiation Medium Components

In some embodiments, the cells described herein are differentiated in media comprising growth factors and cytokines. In some embodiments, the cells are differentiated in media comprising inhibitors. In some embodiments, the cells are differentiated in media comprising one or more of a ROCK inhibitor, GSK inhibitor, WNT pathway activator, WNT pathway inhibitor, Activin-A, activin/nodal inhibitor, TGFβ antagonist, FGF-2, VEGF, FLT3L, IL-3, IL-7, IL-15, BMP-4, SCF, TPO, WNT C-59, IL-2, IL-12, IL-21, IL-18, IL-27, IL-33, TGFβ1, aryl hydrocarbon antagonist and their enhancers: StemRegenin-1, UM729.

In some embodiments, the cells are cultured in a medium comprising at least StemFlex medium. In some embodiments, the cells are cultured in a medium comprising at least StemBrew Basal Media. In some embodiments, the cells are cultured in a medium comprising a StemBrew Supplement. In some embodiments, the cells are cultured in a medium comprising at least albumin polyvinylalcohol essential lipids (APEL) medium. In some embodiments, the cells are cultured in a medium comprising at least STEMdiff™ APEL™ medium. In some embodiments, the cells are cultured in a medium comprising at least STEMdiff™ APEL™ 2 medium. In some embodiments, the term "APEL medium" refers to STEMdiff™ APEL™ medium or STEMdiff™

APEL™ 2 medium. In some embodiments, the cells are cultured in a medium comprising at least DMEM/F12 medium. In some embodiments, the cells are cultured in a medium comprising at least DMEM (high glucose)/F12 medium. In some embodiments, the cells are cultured in a medium comprising at least RPMI medium. In some embodiments, the cells are cultured in a medium comprising at least MCDB131 medium. In some embodiments, the cells are cultured in a medium comprising at least IMDM medium. In some embodiments, the cells are cultured in a media comprising at least the same, or similar components to any one of StemFlex, StemBrew, STEMdiff APEL medium, STEMdiff, APEL 2 medium, DMEM, or DMEM/F12. In some embodiments, the cells are cultured in a media comprising at least the same, or similar components to DMEM (high glucose) or DMEM (high glucose)/F12. In some embodiments, the media comprises one or more of human serum, zinc sulfate, ethanolamine, (3-mercaptoethanol, glucose, nicotinamide, or glutamax (e.g., glutamine substitute). In some embodiments, the media comprises DMEM/F12 and one or more of human serum, zinc sulfate, ethanolamine, β-mercaptoethanol, glucose, nicotinamide, or glutamax. In some embodiments, the media comprises DMEM (high glucose)/F12 and one or more of human serum, zinc sulfate, ethanolamine, β-mercaptoethanol, glucose, nicotinamide, or glutamax.

In some embodiments, the cells are cultured in a medium described herein for one hour to 28 days. In some embodiments, the cells are cultured in a medium described herein for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days.

GSK Inhibitor and WNT Pathway Activators

As used herein, the term "GSK-3 inhibitor" refers to a compound or a group of compounds, capable of inhibiting glycogen synthase kinase 3 (GSK-3; either fully or partially). Glycogen synthase kinase 3 is a serine/threonine protein kinase that mediates the addition of phosphate molecules onto serine and threonine amino acid residues. Phosphorylation of a protein by GSK-3 usually inhibits the activity of its downstream target. GSK-3 has been shown to be integrally tied to pathways of cell proliferation and apoptosis. For example, GSK-3 has been shown to phosphorylate beta-catenin, resulting in beta-catenin being targeted for degradation. GSK-3 is therefore a part of the canonical beta-catenin/Wnt pathway, which signals the cell to divide and proliferate. GSK-3 also participates in several apoptotic signalling pathways by phosphorylating transcription factors that regulate apoptosis. GSK-3 can promote apoptosis by both activating pro-apoptotic factors, such as p53, for example, and inactivating survival-promoting factors through phosphorylation.

In some embodiments, the GSK-3 inhibitor is, but is not limited to, valproic acid sodium salt, staurosporine, KT 5720 (CAS 108068-98-0), GSK-3 Inhibitor IX (CAS 667463-62-9), Ro 31-8220 (CAS 138489-18-6), SB-216763 (CAS 280744-09-4), CID 755673 (CAS 521937-07-5), Kenpaullone (CAS 142273-20-9), lithium chloride, GSK-3beta Inhibitor XII (TWS119; CAS 601514-19-6), GSK-3 Inhibitor XVI (CAS252917-06-9), 1OZ-Hymenialdisine (CAS 82005-12-7), Indirubin (CAS 479-41-4), CHIR-98014 (CAS 252935-94-7), GSK-3beta Inhibitor VI (CAS 62673-69-2), Manzamine A (CAS 104196-68-1), Indirubin-3prime-monoxime (CAS 160807-49-8), GSK-3 Inhibitor X (CAS 740841-15-0), GSK-3 Inhibitor XV, SB-415286 (CAS 264218-23-7), 1-Azakenpaullone (CAS 676596-65-9), TWS 119 ditrifluoroacetate (CAS 601514-19-6), 5-Iodo-indirubin-3'-monoxime, GSK-3beta Inhibitor I (CAS 327036-89-5), 9-Cyanopaullone, Indirubin-5-sulfonic acid sodium salt, GSK-3beta inhibitor VII (CAS 99-73-0), Cdk1/5 inhibitor (CAS 40254-90-8), Hymenidin (CAS 107019-95-4), bisindolylmaleimide X hydrochloride (CAS 131848-97-0), 3F8 (CAS 159109-11-2), isogranulatimide (CAS 244148-46-7), CR8, (R)-isomer (CAS 294646-77-8) L-779,450 (CAS 303727-31-3), indirubin-3prime-monoxime-5-sulphonic acid (CAS 331467-05-1), GSK-3 Inhibitor II (CAS 478482-75-6), GSK-3beta Inhibitor VIII (CAS 487021-52-3), Aloisine A (CAS 496864-16-5), GSK-3beta Inhibitor XI (CAS 626604-39-5), GSK-3 Inhibitor IX (CAS 710323-61-8), Alsterpaullone, 2-Cyanoethyl (CAS 852529-97-0), TCS 2002 (CAS 1005201-24-0), TCS 21311 (CAS 1260181-14-3), A 1070722 (CAS 1384424-80-9), Ro-31-8220 (CAS 138489-18-6), Enzastaurin (CAS 138489-18-6), MeBIO (CAS 667463-95-8), Cdk2/9 Inhibitor (CAS 507487-89-0), Cdk1/2 Inhibitor III (CAS 443798-55-8), PHA 767491 hydrochloride (CAS 845714-00-3), AR-AO 14418-d3, Indole-3-acetamide (CAS 879-37-8), Hymenialdisine Analogue 1 (CAS 693222-51-4), CHIR-99021 (also known as 6-[[2-[[4-(2,4-Dichlorophenyl)-5-(5-methyl-1H-imidazol-2-yl)-2-pyrimidinyl] amino] ethyl] amino]-3-pyridinecarbonitrile and CT99021; CAS 252917-06-9), CHIR-98014 (CAS 556813-39-9), (2'Z,3'E)-6-Bromoindirubin-3'-oxime (Bio; CAS 667463-62-9), Bio-Acetoxime (CAS 667463-85-6), SB216763 (CAS 280744-09-4), and combinations thereof.

In some embodiments, the GSK-3 inhibitor is, but is not limited to, CHIR-99021, (2'Z,3'E)-6-Bromoindirubin-3'-oxime (Bio; CAS 667463-62-9), Kenpaullone (CAS 142273-20-9), GSK-3beta Inhibitor XII (TWS 119; CAS 601514-19-6), Bio-Acetoxime (CAS 667463-85-6), CHIR-98014, SB216763 (CAS 280744-09-4), GSK-3beta Inhibitor VIII (CAS 487021-52-3), and combinations thereof. In some embodiments, the GSK-3 inhibitor is CHIR-99021 or a derivative thereof.

In some embodiments, the GSK-3 inhibitor is present in a concentration of between 0.001 μM to 15 μM. In some embodiments, the GSK3-inhibitor is about 1 μM, about 2 μM, about 3 μM, about 4 μM, about 5 μM, about 6 μM, about 7 μM, about 8 μM, about 9 μM, about 10 μM, about 11 μM, about 12 μM, about 13 μM, about 14 μM, or about 15 μM. In some embodiments, the GSK-3 inhibitor is about 6 μM. In some embodiments, the GSK-3 inhibitor is about 7 μM.

As used herein, a "WNT pathway activator" or "a WNT agonist" is a molecule that mimics or increases WNT signaling. A WNT agonist is not to be restricted to a molecule acting directly on WNT as the molecule may act elsewhere in the WNT signaling pathway.

Non-limiting examples of WNT agonists include small molecules CHIR-99021 (CAS 252917-06-9), a 2-amino-4,6-disubstituted pyrimidine, e.g. BML 284 (CAS 853220-52-7), SKL 2001 (CAS 909089-13-0), WAY 262611 (CAS 1123231-07-1), WAY 316606 (CAS 915759-45-4), SB 216763 (CAS 280744-09-4), IQ 1 (CAS 331001-62-8), QS 11 (CAS 944328-88-5), deoxycholic acid (CAS 83-44-3), BIO (CAS 667463-62-9), kenpaullone (CAS 142273-20-9), or a (hetero) arylpyrimidine. In some embodiments, a WNT agonist is an agonist antibody or functional fragment thereof or an antibody-like polypeptide.

In some embodiments, the WNT agonist is CHIR-99021 ((CHIR) CAS 252917-06-9). In some embodiments, the medium comprises about 2 μM, about 2.5 μM, about 3 μM, about 3.5 μM, about 4.5 μM, about 5 μM, about 5.5 μM, about 6 µM, about 6.5 µM, about 7 µM, about 7.5 µM, about 8 µM, about 8.5 µM, or about 9 µM CHIR-99021. In some embodiments, the medium comprises about 6 µM CHIR-99021. In some embodiments, the medium comprises about 7 µM CHIR-99021.

In some embodiments, the Wnt pathway activator is, but is not limited to, IQ-1 and Wnt3a.

In some embodiments, the Wnt pathway activator, is present in a concentration of between 1 ng/mL to 150 ng/mL, between 10 ng/mL to 100 ng/mL, between 1 ng/mL to 50 ng/mL, between 45 ng/mL to 75 ng/mL, between 60 ng/mL to 110 ng/mL, between 115 ng/mL to 150 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 140 ng/mL, about 145 ng/mL, or about 150 ng/mL.

Rock Inhibitors

Rho associated kinases (ROCK) are serine/threonine kinases that serve downstream effectors of Rho kinases (of which three isoforms exist—RhoA, RhoB and RhoC). ROCK inhibitors suitable for use in compositions contemplated herein include, but are not limited to, polynucleotides, polypeptides, and small molecules. ROCK inhibitors contemplated herein may decrease ROCK expression and/or ROCK activity. Illustrative examples of ROCK inhibitors contemplated herein include, but are not limited to, anti-ROCK antibodies, dominant negative ROCK variants, siRNA, shRNA, miRNA and antisense nucleic acids that target ROCK.

In some embodiments, the ROCK inhibitors include, but are not limited to: thiazovivin, Y27632, Fasudil, AR122-86, RevitaCell™ Supplement, H-1152, Y-30141, Wf-536, HA-1077, hydroxyl-HA-1077, GSK269962A, SB-772077-B, N-(4-Pyridyl)-N'-(2,4,6-trichlorophenyl)urea, 3-(4-Pyridyl)-1H-indole, and (R)-(+)-trans-N-(4-Pyridyl)-4-(1-aminoethyl)-cyclohexanecarboxamide, H-100, and ROCK inhibitors disclosed in U.S. Pat. No. 8,044,201, which is herein incorporated by reference in its entirety.

In some embodiments, the ROCK inhibitor is thiazovivin, Y27632, or pyrintegrin. In some embodiments, the ROCK inhibitor is thiazovivin. In some embodiments, the ROCK inhibitor is Y27632.

In some embodiments, the ROCK inhibitor is present at a concentration of about 1-15 µM, 5-15 µM, 1-30 µM, 5-30 µM, or about 5, 6, 7, 8, 9, 10, 11, 12, 13, 14, 15, 16, 17, 18, 19, 20, 21, 22, 23, 24, 25, 26, 27, 28, 29, or 30 µM, or any range derivable therein. In some embodiments, the ROCK inhibitor is present at a concentration of about 10 µM.

Activin/Nodal Inhibitor

As used herein, an "activin/nodal inhibitor" is a molecule that inhibits or decreases activin signaling. An activin/nodal is not to be restricted to a molecule acting directly on activin as the molecule may act elsewhere in the activin signaling pathway.

In some embodiments, activin/nodal inhibitors include small molecules SB 431542 (CAS 301836-41-9), SB 505124 (CAS 694433-59-5), LDN 193189 (CAS 1062368-24-4), LDN 193719 (CAS 1062368-49-3), Dorsomorphin (CAS 866405-64-3), A 83-01 (CAS 909910-43-6), DMH 1 (CAS 1206711-16-1), RepSox (CAS 446859-33-2), or LY 364947 (CAS 396129-53-6). In some embodiments, the activin/nodal inhibitor is SB 431542.

In some embodiments, an activin/nodal inhibitor is an anti-activin antagonist antibody or functional fragment thereof or an antibody-like polypeptide. In some embodiments, the activin/nodal inhibitor is Follistatin.

In some embodiments, the medium comprises 2 µM, about 2.5 µM, about 3 µM, about 3.5 µM, about 4.5 µM, about 5 µM, about 5.5 µM, about 6 µM, about 6.5 µM, or about 7 µM of activin/nodal inhibitor. In some embodiments, the medium comprises about 2 µM, about 2.5 µM, about 3 µM, about 3.5 µM, about 4.5 µM, about 5 µM, about 5.5 µM, about 6 µM, about 6.5 µM, or about 7 µM SB 431542. In some embodiments, the medium comprises about 5 µM SB 431542.

Porcn Inhibitor

In some embodiments, any media described herein comprises a Porcn Inhibitor. Porcupine (Porcn) is a membrane-bound-O-acyltransferase. Porcn affects Wnt signaling by palmitoleating the Wnts and is essential for Wnt secretion and function. In some embodiments, the Porcn inhibitor is selected from LGK974 (Liu et al., Proc Natl Acad Sci USA. 2013 Dec. 10; 110(50):20224-9; Jiang et al., Proc Natl Acad Sci USA. 2013 Jul. 30; 110(31):12649-54); Wnt C-59 (Proffitt et al., Cancer Res. 2013 Jan. 15; 73(2):502-7); ETC-159 and ETC-131 (aka ETC-1922159, Madan et al., Oncogene. 2016 Apr. 28; 35(17): 2197-2207); IWP compounds including IWP-L6 (Chen et al., Nat Chem Biol. 2009 February; 5(2): 100-7; Wang et al., J Med Chem. 2013 Mar. 28; 56(6):2700-4; Dodge et al., J Biol Chem. 2012 Jun. 29; 287(27):23246-54); GNF6231 (Liu et al., Annals of the Rheumatic Diseases Published Online First: 2 Feb. 2017, doi: 10.1136/annrheumdis-2016-210294); Compounds 3-5 (Duraiswamy et al., J Med Chem. 2015 Aug. 13; 58(15): 5889-99); Compound 6 (Poulsen, et al., J. Chem. Inf. Model., 55 (2015), p. 1435) and other porcupine inhibitors. In some embodiments, the Porcn inhibitor is Wnt C-59.

In some embodiment, the Porcn inhibitor is included in any medium described herein at a concentration of about 0.5-5 µM, about 1-15 µM, about 5-15 µM, about 10-20 µM, about 1-20 µM, or about 1, 2, 3, 4, 5, 6, 7, 8, 9, 10, 11, 12, 13, 14, 15, 16, 17, 18, 19, or 20 µM. In some embodiments, the porcn inhibitor is present in the medium at a concentration of about 2 µM. In some embodiments, Wnt C-59 is included in any medium described herein at a concentration of about 0.5-5 µM, 1-15 µM, 5-15 µM, 10-20 µM, 1-20 µM, or about 1, 2, 3, 4, 5, 6, 7, 8, 9, 10, 11, 12, 13, 14, 15, 16, 17, 18, 19, or 20 µM. In some embodiments, Wnt C-59 is present in the medium at a concentration of about 2 µM.

FGF

In some embodiments, any medium described herein comprises fibroblast growth factor. Basic fibroblast growth factor, also referred to as bFGF or FGF-2, is a growth factor which has been implicated in diverse biological processes, including limb and nervous system development, wound healing, and tumor growth. Previous studies have indicated that bFGF is unlikely to affect hematopoietic cell development or survival (Ratajczak et al., 1996), although bFGF has been used to support feeder-independent growth of human embryonic stem cells (Ludwig et al., (2006).

In some embodiments, the bFGF is FGF2. In some embodiments, the FGF2 is a 146 amino acid FGF2 polypeptide (see e.g., R&D Systems Cat #AFL233-025). In some embodiments, the FGF2 is a 154 amino acid FGF2 polypeptide (see e.g., Cell Guidance Systems Cat #GFH146-10).

In some embodiments, other fibroblast growth factors such as acidic FGF (aFGF), FGF4, FGF8, FGF9, FGF17 or FGF18 may substituted for or included with bFGF, e.g., at the concentrations described above. Alternately, an FGF-2 mimicking compounds may be substituted for FGF-2 to produce substantially or essentially the same effect. FGF-2 mimics include FGF-2 mimicking peptides, antibodies, and small molecules. For example, synthetic peptide F2A4-K-NS mimics the effects of FGF-2 in vitro and in vivo (Lin et al., 2006) and may be substituted for FGF-2 in various embodiments of the medium. FG loop (FGL) peptide is another example of a FGF-2 mimetic which is used in some embodiments of the medium. FGL is a 15 amino acid sequence in the second F3 module of NCAM that represents a part of the binding site of NCAM to the FGFR1. FGL has been shown to bind to and activate FGFR1 and to stimulate neurite outgrowth (Kiselyov et al., 2003).

In some embodiments, the BioSET F2A peptide may also be substituted for FGF-2. The BioSET F2A peptide is a synthetic mimetic of the natural human FGF-2 growth factor. The BioSET F2A peptide and the F2A4-KNS peptide are available from FYI Tornier, Inc., or BioSurface Engineering Technologies, Inc. ("BioSET"). It is envisioned that combinations of FGF-2 mimicking compounds may also be substituted for FGF-2 in various embodiments of the medium.

In some embodiments, FGF is a mammalian FGF. In some embodiments, FGF is mouse FGF. In some embodiments, FGF is human FGF. In some embodiments, FGF is recombinant human FGF. In some embodiments, FGF-2 is a mammalian FGF-2. In some embodiments, FGF-2 is human FGF-2. In some embodiments, FGF-2 is recombinant human FGF-2.

In some embodiments, bFGF is included in any medium described herein at a concentration of from about 5 to about 100 ng/mL, 5 to about 50 ng/mL, from about 5 to about 25 ng/mL, or any range derivable therein. In some embodiments, bFGF is at a concentration of about 2.5, 5, 10, 15, 20, 25, 30, 35, 40, 45, 50, 55, 60, 65, 70, 75, 80, 85, 90, 95, 100, or about 110 ng/mL. In some embodiments, FGF is at a concentration of about 20 ng/mL. In some embodiments, FGF is at a concentration of about 100 ng/mL.

Bone Morphogenic Protein

In some embodiments, any media described herein comprises a bone morphogenic protein (BMP) activator. In some embodiments, the media comprises BMP-4. Bone morphogenetic protein-4 (BMP-4) is a member of the group of bone morphogenic proteins and a ventral mesoderm inducer. BMPs are expressed in adult human bone marrow (BM) and are important for bone remodeling and growth. In some embodiments, inclusion of BMP4 is only needed for the first two to three days in culture, after which time it can be removed from the system with no detrimental effect on differentiation.

In some embodiments, the BMP is BMP2, BMP6, or BMP7.

BMP-4 is important for the modulation of the proliferative and differentiative potential of hematopoietic progenitor cells (Bhardwaj et al., 2001; Bhatia et al., 1999; Chadwick 2003). Additionally, BMP-4 can modulate early hematopoietic cell development in human fetal, neonatal, and adult hematopoietic progenitor cells (Davidson and Zon, 2000; Huber et al., 1998; Marshall et al., 2000). For example, BMP-4 can regulate the proliferation and differentiation of highly purified primitive human hematopoietic cells from adult and neonatal sources (Bhatia et al., 1999), and BMP-4 can promote hematopoietic differentiation in human embryonic stem cells (Chadwick, 2003).

In some embodiments, BMP-4 is a mammalian BMP-4. In some embodiments, BMP-4 is mouse BMP-4. In some embodiments, BMP-4 is human BMP-4. In some embodiments, BMP-4 is recombinant human BMP-4.

In some embodiments, BMP-4 is present in the medium at a concentration of about 5-100 ng/mL, about 20-100 ng/mL, about 20-50 ng/mL, about 10-30 ng/mL, about 15-30 ng/mL, about 20-30 ng/mL, or any range derivable therein. In some embodiments, BMP-4 is included in the medium at a concentration of about 5, 10, 15, 20, 25, 30, 35, 40, 45, or about 50 ng/mL. In some embodiments, BMP-4 is included in the medium at a concentration of about 30 ng/mL.

FLT3L

In some embodiments, any media described herein comprises Flt3 ligand (FLT3L). Flt3 ligand, also referred to as FLT-3 ligand, is the endogenous ligand for FLT3. FLT3 is a receptor tyrosine kinase expressed by immature hematopoietic progenitor cells. The ligand for FLT3 is a transmembrane or soluble protein and is expressed by a variety of cells including hematopoietic and marrow stromal cells; in combination with other growth factors, Flt3 ligand can stimulate the proliferation and development of stem cells, myeloid and lymphoid progenitor cells, dendritic cells and natural killer cells. Activation of the receptor leads to tyrosine phosphorylation of various key adaptor proteins known to be involved in different signal transduction pathways that control proliferation, survival and other processes in hematopoietic cells. FLT3 and mutations affecting FLT3 are also important in pathological diseases, such as the prognosis and therapy of leukemia (Drexler et al., 2004).

In some embodiments, FLT3L is a mammalian FLT3L. In some embodiments, FLT3L is mouse FLT3L. In some embodiments, FLT3L is human FLT3L. In some embodiments, FLT3L is recombinant human FLT3L.

In some embodiments, Flt3 ligand is included in a culture medium at a concentration of from 5 to about 100 ng/mL, 5 to about 50 ng/mL, from about 10 to about 20 ng/mL, from about 10 to about 30 ng/mL, from about 15 to about 30 ng/mL, from about 20 to about 30 ng/mL, or any range derivable therein. In some embodiments, Flt3 ligand is included in the medium at a concentration of about 2.5, 5, 10, 15, 20, 25, 30, 35, 40, 45, or about 50 ng/mL.

In some embodiments, the concentration of FLT3L in the medium is about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, or about 70 ng/mL. In some embodiments, the concentration of FLT3L in the medium is about 15 ng/mL or about 20 ng/mL.

TPO

In some embodiments, any medium described herein comprises thrombopoietin (TPO). TPO is a glycoprotein hormone which is primarily produced in vivo by the liver and kidney and is involved in the in vivo generation of platelets in the bone marrow.

In some embodiments, TPO is a mammalian TPO. In some embodiments, TPO is mouse TPO. In some embodiments, TPO is human TPO. In some embodiments, TPO is recombinant human TPO.

In some embodiments, TPO is included in the medium at a concentration of from about 2.5 to about 100 ng/mL, 5 to about 75 ng/mL, from about 10 to about 50 ng/mL, from about 15 to about 35 ng/mL, at about 25 ng/ml, or any range derivable therein. In some embodiments, TPO is included in the defined culture media at a concentration of about 2.5, 5, 10, 15, 20, 25, 30, 35, 40, 45 or about 50 ng/mL. In some embodiments, the concentration of TPO in the medium is about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL. In some embodiments, the concentration of TPO in the medium is about 20 ng/mL.

IL-3

In some embodiments, any medium described herein comprises IL-3. Interleukin-3 (IL-3) is a hematopoietic growth factor involved in the survival, proliferation and differentiation of multipotent hematopoietic cells.

In some embodiments, IL-3 is a mammalian IL-3. In some embodiments, IL-3 is mouse IL-3. In some embodiments, IL-3 is human IL-3. In some embodiments, IL-3 is recombinant human IL-3.

In some embodiments, IL-3 is included in the medium at a concentration of from 2.5 to about 50 ng/mL, 2.5 to about 50 ng/mL, from about 5 to about 50 ng/mL, from about 5 to about 25 ng/mL, from about 5 to about 15 ng/mL, or any range derivable therein. In some embodiments, IL-3 is included in the medium at a concentration of about 2.5, 5, 10, 15, 20, 25, or about 30 ng/mL. In some embodiments, the concentration of IL-3 in the medium is about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL.

In some embodiment, the IL-3 concentration is 5 ng/mL. In some embodiments, the IL-3 concentration is 40 ng/mL.

VEGF

In some embodiments, any medium described herein comprises VEGF. Vascular endothelial growth factor (VEGF) is an important signaling protein which is involved in formation of the embryonic circulatory system and angiogenesis. VEGF can affect a variety of cell types including vascular endothelium and other cell types (e.g., neurons, cancer cells, kidney epithelial cells). In vitro, VEGF can stimulate endothelial cell mitogenesis and cell migration. VEGF function has also been shown to be important in a variety of disease states including cancer, diabetes, autoimmune diseases, and ocular vascular diseases.

In some embodiments, VEGF is a mammalian VEGF. In some embodiments, VEGF is mouse VEGF. In some embodiments, VEGF is human VEGF. In some embodiments, VEGF is recombinant human VEGF.

In some embodiments, VEGF is included in the medium at a concentration of from about 10-100 ng/mL, about 20-100 ng/mL, about 10-50 ng/mL, about 15-30 ng/mL, about 20-30 ng/mL, about 20-50 ng/mL, or any range derivable therein. In some embodiments, VEGF is included in the defined culture media at a concentration of about 2.5, 5, 10, 15, 20, 25, 30, 35, 40, 45, or about 50 ng/mL. In some embodiments, the VEGF concentration is 20 ng/mL.

IL-15

In some embodiments, any medium described herein comprises IL-15. Interleukin-15 (TL-15) is a cytokine that induces proliferation of natural killer cells.

In some embodiments, IL-15 is a mammalian IL-15. In some embodiments, IL-15 is mouse IL-15. In some embodiments, IL-15 is human IL-15. In some embodiments, IL-15 is recombinant human IL-15.

In some embodiments, the concentration of IL-15 in the medium is about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, or about 70 ng/mL.

In some embodiments, the concentration of IL-15 in the medium is about 1 ng/ml to about 10 ng/mL, about 5 ng/mL to about 15 ng/mL, about 10 ng/mL to about 20 ng/mL, or about 15 ng/mL to about 25 ng/mL. In some embodiments, the concentration of IL-15 in the medium is about 15 ng/mL.

IL-7

In some embodiments, the medium comprises IL-7. Interleukin-7 (IL-7) is a hematopoietic growth factor that stimulates the differentiation of hematopoietic stem cells.

In some embodiments, IL-7 is a mammalian IL-7. In some embodiments, IL-7 is mouse IL-7. In some embodiments, IL-7 is human IL-7. In some embodiments, IL-7 is recombinant human IL-7.

In some embodiments, the IL-7 concentration in the medium is about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, or about 70 ng/mL. In some embodiments, the IL-7 concentration in the medium is about 20 ng/mL.

SCF

In some embodiments, the medium comprises one or more hematopoietic cytokines. In some embodiments, the hematopoietic cytokine is stem cell factor (SCF). Stem cell factor is a cytokine which binds CD117 (c-Kit). SCF is also known as "KIT ligand," "c-kit ligand," or "steel factor." SCF exists in two forms: cell surface bound SCF and soluble (or free) SCF. Soluble SCF is typically produced in vivo by the cleavage of surface bound SCF by metalloproteases. SCF can be important for the survival, proliferation, and differentiation of hematopoietic stem cells and other hematopoietic progenitor cells. In vivo, SCF can change the BFU-E (burst-forming unit-erythroid) cells, which are the earliest erythrocyte precursors in the erythrocytic series, into the CFU-E (colony-forming unit-erythroid).

In some embodiments, SCF is a mammalian SCF. In some embodiments, SCF is mouse SCF. In some embodiments, SCF is human SCF. In some embodiments, SCF is recombinant human SCF.

In some embodiments, SCF is included in the medium at a concentration of from about 5 to about 100 ng/mL, 5 to about 50 ng/mL, from about 10 to about 30 ng/mL, from about 15 to about 30 ng/mL, from about 20 to about 30 ng/mL, or any range derivable therein. In some embodiments, SCF is included in the medium at a concentration of about 2.5, 5, 10, 15, 20, 25, 30, 35, 40, 45, or about 50 ng/mL. In some embodiments, the concentration of SCF in the medium is about 1 ng/mL, about 10 ng/mL, about 20 ng/mL, about 30 ng/mL, about 40 ng/mL, about 50 ng/mL, about 60 ng/mL, about 70 ng/mL, about 80 ng/mL, about 90 ng/mL, about 100 ng/mL, about 110 ng/mL, about 120 ng/mL, about 150 ng/mL, or about 200 ng/mL. In some embodiments, the concentration of SCF in the medium is about 100 ng/mL. In some embodiments, the concentration of SCF in the medium is about 20 ng/mL.

Nicotinamide

In some embodiments, the medium comprises nicotinamide. Nicotinamide is a form of vitamin B3 and aids in the differentiation of NK cells.

In some embodiments, the concentration of nicotinamide in the medium is about 1 mM to 15 mM, from about 2 mM to 10 mM, from about 4 mM to 8 mM, or from about 5 mM to 7 mM. In some embodiments, the concentration of nicotinamide in the medium is about 2 to 8 mM, from about 3 to 8 mM, from about 4 to 8 mM, from about 5 to 8 mM or from about 6 to 7 mM. In some embodiments, the concentration of nicotinamide in the medium is about 1 mM, about 2 mM, about 3 mM, about 4 mM, about 5 mM, about 6 mM, about 7 mM, about 8 mM, about 9 mM, about 10 mM, about 12 mM, or about 15 mM. In some embodiments, the concentration of nicotinamide in the medium is about 4.5 mM, about 5.5 mM, about 6.6 mM, about 7.5 mM or about 8.5 mM. In some embodiments, the concentration of nicotinamide in the medium is about 6.5 mM.

Additional Components

In some embodiments, the medium comprises one or more of glucose, ethanolamine, zinc sulfate, human serum, sodium selenite, ascorbic acid, and β-mercaptoethanol. In some embodiments, the medium comprises one or more of glucose, ethanolamine, zinc sulfate, human serum, sodium selenite, ascorbic acid, and β-mercaptoethanol in an amount additional to any amount present in the base medium.

In various embodiments, the medium comprises glucose. In some embodiments, the media may comprise a total glucose concentration of about 15 mM to 40 mM. In some embodiments, the media may comprise a total glucose concentration of about 15 mM to 35 mM, about 15 mM to 30 mM, about 15 mM to 25 mM, about 15 mM to 20 mM, about 20 mM to 40 mM, about 20 mM to 35 mM, about 20 mM to 30 mM, about 20 mM to 25 mM, or about 25 mM to 30 mM. In some embodiments, the media may comprise a total glucose concentration of about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, or about 40 mM glucose. In some embodiments, the media may comprise a total glucose concentration of about 27 mM glucose. In some embodiments, the media may comprise a total glucose concentration of about 20 mM. In any of these embodiments, the glucose may be provided to the medium from a base media (e.g., DMEM/F12 or DMEM (high glucose)/F12) and/or may be added to the medium in a supplement ("added glucose"). In some embodiments, the media may comprise about 2 to 40 mM of glucose provided from one or more commercial sources (e.g., base medium DMEM/F12 or DMEM (high glucose)/F12). In some embodiments, the medium may contain about 5 to 15 mM or about 5 to 25 mM of glucose sourced from a base medium (e.g., DMEM, DMEM (high glucose), F12). In some embodiments, the medium may comprise about 10 to 15 mM or about 10 to 25 mM of glucose sourced from a base medium (e.g., DMEM/F12, DMEM (high glucose)/F12). In some embodiments, the medium may comprise 1 to 15 mM of glucose in addition to that provided in the base medium. For example, in some embodiments, an additional 1 to 15 mM or an additional 2 to 12 mM of glucose is added to the medium. In some embodiments, an additional 1 to 15 mM, 1 to 10 mM, 2 to 12 mM, 2 to 10 mM, 5 to 15 mM, or 5 to 10 mM of glucose is added to the medium. In some embodiments, about 0.5 mM, about 1.0 mM, about 1.5 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.5 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, about 5.0 mM, about 6 mM, about 7 mM, about 8 mM, about 9 mM, about 10 mM, about 10.10 mM, about 10.25 mM, about 10.5 mM, about 10.75 mM, about 11 mM, about 12 mM, about 13 mM, about 14 mM, or about 15 mM of glucose is added to the medium. In some embodiments, about 2.3 mM of glucose is added to the medium. In some embodiments, about 4.66 mM of glucose is added to the medium. In some embodiments, about 10.25 mM of glucose is added to the medium.

In some embodiments, ethanolamine is added to the medium at a concentration of about 10-100 μM. In some embodiments, ethanolamine is added to the medium at a concentration of about 50 μM. In some embodiments, zinc sulfate is added to the medium at a concentration of about 1.7 μM to 40 μM. In some embodiments, zinc sulfate is added to the medium at a concentration of about 20 μM to 40 μM. In some embodiments, the medium comprises about 37 μM of zinc sulfate. In some embodiments, the medium comprises about 36 μM (e.g., 36.2 μM) of zinc sulfate. In some embodiments, the medium comprises 2% to 40% human serum. In some embodiments, the medium comprises 20-40% human serum. In some embodiments, the medium comprises 2-20% human serum. In some embodiments, the medium comprises about 15% human serum. In some embodiments, the medium comprises about 20% of human serum. In some embodiments, the medium comprises 0 μM to 50 μM β-mercaptoethanol. In some embodiments, the medium comprises 0 μM to 7.5 μM β-mercaptoethanol. In some embodiments, the medium comprises 0 μM-5 μM β-mercaptoethanol. In some embodiments, the medium comprises 0.1 μM-5 μM β-mercaptoethanol. In some embodiments, the medium comprises about 1 μM β-mercaptoethanol. In some embodiments, the medium does not comprise β-mercaptoethanol. In some embodiments, sodium selenite is added to the medium at a concentration of about 1 ng/mL to 10 ng/mL. In some embodiments, the medium comprises about 5 ng/mL sodium selenite. In some embodiments, ascorbic acid is added to the medium at a concentration of about 1 to 30 μg/mL. In some embodiments, the medium comprises about 15 μg/mL of ascorbic acid. In some embodiments, the medium comprises about 20 μg/mL ascorbic acid.

In some embodiments, a medium described herein comprises glucose, zinc sulfate, human serum, ethanolamine, and β-mercaptoethanol. In some embodiments, the medium described herein comprises (i) a total concentration of glucose of about 2 mM to about 40 mM; (ii) a concentration of about 10 μM to about 100 μM of ethanolamine; (iii) a concentration of about 1.7 μM to about 40 μM zinc sulfate; (iv) a concentration of about 2% to 40% human serum; and/or (v) a concentration of about 0.1 μM to 50 μM β-mercaptoethanol. In some embodiments, the medium described herein comprises glucose, zinc sulfate, human serum, ethanolamine, and β-mercaptoethanol. In some embodiments the medium described herein comprises (i) a total concentration of about 27 mM of glucose; (ii) a concentration of about 50 μM of ethanolamine; (iii) a concentration of about 37 μM zinc sulfate; (iv) a concentration of about 15% human serum; and (v), a concentration of about 1 μM β-mercaptoethanol.

In some embodiments, a medium described herein comprises glucose, zinc sulfate, human serum, ethanolamine, sodium selenite, ascorbic acid or any combination thereof. In some embodiments, a medium described herein comprises glucose, zinc sulfate, human serum, ethanolamine or any combination thereof. In some embodiments, a medium described herein comprises (i) a total concentration of about 2 mM to about 40 mM of glucose; (ii) a concentration of about 10 μM to about 100 μM of ethanolamine; (iii) a concentration of about 1.7 μM to about 40 μM zinc sulfate; and (iv) a concentration of about 2% to 40% human serum.

In some embodiments, a medium described herein comprises (i) a total concentration of about 20 mM of glucose; (ii) a concentration of about 50 µM of ethanolamine; (iii) a concentration of about 36.2 µM or 37 µM zinc sulfate; (iv) and a concentration of about 20% human serum.

In some embodiments, a medium described herein comprises glucose, zinc sulfate, human serum, ethanolamine, sodium selenite, ascorbic acid or any combination thereof. In some embodiments, a medium described herein comprises glucose, zinc sulfate, human serum, ethanolamine or any combination thereof. In some embodiments, a medium described herein comprises (i) an total concentration of about 2 mM to about 40 mM of glucose; (ii) a concentration of about 10 µM to about 100 µM of ethanolamine; (iii) a concentration of about 1.7 µM to about 40 µM zinc sulfate; and (iv) a concentration of about 2% to 40% human serum. In some embodiments, a medium described herein comprises (i) a total concentration of about 20 mM of glucose; (ii) a concentration of about 50 µM of ethanolamine; (iii) a concentration of about 37 µM zinc sulfate; (iv) and a concentration of about 15% human serum.

In some embodiments, a medium described herein comprises DMEM/F12 medium and a supplement of glucose, zinc sulfate, human serum, ethanolamine, β-mercaptoethanol, or any combination thereof. DMEM (high glucose) In some embodiments, the supplement provides (i) an additional concentration of glucose of about 2 mM to about 40 mM; (ii) an additional concentration of about 10 µM to about 100 µM of ethanolamine; (iii) an additional concentration of about 1.7 µM to about 40 µM zinc sulfate; (iv) an additional concentration of about 2% to 40% human serum; and/or (v) an additional concentration of about 0.1 µM to 50 µM 3-mercaptoethanol. In some embodiments, the supplement provides an additional concentration of glucose, zinc sulfate, human serum, ethanolamine, and β-mercaptoethanol. In some embodiments, the supplement provides (i) an additional concentration of about 10.25 mM of glucose; (ii) an additional concentration of about 50 µM of ethanolamine; (iii) an additional concentration of about 37 µM zinc sulfate; (iv) an additional concentration of about 15% human serum; and (v), an additional concentration of about 1 µM β-mercaptoethanol.

In some embodiments, a medium described herein comprises DMEM/F12 medium and a supplement of glucose, zinc sulfate, human serum, ethanolamine, sodium selenite, ascorbic acid or any combination thereof. DMEM (high glucose) In some embodiments, a medium described herein comprises DMEM/F12 medium and a supplement of glucose, zinc sulfate, human serum, ethanolamine or any combination thereof. In some embodiments, the supplement provides (i) an additional concentration of about 2 mM to about 20 mM of glucose; (ii) an additional concentration of about 10 µM to about 100 µM of ethanolamine; (iii) an additional concentration of about 1.7 µM to about 40 µM zinc sulfate; and (iv) an additional concentration of about 2% to 40% human serum. In some embodiments, the supplement provides (i) an additional concentration of about 4.66 mM of glucose; (ii) an additional concentration of about 50 µM of ethanolamine; (iii) an additional concentration of about 36.2 µM or 37 µM zinc sulfate; (iv) and an additional concentration of about 20% human serum.

In some embodiments, a medium described herein comprises DMEM/F12 medium and a supplement of glucose, zinc sulfate, human serum, ethanolamine, sodium selenite, ascorbic acid or any combination thereof. DMEM (high glucose) In some embodiments, a medium described herein comprises DMEM/F12 medium and a supplement of glucose, zinc sulfate, human serum, ethanolamine or any combination thereof. DMEM (high glucose) In some embodiments, the supplement provides (i) an additional concentration of about 2 mM to about 40 mM of glucose; (ii) an additional concentration of about 10 µM to about 100 µM of ethanolamine; (iii) an additional concentration of about 1.7 µM to about 40 µM zinc sulfate; and (iv) an additional concentration of about 2% to 40% human serum. In some embodiments, the supplement provides (i) an additional concentration of about 2.3 mM of glucose; (ii) an additional concentration of about 50 µM of ethanolamine; (iii) an additional concentration of about 37 µM zinc sulfate; (iv) and an additional concentration of about 15% human serum.

Exemplary Differentiation Medium Compositions

In some embodiments, the cells described herein are cultured in one, two, three, four, five, six, seven or eight media. In some embodiments, the cells described herein are cultured in a first medium, followed by a second medium, a third medium, a fourth medium, a fifth medium, a sixth medium, and a seventh medium. In some embodiments, the cells described herein are cultured in a first medium, followed by a second medium, a third medium, a fourth medium, a fifth medium, a sixth medium, a seventh medium and an eighth medium. In some embodiments, the cells are cultured in a medium described herein for one hour to 28 days. In some embodiments, the cells are cultured in a medium described herein for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days. In some embodiments, the cells are cultured in a medium described herein for 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18, hours, 19 hours, 20 hours, 21 hours, 22 hours, or 23 hours.

In some embodiments, a method for differentiation of a population of stem cells into a population comprising HSPCs (e.g., Stage I) utilizes the first, second, third and fourth mediums described herein. In some embodiments, a method for differentiation of a population comprising HSPCs into a population comprising NK cells (e.g., Stage II) utilizes the fifth, sixth and seventh mediums described herein. In some embodiments, an alternate method for differentiation of a population comprising HSPCs into a population comprising NK cells (e.g., Stage II) utilizes the fifth, sixth, seventh, and eight mediums described herein.

In some embodiments, the concentrations of medium components described herein are the total concentration of the component in the media. In some embodiments, the concentration of the medium component described herein is added in addition to any amount of the same component already present in the described medium. For example, a base medium containing a growth factor may have an additional supplement of the same growth factor added to the medium to yield a higher concentration of said growth factor. Additionally, in other examples, the concentration described is the final concentration of a factor in the medium.

First Medium

In some embodiments, a population of stem cells are cultured in a first medium comprising any of the ROCK inhibitors described herein. In some embodiments, stem cells are cultured in the first medium comprising the ROCK inhibitor thiazovivin. In some embodiments, stem cells are cultured in the ROCK inhibitor Y-27632 (TOCRIS). In some embodiments, the first medium comprises a concentration of about 10 μM of the ROCK inhibitor. In some embodiments, the first medium comprises StemFlex™ medium. In some embodiments, the first medium comprises StemBrew™ Basal Media. In some embodiments, the first medium comprises StemFlex™ Supplement. In some embodiments, the first medium comprises StemBrew™ Supplement. In some embodiments, the first medium comprises StemFlex™ medium and a ROCK inhibitor. In some embodiments, the first medium comprises StemBrew media and a ROCK inhibitor. In some embodiments, the first medium comprises StemFlex™ medium and thiazovivin. In some embodiments, the first medium comprises StemBrew media and thiazovivin. In some embodiments, the first medium comprises StemFlex™ medium and Y27632. In some embodiments, the first medium comprises StemBrew media and Y27632. In some embodiments, the first medium comprises StemFlex™ medium and a concentration of about 10 μM of thiazovivin. In some embodiments, the first medium comprises StemFlex™ medium and a concentration of about 10 μm of Y27632. In some embodiments, the first medium comprises StemBrew medium and a concentration of about 10 μM of thiazovivin. In some embodiments, the first medium comprises StemBrew medium and a concentration of about 10 μM of Y27632.

In some embodiments, stem cells are cultured in the first medium for a time and under conditions sufficient to form stem cell aggregates. In some embodiments, cells are cultured in the first medium for 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, or 48 hours. In some embodiments, stem cells are cultured in the first medium for 12-48 hours. In some embodiments, stem cells are cultured in the first medium for 16-20 hours.

In some embodiments, the first medium comprises the composition set forth in Table 18A or Table 18B. In some embodiments, the cells are cultured in the media in Table 18A or 18B for 12-48 hours. In some embodiments, the cells are cultured in the media in Table 18A or 18B for 16-20 hours.

TABLE 18A

Exemplary First-Medium composition

| Component | Working Conc. |
|---|---|
| STEMFLEX ™ Basal | 90% |
| STEMFLEX ™ Supplement | 1X |
| ROCK Inhibitor | 10 μM |

TABLE 18B

Exemplary First Medium composition

| Component | Working Conc. |
|---|---|
| StemBrew Basal Media | 90% |
| StemBrew Supplement | 1X |
| ROCK Inhibitor | 10 μM |

Second Medium

In some embodiments, cells are cultured in a second medium comprising a bone morphogenetic protein (BMP). In some embodiments, cells are cultured in a second medium comprising a ROCK inhibitor and a BMP. In some embodiments, cells are cultured in the second medium comprising the ROCK inhibitor thiazovivin and a BMP. In some embodiments, cells are cultured in a second medium comprising the ROCK inhibitor Y27632 and a BMP. In some embodiments, cells are cultured in the second medium comprising a ROCK inhibitor and BMP-4. In some embodiments, cells are cultured in a second medium comprising the ROCK inhibitor Y27632 and BMP-4. In some embodiments, cells are cultured in the second medium comprising the ROCK inhibitor thiazovivin and BMP-4. In some embodiments, the second medium comprises a concentration of about 10 μM of the ROCK inhibitor. In some embodiments, the second medium comprises a concentration of about 30 ng/mL of BMP-4. In some embodiments, the second medium comprises APEL medium. In some embodiments, the second medium comprises APEL medium, a ROCK inhibitor and a BMP. In some embodiments, the second medium comprises APEL medium, a ROCK inhibitor and BMP-4. In some embodiments, the second medium comprises APEL medium, Thiazovivin, and a BMP. In some embodiments, the second medium comprises APEL medium, Thiazovivin, and BMP-4. In some embodiments, the second medium comprises APEL medium, Y27632, and a BMP. In some embodiments, the second medium comprises APEL medium, Y27632, and BMP-4. In some embodiments, the second medium comprises APEL medium and a BMP. In some embodiments, the second medium comprises APEL medium and BMP-4.

In some embodiments, cells are cultured in the second medium for 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours. In some embodiments, cells are cultured in the second medium for up to 24 hours. In some embodiments, cells are cultured in the second medium for 6-10 hours.

In some embodiments, cells are cultured in the second medium after being cultured in the first medium described supra.

In some embodiments, the second medium comprises the composition set forth in Table 19A or Table 19B. In some embodiments, the cells are cultured in the media in Table 19A or Table 19B for up to 24 hours. In some embodiments, the cells are cultured in the media in Table 19A or Table 19B for 4-24 hours. In some embodiments, the cells are cultured in the media in Table 19A or Table 19B for 6-10 hours. In some embodiments, the cells are cultured in the media in Table 19A or Table 19B after being cultured in the media in Table 18A or 18B.

TABLE 19A

Exemplary Second-Medium composition

| Component | Working Conc. |
|---|---|
| STEMdiff APEL 2 Medium | 100% |
| rh BMP-4 | 30 ng/mL |
| ROCK Inhibitor | 10 μM |

TABLE 19B

| Exemplary Second-Medium composition | |
|---|---|
| Component | Working Conc. |
| STEMdiff APEL 2 Medium | 100% |
| rh BMP-4 | 30 ng/mL |

Third Medium

In some embodiments, cells are cultured in a third medium comprising FGF, a bone morphogenetic protein, a WNT pathway activator, and Activin-A. In some embodiments, the bone morphogenic protein in the third medium is BMP-4. In some embodiments, the WNT pathway activator in the third medium is CHIR-99021. In some embodiments, the FGF is bFGF or FGF-2. In some embodiments, the third medium comprises a concentration of about 100 ng/mL of FGF. In some embodiments, the third medium comprises a concentration of about 30 ng/mL of BMP-4. In some embodiments, the third medium comprises a concentration of about 2.5 µM to about 3.5 µM of CHIR-99021. In some embodiments, the third medium comprises a concentration of about 6 µM of CHIR-99021. In some embodiments, the third medium comprises a concentration of about 7 µM of CHIR-99021. In some embodiments, the third medium comprises a concentration of about 5 ng/mL of Activin-A. In some embodiments, the third medium comprises APEL medium. In some embodiments, the third medium comprises APEL medium, FGF, BMP-4, CHIR-99021, and Activin A.

In some embodiments, cells are cultured in the third medium for 1-3 days. In some embodiments, cells are cultured in the third medium for 1 day, 2 days, or 3 days. In some embodiments, cells are cultured in the third medium for 2 days.

In some embodiments, cells are cultured in the third medium after being cultured in the first and second media described supra.

In some embodiments, the third medium comprises the composition set forth in Table 20A or Table 20B. In some embodiments, the cells are cultured in the third media in Table 20A or Table 20B for 1-3 Days. In some embodiments, the cells are cultured in the third media in Table 20A or Table 20B for about 2 days. In some embodiments, the cells are cultured in the media in Table 20A or Table 20B after being cultured in the media in Tables 18A or 18B and 19A or 19B. In some embodiments, the cells are cultured in the third media in Table 20A after being cultured in the media in Tables 18A and 19A. In some embodiments, the cells are cultured in the third media in Table 20B after being cultured in the media in Tables 18B and 19A. In some embodiments, the cells are cultured in the third media in Table 20A after being cultured in the media in Tables 18A and 19B. In some embodiments, the cells are cultured in the third media in Table 20B after being cultured in the media in Tables 18B and 19B.

TABLE 20A

| Exemplary Third-Medium composition | |
|---|---|
| Component | Working Conc. |
| STEMdiff APEL 2 Medium | 100% |
| rh BMP-4 | 30 ng/mL |
| rh FGF2 | 100 ng/mL |
| CHIR-99021 | 6 µM |
| Activin-A | 5 ng/mL |

TABLE 20B

| Exemplary Third-Medium composition | |
|---|---|
| Component | Working Conc. |
| STEMdiff APEL 2 Medium | 100% |
| rh BMP-4 | 30 ng/mL |
| rh FGF2 | 100 ng/mL |
| CHIR-99021 | 7 µM |
| Activin-A | 5 ng/mL |

Fourth Medium

In some embodiments, cells are cultured in a fourth medium comprising FGF, VEGF, TPO, SCF, IL-3, FLT3L, a Porcn inhibitor, and an activin/nodal inhibitor. In some embodiments, the Porcn inhibitor in the fourth medium is WNT C-59. In some embodiments, cells are cultured in a fourth medium comprising FGF, VEGF, TPO, SCF, IL-3, FLT3L, and an activin/nodal inhibitor. In some embodiments, the activin/nodal inhibitor in the fourth medium is SB-431542. In some embodiments, the fourth medium comprises a concentration of about 10-20 ng/mL of FGF. In some embodiments, the fourth medium comprises a concentration of about 20 ng/mL of FGF. In some embodiments, the fourth medium comprises a concentration of about 20 ng/mL of VEGF. In some embodiments, the fourth medium comprises a concentration of about 20 ng/mL of TPO. In some embodiments, the fourth medium comprises a concentration of about 100 ng/mL of SCF. In some embodiments, the fourth medium comprises a concentration of about 40 ng/mL of IL-3. In some embodiments, the fourth medium comprises a concentration of about 20 ng/mL of FLT3L. In some embodiments, the fourth medium comprises a concentration of about 0-2 µM of WNT C-59. In some embodiments, the fourth medium comprises a concentration of about 2 µM of WNT C-59. In some embodiments, the fourth medium does not comprise any WNT C-59. In some embodiments, the fourth medium comprises a concentration of about 5 µM of SB-431542. In some embodiments, the fourth medium comprises APEL medium. In some embodiments, the fourth medium comprises APEL medium, FGF, VEGF, TPO, SCF, TL-3, FLT3L, a Porcn inhibitor, and an activin/nodal inhibitor. In some embodiments, the fourth medium comprises APEL medium, FGF, VEGF, TPO, SCF, TL-3, FLT3L, and an activin/nodal inhibitor. In some embodiments, the fourth medium comprises APEL medium, FGF, VEGF, TPO, SCF, TL-3, FLT3L, WNT C-59, and SB-431542. In some embodiments, the fourth medium comprises APEL medium, FGF, VEGF, TPO, SCF, TL-3, FLT3L, and SB-431542.

In some embodiments, cells are cultured in the fourth medium for 1-3 days. In some embodiments, cells are cultured in the fourth medium for 1 day, 2 days, or 3 days. In some embodiments, cells are cultured in the fourth medium for about 2 days.

In some embodiments, the fourth media comprises the composition set forth in Table 21A or 21B. In some embodiments, the cells are cultured in the fourth media in Table 21A or 21B for 1-3 days. In some embodiments, the cells are cultured in the fourth media in Table 21A or 21B for about 2 days. In some embodiments, the cells are cultured in the media in Table 21A or 21B after being cultured in the media in Tables 18A/18B-20A/20B. For example, in some embodiments, the cells are cultured in the media in Table 21A after being cultured in the media in Tables 18A, 19A, and 20A. In some embodiments, the cells are cultured in the media in Table 21B after being cultured in the media in Tables 18B, 19A, and 20B. For example, in some embodiments, the cells are cultured in the media in Table 21A after being cultured in the media in Tables 18A, 19B, and 20A. In some embodiments, the cells are cultured in the media in Table 21B after being cultured in the media in Tables 18B, 19B, and 20B.

TABLE 21A

Exemplary Fourth-Medium composition

| Component | Working Conc. |
|---|---|
| STEMdiff APEL 2 Medium | 100% |
| rh FGF2 | 20 ng/mL |
| rh VEGF165 | 20 ng/mL |
| rh TPO | 20 ng/mL |
| rh SCF | 100 ng/mL |
| rh IL-3 | 40 ng/mL |
| rh Flt3L | 20 ng/mL |
| WNT C-59 | 2 µM |
| SB431542 | 5 µM |

TABLE 21B

Exemplary Fourth-Medium composition.

| Component | Working Conc. |
|---|---|
| STEMdiff APEL 2 Medium | 100% |
| rh FGF2 | 20 ng/mL |
| rh VEGF165 | 20 ng/mL |
| rh TPO | 20 ng/mL |
| rh SCF | 100 ng/mL |
| rh IL-3 | 40 ng/mL |
| rh Flt3L | 20 ng/mL |
| SB431542 | 5 µM |

Fifth Medium

In some embodiments, the cells are cultured in a fifth medium comprising FGF, VEGF, TPO, SCF, IL-3, and FLT3L. In some embodiments, the fifth medium comprises a concentration of about 20 ng/mL of FGF. In some embodiments, the fifth medium comprises a concentration of about 20 ng/mL of VEGF. In some embodiments, the fifth medium comprises a concentration of about 20 ng/mL of TPO. In some embodiments, the fifth medium comprises a concentration of about 100 ng/mL of SCF. In some embodiments, the fifth medium comprises a concentration of about 40 ng/mL of IL-3. In some embodiments, the fifth medium comprises a concentration of about 10-20 ng/mL of FLT3L. In some embodiments, the fifth medium comprises a concentration of about 20 ng/mL of FLT3L In some embodiments, the fifth medium comprises at least APEL medium. In some embodiments, the fifth medium comprises APEL, FGF, VEGF, TPO, SCF, IL-3 and FLT3L.

In some embodiments, cells are cultured in the fifth medium for 1-3 days. In some embodiments, the cells are cultured in the fifth medium for 1 day, 2 days, or 3 days. In some embodiments, cells are cultured in the fifth medium for about 2 days.

In some embodiments, the fifth medium comprises the composition set forth in Table 22. In some embodiments, the cells are cultured in the fifth medium in Table 22 for 2 days. In some embodiments, the cells are cultured in the fifth media in Table 22 for about 2 days. In some embodiments, the cells are cultured in the media in Table 22 after being cultured in the media in Tables 18A, 19A, 20A, and 21A. In some embodiments, the cells are cultured in the media in Table 22 after being cultured in the media in Tables 18B, 19A, 20B, and 21B. In some embodiments, the cells are cultured in the media in Table 22 after being cultured in the media in Tables 18A, 19B, 20A, and 21A. In some embodiments, the cells are cultured in the media in Table 22 after being cultured in the media in Tables 18B, 19B, 20B, and 21B.

TABLE 22

Exemplary Fifth-Medium composition

| Component | Working Conc. |
|---|---|
| STEMdiff APEL 2 Medium | 100% |
| rh FGF2 | 20 ng/mL |
| rh VEGF165 | 20 ng/mL |
| rh TPO | 20 ng/mL |
| rh SCF | 100 ng/mL |
| rh IL-3 | 40 ng/mL |
| rh Flt3L | 20 ng/mL |

Sixth Medium

In some embodiments, cells are cultured in a sixth medium comprising IL-3, IL-7, FLT3L, IL-15, and SCF. In some embodiments, the sixth medium comprises a concentration of about 5 ng/mL of IL-3. In some embodiments, the sixth medium comprises a concentration of about 20 ng/mL of IL-7. In some embodiments, the sixth medium comprises a concentration of about 10-20 ng/mL of FLT3L. In some embodiments, the sixth medium comprises a concentration of about 15 ng/mL of FLT3L. In some embodiments, the sixth medium comprises a concentration of about 10-20 ng/mL of IL-15. In some embodiments, the sixth medium comprises a concentration of about 15 ng/mL of IL-15. In some embodiments, the sixth medium comprises a concentration of about 20 ng/mL of SCF. In some embodiments, the sixth medium comprises a concentration of about 20 ng/mL of FLT3L.

In some embodiments, the sixth medium comprises human serum, zinc sulfate, ethanolamine, β-mercaptoethanol, glucose, and glutamax (e.g., glutamine substitute) in addition to any amounts present in the base medium. In some embodiments, the sixth medium comprises about 15% human serum. In some embodiments, the sixth medium comprises a concentration of about 37 µM of zinc sulfate. In some embodiments, the sixth medium comprises a concentration of about 50 µM of ethanolamine. In some embodiments, the sixth medium comprises a concentration of about 1 µM of β-mercaptoethanol. In some embodiments, the sixth medium comprises a total concentration of about 27 mM of glucose. This concentration is inclusive of glucose sourced from other components in the medium (e.g., DMEM, DMEM (high glucose), and/or F-12 supplement) as well as additional glucose added to the medium ("added glucose"). In some cases, the sixth medium comprises about 1 to 15 mM of "added glucose." In some cases, the sixth medium comprises about 10.25 mM of "added glucose." In some embodiments, the sixth medium comprises a concentration of 1× glutamax.

In some embodiments, the sixth medium comprises human serum, zinc sulfate, ethanolamine, glucose, and glutamax in addition to any amounts present in the base medium. In some embodiments, the sixth medium comprises about 20% human serum. In some embodiments, the sixth medium comprises a concentration of about 36.2 µM of zinc sulfate. In some embodiments, the sixth medium comprises a concentration of about 50 µM of ethanolamine. In some embodiments, the sixth medium comprises a total concentration of about 20 mM of glucose. This concentration is inclusive of glucose sourced from other components in the medium (e.g., DMEM, DMEM (high glucose), and/or F-12 supplement) as well as additional glucose added to the medium ("added glucose"). In some cases, the sixth medium comprises about 1 to 5 mM of "added glucose." In some cases, the sixth medium comprises about 4.66 mM of "added glucose." In some embodiments, the sixth medium comprises a concentration of 1× glutamax.

In some embodiments, the sixth medium comprises DMEM/F12 medium. In some embodiments, DMEM/F12 medium is the base medium. In some embodiments, the sixth medium comprises DMEM/F12 medium, IL-3, IL-7, FLT3L, IL-15, and SCF. In some embodiments, the sixth medium comprises DMEM/F12 medium, IL-3, IL-7, FLT3L, IL-15, SCF, human serum, zinc sulfate, ethanolamine, β-mercaptoethanol, glucose, and glutamax. In some embodiments, the sixth medium comprises DMEM/F12 medium, IL-3, IL-7, FLT3L, IL-15, SCF, human serum, zinc sulfate, ethanolamine, glucose, and glutamax.

In some embodiments, the sixth medium comprises DMEM (high glucose)/F12 medium. In some embodiments, DMEM (high glucose)/F12 medium is the base medium. In some embodiments, the sixth medium comprises DMEM (high glucose)/F12 medium, IL-3, IL-7, FLT3L, IL-15, and SCF. In some embodiments, the sixth medium comprises DMEM (high glucose)/F12 medium, IL-3, IL-7, FLT3L, IL-15, SCF, human serum, zinc sulfate, ethanolamine, β-mercaptoethanol, glucose, and glutamax. In some embodiments, the sixth medium comprises DMEM (high glucose)/F12 medium, IL-3, IL-7, FLT3L, IL-15, SCF, human serum, zinc sulfate, ethanolamine, glucose, and glutamax.

In some embodiments, cells are cultured in the sixth medium for 1 day, 2 days, 3 days, 4 days, 5 days, 6 days, 7 days or 8 days. In some embodiments, the cells are cultured in the sixth medium for up to 8 days. In some embodiments, the cells are cultured in the sixth medium for 6-8 days. In some embodiments, the cells are cultured in the sixth medium for 8 days.

In some embodiments, the sixth medium comprises the composition set forth in Table 23A or 23B. In some embodiments, the cells are cultured in the sixth media in Table 23A or 23B for up to 8 days. In some embodiments, the cells are cultured in the sixth media in Table 23A or 23B for 6-8 days. In some embodiments, the cells are cultured in the media in Table 23A or 23B after being cultured in the media in Tables 18A/18B-22. For example, in some embodiments, the cells are cultured in the media in Table 23A after being cultured in the media in Tables 18A, 19A, 20A, 21A, and 22. In additional embodiments, the cells are cultured in the media in Table 23B after being cultured in the media in Tables 18B, 19A, 20B, 21B and 22. In some embodiments, the cells are cultured in the media in Table 23A after being cultured in the media in Tables 18A, 19B, 20A, 21A, and 22. In additional embodiments, the cells are cultured in the media in Table 23B after being cultured in the media in Tables 18B, 19B, 20B, 21B and 22.

TABLE 23A

Exemplary Sixth-Medium composition

| Component | Working Conc. |
|---|---|
| DMEM (high glucose, GlutaMAX) | 55.47% |
| F-12 with GlutaMAX | 27.74% |
| GlutaMAX | 1X |
| Glucose* | 10.25 mM |
| Human AB serum | 15% |
| Zinc sulfate | 37 μM |

TABLE 23A-continued

Exemplary Sixth-Medium composition

| Component | Working Conc. |
|---|---|
| Ethanolamine | 50 μM |
| Ascorbic acid | 20 μg/mL |
| Sodium selenite | 5 ng/mL |
| β-mercaptoethanol | 1 μM |
| rh IL-3 | 5 ng/mL |
| rh IL-7 | 20 ng/mL |
| rh Flt3L | 15 ng/mL |
| rh IL-15 | 15 ng/mL |
| rh SCF | 20 ng/mL |

*Total glucose concentration in medium is 27 mM (accounting for glucose in DMEM (high glucose) medium, F12 supplement and any added glucose).

TABLE 23B

Exemplary Sixth Medium.

| Component | Working Conc. |
|---|---|
| DMEM (high glucose, GlutaMAX) | 50.3% |
| F-12 with GlutaMAX | 28% |
| GlutaMAX | 1X |
| Glucose* | 4.66 mM |
| Human AB serum | 20% |
| Zinc sulfate | 36.2 μM |
| Ethanolamine | 50 μM |
| Ascorbic acid | 15 μg/mL |
| Sodium selenite | 5 ng/mL |
| rh IL-3 | 5 ng/mL |
| rh IL-7 | 20 ng/mL |
| rh Flt3L | 15 ng/mL |
| rh IL-15 | 15 ng/mL |
| rh SCF | 20 ng/mL |

*Total glucose concentration in medium is 20 mM (accounting for glucose in DMEM (high glucose) medium, F12 supplement and any added glucose).

Seventh Medium

In some embodiments, cells are cultured in a seventh medium comprising IL-7, FLT3L, IL-15, and SCF. In some embodiments, the seventh medium comprises a concentration of about 20 ng/mL of IL-7. In some embodiments, the seventh medium comprises a concentration of about 10-20 ng/mL of FLT3L. In some embodiments, the seventh medium comprises a concentration of about 15 ng/mL of FLT3L. In some embodiments, the seventh medium comprises a concentration of about 10-20 ng/mL of IL-15. In some embodiments, the seventh medium comprises a concentration of about 15 ng/mL of IL-15. In some embodiments, the seventh medium comprises a concentration of about 20 ng/mL of SCF.

In some embodiments, the seventh medium comprises human serum, zinc sulfate, ethanolamine, β-mercaptoethanol, glucose, and glutamax in addition to any amounts present in the base medium. In some embodiments, the seventh medium comprises about 15% human serum. In some embodiments, the seventh medium comprises a concentration of about 37 μM of zinc sulfate. In some embodiments, the seventh medium comprises a concentration of about 50 μM of ethanolamine. In some embodiments, the seventh medium comprises a concentration of about 1 μM of β-mercaptoethanol. In some embodiments, the seventh medium comprises a total concentration of about 27 mM of glucose. This concentration is inclusive of glucose sourced from other components in the medium (e.g., DMEM, DMEM (high glucose), and/or F-12 supplement) as well as additional glucose added to the medium ("added glucose"). In some cases, the seventh medium comprises about 1 to 15 mM of "added glucose." In some cases, the seventh medium comprises about 10.25 mM of "added glucose." In some embodiments, the seventh medium comprises a concentration of 1× glutamax.

In some embodiments, the seventh medium comprises human serum, zinc sulfate, ethanolamine, glucose, and glutamax in addition to any amounts present in the base medium. In some embodiments, the seventh medium comprises about 20% human serum. In some embodiments, the seventh medium comprises a concentration of about 37 µM of zinc sulfate. In some embodiments, the seventh medium comprises a concentration of about 50 µM of ethanolamine. In some embodiments, the seventh medium comprises a total concentration of about 20 mM of glucose. This concentration is inclusive of glucose sourced from other components in the medium (e.g., DMEM, DMEM (high glucose), and/or F-12 supplement) as well as additional glucose added to the medium ("added glucose"). In some cases, the seventh medium comprises about 1 to 5 mM of "added glucose." In some cases, the seventh medium comprises about 4.66 mM of "added glucose." In some embodiments, the seventh medium comprises a concentration of 1× glutamax.

In some embodiments, the seventh medium comprises DMEM/F12 medium. In some embodiments, DMEM/F12 medium is the base medium. In some embodiments, the seventh medium comprises DMEM/F12 medium, IL-7, FLT3L, IL-15, and SCF. In some embodiments, the seventh medium comprises DMEM/F12 medium, IL-7, FLT3L, IL-15, SCF, human serum, zinc sulfate, ethanolamine, β-mercaptoethanol, glucose, and glutamax. In some embodiments, the seventh medium comprises DMEM/F12 medium, IL-7, FLT3L, IL-15, SCF, human serum, zinc sulfate, ethanolamine, glucose, and glutamax.

In some embodiments, the seventh medium comprises DMEM (high glucose)/F12 medium. In some embodiments, DMEM (high glucose)/F12 medium is the base medium. In some embodiments, the seventh medium comprises DMEM (high glucose)/F12 medium, IL-7, FLT3L, IL-15, and SCF. In some embodiments, the seventh medium comprises DMEM (high glucose)/F12 medium, IL-7, FLT3L, IL-15, SCF, human serum, zinc sulfate, ethanolamine, 0-mercaptoethanol, glucose, and glutamax. In some embodiments, the seventh medium comprises DMEM (high glucose)/F12 medium, IL-7, FLT3L, IL-15, SCF, human serum, zinc sulfate, ethanolamine, glucose, and glutamax.

In some embodiments, the cells are cultured in the seventh medium for up to 6 days. In some embodiments, the cells are cultured in the seventh medium for 6 days. In some embodiments, the cells are cultured in the seventh medium for 14 days. In some embodiments, the cells are cultured in the seventh medium for at least 6 days and up to 21 to 28 days. In some embodiments, the cells are cultured in the seventh medium for 6-28 days.

In some embodiments, the seventh medium comprises the composition set forth in Table 24A or 24B. In some embodiments, the cells are cultured in the seventh media in Table 24A or 24B for at least 6 days. In some embodiments, the cells are cultured in the seventh media in Table 24A for 6-28 days. In some embodiments, the cells are cultured in the seventh media in Table 24A for 14-28 days. In some embodiments, the cells are cultured in the seventh media in Table 24A for up to 14 days, up to 21 days, up to 22 days, up to 23 days, up to 24 days, up to 25 days, up to 26 days, up to 27 days, or up to 28 days. In some embodiments, the cells are cultured in the seventh media in Table 24B for up to 6 days. In some embodiments, the cells are cultured in the seventh media in Table 24B for 6 days. In some embodiments, the cells are cultured in the media in Table 24A or 24B after being cultured in the media in Tables 18A-23B. For example, the cells can be cultured in the media in Table 24A after being cultured in the media in Tables 18A, 19A, 20A, 21A, 22 and 23A. As another example, the cells can be cultured in the media in Table 24B after being cultured in the media in Tables 18B, 19A, 20B, 21B, 22 and 23B. For example, the cells can be cultured in the media in Table 24A after being cultured in the media in Tables 18A, 19B, 20A, 21A, 22 and 23A. As another example, the cells can be cultured in the media in Table 24B after being cultured in the media in Tables 18B, 19B, 20B, 21B, 22 and 23B.

TABLE 24A

Exemplary Seventh-Medium composition.

| Component | Working Conc. |
| --- | --- |
| DMEM (high glucose, GlutaMAX) | 55.47% |
| F-12 with GlutaMAX | 27.74% |
| GlutaMAX | 1X |
| Glucose* | 10.25 mM |
| Human AB serum | 15% |
| Zinc sulfate | 37 µM |
| Ethanolamine | 50 µM |
| Ascorbic acid | 20 µg/mL |
| Sodium selenite | 5 ng/mL |
| β-mercaptoethanol | 1 µM |
| rh IL-7 | 20 ng/mL |
| rh Flt3L | 15 ng/mL |
| rh IL-15 | 15 ng/mL |
| rh SCF | 20 ng/mL |

*Total glucose concentration in medium is 27 mM (accounting for glucose in DMEM (high glucose) medium, F12 supplement and any added glucose).

TABLE 24B

Exemplary Seventh Medium composition.

| Component | Working Conc. |
| --- | --- |
| DMEM (high glucose, GlutaMAX) | 50.3% |
| F-12 with GlutaMAX | 28% |
| GlutaMAX | 1X |
| Glucose | 4.66 mM |
| Human AB serum | 20% |
| Zinc sulfate | 37 µM |
| Ethanolamine | 50 µM |
| Ascorbic acid | 15 µg/mL |
| Sodium selenite | 5 ng/mL |
| rh IL-7 | 20 ng/mL |
| rh Flt3L | 15 ng/mL |
| rh IL-15 | 15 ng/mL |
| rh SCF | 20 ng/mL |

*Total glucose concentration in medium is 20 mM (accounting for glucose in DMEM (high glucose) medium, F12 supplement and any added glucose).

Eighth Medium

In some embodiments, cells are cultured in an eighth medium comprising IL-7, FLT3L, IL-15, SCF and nicotinamide. In some embodiments, cells are cultured in an eighth medium comprising IL-7, FLT3L, IL-15, and SCF. In some embodiments, the eighth medium comprises a concentration of about 10 ng/mL of IL-7. In some embodiments, the eighth medium comprises a concentration of about 5-20 ng/mL of FLT3L. In some embodiments, the eighth medium comprises a concentration of about 7.5 ng/mL of FLT3L. In some embodiments, the eighth medium comprises a concentration of about 10-40 ng/mL of IL-15. In some embodiments, the eighth medium comprises a concentration of about 15 ng/mL of IL-15. In some embodiments, the eighth medium comprises a concentration of about 20 ng/mL of SCF. In some embodiments, the eighth medium comprises about 5 to 10 mM of nicotinamide. In some embodiments, the eight medium comprises about 6.5 mM of nicotinamide. In some embodiments, the eighth medium does not comprise any nicotinamide.

In some embodiments, the eighth medium comprises human serum, zinc sulfate, ethanolamine, glucose, and glutamax in addition to any amounts present in the base medium. In some embodiments, the eighth medium comprises about 10% human serum. In some embodiments, the eighth medium comprises a concentration of about 37 µM of zinc sulfate. In some embodiments, the eighth medium comprises a concentration of about 50 µM of ethanolamine. In some embodiments, the eighth medium comprises a total concentration of about 20 mM of glucose. This concentration is inclusive of glucose sourced from other components in the medium (e.g., DMEM, DMEM (high glucose), and/or F-12 supplement) as well as additional glucose added to the medium ("added glucose"). In some cases, the eighth medium comprises about 1 to 5 mM of "added glucose." In some cases, the eighth medium comprises about 2.3 mM of "added glucose." In some embodiments, the eighth medium comprises a concentration of 1× glutamax.

In some embodiments, the eighth medium comprises DMEM/F12 medium. In some embodiments, DMEM/F12 medium is the base medium. In some embodiments, the eighth medium comprises DMEM/F12 medium, IL-7, FLT3L, IL-15, SCF and nicotinamide. In some embodiments, the eighth medium comprises DMEM/F12 medium, IL-7, FLT3L, IL-15, and SCF. In some embodiments, the eighth medium comprises DMEM/F12 medium, IL-7, FLT3L, IL-15, SCF, nicotinamide, human serum, zinc sulfate, ethanolamine, glucose, and glutamax. In some embodiments, the eighth medium comprises DMEM/F12 medium, IL-7, FLT3L, IL-15, SCF, human serum, zinc sulfate, ethanolamine, glucose, and glutamax. In some embodiments, the eighth medium does not comprise nicotinamide.

In some embodiments, the eighth medium comprises DMEM (high glucose)/F12 medium. In some embodiments, DMEM (high glucose)/F12 medium is the base medium. In some embodiments, the eighth medium comprises DMEM (high glucose)/F12 medium, IL-7, FLT3L, IL-15, SCF and nicotinamide. In some embodiments, the eighth medium comprises DMEM (high glucose)/F12 medium, IL-7, FLT3L, IL-15, and SCF. In some embodiments, the eighth medium comprises DMEM (high glucose)/F12 medium, IL-7, FLT3L, IL-15, SCF, nicotinamide, human serum, zinc sulfate, ethanolamine, glucose, and glutamax. In some embodiments, the eighth medium comprises DMEM (high glucose)/F12 medium, IL-7, FLT3L, IL-15, SCF, human serum, zinc sulfate, ethanolamine, glucose, and glutamax. In some embodiments, the eighth medium does not comprise nicotinamide.

In some embodiments, the cells are cultured in the eighth medium for at least 6 days and up to 10 to 16 days total. In some embodiments, the cells are cultured in the eighth medium for 8 days. In some embodiments, the cells are cultured in the eighth medium for 8 to 16 days.

In some embodiments, the eighth medium comprises the composition set forth in Table 25A or Table 25B. In some embodiments, the cells are cultured in the eighth media in Table 25A or Table 25B for at least 6 days. In some embodiments, the cells are cultured in the eighth media in Table 25A or Table 25B for 8 days. In some embodiments, the cells are cultured in the eighth media in Table 25A or Table 25B for 8-28 days. In some embodiments, the cells are cultured in the media in Table 25A or Table 25B after being cultured in the media in Tables 18B, 19A, 20B, 21B, 22, 23B, and 24B. In some embodiments, the cells are cultured in the media in Table 25A or Table 25B after being cultured in the media in Tables 18B, 19B, 20B, 21B, 22, 23B, and 24B.

TABLE 25A

Exemplary Eighth-Medium composition

| Component | Working Conc. |
|---|---|
| DMEM (high glucose, GlutaMAX) | 60.5% |
| F-12 with GlutaMAX | 28% |
| GlutaMAX | 1X |
| Glucose* | 2.3 mM |
| Human AB serum | 10% |
| Zinc sulfate | 37 µM |
| Ethanolamine | 50 µM |
| Ascorbic acid | 15 µg//mL |
| Sodium selenite | 5 ng/mL |
| Nicotinamide | 6.5 mM |
| rh IL-7 | 10 ng/mL |
| rh Flt3L | 7.5 ng/mL |
| rh IL-15 | 15 ng/mL |
| rh SCF | 20 ng/mL |

*Total glucose concentration in medium is 20 mM (accounting for glucose in DMEM (high glucose) medium, F12 supplement and any added glucose).

TABLE 25B

Exemplary Eighth-Medium composition

| Component | Working Conc. |
|---|---|
| DMEM (high glucose, GlutaMAX) | 60.5% |
| F-12 with GlutaMAX | 28% |
| GlutaMAX | 1X |
| Glucose* | 2.3 mM |
| Human AB serum | 10% |
| Zinc sulfate | 37 µM |
| Ethanolamine | 50 µM |
| Ascorbic acid | 15 µg//mL |
| Sodium selenite | 5 ng/mL |
| rh IL-7 | 10 ng/mL |
| rh Flt3L | 7.5 ng/mL |
| rh IL-15 | 15 ng/mL |
| rh SCF | 20 ng/mL |

*Total glucose concentration in medium is 20 mM (accounting for glucose in DMEM (high glucose) medium, F12 supplement and any added glucose).

Exemplary Differentiation Methods

Provided herein, in some embodiments, are methods for generating HSPCs from stem cells (e.g., iPSCs). In some embodiments, the method includes:

(a) culturing a population of stem cells in a first medium comprising an amount of a ROCK inhibitor under conditions sufficient to form a population comprising cell aggregates;

(b) culturing the population comprising aggregates in a second medium comprising an amount of BMP-4, and optionally an amount of a ROCK inhibitor;

(c) culturing the population comprising aggregates in a third medium comprising an amount of BMP-4, FGF2, a WNT pathway activator, and Activin A;

(d) culturing the population comprising aggregates in a fourth medium comprising an amount of FGF2, VEGF, TPO, SCF, IL-3, FLT3L, WNT C-59 and an activin/nodal inhibitor to form a cell population comprising HSPCs.

In some embodiments, steps (a)-(d) occurs between 4-9 days. In some embodiments, the cell population is cultured in step (a) for 12-48 hours. In some embodiments, the population comprising aggregates is cultured in step (b) for up to 24 hours. In some embodiments, the population comprising aggregates is cultured in step (c) for 1-3 days. In some embodiments, the population comprising aggregates is cultured in step (d) for 1-3 days. In some embodiments, the cell population is cultured in step (a) for 16-20 hours; the population comprising aggregates is cultured in step (b) for 6-10 hours; the population comprising aggregates is cultured in step (c) for 2 days; and the population comprising aggregates is cultured in step (d) for 2 days.

Provided herein, in some embodiments, are alternative methods for generating HSPCs from stem cells (e.g., iPSCs). In some embodiments, the method includes:

(a) culturing a population of stem cells in a first medium comprising an amount of a ROCK inhibitor under conditions sufficient to form a population comprising cell aggregates;

(b) culturing the population comprising aggregates in a second medium comprising an amount of BMP-4, and optionally an amount of a ROCK inhibitor;

(c) culturing the population comprising aggregates in a third medium comprising an amount of BMP-4, FGF2, a WNT pathway activator, and Activin A;

(d) culturing the population comprising aggregates in a fourth medium comprising an amount of FGF2, VEGF, TPO, SCF, IL-3, FLT3L and an activin/nodal inhibitor to form a cell population comprising HSPCs.

In some embodiments, steps (a)-(d) occurs between 4-9 days. In some embodiments, the cell population is cultured in step (a) for 12-48 hours. In some embodiments, the population comprising aggregates is cultured in step (b) for up to 24 hours. In some embodiments, the population comprising aggregates is cultured in step (c) for 1-3 days. In some embodiments, the population comprising aggregates is cultured in step (d) for 1-3 days. In some embodiments, the cell population is cultured in step (a) for 16-20 hours; the population comprising aggregates is cultured in step (b) for 6-10 hours; the population comprising aggregates is cultured in step (c) for 2 days; and the population comprising aggregates is cultured in step (d) for 2 days.

Provided herein, in some embodiments, are methods for generating Natural Killer (NK) cells from stem cells. In some embodiments, the method includes:

(a) culturing a population of stem cells in a first medium comprising an amount of a ROCK inhibitor under conditions sufficient to form a population comprising cell aggregates;

(b) culturing the population comprising aggregates in a second medium comprising an amount of BMP-4, and optionally an amount of a ROCK inhibitor;

(c) culturing the population comprising aggregates in a third medium comprising an amount of BMP-4, FGF2, a WNT pathway activator, and Activin A;

(d) culturing the population comprising aggregates in a fourth medium comprising an amount of FGF2, VEGF, TPO, SCF, IL-3, FLT3L, WNT C-59 and an activin/nodal inhibitor to form a cell population comprising HSPCs;

(e) culturing the cell population in a fifth medium comprising an amount of FGF2, VEGF, TPO, SCF, IL-3 and FLT3L;

(f) culturing the cell population in a sixth medium comprising an amount of IL-3, IL-7, FLT3L, IL-15 and SCF; and (g) culturing the cell population in a seventh medium comprising an amount IL-7, FLT3L, IL-15 and SCF for a time sufficient to generate NK cells. In some embodiments, the second medium further includes a ROCK inhibitor. In some embodiments, the ROCK inhibitor is thiazovivin. In some embodiments, the ROCK inhibitor is Y27632. In some embodiments, the WNT pathway activator is CHIR-99021. In some embodiments, the activin/nodal inhibitor is SB-431542.

In some embodiments, steps (a)-(g) occurs between 20-35 days. In some embodiments steps (a)-(g) occur in less than 20 days. In some embodiments, the cell population is cultured in step (a) for 12-48 hours. In some embodiments, the population comprising aggregates is cultured in step (b) for up to 24 hours. In some embodiments, the population comprising aggregates is cultured in step (c) for 1-3 days. In some embodiments, the population comprising aggregates is cultured in step (d) for 1-3 days. In some embodiments, the cell population is cultured in step (e) for 1-3 days. In some embodiments, the cell population is cultured in step (f) for up to 7 days. In some embodiments, the cell population is cultured in step (g) for at least 6 days and up to 21-28 days total. In some embodiments, the cell population is cultured in step (a) for 16-20 hours; the population comprising aggregates is cultured in step (b) for 6-10 hours; the population comprising aggregates is cultured in step (c) for 2 days; the population comprising aggregates is cultured in step (d) for 2 days; the cell population is cultured in step (e) for 2 days; the cell population is cultured in step (f) for 4 days; and/or the cell population is cultured in step (g) for 14-28 days.

In some embodiments, the method is carried out under suspension agitation. In some embodiments, the suspension agitation includes rotation. In some embodiments, the first and second media include StemFlex medium. In some embodiments, the third, fourth and fifth media include APEL medium. In some embodiments, the sixth and seventh media comprise DMEM/F12 medium. In some embodiments, the sixth and seventh media comprise DMEM with high glucose and GlutaMAX (Thermo Fisher, 10566016). In some embodiments, the sixth and seventh media comprise F-12 with GlutaMAX (Thermo Fisher, 31765035). In some embodiments, the sixth and seventh media include human serum, zinc sulfate, ethanolamine, β-mercaptoethanol, glucose, or any combination thereof. In some embodiments, the sixth medium comprises about 15% of human AB serum. In some embodiments, the sixth medium comprises about 37 µM of zinc sulfate. In some embodiments, the sixth medium comprises a concentration of about 50 µM of ethanolamine. In some embodiments, the sixth medium comprises about 20 µg/mL of ascorbic acid. In some embodiments, the sixth medium comprises about 5 ng/mL of sodium selenite. In some embodiments, the sixth medium comprises a concentration of about 1 µM of β-mercaptoethanol. In some embodiments, the sixth medium comprises a concentration of about 27 mM of glucose. In some embodiments, the sixth medium comprises a concentration of about 27 mM of glucose, including about 10.25 mM of added glucose (above glucose in DMEM, DMEM (high glucose), or F12 media). In some embodiments, the seventh medium comprises about 15% human serum. In some embodiments, the seventh medium comprises a concentration of about 37 µM of zinc sulfate. In some embodiments, the seventh medium comprises a concentration of about 50 µM of ethanolamine. In some embodiments, the seventh medium comprises a concentration of about 1 µM of β-mercaptoethanol. In some embodiments, the seventh medium comprises a concentration of about 27 mM of glucose. In some embodiments, the seventh medium comprises a concentration of about 27 mM of glucose, including about 10.25 mM of added glucose (above glucose in DMEM, DMEM (high glucose), or F12 media). In some embodiments, the seventh medium comprises a concentration of 1× glutamax.

In some embodiments, the first medium includes 10 µM of the ROCK inhibitor. In some embodiments, the second medium includes 30 ng/mL BMP-4 and 10 µM of a ROCK inhibitor. In some embodiments, the third medium includes 30 ng/mL BMP-4, 100 ng/mL FGF2, 6 µM CHIR-99021, and 2.5-5 ng/mL Activin A.

In some embodiments, half of the third medium is added to the stem cell aggregates. In some embodiments, the fourth and fifth media include 20 ng/mL FGF, 20 ng/mL VEGF, 20 ng/mL TPO, 100 ng/mL SCF, 40 ng/mL IL-3, and 10-20 ng/mL FLT3L. In some embodiments, the fourth medium further includes 2 µM WNT C-59 and 5 µM SB-431542. In some embodiments, the sixth and seventh media includes 20 ng/mL IL-7, 10-20 ng/mL FLT3L, 10-20 ng/mL IL-15, and 20 ng/mL SCF. In some embodiments, the sixth medium includes 5 ng/mL IL-3.

Provided herein, in some embodiments, are alternative methods for generating NK cells from stem cells. In some embodiments, the method includes:

(a) culturing a population of stem cells in a first medium comprising an amount of a ROCK inhibitor under conditions sufficient to form a population comprising cell aggregates;

(b) culturing the population comprising aggregates in a second medium comprising an amount of BMP-4, and optionally an amount of a ROCK inhibitor;

(c) culturing the population comprising aggregates in a third medium comprising an amount of BMP-4, FGF2, a WNT pathway activator, and Activin A;

(d) culturing the population comprising aggregates in a fourth medium comprising an amount of FGF2, VEGF, TPO, SCF, IL-3, FLT3L, and an activin/nodal inhibitor to form a cell population comprising HSPCs;

(e) culturing the cell population in a fifth medium comprising an amount of FGF2, VEGF, TPO, SCF, IL-3 and FLT3L;

(f) culturing the cell population in a sixth medium comprising an amount of IL-3, IL-7, FLT3L, IL-15 and SCF;

(g) culturing the cell population in a seventh medium comprising an amount IL-7, FLT3L, IL-15 and SCF; and;

(h) culturing the cell population in an eighth medium comprising an amount of IL-7, FLT3L, IL-15, SCF and, optionally, nicotinamide for a time sufficient to generate NK cells.

In some embodiments, the second medium further includes a ROCK inhibitor. In some embodiments, the ROCK inhibitor is thiazovivin. In some embodiments, the ROCK inhibitor is Y27632. In some embodiments, the WNT pathway activator is CHIR-99021. In some embodiments, the activin/nodal inhibitor is SB-431542.

In some embodiments, steps (a)-(g) occurs between 20-35 days. In some embodiments, steps (a)-(h) occurs between 20-35 days. In some embodiments, steps (a)-(h) occurs between 23-40 days. In some embodiments, steps (a)-(h) occurs between 23-30 days. In some embodiments, the cell population is cultured in step (a) for about 12-48 hours. In some embodiments, the population comprising aggregates is cultured in step (b) for up to about 24 hours. In some embodiments, the population comprising aggregates is cultured in step (c) for about 1-3 days. In some embodiments, the population comprising aggregates is cultured in step (d) for about 1-3 days. In some embodiments, the cell population is cultured in step (e) for about 1-3 days. In some embodiments, the cell population is cultured in step (f) for up to about 8 days. In some embodiments, the cell population is cultured in step (g) for up to about 6 days. In some embodiments, the cell population is cultured in step (h) for at least about 8 days and up to 10-16 days total. In some embodiments, the cell population is cultured in step (a) for about 16-20 hours; the population comprising aggregates is cultured in step (b) for about 6-10 hours; the population comprising aggregates is cultured in step (c) for about 2 days; the population comprising aggregates is cultured in step (d) for about 2 days; the cell population is cultured in step (e) for about 2 days; the cell population is cultured in step (f) for about 8 days; the cell population is cultured in step (g) for about 6 days; and/or the cell population is cultured in step (h) for about 8 days.

In some embodiments, the method is carried out under suspension agitation. In some embodiments, the suspension agitation includes rotation. In some embodiments, the first and second media include StemBrew medium. In some embodiments, the first media includes StemBrew medium. In some embodiments, the third, fourth and fifth media include APEL medium. In some embodiments, the second, third, fourth and fifth media include APEL medium. In some embodiments, the sixth, seventh and eighth media comprise DMEM/F12 medium. In some embodiments, the sixth, seventh and eighth media comprise DMEM with high glucose and GlutaMAX (Thermo Fisher, 10566016). In some embodiments, the sixth, seventh and eighth media comprise F-12 with GlutaMAX (Thermo Fisher, 31765035).

In some embodiments, the sixth, seventh and eighth media include human serum, zinc sulfate, ethanolamine, glucose, or any combination thereof. In some embodiments, the sixth medium comprises about 20% of human AB serum. In some embodiments, the sixth medium comprises about 36.2 µM of zinc sulfate. In some embodiments, the sixth medium comprises a concentration of about 50 µM of ethanolamine. In some embodiments, the sixth medium comprises about 15 µg/mL of ascorbic acid. In some embodiments, the sixth medium comprises about 5 ng/mL of sodium selenite. In some embodiments, the seventh medium comprises a total concentration of about 20 mM of glucose. In some embodiments, the seventh medium comprises a concentration of about 20 mM of glucose, including about 4.66 mM of added glucose (above glucose in DMEM, DMEM (high glucose), or F12 media). In some embodiments, the seventh medium comprises about 20% human serum. In some embodiments, the seventh medium comprises a concentration of about 37 µM of zinc sulfate. In some embodiments, the seventh medium comprises a concentration of about 50 µM of ethanolamine. In some embodiments, the seventh medium comprises a total concentration of about 20 mM of glucose. In some embodiments, the seventh medium comprises a concentration of about 20 mM of glucose, including about 4.66 mM of added glucose (above glucose in DMEM, DMEM (high glucose), or F12 media). In some embodiments, the seventh medium comprises a concentration of 1× glutamax. In some embodiments, the eighth medium comprises about 10% human serum. In some embodiments, the eighth medium comprises a concentration of about 37 µM of zinc sulfate. In some embodiments, the eighth medium comprises a concentration of about 50 µM of ethanolamine. In some embodiments, the eighth medium comprises a total concentration of about 20 mM of glucose. In some embodiments, the eighth medium comprises a concentration of about 20 mM of glucose, including about 2.3 mM of added glucose (above glucose in DMEM, DMEM (high glucose), or F12 media). In some embodiments, the eighth medium comprises a concentration of 1× glutamax. In some embodiments, the eighth medium comprises nicotinamide. In some embodiments, the eighth medium comprises a concentration of about 1-10 mM of nicotinamide. In some embodiments, the eighth medium comprises a concentration of about 6.5 mM nicotinamide. In some embodiments, the eighth medium does not comprise nicotinamide.

In some embodiments, the first medium includes 10 µM of the ROCK inhibitor. In some embodiments, the second medium includes 30 ng/mL BMP-4 and 10 µM of a ROCK inhibitor. In some embodiments, the second medium includes 30 ng/mL BMP-4. In some embodiments, the third medium includes 30 ng/mL BMP-4, 100 ng/mL FGF2, 7 µM CHIR-99021, and 2.5-5 ng/mL Activin A.

In some embodiments, half of the third medium is added to the stem cell aggregates. In some embodiments, the fourth and fifth media include 20 ng/mL FGF, 20 ng/mL VEGF, 20 ng/mL TPO, 100 ng/mL SCF, 40 ng/mL IL-3, and 10-20 ng/mL FLT3L. In some embodiments, the fourth medium further includes 5 µM SB-431542. In some embodiments, the sixth and seventh media includes 20 ng/mL IL-7, 10-20 ng/mL FLT3L, 10-20 ng/mL IL-15, and 20 ng/mL SCF. In some embodiments, the sixth medium includes 5 ng/mL IL-3.

In some embodiments, the eighth medium comprises 10-20 ng/mL IL-7, 5-20 ng/mL FLT3L, 10-40 ng/mL IL-15, and 20-40 ng/mL of SCF. In some embodiments, the eighth medium comprises 10 ng/mL IL-7, 7.5 ng/mL FLT3L, 15 ng/mL IL-15, and 20 ng/mL of SCF. In some embodiments, the eighth medium comprises 20 ng/mL IL-7, 15 ng/mL FLT3L, 30 ng/mL IL-15 and 40 ng/mL of SCF. In some embodiments, about 50 mL of the eighth medium comprising high amounts of IL-7, FLT3L, IL-15 and SCF (e.g., 20 ng/mL IL-7, 15 ng/mL FLT3L, 30 ng/mL IL-15 and 40 ng/mL of SCF) replaces the eighth medium comprising low amounts of IL-7, FLT3L, IL-15, and SCF (e.g., 10 ng/mL IL-7, 7.5 ng/mL FLT3L, 15 ng/mL IL-15, and 20 ng/mL of SCF). In some embodiments, the eighth medium includes 1-10 mM of nicotinamide. In some embodiments, the eighth medium comprises 6.5 mM of nicotinamide. In some embodiments, the eighth medium does not comprise nicotinamide.

In some embodiments, a method for differentiating stem cells into HSPCs includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days; and (d) culturing the aggregates in a fourth medium comprising an amount of FGF2, VEGF, TPO, SCF, IL-3, FLT3L, WNT C-59 and an activin/nodal inhibitor for 1-3 days to form a cell population comprising HSPCs.

In some embodiments, an alternative method for differentiating stem cells into HSPCs includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days; and (d) culturing the aggregates in a fourth medium comprising an amount of FGF2, VEGF, TPO, SCF, IL-3, FLT3L and an activin/nodal inhibitor for 1-3 days to form a cell population comprising HSPCs.

In some embodiments, a method for differentiating stem cells into HSPCs includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days; and (d) culturing the aggregates in a fourth medium comprising an amount of FGF2, VEGF, TPO, SCF, IL-3, FLT3L, WNT C-59 and an activin/nodal inhibitor for about 2 days to form a cell population comprising HSPCs.

In some embodiments, an alternative method for differentiating stem cells into HSPCs includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days; and (d) culturing the aggregates in a fourth medium comprising an amount of FGF2, VEGF, TPO, SCF, IL-3, FLT3L and an activin/nodal inhibitor for about 2 days to form a cell population comprising HSPCs.

In some embodiments, a method for differentiating stem cells into HSPCs includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL; and (d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, WNT C-59 at a concentration of about 2 µM and SB-431542 at a concentration of about 5 µM to form a cell population comprising HSPCs.

In some embodiments, an alternative method for differentiating stem cells into HSPCs includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL; and (d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, and SB-431542 at a concentration of about 5 µM to form a cell population comprising HSPCs.

In some embodiments, a method for differentiating stem cells into HSPCs includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL, for 1-3 days; and (d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, WNT C-59 at a concentration of about 2 µM and SB-431542 at a concentration of about 5 µM for 1-3 days to form a cell population comprising HSPCs.

In some embodiments, an alternative method for differentiating stem cells into HSPCs includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for 1-3 days; and (d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL and SB-431542 at a concentration of about 5 µM for 1-3 days to form a cell population comprising HSPCs.

In some embodiments, a method for differentiating stem cells into HSPCs includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and, optionally, a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL, for about 2 days; and (d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, WNT C-59 at a concentration of about 2 µM and SB-431542 at a concentration of about 5 µM for about 2 days to form a cell population comprising HSPCs;

In some embodiments, an alternative method for differentiating stem cells into HSPCs includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and, optionally, a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for about 2 days; and (d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, and SB-431542 at a concentration of about 5 µM for about 2 days to form a cell population comprising HSPCs.

In some embodiments, a method for differentiating stem cells into NK cells includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days;

(d) culturing the aggregates in a fourth medium comprising an amount of FGF2, VEGF, TPO, SCF, IL-3, FLT3L, WNT C-59 and an activin/nodal inhibitor for 1-3 days to form a cell population comprising HSPCs;

(e) culturing the cell population in a fifth medium comprising an amount of FGF2, VEGF, TPO, SCF, IL-3 and FLT3L for 1-3 days;

(f) culturing the cell population in a sixth medium comprising an amount of IL-3, IL-7, FLT3L, IL-15 and SCF for up to 8 days; and (g) culturing the cell population in a seventh medium comprising an amount IL-7, FLT3L, IL-15 and SCF for at least 6 days and up to 14-28 days total to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days;

(d) culturing the aggregates in a fourth medium comprising an amount of FGF2, VEGF, TPO, SCF, IL-3, FLT3L, and an activin/nodal inhibitor for 1-3 days to form a cell population comprising HSPCs;

(e) culturing the cell population in a fifth medium comprising an amount of FGF2, VEGF, TPO, SCF, IL-3 and FLT3L for 1-3 days;

(f) culturing the cell population in a sixth medium comprising an amount of IL-3, IL-7, FLT3L, IL-15 and SCF for up to 8 days;

(g) culturing the cell population in a seventh medium comprising an amount IL-7, FLT3L, IL-15 and SCF for up to 6 days; and (h) culturing the cell population in an eighth medium comprising an amount of IL-7, FLT3L, IL-15, and SCF for at least 6 days and up to 8-16 days total to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days;

(d) culturing the aggregates in a fourth medium comprising an amount of FGF2, VEGF, TPO, SCF, IL-3, FLT3L, and an activin/nodal inhibitor for 1-3 days to form a cell population comprising HSPCs;

(e) culturing the cell population in a fifth medium comprising an amount of FGF2, VEGF, TPO, SCF, IL-3 and FLT3L for 1-3 days;

(f) culturing the cell population in a sixth medium comprising an amount of IL-3, IL-7, FLT3L, IL-15 and SCF for up to 8 days;

(g) culturing the cell population in a seventh medium comprising an amount IL-7, FLT3L, IL-15 and SCF for up to 6 days; and (h) culturing the cell population in an eighth medium comprising an amount of IL-7, FLT3L, IL-15, SCF and nicotinamide for at least 6 days and up to 8-16 days total to generate NK cells.

In some embodiments, a method for differentiating stem cells into NK cells includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days;

(d) culturing the aggregates in a fourth medium comprising an amount of FGF2, VEGF, TPO, SCF, IL-3, FLT3L, WNT C-59 and an activin/nodal inhibitor for about 2 days to form a cell population comprising HSPCs;

(e) culturing the cell population in a fifth medium comprising an amount of FGF2, VEGF, TPO, SCF, IL-3 and FLT3L for about 2 days;

(f) culturing the cell population in a sixth medium comprising an amount of IL-3, IL-7, FLT3L, IL-15 and SCF for 6-8 days; and (g) culturing the cell population in a seventh medium comprising an amount IL-7, FLT3L, IL-15 and SCF for at least 6-28 days total to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days;

(d) culturing the aggregates in a fourth medium comprising an amount of FGF2, VEGF, TPO, SCF, IL-3, FLT3L and an activin/nodal inhibitor for about 2 days to form a cell population comprising HSPCs;

(e) culturing the cell population in a fifth medium comprising an amount of FGF2, VEGF, TPO, SCF, IL-3 and FLT3L for about 2 days;

(f) culturing the cell population in a sixth medium comprising an amount of IL-3, IL-7, FLT3L, IL-15 and SCF for 6-8 days; and (g) culturing the cell population in a seventh medium comprising an amount IL-7, FLT3L, IL-15 and SCF for 6 day; and (h) culturing the cell population in an eighth medium comprising an amount of IL-7, FLT3L, IL-15, SCF and nicotinamide for at least 10-16 days to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days;

(d) culturing the aggregates in a fourth medium comprising an amount of FGF2, VEGF, TPO, SCF, IL-3, FLT3L and an activin/nodal inhibitor for about 2 days to form a cell population comprising HSPCs;

(e) culturing the cell population in a fifth medium comprising an amount of FGF2, VEGF, TPO, SCF, IL-3 and FLT3L for about 2 days;

(f) culturing the cell population in a sixth medium comprising an amount of IL-3, IL-7, FLT3L, IL-15 and SCF for 6-8 days; and (g) culturing the cell population in a seventh medium comprising an amount IL-7, FLT3L, IL-15 and SCF for 6 day; and (h) culturing the cell population in an eighth medium comprising an amount of IL-7, FLT3L, IL-15, and SCF for at least 10-16 days to generate NK cells.

In some embodiments, a method for differentiating stem cells into NK cells includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, WNT C-59 at a concentration of about 2 µM and SB-431542 at a concentration of about 5 µM to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL; and (g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for a time sufficient to generate NK cells.

In some embodiments, an alternative method for differentiating stem cells into NK cells includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, SB-431542 at a concentration of about 5 µM to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL; and (g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL;

(h) culturing the cell population in an eighth medium comprising an amount IL-7 at a concentration of about 10-20 ng/mL, FLT3L at a concentration of 5-20 ng/mL, IL-15 at a concentration of about 10-30 ng/mL, SCF at a concentration of about 20-40 ng/mL and nicotinamide at a concentration of about 5-10 mM for a time sufficient to generate NK cells.

In some embodiments, an alternative method for differentiating stem cells into NK cells includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, SB-431542 at a concentration of about 5 µM to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL; and (g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL;

(h) culturing the cell population in an eighth medium comprising an amount IL-7 at a concentration of about 10-20 ng/mL, FLT3L at a concentration of 5-20 ng/mL, IL-15 at a concentration of about 10-30 ng/mL, and SCF at a concentration of about 20-40 ng/mL for a time sufficient to generate NK cells.

In some embodiments, a method for differentiating stem cells into NK cells includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL, for 1-3 days;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, WNT C-59 at a concentration of about 2 µM and SB-431542 at a concentration of about 5 µM for 1-3 days to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for 1-3 days;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for up to 8 days; and (g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for at least 6 days and up to 21-28 total days to generate NK cells.

In some embodiments, an alternative method for differentiating stem cells into NK cells includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for 1-3 days;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, SB-431542 at a concentration of about 5 µM for 1-3 days to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for 1-3 days;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for up to 8 days; and (g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for up to 6 days; and (h) culturing the cell population in an eighth medium comprising an amount IL-7 at a concentration of about 10-20 ng/mL, FLT3L at a concentration of 5-20 ng/mL, IL-15 at a concentration of about 10-30 ng/mL, SCF at a concentration of about 20-40 ng/mL and nicotinamide at a concentration of about 5-10 mM for at least 6 days and up to 10-16 total days to generate NK cells.

In some embodiments, an alternative method for differentiating stem cells into NK cells includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for 1-3 days;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, SB-431542 at a concentration of about 5 µM for 1-3 days to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for 1-3 days;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for up to 8 days;

(g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for up to 6 days; and (h) culturing the cell population in an eighth medium comprising an amount IL-7 at a concentration of about 10-20 ng/mL, FLT3L at a concentration of 5-20 ng/mL, IL-15 at a concentration of about 10-30 ng/mL, and SCF at a concentration of about 20-40 ng/mL for at least 6 days and up to 10-16 total days to generate NK cells.

In some embodiments, a method for differentiating stem cells into NK cells includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and optionally a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL, for about 2 days;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, WNT C-59 at a concentration of about 2 µM and SB-431542 at a concentration of about 5 µM for about 2 days to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for about 2 days;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for 6-8 days; and (g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for 6-28 days to generate NK cells.

In some embodiments, an alternative method for differentiating stem cells into NK cells includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and optionally a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for about 2 days;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, and SB-431542 at a concentration of about 5 µM for about 2 days to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for about 2 days;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for 6-8 days;

(g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for 6 days; and (h) culturing the cell population in an eighth medium comprising an amount IL-7 at a concentration of about 10-20 ng/mL, FLT3L at a concentration of 5-20 ng/mL, IL-15 at a concentration of about 10-30 ng/mL, SCF at a concentration of about 20-40 ng/mL and nicotinamide at a concentration of about 5-10 mM for 10-16 days to generate NK cells.

In some embodiments, an alternative method for differentiating stem cells into NK cells includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and optionally a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for about 2 days;

(d) culturing the aggregates in a fourth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, FLT3L at a concentration of about 10-20 ng/mL, and SB-431542 at a concentration of about 5 µM for about 2 days to form a cell population comprising HSPCs;

(e) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for about 2 days;

(f) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for 6-8 days;

(g) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for 6 days; and (h) culturing the cell population in an eighth medium comprising an amount IL-7 at a concentration of about 10-20 ng/mL, FLT3L at a concentration of 5-20 ng/mL, IL-15 at a concentration of about 10-30 ng/mL, and SCF at a concentration of about 20-40 ng/mL for 10-16 days to generate NK cells.

In some embodiments, a method for differentiating stem cells into NK cells includes:

(a) culturing a population of stem cells in a first medium comprising an amount of a ROCK inhibitor under conditions sufficient to form aggregates;

(b) culturing the aggregates in a second medium comprising an amount of BMP-4, and optionally an amount of a ROCK inhibitor;

(c) culturing the aggregates in a third medium comprising an amount of BMP-4, FGF2, a WNT pathway activator, and Activin A;

(d) culturing the cell population in a fifth medium comprising an amount of FGF2, VEGF, TPO, SCF, IL-3 and FLT3L to form a cell population comprising HSPCs;

(e) culturing the cell population in a sixth medium comprising an amount of IL-3, IL-7, FLT3L, IL-15 and SCF; and (f) culturing the cell population in a seventh medium comprising an amount IL-7, FLT3L, IL-15 and SCF for a time sufficient to generate NK cells.

In some embodiments, an alternative method for differentiating stem cells into NK cells includes:

(a) culturing a population of stem cells in a first medium comprising an amount of a ROCK inhibitor under conditions sufficient to form aggregates;

(b) culturing the aggregates in a second medium comprising an amount of BMP-4, and optionally an amount of a ROCK inhibitor;

(c) culturing the aggregates in a third medium comprising an amount of BMP-4, FGF2, a WNT pathway activator, and Activin A;

(d) culturing the cell population in a fifth medium comprising an amount of FGF2, VEGF, TPO, SCF, IL-3 and FLT3L to form a cell population comprising HSPCs;

(e) culturing the cell population in a sixth medium comprising an amount of IL-3, IL-7, FLT3L, IL-15 and SCF;

(f) culturing the cell population in a seventh medium comprising an amount IL-7, FLT3L, IL-15 and SCF; and (g) culturing the cell population in an eighth medium comprising an amount of IL-7, FLT3L, IL-15, SCF and nicotinamide for a time sufficient to generate NK cells.

In some embodiments, an alternative method for differentiating stem cells into NK cells includes:

(a) culturing a population of stem cells in a first medium comprising an amount of a ROCK inhibitor under conditions sufficient to form aggregates;

(b) culturing the aggregates in a second medium comprising an amount of BMP-4, and optionally an amount of a ROCK inhibitor;

(c) culturing the aggregates in a third medium comprising an amount of BMP-4, FGF2, a WNT pathway activator, and Activin A;

(d) culturing the cell population in a fifth medium comprising an amount of FGF2, VEGF, TPO, SCF, IL-3 and FLT3L to form a cell population comprising HSPCs;

(e) culturing the cell population in a sixth medium comprising an amount of IL-3, IL-7, FLT3L, IL-15 and SCF;

(f) culturing the cell population in a seventh medium comprising an amount IL-7, FLT3L, IL-15 and SCF; and (g) culturing the cell population in an eighth medium comprising an amount of IL-7, FLT3L, IL-15, and SCF and for a time sufficient to generate NK cells.

In some embodiments, a method for differentiating stem cells into NK cells includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days;

(d) culturing the cell population in a fifth medium comprising an amount of FGF2, VEGF, TPO, SCF, IL-3 and FLT3L for 5-7 days to form a cell population comprising HSPCs;

(e) culturing the cell population in a sixth medium comprising an amount of IL-3, IL-7, FLT3L, IL-15 and SCF for up to 8 days; and (f) culturing the cell population in a seventh medium comprising an amount IL-7, FLT3L, IL-15 and SCF for at least 6 days and up to 21-28 days total to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days;

(d) culturing the cell population in a fifth medium comprising an amount of FGF2, VEGF, TPO, SCF, IL-3 and FLT3L for 5-7 days to form a cell population comprising HSPCs;

(e) culturing the cell population in a sixth medium comprising an amount of IL-3, IL-7, FLT3L, IL-15 and SCF for up to 8 days;

(f) culturing the cell population in a seventh medium comprising an amount IL-7, FLT3L, IL-15 and SCF for up to 6 days; and (g) culturing the cell population in an eighth medium comprising an amount of IL-7, FLT3L, IL-15, SCF and nicotinamide for at least 6 days and up to 10-16 days to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 12-24 hours;

(b) culturing the aggregates in a second medium comprising an amount of BMP-4, and optionally an amount of a ROCK inhibitor, for up to 24 hours;

(c) culturing the aggregates in a third medium comprising an amount of BMP-4, FGF2, a WNT pathway activator, and Activin A for 1-3 days;

(d) culturing the cell population in a fifth medium comprising an amount of FGF2, VEGF, TPO, SCF, IL-3 and FLT3L for 5-7 days to form a cell population comprising HSPCs;

(e) culturing the cell population in a sixth medium comprising an amount of IL-3, IL-7, FLT3L, IL-15 and SCF for up to 8 days;

(f) culturing the cell population in a seventh medium comprising an amount IL-7, FLT3L, IL-15 and SCF for up to 6 days; and (g) culturing the cell population in an eighth medium comprising an amount of IL-7, FLT3L, IL-15, and SCF for at least 6 days and up to 10-16 days to generate NK cells.

In some embodiments, a method for differentiating stem cells into NK cells includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days;

(d) culturing the cell population in a fifth medium comprising an amount of FGF2, VEGF, TPO, SCF, IL-3 and FLT3L for about 6 days to form a cell population comprising HSPCs;

(e) culturing the cell population in a sixth medium comprising an amount of IL-3, IL-7, FLT3L, IL-15 and SCF for 6-8 days; and (f) culturing the cell population in a seventh medium comprising an amount IL-7, FLT3L, IL-15 and SCF for at least 6-28 days total to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days;

(d) culturing the cell population in a fifth medium comprising an amount of FGF2, VEGF, TPO, SCF, IL-3 and FLT3L for about 6 days to form a cell population comprising HSPCs;

(e) culturing the cell population in a sixth medium comprising an amount of IL-3, IL-7, FLT3L, IL-15 and SCF for 6-8 days;

(f) culturing the cell population in a seventh medium comprising an amount IL-7, FLT3L, IL-15 and SCF for about 6 days; and (g) culturing the cell population in an eighth medium comprising an amount of IL-7, FLT3L, IL-15, SCF and nicotinamide for at least 10-16 days total to generate NK cells.

In some embodiments, an alternative method for differentiating stem cells into NK cells includes:

(a) culturing a population of stem cells in a first medium comprising an amount of a ROCK inhibitor under conditions sufficient to form aggregates for 16-20 hours;

(b) culturing the aggregates in a second medium comprising an amount of BMP-4, and optionally an amount of a ROCK inhibitor, for 6-10 hours;

(c) culturing the aggregates in a third medium comprising an amount of BMP-4, FGF2, a WNT pathway activator, and Activin A for about 2 days;

(d) culturing the cell population in a fifth medium comprising an amount of FGF2, VEGF, TPO, SCF, IL-3 and FLT3L for about 6 days to form a cell population comprising HSPCs;

(e) culturing the cell population in a sixth medium comprising an amount of IL-3, IL-7, FLT3L, IL-15 and SCF for 6-8 days;

(f) culturing the cell population in a seventh medium comprising an amount IL-7, FLT3L, IL-15 and SCF for about 6 days; and (g) culturing the cell population in an eighth medium comprising an amount of IL-7, FLT3L, IL-15, and SCF for at least 10-16 days total to generate NK cells In some embodiments, a method for differentiating stem cells into NK cells includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL; and (f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for a time sufficient to generate NK cells.

In some embodiments, an alternative method for differentiating stem cells into NK cells includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL;

(f) culturing the cell population in a seventh medium comprising an amount of IL-7 at a concentration of about 20 ng/mL, FLT3L at a concentration of 10-20 ng/mL, IL-15 at a concentration of about 10-20 ng/mL and SCF at a concentration of about 20 ng/mL; and (g) culturing the cell population in an eighth medium comprising an amount IL-7 at a concentration of about 10-20 ng/mL, FLT3L at a concentration of 5-20 ng/mL, IL-15 at a concentration of about 10-30 ng/mL, SCF at a concentration of about 20-40 ng/mL, and, nicotinamide at a concentration of about 5-10 mM, for a time sufficient to generate NK cells.

In some embodiments, an alternative method for differentiating stem cells into NK cells includes:

(a) culturing a population of stem cells in a first medium comprising a ROCK inhibitor at a concentration of about 10 µM under conditions sufficient to form aggregates;

(b) culturing the aggregates in a second medium comprising BMP-4 at a concentration of about 30 ng/mL, and optionally a ROCK inhibitor at a concentration of about 10 µM;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL;

(f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL; and (g) culturing the cell population in an eighth medium comprising an amount IL-7 at a concentration of about 10-20 ng/mL, FLT3L at a concentration of 5-20 ng/mL, IL-15 at a concentration of about 10-30 ng/mL and SCF at a concentration of about 20-40 ng/mL for a time sufficient to generate NK cells.

In some embodiments, a method for differentiating stem cells into NK cells includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL, for 1-3 days;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for 5-7 days to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for up to 8 days; and (f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for at least 6 days and up to 21-28 total days to generate NK cells.

In some embodiments, an alternative method for differentiating stem cells into NK cells includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for 1-3 days;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for 5-7 days to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for up to 8 days;

(f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for up to 6 days; and (g) culturing the cell population in an eighth medium comprising an amount of IL-7 at a concentration of about 10-20 ng/mL, FLT3L at a concentration of 5-20 ng/mL, IL-15 at a concentration of about 10-30 ng/mL, SCF at a concentration of about 20-40 ng/mL, and nicotinamide at a concentration of about 5-10 mM for at least 6 days and up to 10-16 total days to generate NK cells.

In some embodiments, an alternative method for differentiating stem cells into NK cells includes:

(a) culturing a population of stem cells in a first medium comprising a ROCK inhibitor at a concentration of about 10 µM for 12-48 hours to form aggregates;

(b) culturing the aggregates in a second medium comprising BMP-4 at a concentration of about 30 ng/mL, and optionally a ROCK inhibitor at a concentration of about 10 µM, for up to 24 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for 1-3 days;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for 5-7 days to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for up to 8 days;

(f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for up to 6 days; and (g) culturing the cell population in an eighth medium comprising an amount of IL-7 at a concentration of about 10-20 ng/mL, FLT3L at a concentration of 5-20 ng/mL, IL-15 at a concentration of about 10-30 ng/mL, and SCF at a concentration of about 20-40 ng/mL, for at least 6 days and up to 10-16 total days to generate NK cells.

In some embodiments, a method for differentiating stem cells into NK cells includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and optionally a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 6 µM and Activin A at a concentration of about 2.5-5.0 ng/mL, for about 2 days;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for about 6 days to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for 6-8 days; and (f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for 6-28 days to generate NK cells.

In some embodiments, the HSPCs of step (d) express CD34. In some embodiments, the NK cells express CD56. In some embodiments, the NK cells express at least one activating receptor. In some embodiments, the at least one activating receptor is selected from the group of NKp44, NKp46, CD16, KIR2DL4, and any combination thereof. In some embodiments, the NK cells express at least one inhibitory receptor. In some embodiments, the at least one inhibitory receptor is selected from the group of CD94, NKG2A, KIR3DL2, and any combination thereof.

In some embodiments, an alternative method for differentiating stem cells into NK cells includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and optionally a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for about 2 days;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for about 6 days to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for 6-8 days;

(f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for about 6 days; and (g) culturing the cell population in an eighth medium comprising an amount of IL-7 at a concentration of about 10-20 ng/mL, FLT3L at a concentration of 5-20 ng/mL, IL-15 at a concentration of about 10-30 ng/mL, SCF at a concentration of about 20-40 ng/mL, and nicotinamide at a concentration of about 5 to 10 mM for 8 days or 8-16 days to generate NK cells.

In some embodiments, the HSPCs of step (d) express CD34. In some embodiments, the NK cells express CD56. In some embodiments, the NK cells express at least one activating receptor. In some embodiments, the at least one activating receptor is selected from the group of NKp44, NKp46, CD16, KIR2DL4, and any combination thereof. In some embodiments, the NK cells express at least one inhibitory receptor. In some embodiments, the at least one inhibitory receptor is selected from the group of CD94, NKG2A, KIR3DL2, and any combination thereof.

In some embodiments, an alternative method for differentiating stem cells into NK cells includes:

(a) culturing a population of stem cells in a first medium comprising a ROCK inhibitor at a concentration of about 10 µM for 16-20 hours to form aggregates;

(b) culturing the aggregates in a second medium comprising BMP-4 at a concentration of about 30 ng/mL, and optionally a ROCK inhibitor at a concentration of about 10 µM, for 6-10 hours;

(c) culturing the aggregates in a third medium comprising BMP-4 at a concentration of about 30 ng/mL, FGF2 at a concentration of about 100 ng/mL, CHIR-99021 at a concentration of about 7 µM and Activin A at a concentration of about 2.5-5.0 ng/mL, for about 2 days;

(d) culturing the cell population in a fifth medium comprising FGF2 at a concentration of about 20 ng/mL, VEGF at a concentration of about 20 ng/mL, TPO at a concentration of about 20 ng/mL, SCF at a concentration of about 100 ng/mL, IL-3 at a concentration of about 40 ng/mL, and FLT3L at a concentration of about 10-20 ng/mL, for about 6 days to form a cell population comprising HSPCs;

(e) culturing the cell population in a sixth medium comprising an amount of IL-3 at a concentration of about 5 ng/mL, IL-7 at a concentration of about 20 ng/mL, FLT3L at a concentration of 10-20 ng/mL, IL-15 at a concentration of about 10-20 ng/mL and SCF at a concentration of about 20 ng/mL, for 6-8 days;

(f) culturing the cell population in a seventh medium comprising an amount IL-7 at a concentration of about 20 ng/mL, FLT3L at a concentration of 10-20 ng/mL, IL-15 at a concentration of about 10-20 ng/mL and SCF at a concentration of about 20 ng/mL for about 6 days; and (g) culturing the cell population in an eighth medium comprising an amount of IL-7 at a concentration of about 10-20 ng/mL, FLT3L at a concentration of 5-20 ng/mL, IL-15 at a concentration of about 10-30 ng/mL, and SCF at a concentration of about 20-40 ng/mL for 8 days or 8-16 days to generate NK cells.

In some embodiments, the HSPCs of step (d) express CD34. In some embodiments, the NK cells express CD56. In some embodiments, the NK cells express at least one activating receptor. In some embodiments, the at least one activating receptor is selected from the group of NKp44, NKp46, CD16, KIR2DL4, and any combination thereof. In some embodiments, the NK cells express at least one inhibitory receptor. In some embodiments, the at least one inhibitory receptor is selected from the group of CD94, NKG2A, KIR3DL2, and any combination thereof.

In some embodiments, inducible pluripotent stem cells (iPSC) are thawed and prepared for differentiation culture. Methods for culturing and maintaining iPSC and other stem cell types are known in the art. In some embodiments, iPSCs are cultured in StemFlex™ Basal Media and StemFlex™ Supplement. In some embodiments, prior to inducing differentiation iPSCs are cultured in a medium comprising a low concentration of a ROCK inhibitor (e.g., thiazovivin or Y27632). In some embodiments, iPSCs are cultured in a medium comprising 2 µM of a ROCK inhibitor (e.g., thiazovivin or Y27632). In some embodiments, after culture in StemFlex™ Basal Media and StemFlex™ Supplement cells are resuspended in the media in Table 18A or 18B. In some embodiments, cells are cultured in the media in Table 18A or 18B for 16 to 20 hours. In some embodiments, cells are removed from the Table 18A or 18B media and are resuspended in the Table 19A or 19B media and cultured for about 8 hours. In some embodiments, after culturing in the media in Table 19A or 19B after about 8 hours, the media is diluted in half by the addition of the media in Table 20A or 20B, cells are then cultured for about 48 hours. In some embodiments, after culture for 48 hours in the media in Table 20A or 20B cells are transferred to the media in Table 21A or 21B and cultured for about 48 hours. In some embodiments, after culture for about 48 hours in the media in Table 21A or 21B, cells are transferred to the media in Table 22 and cultured for about 48 hours. In some embodiments, after culture for about 48 hours in the media in Table 22, cells are transferred to the medium in Table 23A or 23B and cultured for about 4 days. In some embodiments, after culture for about 4 days in the media in Table 23A or 23B, half of the media is replaced with fresh media from Table 23A or 23B and cells are cultured for an additional 4 days. In some embodiments, after culture for about 4 days in the media in Table 23A or 23B, cells are transferred to the media in Table 24A or 24B are cultured for about 3 days and a full media change occurs every 2-3 days for up to 28 days. In some embodiments, NK cells are formed during culture with media in Table 24A or 24B. In some embodiments, after culturing in the media in Tables 23A or 23B, cells are transferred to the media in Table 24A or 24B and are cultured for up to 6 days followed by a full media change to the media in Table 25A or Table 25B, wherein a full media change occurs every 2-3 days for up to 10-16 days. In some embodiments, a partial media change is performed with the media in Table 25A or Table 25B at a time during the 10-16 days duration. In some embodiments, NK cells are formed during culture with media in Table 25A or Table 25B.

In some embodiments, iPSCs are thawed and prepared for differentiation, in StemFlex™ Basal Media and StemFlex™ Supplement, then cells are cultured sequentially in the following order a) following culture in StemFlex™ Basal Media and StemFlex™ Supplement cells are resuspended and cultured in in the media in Table 18A for 16 to 20 hours; b) cells are removed from the Table 18A media and are resuspended in the Table 19 media and cultured for about 8 hours; c) after culturing in the media in Table 19A or 19B for about 8 hours, the media is diluted in half by the addition of the media in Table 20A, cells are then cultured for about 48 hours; d) after culture for about 48 hours in the media in Table 20A cells are transferred to the media in Table 21A and cultured for about 48 hours; e) after culture for about 48 hours in the media in Table 21A, cells are transferred to the media in Table 22 and cultured for about 48 hours; f) after culture for about 48 hours in the media in Table 22, cells are transferred to the medium in Table 23A and cultured for about 4 days; g) after culture for about 4 days in the media in Table 23A, half of the media is replaced with fresh media from Table 23A and cells are cultured for an additional 4 days; h) after culture for about 4 days in the media in Table 23A, cells are transferred to the media in Table 24A are cultured for about 3 days and a full media change occurs every 2-3 days for up to 28 days; i) NK cells are formed.

In some embodiments, iPSCs are thawed and prepared for differentiation, in StemBrew™ Basal Media and StemBrew™ Supplement, then cells are cultured sequentially in the following order a) following culture in StemBrew™ Basal Media and StemBrew™ Supplement cells are resuspended and cultured in in the media in Table 18B for 16 to 20 hours; b) cells are removed from the Table 18B media and are resuspended in the Table 19A or 19B media and cultured for about 8 hours; c) after culturing in the media in Table 19 for about 8 hours, the media is diluted in half by the addition of the media in Table 20B, cells are then cultured for about 48 hours; d) after culture for about 48 hours in the media in Table 20B cells are transferred to the media in Table 21B and cultured for about 48 hours; e) after culture for about 48 hours in the media in Table 21B, cells are transferred to the media in Table 22 and cultured for about 48 hours; f) after culture for about 48 hours in the media in Table 22, cells are transferred to the medium in Table 23B and cultured for about 4 days; g) after culture for about 4 days in the media in Table 23B, the media is replaced with fresh media from Table 23B and cells are cultured for an additional 4 days; h) after culture for about 4 days in the media in Table 23B, cells are transferred to the media in Table 24B are cultured for about 6 days, with fresh media from Table 24B changed after 3 days; i) after culture for about 6 days in the media in Table 24B cells are transferred to the media in Table 25A or Table 25B and a full media change occurs every 2-3 days for up to 16 days; i) NK cells are formed.

In some embodiments, cells are cultured in aggregates. In some embodiments, cells are cultured in aggregates until day 5 of differentiation. In some embodiments, aggregates are present in the culture as late as day 20 of differentiation. In some embodiments, single cells emerge during differentiation. In some embodiments, single cells emerge on day 6, 7, 8, 9, 10, 11, 12, 13, 14, 15, 16, 17, 18, 19, or 20 of differentiation. In some embodiments, cell aggregates dissociate into single cells during culture. In some embodiments, aggregates dissociate into single cells on any one of days 6, 7, 8, 9, 10, 11, 12, 13, 14, 15, 16, 17, 18, 19, and 20.

In some embodiments, aggregates are about 50 μm to about 200 μm in diameter. In some embodiments, aggregates are about 100 μm to about 200 μm in diameter. In some embodiments, aggregates are less than about 100 μm in diameter. In some embodiments, aggregates are about 50 μm to about 100 μm in diameter. In some embodiments, aggregates are about 60 μm to about 100 μm in diameter.

In some embodiments, at least 99%, at least 90%, at least 80%, at least 70%, at least 60%, at least 50%, at least 40%, at least 30%, at least 20%, at least 10%, at least 5%, or at least 1% of the cells in culture are in aggregates. In some embodiments, at least 99%, at least 90%, at least 80%, at least 70%, at least 60%, at least 50%, at least 40%, at least 30%, at least 20%, at least 10%, at least 5%, or at least 1% of the cells in culture are single cells.

Differentiating Cell Phenotypes

Throughout differentiation from stem cell to natural killer cell, or any intermediate cell types therein, cells express a variety of phenotypic markers. Similarly, differentiation from stem cell to HSPC or HSPC to NK cell provide one or more markers of cell types during differentiation. In some embodiments, at day 0 of differentiation, cells are Oct3/4+ and Sox2+. In some embodiments, cells are Oct3/4$^+$ and Sox2$^+$ on any one of day 1, 2, 3, or 4 of differentiation. In some embodiments, cells lose Oct3/4 and Sox2 expression beginning at day 2. In some embodiments, cells express CD34 beginning at day 3. In some embodiments, at any one or more of day 4, 5, 6, 7 or 8 of differentiation, HSCs are CD34$^+$/CD43$^+$/CD45$^-$. In some embodiments, at day 6 of differentiation, HSCs are CD34$^+$/CD43$^+$/CD45$^-$. In some embodiments, at one or more of day 10, 11, 12, 13, 14, cells are CD34$^+$/CD43$^+$/CD45$^+$. In some embodiments, at any one or more of days 12, 13, 14, 15, or 16, CLPs are CD34$^-$/CD45$^+$/CD38$^+$/CD117$^+$/CD7$^+$. In some embodiments, at day 14 of differentiation, CLPs are CD34$^-$/CD45$^+$/CD38$^+$/CD117$^+$/CD7$^+$. In some embodiments, on any one or more of days 17, 18, 19, 20, 21, or 22 of differentiation, immature NK cells are CD34$^-$/CD45$^+$/CD56$^+$/NKp46$^+$/CD94$^+$/NKG2A$^+$. In some embodiments, on day 20 of differentiation, immature NK cells are CD34$^-$/CD45$^+$/CD56$^+$/NKp46$^+$/CD94$^+$/NKG2A$^+$. In some embodiments on any one or more of days 26, 27, 28, 29, or 30 of differentiation, NK cells are CD45$^+$/CD56$^+$/NKp44$^+$/NKp46$^+$/CD94$^+$/NKG2A$^+$/NKG2D$^+$/CD16$^{-/+}$/and KIR$^{-/+}$. In some embodiments, NK cells formed in step (c) or step (d) of Stage II are CD45$^+$/CD56$^+$/NKp44$^+$/NKp46$^+$/CD94$^+$/NKG2A$^+$/NKG2D$^+$/CD16$^+$/KIR$^+$. In some embodiments, NK cells formed in step (c) or step (d) of Stage II are CD45$^+$/CD56$^+$/NKp44$^+$/NKp46$^+$/CD94$^+$/NKG2A$^+$/NKG2D$^+$/CD16/KIR$^-$. In some embodiments, NK cells formed in step (c) or step (d) of Stage II are CD45$^+$/CD56$^+$/NKp44$^+$/NKp46$^+$/CD94$^+$/NKG2A$^+$/NKG2D$^+$/CD16/KIR$^-$. In some embodiments, NK cells formed in step (c) or step (d) of Stage II are CD45$^+$/CD56$^+$/NKp44$^+$/NKp46$^+$/CD94$^+$/NKG2A$^+$/NKG2D$^+$/CD16$^-$/KIR$^+$. In some embodiments on day 28 of differentiation, NK cells are CD45$^+$/CD56$^+$/NKp44$^+$/NKp46$^+$/CD94$^+$/NKG2A$^+$/NKG2D$^+$/CD16$^{-/+}$/KIR$^{-/+}$. In some embodiments, the differentiated NK cells do not express CD3. In some embodiments, on days 21 and 35, differentiated NK cells do not express CD3.

In some embodiments, on day 6 at least about 38-55% of the cells are CD34$^+$. In some embodiments, at least about 29%-49% of cells are CD34$^+$/CD45$^+$. In some embodiments, at day 14, at least about 19-45% of cells are CD7$^+$/CD45$^+$. In some embodiments, at day 17 about 50% of cells are CD56$^+$/CD45$^+$. In some embodiments, at day 20, at least about 70% of cells are CD56$^+$/CD45$^+$.

In some embodiments, about 20-60% of differentiating cells are CD34$^+$/CD43$^-$ on day 6 of differentiation. In some embodiments, 0 to about 5% of differentiating cells are CD34$^+$/CD43$^+$ on day 6 of differentiation. In some embodiments, about 15% to about 25% of differentiating cells are CD34$^+$/CD43$^+$ on day 10 of differentiation. In some embodiments, about 45% to about 55% of differentiating cells are CD34$^+$/CD43$^-$ on day 10 of differentiation.

In some embodiments, about 50% to about 60% of differentiating cells are CD45$^+$/CD56$^-$ on day 10 of differentiation. In some embodiments, about 50% to about 75% of differentiating cells are CD45$^+$/CD56$^-$ on day 14 of differentiation. In some embodiments, about 5% to about 40% of differentiating cells are CD45$^+$/CD56$^+$ on day 14 of differentiation. In some embodiments, about 50% of differentiating cells are CD45$^+$/CD56$^+$ on day 17 of differentiation. In some embodiments, about 20% to about 30% of differentiating cells are CD45$^+$/CD56$^-$ on day 20 of differentiation. In some embodiments, about 65% to about 90% of differentiating cells are CD45$^+$/CD56$^+$ on day 20 of differentiation. In some embodiments, about 95% to 100% of differentiating cells are CD45$^+$/CD56$^+$ on day 28 of differentiation. In some embodiments, about 95% to 100% of differentiating cells are CD45$^+$/CD56$^+$ on day 35 of differentiation.

In some embodiments, differentiating cells lose Sox2 expression by day 1, 2, 3, or 4 of differentiation. In some embodiments, differentiating cells lose Oct3/4 expression by day 1, 2, 3, or 4 of differentiation. In some embodiments, by day 6 of differentiation, cells do not express OCT3/4. In some embodiments, by day 6 of differentiation, cells do no express Sox2.

In some embodiments, about 35% to about 45% of differentiating cells express NKp44 on day 21 of differentiation. In some embodiments, about 70% to about 80% of differentiating cells express NKp44 on day 28 of differentiation. In some embodiments, about 75% to about 85% of differentiation cells express NKp44 on day 37 of differentiation. In some embodiments, about 60% to about 70% of differentiating cells express NKp46 on day 21 of differentiation. In some embodiments, about 75% to about 85% of differentiating cells express NKp46 on day 28 of differentiation. In some embodiments, about 70% to about 80% of differentiation cells express NKp46 on day 37 of differentiation. In some embodiments, about 15% to about 30% of differentiating cells express CD16 on day 21 of differentiation. In some embodiments, about 10% to about 30% of differentiating cells express CD16 on day 28 of differentiation. In some embodiments, about 1% to about 10% of differentiation cells express CD16 on day 37 of differentiation. In some embodiments, differentiating cells do not express KIR2DL4 on day 21 of differentiation. In some embodiments, about 2% to about 5% of differentiating cells differentiating cells express KIR2DL4 on day 28 of differentiation. In some embodiments, about 20% to about 40% of differentiating cells express KIR2DL4 on day 37 of differentiation. In some embodiments, about 75% to about 85% of differentiating cells express CD94 on day 21 of differentiation. In some embodiments, about 80% to about 90% of differentiating cells express CD94 on day 28 of differentiation. In some embodiments, about 65% to about 80% of differentiation cells express CD94 on day 37 of differentiation. In some embodiments, about 70% to about 80% of differentiating cells express NKG2A on day 21 of differentiation. In some embodiments, about 75% to about 85% of differentiating cells express NKG2A on day 28 of differentiation. In some embodiments, about 70% to about 80% of differentiation cells express NKG2A on day 37 of differentiation. In some embodiments, differentiating cells do no express KIR3DL2 on day 21 of differentiation. In some embodiments, differentiating cells do not express KIR3DL2 on day 28 of differentiation. In some embodiments, 0% to about 5% of differentiation cells express KIR3DL2 on day 37 of differentiation.

In some embodiments, on day 20 of differentiation, cells have an about 10 to about 100-fold change increase normalized to day 0 of one or more of EOMES, NFIL3, FCGR3A, KIR2DL1, KIR2DS4, KIR2DL3, KIR3DL1, KIR3DL2, IL15, IL18, IL2RA, KLRF1 (NKP80), SLAMF7. In some embodiments, on day 35 of differentiation, cells have about 10 to about 100-fold change increase normalized to ay 0 of one or more of EOMES, NFIL3, FCGR3A, GZMM, IL15, KLRF1 (NKP80), KLRD1 (CD94).

In some embodiments, on day 20 of differentiation, cells have about 100 to about 1000-fold change increase normalize to day 0 of one or more of TBX21, NCR1, NCR2, CCR5, CD226 (DNAM-1), GZMM, IL2RB, KLRD1 (CD94). In some embodiments, on day 35 of differentiation, cells have about 100 to about 1000-fold change increase normalized to day 0 of one or more of TBX21, NCR1, NCR2, KIR2DL1, KIR3DL1, KIR3DL2, IL2RA, IL2RB, SLAMF7.

In some embodiments, on day 20 of differentiation, cells have greater than 1000-fold change increase normalized to day 0 of one or more of GZMA, GZMH, GZMK, NCR3, CCL3, CCL4, CCL5, CCR1, IL2RG, KLRB1, KLRC1 (NKG2A), KLRC2 (NKG2C). In some embodiments, on day 35 of differentiation, cells have great than a 1000-fold change increase compared to day 0 of one or more of GZMA, GZMH, GZMK, NCR3, CCL3, CCL4, CCL5, CCR1, CCR5, CD226 (DNAM-1), IL2RG, KIR2DL1, KIR2DS4, KLRB1, KLRC1 (NKG2A), KLRC2 (NKG2C).

In some embodiments, about 25% to about 35% of differentiating cells express Granzyme B on day 16 of differentiation. In some embodiments about 25% to about 35% of differentiating cells express Perforin on day 16 of differentiation. In some embodiments, about 90% to about 95% of differentiating cells express Granzyme B on day 24 of differentiation. In some embodiments, about 75% to about 80% of differentiating cells express Perforin on day 24 of differentiation.

In some embodiments, differentiating cells in media with GSK3b blockers increases CD34 expression. In some embodiments, differentiating cells in media with CHIR-99021 and/or Activin A enhances CD34 expression.

In some embodiments, NK cells are CD45$^+$/CD56$^+$. In some embodiments, on day 17 of differentiation the culture comprises CD45$^+$/CD56$^+$ cells.

Differentiated Natural Killer Cells

Natural killer (NK) cells are a subpopulation of lymphocytes which play a critical role in the innate immune system. NK cells have cytotoxicity against a variety of cells including but not limited to tumor cells and virus-infected cells. In some embodiments, the stem cells described herein are differentiated to NK cells. In some embodiments, iPSCs are differentiated into NK cells. In some embodiments HSPCs are differentiated into NK cells.

NK cells have been shown to secrete cytokines. In some embodiments, an NK cell differentiated or obtained by using the methods described herein secretes at least one cytokine to the same or similar levels as an endogenous NK cell. In some embodiments, an NK cell differentiated or obtained by using the methods described herein secretes at least one cytokine to the same or similar levels as a wild-type NK cell line (e.g. NK-92, NK-YS, KHYG-1, NKL, NKG, SNK-6, and IMC-1). In some embodiments, an NK cell differentiated or obtained by using the methods described herein secretes at least one cytokine to the same or similar levels as an NK cell derived using any differentiation method known to those of skill in the art. In some embodiments, an NK cell differentiated or obtained by using the methods described herein secretes at least one cytokine to the same or similar levels as an NK cell derived from human embryonic stem cells (hESCs), peripheral blood (PB-NK), umbilical cord blood (UCB-NK), or bone marrow (BM-NK). In some embodiments, an NK cell differentiated or obtained by using the methods described herein secretes at least one cytokine to the same or similar levels as a tissue resident or tumor infiltrating NK cell. In some embodiments, the NK cells differentiated or obtained by using the methods described herein secrete TNF-α, IL-10, IFN-γ, GM-CSF, TGF-β IL-5, IL13, or any combination thereof.

NK cells have been shown to secrete chemokines. In some embodiments, an NK cell differentiated or obtained by using the methods described herein secretes at least one chemokine to the same or similar levels as an endogenous NK cell. In some embodiments, an NK cell differentiated or obtained by using the methods described herein secretes at least one chemokine to the same or similar levels as a wild-type NK cell line (e.g. NK-92, NK-YS, KHYG-1, NKL, NKG, SNK-6, and IMC-1). In some embodiments, an NK cell differentiated or obtained by using the methods described herein secretes at least one chemokine to the same or similar levels as an NK cell derived using any differentiation method known to those of skill in the art. In some embodiments, an NK cell differentiated or obtained by using the methods described herein secretes at least one chemokine to the same or similar levels as an NK cell derived from human embryonic stem cells (hESCs), peripheral blood (PB-NK), umbilical cord blood (UCB-NK), or bone marrow (BM-NK). In some embodiments, an NK cell differentiated or obtained by using the methods described herein secretes at least one chemokine to the same or similar levels as a tissue resident or tumor infiltrating NK cell. In some embodiments, the NK cells differentiated or obtained by using the methods described herein secrete CCL1, CCL2, CCL3, CCL4, CCL5, CXCL8, MIP-1α, MIP-1β, IL-8, RANTES, or any combination thereof. Methods of measuring cytokines and chemokines are known to those of skill in the art. Examples of methods include but are not limited to quantitative polymerase chain reaction (q-PCR), enzyme-linked immunosorbent assay (ELISA), or flow cytometry analysis.

NK cells have both activating and inhibitory receptors that regulate their function. In some embodiments, an NK cell differentiated or obtained by using the methods described herein expresses at least one activating receptor similar to, or at the same level as an endogenous NK cell, a wild-type NK cell line, an NK cell derived from a sample or tissue as described herein, and/or an NK cell derived from a differentiation method known to one of skill in the art. In some embodiments, the NK cells differentiated or obtained by using the methods described herein express any one or more of the activating receptors: NKG2D, NKG2C, Ly49D, Ly49H, KIR2DL4, KIR2DS1, KIR2DS2, KIR2DS3, KIR2DS4, KIR2DS5, KIR3DS1, NKp30, NKp46, NKp44, NKR-P1C, NKR-P1F, NKR-P1G, or DNAM-1. In some embodiments, a function of a differentiated NK cell associated with at least one activating receptor is induced upon stimulation of the activating receptor at the same or similar level as an endogenous NK cell, a wild-type NK cell line, an NK cell derived from a sample or tissue as described herein, and/or an NK cell derived from a differentiation method known to one of skill in the art. In some embodiments, an NK cell differentiated or obtained by using the methods described herein expresses at least one inhibitory receptor similar to, or at the same level as an endogenous NK cell, a wild-type NK cell line, an NK cell derived from a sample or tissue as described herein, and/or an NK cell derived from a differentiation method known to one of skill in the art. In some embodiments, the NK cells differentiated or obtained by using the methods described herein express any one or more of the inhibitory receptors: Ly49A, Ly49C, Ly49I, Ly49P, KIR2DL1, KIR2DL2, KIR2DL3, KIR3DL1, KIR3DL2, NKR-P1A, NKR-P1B, NKR-P1D, NKG2A, ILT2, or CD244. In some embodiments, a function of a differentiated NK cell associated with at least one inhibitory receptor is induced upon stimulation of the activating receptor at the same or similar level as an endogenous NK cell, a wild-type NK cell line, an NK cell derived from a sample or tissue as described herein, and/or an NK cell derived from a differentiation method known to one of skill in the art.

In some embodiments, the differentiated NK cells express at least one, two, three, four, five, six, seven, eight or all of the following markers: CD45, CD56, CD94, NKG2A, CD16, NKp44, NKp46, KIR2DL4, and KIR3DL2. In some embodiments, the differentiated NK cells express at least one, two, three, four, five or all of the following markers: CD56, NKp44, NKp46, CD94, NKG2A and KIR2DL4. In some embodiments, the differentiated NK cells have at least 25%, at least 30%, at least 40%, at least 50%, at least 60%, at least 70%, at least 80%, at least 90%, at least 95% or at least 99% of the cell population expressing one, two, three, four, five, six, seven, eight or all of the following markers: CD45, CD56, CD94, NKG2A, CD16, NKp44, NKp46, KIR2DL4, and KIR3DL2. In some embodiments, the differentiated NK cells have at least 25%, at least 30%, at least 40%, at least 50%, at least 60%, at least 70%, at least 80%, at least 90%, at least 95% or at least 99% of the cell population expressing one, two, three, four, five or all of the following markers: CD56, NKp44, NKp46, CD94, NKG2A and KIR2DL4.

In some embodiments, the differentiated NK cells express at least one, two, three or all of the following markers: CD38, CD96, DNAM-1, and ICAM-1. In some embodiments, the differentiated NK cells express at least one, two, three or all of the following markers: CD38, CD96, DNAM-1, and ICAM-1. In some embodiments, the differentiated NK cells have at least 25%, at least 30%, at least 40%, at least 50%, at least 60%, at least 70%, at least 80%, at least 90%, at least 95% or at least 99% of the cell population expressing one, two, three or all of the following markers: CD38, CD96, DNAM-1, and ICAM-1. In some embodiments, the differentiated NK cells have at least 25%, at least 30%, at least 40%, at least 50%, at least 60%, at least 70%, at least 80%, at least 90%, at least 95% or at least 99% of the cell population expressing one, two, three or all of the following markers: CD38, CD96, DNAM-1, and ICAM-1.

In some embodiments, the differentiated NK cells express at least one, two, three or all of the following markers: NKG2D, TIM3, CD16, and CD25. In some embodiments, the differentiated NK cells express at least one, two, three or all of the following markers: NKG2D, TIM3, CD16, and CD25. In some embodiments, the differentiated NK cells have at least 10%, at least 15%, at least 20%, at least 25%, at least 30%, at least 40%, at least 50%, at least 60%, at least 70%, at least 80%, at least 90%, at least 95% or at least 99% of the cell population expressing one, two, three or all of the following markers: NKG2D, TIM3, CD16, and CD25. In some embodiments, the differentiated NK cells have at least 10%, at least 15%, at least 20%, at least 25%, at least 30%, at least 40%, at least 50%, at least 60%, at least 70%, at least 80%, at least 90%, at least 95% or at least 99% of the cell population expressing one, two, three or all of the following markers: NKG2D, TIM3, CD16, and CD25.

In some embodiments, the NK cells differentiated herein have the same or similar functional capacity to that of endogenous NK cells, a wild-type NK cell line, an NK cell derived from a sample or tissue as described herein, and/or an NK cell derived from a differentiation method known to one of skill in the art.

In some embodiments, the differentiated NK cells are capable of being activated. In some embodiments, the differentiated NK cells are capable of being activated to the same or similar level as endogenous NK cells, a wild-type NK cell line, an NK cell derived from a sample or tissue as described herein, and/or an NK cell derived from a differentiation method known to one of skill in the art. Activation refers to NK cells that have received an activating signal and have the potential for killing target cells. NK cell cytotoxicity and activation contribute to their anti-tumor activity. In some embodiments, the NK cells have the same or similar anti-tumor activity as an endogenous NK cell, a wild-type NK cell line, an NK cell derived from a sample or tissue as described herein, and/or an NK cell derived from a differentiation method known to one of skill in the art.

The cytotoxic response of NK cells involves a process known as degranulation. Degranulation leads to the release of cytotoxic molecules such as perforin and granzyme which mediate apoptosis of target cells. An additional maker of NK cell degranulation is CD107a. Following stimulation of NK cells after contact with MHC devoid targets, CD107a is upregulated on the cell surface. In some embodiments, the differentiated NK cells express CD107a to the same or similar levels as endogenous NK cells, a wild-type NK cell line, an NK cell derived from a sample or tissue as described herein, and/or an NK cell derived from a differentiation method known to one of skill in the art. Measurement of Perforin, Granzyme, and CD107a are used in the art as a readout of cytotoxic activity. Methods of measuring Perforin, Granzyme, and CD107a are known in the art and include but are not limited to, flow cytometric detection, colorimetric assays (see e.g., Hagn et al. 2014 J Vis. Exp. 93:52419), and Western blot analysis.

Additional methods to measure the cytotoxicity of NK cells include, but are not limited to, in vitro analysis of effector:target cell killing. Target cell death is measured using methods including culturing the chromium release assay, apoptosis assays, or counting total cell number. In some embodiments, the NK cells have the same or similar cytotoxicity as endogenous NK cells, a wild-type NK cell line, an NK cell derived from a sample or tissue as described herein, and/or an NK cell derived from a differentiation method known to one of skill in the art. In some embodiments, the NK cells kill target cells at the same or similar rate as endogenous NK cells, a wild-type NK cell line, an NK cell derived from a sample or tissue as described herein, and/or an NK cell derived from a differentiation method known to one of skill in the art.

In any of the embodiments provided herein, the target cells may include tumor cells (e.g., myelogenous leukemia cells, lymphoma cells, melanoma cells, or other metastatic tumor cells. In some embodiments, the target cells may comprise immortalized tumor cells such as immortalized myelogenous leukemia cells (e.g., K-562 cells), or immortalized Hodgkin lymphoma cells (e.g., L-428, L-540, or KM-H2 cells). In some embodiments, the target cells may comprise tumor cells from chronic lymphocytic leukemia (CLL), non-Hodgkin lymphomas (e.g., diffuse large B-cell lymphoma (DLBCL), high grade B-cell lymphoma, transformed follicular lymphoma (FL), grade 3B FL, and Richter's transformation of CLL), and acute lymphoblastic leukemia (ALL). In some embodiments, the target cells may comprise tumor cells from Hodgkin lymphoma. In various embodiments, the target cells may be cultured in vitro.

In some embodiments, the differentiated NK cells use antibody-dependent cytotoxicity (ADCC) at the same or similar levels to endogenous NK cells, a wild-type NK cell line, an NK cell derived from a sample or tissue as described herein, and/or an NK cell derived from a differentiation method known to one of skill in the art. NK cells express Fcγ receptors on their surface that are activated by binding to antibodies on target cells. Receptor activation activates the release of cytokines from the NK cell. In some embodiments, the NK cells have the same, or similar ADCC to that of endogenous NK cells, a wild-type NK cell line, an NK cell derived from a sample or tissue as described herein, and/or an NK cell derived from a differentiation method known to one of skill in the art. Assays to measure ADCC are known in the art and involved culturing NK cells with a target cell. Binding of the receptor to an antibody on the target cell initiates ADCC which is measured by chromium release assay.

In some embodiments, the differentiated NK cells proliferate at the same rate as endogenous NK cells, a wild-type NK cell line, an NK cell derived from a sample or tissue as described herein, and/or an NK cell derived from a differentiation method known to one of skill in the art. Proliferation is measured using methods known in the art. Methods include but are not limited to manual counting of cell numbers, measurement of proliferation markers such as Ki67, DNA labeling and cell cycle analysis.

In some embodiments, the differentiated NK cells do not exhibit exhaustion or exhibit a low level of exhaustion (e.g., a level of exhaustion markers associated with a functional NK cell). In some embodiments, exhaustion is detected by detecting a reduced expression of IFNγ, granzyme B, perforin, CD107a, and/or TNFα in cells. In some embodiments, exhaustion is detected by detecting increased expression (e.g., on the surface of the cell) of an exhaustion marker, e.g., PD-1, LAG-3, TIGIT and/or TIM-3.

In some embodiments, the differentiated NK cells persist in vitro or in vivo In some embodiments, persistence of the cells is assessed by analyzing their presence and quantity in one or more tissue samples that are collected from a subject following administration of the cells to the subject. In some embodiments, persistence is defined as the longest duration of time from administration to a time wherein a detectable level of the cells is present in a given tissue type (e.g., peripheral blood). In some embodiments, persistence is defined as the continued absence of disease (e.g., complete response or partial response). Determination of the absence of disease and response to treatment are known to those of skill in the art and described herein.

Genome Editing

In some embodiments, a cell described herein comprises at least one gene edit and is referred to as an "engineered cell." In some embodiments, a stem or progenitor cell comprises at least one gene edit, and that edit is maintained through differentiation. In some embodiments, a stem or progenitor cell comprises at least one gene edit, and that edit is maintained through differentiation into an NK cell such that the NK cell comprises the gene edit.

Genome editing generally refers to the process of modifying the nucleotide sequence of a genome, preferably in a precise or pre-determined manner. In some embodiments, genome editing methods, e.g., the CRISPR-endonuclease system, are used to genetically modify a cell as described herein, e.g., to create a gene-edited iPSC cell. In some embodiments, genome editing methods e.g., the CRISPR-endonuclease system, are used to genetically modify a cell as described herein. Any genome editing method to known to one of skill in the art is useful for engineering the cells described herein.

Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ), as described in Cox et al., "Therapeutic genome editing: prospects and challenges,", Nature Medicine, 2015, 21(2), 121-31. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor sequence can be an exogenous polynucleotide, such as a plasmid, a single-strand oligonucleotide, a double-stranded oligonucleotide, a duplex oligonucleotide or a virus, that has regions (e.g., left and right homology arms) of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process; see, e.g., Cho and Greenberg, Nature, 2015, 518, 174-76; Kent et al., Nature Structural and Molecular Biology, 2015, 22(3):230-7; Mateos-Gomez et al., Nature, 2015, 518, 254-57; Ceccaldi et al., Nature, 2015, 528, 258-62. In some instances, it may be possible to predict likely repair outcomes based on analysis of potential microhomologies at the site of the DNA break.

Each of these genome editing mechanisms can be used to create desired genetic modifications. A step in the genome editing process can be to create one or two DNA breaks, the latter as double-strand breaks or as two single-stranded breaks, in the target locus as near the site of intended mutation. This can be achieved via the use of endonucleases.

Exemplary Gene Edits

In some embodiments, an engineered cell (e.g., an NK cell derived from a gene-edited iPSC) evades an immune response and/or survives following engraftment into a subject at higher success rates than an unmodified cell. In some embodiments, an engineered cell is hypoimmunogenic. In some embodiments, an engineered cell has improved (i) persistency; (ii) immune evasiveness; (iii) cytotoxic activity;

(iv) ADCC activity; and/or (v) anti-tumor activity, as compared to an unmodified or wild-type cell.

In certain embodiments, any cells described herein can be gene-edited using any of the gene-editing methods. In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell.

In some embodiments, the cells described herein are gene-edited to disrupt one or more of the genes encoding an MHC-I or MHC-II human leukocyte antigen, a component of a MHC-I or MHC-II complex, or a transcriptional regulator of a MHC-I or MHC-II complex. In some embodiments, the cells described herein are gene-edited to disrupt one or more of the genes encoding an MHC-I or MHC-II human leukocyte antigen. In some embodiments, the cells described herein are gene-edited to disrupt one or more of the genes encoding one or more components of a MHC-I or MHC-II complex. In some embodiments, the cells described herein are gene-edited to disrupt one or more of the genes encoding one or more transcriptional regulator of a MHC-I or MHC-II complex.

In some embodiments, the cells described herein are gene-edited to disrupt one or more genes including but not limited to: beta-2-microglobulin (B2M), class II major histocompatibility complex transactivator (CIITA), ADAM metallopeptidase domain 17 (ADAM17), cytokine inducible SH2 containing protein (CISH), Regnasel, Fas cell surface death receptor (FAS), T cell immunoreceptor with Ig and ITIM domains (TIGIT), programmed cell death 1 (PD-1), NKG2-A type II integral membrane protein-like (NKG2A), CD70, aurora like protein kinase 4 (ALK4), and/or type I activin receptor (e.g., conditionally). In some embodiments, the cells described herein are gene-edited to improve immune evasiveness. In some embodiments, immune evasiveness is improved by disrupting a gene encoding a polypeptide associated with inducing an immune response. In some embodiments, immune evasiveness is improved by disrupting B2M and/or CIITA gene(s).

In some embodiments, the cells described herein are gene-edited to improve persistence of the cell or differentiated cell. In some embodiments, persistence is improved by gene-editing a cell to insert a polynucleotide encoding, without limitation, one or more of the following: interleukin 15 (IL15), interleukin 15 receptor, alpha chain (IL15Ra), Serpin Family B Member 9 (SERPINB9), and class I histocompatibility antigen, alpha chain E (HLA-E).

In some embodiments, the cells described herein are gene-edited to improve antibody-dependent cellular cytotoxicity (ADCC) of the cell or differentiated cell. Natural Killer cells express Fcγ receptors on their surface which bind to target cells by recognizing antibodies (e.g. IgG) on the surface. The binding induces a signal cascade resulting in cytokine production and cytotoxic activation of the NK cell (ADCC). Increased ADCC contributes to the anti-tumor activity of an NK cell. One example of the Fcγ receptors is CD16. Increased expression of CD16 on the surface or NK cells increases their ADCC potential. In some embodiments, the cells described herein are gene-edited to insert a polynucleotide encoding CD16 (e.g., a high affinity non-cleavable CD16).

In some embodiments, the cells described herein are gene-edited to insert a polynucleotide encoding one or more chimeric antigen receptors (CARs). CARs are designed to enhance a cells ability to recognize, bind to, and kill tumor cells. In some embodiments, the CAR enhances the NK cells ability to recognize tumor cells. In some embodiments, the CAR enhances the NK cells anti-tumor activity. In some embodiments, and without limitation, the CAR is a TNF receptor superfamily member 17 (BCMA) CAR, CD30 CAR, CD19 CAR, CD33 CAR, NKG2D CAR (or a CAR or receptor comprising an NKG2D ectodomain), CAR CD70 CAR, NKp30 CAR, CD73 CAR, G protein coupled receptor 87 (GPR87) CAR and solute carrier family 7 member 11 (SLC7A11 (xCT)) CAR.

CRISPR Endonuclease System

The CRISPR-endonuclease system is a naturally occurring defense mechanism in prokaryotes that has been repurposed as a RNA-guided DNA-targeting platform used for gene editing. Accordingly, in some embodiments, a CRISPR-endonuclease system is utilized to introduce a gene edit into a cell. CRISPR systems include Types I, II, III, IV, V, and VI systems. In some embodiments, the CRISPR system is a Type II CRISPR/Cas9 system. In some embodiments, the CRISPR system is a Type V CRISPR/Cprf system. CRISPR systems rely on a DNA endonuclease, e.g., Cas9, and two noncoding RNAs—crisprRNA (crRNA) and trans-activating RNA (tracrRNA)—to target the cleavage of DNA.

The crRNA drives sequence recognition and specificity of the CRISPR-endonuclease complex through Watson-Crick base pairing, typically with a ~20 nucleotide (nt) sequence in the target DNA. Changing the sequence of the 5' 20 nt in the crRNA allows targeting of the CRISPR-endonuclease complex to specific loci. The CRISPR-endonuclease complex only binds DNA sequences that contain a sequence match to the first 20 nt of the single-guide RNA (sgRNA) if the target sequence is followed by a specific short DNA motif (with the sequence NGG) referred to as a protospacer adjacent motif (PAM).

TracrRNA hybridizes with the 3' end of crRNA to form an RNA-duplex structure that is bound by the endonuclease to form the catalytically active CRISPR-endonuclease complex, which can then cleave the target DNA.

Once the CRISPR-endonuclease complex is bound to DNA at a target site, two independent nuclease domains within the endonuclease each cleave one of the DNA strands three bases upstream of the PAM site, leaving a double-strand break (DSB) where both strands of the DNA terminate in a base pair (a blunt end).

In some embodiments, the endonuclease is a Cas9 (CRISPR associated protein 9). In some embodiments, the Cas9 endonuclease is from Streptococcuspyogenes, although other Cas9 homologs may be used, e.g., *S. aureus* Cas9, *N. meningitidis* Cas9, *S. thermophilus* CRISPR 1 Cas9, *S. thermophilus* CRISPR 3 Cas9, or *T. denticola* Cas9. In some embodiments, the CRISPR endonuclease is Cpf1, e.g., *L. bacterium* ND2006 Cpf1 or *Acidaminococcus* sp. BV3L6 Cpf1. In some embodiments, the endonuclease is Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease. In some embodiments, wild-type variants may be used. In some embodiments, modified versions (e.g., a homolog thereof, a recombination of the naturally occurring molecule thereof, codon-optimized thereof, or modified versions thereof) of the preceding endonucleases may be used.

The CRISPR nuclease can be linked to at least one nuclear localization signal (NLS). The at least one NLS can be located at or within 50 amino acids of the amino-terminus of the CRISPR nuclease and/or at least one NLS can be located at or within 50 amino acids of the carboxy-terminus of the CRISPR nuclease.

Exemplary CRISPR/Cas polypeptides include the Cas9 polypeptides as published in Fonfara et al., "Phylogeny of Cas9 determines functional exchangeability of dual-RNA and Cas9 among orthologous type II CRISPR-Cas systems," Nucleic Acids Research, 2014, 42: 2577-2590. The CRISPR/Cas gene naming system has undergone extensive rewriting since the Cas genes were discovered. Fonfara et al. also provides PAM sequences for the Cas9 polypeptides from various species.

Zinc Finger Nucleases

In some embodiments, a zinc finger nuclease (ZFN) is used to introduce a gene edit into a cell. ZFNs are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci, 1999 96(6):2758-63; Dreier B et al., J Mol Biol., 2000, 303(4):489-502; Liu Q et al., J Biol Chem., 2002, 277(6):3850-6; Dreier et al., J Biol Chem., 2005, 280(42):35588-97; and Dreier et al., J Biol Chem. 2001, 276(31):29466-78.

Transcription Activator-Like Effector Nucleases (TALENs)

In some embodiments, TALENs are utilized to introduce a gene edit into a cell. TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9 or CRISPR/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science, 2009 326(5959):1509-12; Mak et al., Science, 2012, 335(6069):716-9; and Moscou et al., Science, 2009, 326(5959):1501. The use of TALENs based on the "Golden Gate" platform, or cloning scheme, has been described by multiple groups; see, e.g., Cermak et al., Nucleic Acids Res., 2011, 39(12):e82; Li et al., Nucleic Acids Res., 2011, 39(14):6315-25; Weber et al., PLoS One., 2011, 6(2):e16765; Wang et al., J Genet Genomics, 2014, 41(6):339-47; and Cermak T et al., Methods Mol Biol., 2015 1239:133-59.

Homing Endonucleases

In some embodiments, a homing endonuclease (HE) is used to introduce a gene edit into a cell. HEs are sequence-specific endonucleases that have long recognition sequences (14-44 base pairs) and cleave DNA with high specificity—often at sites unique in the genome. There are at least six known families of HEs as classified by their structure, including GIY-YIG, His-Cis box, H-N-H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology, 2014, 24(8):663-80; Belfort and Bonocora, Methods Mol Biol., 2014, 1123:1-26; and Hafez and Hausner, Genome, 2012, 55(8):553-69.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., Nucleic Acids Res., 2014, 42: 2591-2601; Kleinstiver et al., G3, 2014, 4:1155-65; and Boissel and Scharenberg, Methods Mol. Biol., 2015, 1239: 171-96.

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., Nucleic Acids Res., 2014, 42, 8816-29. It is anticipated that other combinations of existing nuclease-based approaches will evolve and be useful in achieving the targeted genome modifications described herein.

dCas9-FokI or dCpf1-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from S. pyogenes). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech, 2014, 32: 569-76; and Guilinger et al., Nature Biotech., 2014, 32: 577-82. Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

RNA-Guided Endonucleases

The RNA-guided endonuclease systems as used herein can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary endonuclease, e.g., Cas9 from S. pyogenes, US2014/0068797 Sequence ID No. 8 or Sapranauskas et al., Nucleic Acids Res, 39(21): 9275-9282 (2011). The endonuclease can comprise at least 70, 75, 80, 85, 90, 95, 97, 99, or 100% identity to a wild-type endonuclease (e.g., Cas9 from S. pyogenes, supra) over 10 contiguous amino acids. The endonuclease can comprise at most: 70, 75, 80, 85, 90, 95, 97, 99, or 100% identity to a wild-type endonuclease (e.g., Cas9 from S. pyogenes, supra) over 10 contiguous amino acids. The endonuclease can comprise at least: 70, 75, 80, 85, 90, 95, 97, 99, or 100% identity to a wild-type endonuclease (e.g., Cas9 from S. pyogenes, supra) over 10 contiguous amino acids in a HNH nuclease domain of the endonuclease. The endonuclease can comprise at most: 70, 75, 80, 85, 90, 95, 97, 99, or 100% identity to a wild-type endonuclease (e.g., Cas9 from S. pyogenes, supra) over 10 contiguous amino acids in a HNH nuclease domain of the endonuclease. The endonuclease can comprise at least: 70, 75, 80, 85, 90, 95, 97, 99, or 100% identity to a wild-type endonuclease (e.g., Cas9 from S. pyogenes, supra) over 10 contiguous amino acids in a RuvC nuclease domain of the endonuclease. The endonuclease can comprise at most: 70, 75, 80, 85, 90, 95, 97, 99, or 100% identity to a wild-type endonuclease (e.g., Cas9 from S. pyogenes, supra) over 10 contiguous amino acids in a RuvC nuclease domain of the endonuclease.

The endonuclease can comprise a modified form of a wild-type exemplary endonuclease. The modified form of the wild-type exemplary endonuclease can comprise a mutation that reduces the nucleic acid-cleaving activity of the endonuclease. The modified form of the wild-type exemplary endonuclease can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary endonuclease (e.g., Cas9 from S. pyogenes, supra). The modified form of the endonuclease can have no substantial nucleic acid-cleaving activity. When an endonuclease is a modified form that has no substantial nucleic acid-cleaving activity, it is referred to herein as "enzymatically inactive."

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagine, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon.

Mutations can cause changes to regulatory regions of genes or loci that affect expression of one or more genes.

Guide RNAs

In some embodiments, a guide RNA (gRNA) that can direct the activities of an associated endonuclease to a specific target site within a polynucleotide is used to introduce a gene edit into a cell. A guide RNA can comprise at least a spacer sequence that hybridizes to a target nucleic acid sequence of interest, and a CRISPR repeat sequence. In CRISPR Type II systems, the gRNA also comprises a second RNA called the tracrRNA sequence. In the CRISPR Type II guide RNA (gRNA), the CRISPR repeat sequence and tracrRNA sequence hybridize to each other to form a duplex. In CRISPR Type V systems, the gRNA comprises a crRNA that forms a duplex. In some embodiments, a gRNA can bind an endonuclease, such that the gRNA and endonuclease form a complex. The gRNA can provide target specificity to the complex by virtue of its association with the endonuclease. The genome-targeting nucleic acid thus can direct the activity of the endonuclease.

Exemplary guide RNAs include a spacer sequences that comprises 15-200 nucleotides wherein the gRNA targets a genome location based on the GRCh38 human genome assembly. As is understood by the person of ordinary skill in the art, each gRNA can be designed to include a spacer sequence complementary to its genomic target site or region. See Jinek et al., Science, 2012, 337, 816-821 and Deltcheva et al., Nature, 2011, 471, 602-607.

The gRNA can be a double-molecule guide RNA. The gRNA can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

In some embodiments, a sgRNA comprises a 20 nucleotide spacer sequence at the 5' end of the sgRNA sequence. In some embodiments, a sgRNA comprises a less than a 20 nucleotide spacer sequence at the 5' end of the sgRNA sequence. In some embodiments, a sgRNA comprises a more than 20 nucleotide spacer sequence at the 5' end of the sgRNA sequence. In some embodiments, a sgRNA comprises a variable length spacer sequence with 17-30 nucleotides at the 5' end of the sgRNA sequence. In some embodiments, a sgRNA comprises a spacer extension sequence with a length of more than 1, 5, 10, 15, 20, 25, 30, 35, 40, 45, 50, 60, 70, 80, 90, 100, 120, 140, 160, 180, or 200 nucleotides. In some embodiments, a sgRNA comprises a spacer extension sequence with a length of less than 3, 5, 10, 15, 20, 25, 30, 35, 40, 45, 50, 60, 70, 80, 90, or 100 nucleotides.

In some embodiments, a sgRNA comprises a spacer extension sequence that comprises another moiety (e.g., a stability control sequence, an endoribonuclease binding sequence, or a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

In some embodiments, a sgRNA comprises a spacer sequence that hybridizes to a sequence in a target polynucleotide. The spacer of a gRNA can interact with a target polynucleotide in a sequence-specific manner via hybridization (i.e., base pairing). The nucleotide sequence of the spacer can vary depending on the sequence of the target nucleic acid of interest.

In a CRISPR-endonuclease system, a spacer sequence can be designed to hybridize to a target polynucleotide that is located 5' of a PAM of the endonuclease used in the system. The spacer may perfectly match the target sequence or may have mismatches. Each endonuclease, e.g., Cas9 nuclease, has a particular PAM sequence that it recognizes in a target DNA. For example, S. pyogenes Cas9 recognizes a PAM that comprises the sequence 5'-NRG-3', where R comprises either A or G, where N is any nucleotide and N is immediately 3' of the target nucleic acid sequence targeted by the spacer sequence.

A target polynucleotide sequence can comprise 20 nucleotides. The target polynucleotide can comprise less than 20 nucleotides. The target polynucleotide can comprise more than 20 nucleotides. The target polynucleotide can comprise at least: 5, 10, 15, 16, 17, 18, 19, 20, 21, 22, 23, 24, 25, 30 or more nucleotides. The target polynucleotide can comprise at most: 5, 10, 15, 16, 17, 18, 19, 20, 21, 22, 23, 24, 25, 30 or more nucleotides. The target polynucleotide sequence can comprise 20 bases immediately 5' of the first nucleotide of the PAM.

A spacer sequence that hybridizes to a target polynucleotide can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

A tracrRNA sequence can comprise nucleotides that hybridize to a minimum CRISPR repeat sequence in a cell. A minimum tracrRNA sequence and a minimum CRISPR repeat sequence may form a duplex, i.e. a base-paired double-stranded structure. Together, the minimum tracrRNA sequence and the minimum CRISPR repeat can bind to an RNA-guided endonuclease. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from S. pyogenes) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

In some embodiments, a tracrRNA may be a 3' tracrRNA. In some embodiments, a 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from S. pyogenes).

In some embodiments, a gRNA may comprise a tracrRNA extension sequence. A tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, or 200 nucleotides. The tracrRNA extension sequence can have a length from about 20 to about 5000 or more nucleotides. The tracrRNA extension sequence can have a length of less than 5, 10, 15, 20, 25, 30, 35, 40, 45, 50, 60, 70, 80, 90, or 100 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt.

In some embodiments, a sgRNA may comprise a linker sequence with a length from about 3 nucleotides to about 100 nucleotides. In Jinek et al., supra, for example, a simple 4 nucleotide "tetraloop" (-GAAA-) was used (Jinek et al., Science, 2012, 337(6096):816-821). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used (Jinek et al., Science, 2012, 337(6096):816-821), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

In some embodiments, a sgRNA does not comprise a uracil, e.g., at the 3' end of the sgRNA sequence. In some embodiments, a sgRNA does comprise one or more uracils, e.g., at the 3' end of the sgRNA sequence. In some embodiments, a sgRNA comprises 1, 2, 3, 4, 5, 6, 7, 8, 9, or 10 uracils (U) at the 3' end of the sgRNA sequence.

A sgRNA may be chemically modified. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, chemical modifications enhance stability, reduce the likelihood or degree of innate immune response, and/or enhance other attributes, as described in the art.

In some embodiments, a modified gRNA may comprise a modified backbones, for example, phosphorothioates, phosphotriesters, morpholinos, methyl phosphonates, short chain alkyl or cycloalkyl intersugar linkages or short chain heteroatomic or heterocyclic intersugar linkages.

Morpholino-based compounds are described in Braasch and David Corey, Biochemistry, 2002, 41(14): 4503-4510; Genesis, 2001, Volume 30, Issue 3; Heasman, Dev. Biol., 2002, 243: 209-214; Nasevicius et al., Nat. Genet., 2000, 26:216-220; Lacerra et al., Proc. Natl. Acad. Sci., 2000, 97: 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122: 8595-8602.

In some embodiments, a modified gRNA may comprise one or more substituted sugar moieties, e.g., one of the following at the 2' position: OH, SH, SCH$_3$, F, OCN, OCH$_3$, OCH$_3$ O(CH$_2$)$_n$ CH$_3$, O(CH$_2$)$_n$ NH$_2$, or O(CH$_2$)$_n$ CH$_3$, where n is from 1 to about 10; C1 to C10 lower alkyl, alkoxyalkoxy, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$ CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; 2'-O-(2-methoxyethyl); 2'-methoxy (2'-O—CH$_3$); 2'-propoxy (2'-OCH$_2$ CH$_2$CH$_3$); and 2'-fluoro (2'-F). Similar modifications may also be made at other positions on the gRNA, particularly the 3' position of the sugar on the 3' terminal nucleotide and the 5' position of 5' terminal nucleotide. In some examples, both a sugar and an internucleoside linkage, i.e., the backbone, of the nucleotide units can be replaced with novel groups.

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A., DNA Replication, W. H. Freeman & Co., San Francisco, pp 75-77, 1980; Gebeyehu et al., Nucl. Acids Res. 1997, 15:4513. A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Complexes of a Genome-Targeting Nucleic Acid and an Endonuclease

A gRNA interacts with an endonuclease (e.g., a RNA-guided nuclease such as Cas9), thereby forming a complex. The gRNA guides the endonuclease to a target polynucleotide.

The endonuclease and gRNA can each be administered separately to a cell or a subject. In some embodiments, the endonuclease can be pre-complexed with one or more guide RNAs, or one or more crRNA together with a tracrRNA. The pre-complexed material can then be administered to a cell or a subject. Such pre-complexed material is known as a ribonucleoprotein particle (RNP). The endonuclease in the RNP can be, for example, a Cas9 endonuclease or a Cpf1 endonuclease. The endonuclease can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to endonuclease in the RNP can be 1:1. For example, the weight ratio of sgRNA to Cas9 endonuclease in the RNP can be 1:1.

Base Editing

In some embodiments, a gene is edited in a cell using base editing. Base Editing is a technique enabling the conversion of one nucleotide into another without double-stranded breaks in the DNA. Base editing allows for conversion of a C to T, G to A, or vice versa. An example editor for cytosine includes rAPOBEC1 which is fused to a catalytically inactive form of Cas9. The Cas9 helps to bind a site of interest and the rAPOBEC1 cytidine deaminase induces the point mutation. Conversion of adenine requires a mutant transfer RNA adenosine deaminase (TadA), a Cas9 nikase, and a sgRNA. The construct is able to introduce the site-specific mutation without introducing a strand break. In some embodiments, Base Editing is used to introduce one or more mutations in a cell described herein.

Kits

In some embodiments, the disclosure provides kits for differentiating of stem cells and/or progenitor cells into Natural Killer (NK) cells. In some embodiments, the disclosure provides kits for differentiating stem cells and/or progenitor cells into HSPCs. In some embodiments, the disclosure provides kits for differentiating HSPCs into NK cells.

In some embodiments, the kits for differentiating cells comprise media or components to make media and instructions for use in differentiating cells. In some embodiments, a kit comprises a first medium, a second medium, a third medium, and a fourth medium, and instructions for differentiating HSPCs from stem cells. In some embodiments, a kit comprises the components to make the mediums in Table 18A or 18B, Table 19A or 19B, Table 20A or 20B, and Table 21A or 21B, and instructions for differentiating HSPCs from stem cells. In some embodiments, a kit comprises a first medium, a second medium, a third medium, a fourth medium, a fifth medium, a sixth medium, and a seventh medium and instructions for differentiating natural killer cells from stem cells.

In some embodiments, a kit comprises the components to make the mediums in Table 18A or 18B, Table 19A or 19B, Table 20A or 20B, Table 21A or 21B, Table 22, Table 23A or 23B, Table 24A or 24B and Table 25A or Table 25B and instructions for differentiating natural killer cells from stem cells. In some embodiments, a kit comprises the components to make the mediums in Table 18A, Table 19A or 19B, Table 20A, Table 21A, Table 22, Table 23A, and Table 24A and instructions for differentiating natural killer cells from stem cells. In some embodiments, a kit comprises the components to make the mediums in Table 18B, Table 19A or 19B, Table 20B, Table 21B, Table 22, Table 23B, Table 24B and Table 25A or 25B and instructions for differentiating natural killer cells from stem cells.

In some embodiments, the kit comprises one or more base media and a ROCK inhibitor. In some embodiments, the kit comprises a base media, a ROCK inhibitor, and BMP-4. In some embodiments, the kit comprises a base media and BMP-4. In some embodiments, the kit comprises a base media, BMP-4, FGF2, a WNT pathway activators, and Activin A. In some embodiments, the kit comprises FGF2, VEGF, TPO, SCF, IL-3, FLT3L, WNT C-59, and an activin/nodal inhibitor. In some embodiments, kit comprises FGF2, VEGF, TPO, SCF, IL-3, FLT3L, WNT C-59, and an activin/nodal inhibitor, and instructions for differentiation hematopoietic stem and progenitor cells (HSPCs) from stem cells. In some embodiments, the kit comprises a base medium, FGF2, VEGF, TPO, SCF, IL-3, and FLT3L. In some embodiments, the kit comprises a base medium, IL-3, IL-7, FLT3L, IL-15 and SCF. In some embodiments, the kit comprises a base medium, IL-7, FLT3L, IL-15 and SCF. In some embodiments, the kit comprises a base medium, IL-7, FLT3L, IL-15, SCF and nicotinamide. In some embodiments, the kit comprises instructions for differentiating NK cells from stem cells.

In some embodiments, the kit comprises at least a ROCK inhibitor, BMP-4, FGF2, WNT pathway activators, Activin A, VEGF, TPO, SCF, IL-3, FLT3L, WNT C-59, an activin/nodal inhibitor, and instructions for differentiating HSPCs from stem cells. In some embodiments, the kit comprises at least a ROCK inhibitor, BMP-4, FGF2, WNT pathway activators, Activin A, VEGF, TPO, SCF, IL-3, FLT3L, WNT C-59, an activin/nodal inhibitor, IL-7, IL-15, and instructions for differentiating NK cells from stem cells. In some embodiments, the kit comprises at least FGF2, VEGF, TPO, SCF, IL-3, FLT3L, IL-7, IL-15, and instructions for differentiating NK cells from HSPCs.

Treatment Methods

Provided herein, in some embodiments, are methods for treating a disease or disorder using a differentiated NK cell described herein or a population of cells comprising differentiated NK cells described herein. Also provided are methods for treating a disease or disorder using a differentiated stem cell or a population of cells comprising differentiated stem cells as described herein (i.e. hematopoietic stem and progenitor cells). In some embodiments, the disease or disorder is a cancer, an autoimmune disease, and/or an infectious disease. In some embodiments, a subject has a cancer and an autoimmune disease. In some embodiments, a subject has a cancer and an infectious disease. In some embodiments, a subject has an autoimmune disease and an infectious disease.

In some embodiments, a cell population comprising differentiated NK cells is used to treat an infectious disease in a subject. In some embodiments, a cell population comprising differentiated stem cells is used to treat an infectious disease in a subject. In some embodiments, differentiated NK cells are engineered to comprise a CAR that binds to a pathogen, such that the NK cells are activated and targets the pathogen. In some embodiments, a cell population comprising differentiated NK cells is used to treat an infectious disease in a subject that is immunocompromised. In some embodiments, a cell population comprising differentiated stem cells is used to treat an infectious disease in a subject that is immunocompromised. In some embodiments, an immunocompromised subject has reduced NK cell numbers and/or functional NK cell impairment. In some embodiments, a subject is immunocompromised due to a cancer and/or cancer treatment, or due to an autoimmune disease. As used herein, the term "infectious disease" includes all diseases which are caused by infection with viruses or pathogenic bacteria and can be infected through respiratory organ, blood or skin contact. Non-limiting examples of such infectious diseases include, but are not limited to, hepatitis B, hepatitis C, human papilloma virus (HPV) infection, cytomegalovirus infection, viral respiratory disease, influenza and so on.

In some embodiments, a cell population comprising differentiated NK cells is used to treat an autoimmune disease in a subject. In some embodiments, a cell population comprising differentiated stem cells is used to treat an autoimmune disease in a subject. As used herein, the term "autoimmune disease" refers to a class of diseases or disorders in which a subject's own antibodies react with host tissue or in which immune effector T cells are autoreactive to endogenous self-peptides and cause destruction of tissue. In some embodiments, the differentiated NK cells are engineered to express a CAR polypeptide that binds to immune effector T cells to prevent their activity.

In some embodiments, the differentiated NK cells described herein have endogenous anti-cancer cell activity. In some embodiments, the differentiated stem cells described herein have endogenous anti-cancer cell activity. In some embodiments, the differentiated NK cells comprise a CAR polypeptide, thus providing anti-cancer cell activity.

In some embodiments, a cell population comprising differentiated NK cells is used to treat a cancer. In some embodiments, a cell population comprising differentiated stem cells is used to treat a cancer. In some embodiments, the cancer is a leukemia. Non-limiting examples of leukemias that may be treated as provided herein include chronic lymphocytic leukemia (CLL), non-Hodgkin lymphomas (e.g., diffuse large B-cell lymphoma (DLBCL), high grade B-cell lymphoma, transformed follicular lymphoma (FL), grade 3B FL, and Richter's transformation of CLL), and acute lymphoblastic leukemia (ALL). In some embodiments, provided herein is a method of treating cancer in a subject (e.g., human) in need thereof, comprising administering a cell population comprising differentiated NK cells described herein to the subject (e.g., wherein the subject has or has been diagnosed with cancer). In some embodiments, provided herein is a method of treating a non-Hodgkin lymphoma (e.g., diffuse large B-cell lymphoma (DLBCL), high grade B-cell lymphoma, transformed follicular lymphoma (FL), grade 3B FL, and Richter's transformation of CLL) in a subject (e.g., human) in need thereof, comprising administering a cell population comprising differentiated NK cells described herein to the subject (e.g., wherein the subject has or has been diagnosed with a non-Hodgkin lymphoma, or is at risk of a non-Hodgkin lymphoma). In some embodiments, provided herein is a method of treating a non-Hodgkin lymphoma (e.g., diffuse large B-cell lymphoma (DLBCL), high grade B-cell lymphoma, transformed follicular lymphoma (FL), grade 3B FL, and Richter's transformation of CLL) in a subject (e.g., human) in need thereof, comprising administering a cell population comprising differentiated stem cells described herein to the subject (e.g., wherein the subject has or has been diagnosed with a non-Hodgkin lymphoma, or is at risk of a non-Hodgkin lymphoma). In some embodiments, the subject (e.g., a human) has (e.g., has been diagnosed with) a relapsed and/or refractory non-Hodgkin lymphoma. In some embodiments, the subject (e.g., a human) has (e.g., has been diagnosed with) a non-relapsed or early stage non-Hodgkin lymphoma. In some embodiments, provided herein is a method of treating chronic lymphocytic leukemia (CLL) or acute lymphoblastic leukemia (ALL) in a subject (e.g., human) in need thereof, comprising administering a cell population comprising differentiated NK cells described herein to the subject (e.g., wherein the subject has or has been diagnosed with CLL or ALL). In some embodiments, provided herein is a method of treating chronic lymphocytic leukemia (CLL) or acute lymphoblastic leukemia (ALL) in a subject (e.g., human) in need thereof, comprising administering a cell population comprising differentiated stem cells described herein to the subject (e.g., wherein the subject has or has been diagnosed with CLL or ALL). In some embodiments, the subject (e.g., a human) has (e.g., has been diagnosed with) a relapsed and/or refractory CLL or ALL. In some embodiments, the subject (e.g., a human) has (e.g., has been diagnosed with) a non-relapsed or early stage CLL or ALL. In some embodiments, the cell population is administered at any dose described herein, in particular, in a therapeutically effective amount. In some embodiments, a human being treated is an adult, e.g., a human over 18 years of age. In some embodiments, a human being treated is under 18 years of age.

In some embodiments, the methods comprise delivering the cell population comprising differentiated NK cells of the present disclosure to a subject having a cancer (e.g., leukemia).

The step of administering may include the placement (e.g., transplantation) of cells, e.g., NK cells, into a subject, by a method or route that results in at least partial localization of the introduced cells at a desired site, such as tumor, such that a desired effect(s) is produced. In some embodiments, the step of administering may include placement of differentiated stem cells, as described herein. In some embodiments, cells are administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life-time of the subject, i.e., long-term engraftment. For example, in some embodiments, an effective amount of NK cell is administered via a systemic route of administration, such as an intraperitoneal or intravenous route. In some embodiments, an effective amount of differentiated stem cells is administered via a systemic route of administration, such as an intraperitoneal or intravenous route.

A subject may be any subject for whom diagnosis, treatment, or therapy is desired. In some embodiments, the subject is a mammal. In some embodiments, the subject is a human.

In some embodiments, a cell population comprising NK cells being administered according to the methods described herein comprises gene edited cells (e.g., NK cells) differentiated from gene-edited stem cells (e.g., iPSC cells). In some embodiments, a cell population comprising stem cells being administered according to the methods described herein comprises gene edited cells (e.g., hematopoietic stem and progenitor cells) differentiated from gene-edited stem cells (e.g., iPSC cells).

In some embodiments, a cell population (e.g. comprising NK cells) being administered according to the methods described herein does not induce toxicity in the subject, e.g., the NK cells do not induce toxicity in non-cancer cells. In some embodiments, a cell population (e.g., comprising NK cells) being administered does not trigger complement mediated lysis, or does not stimulate antibody-dependent cell mediated cytotoxicity (ADCC).

In some embodiments, the subject being treated has no chronic immune suppression.

An effective amount refers to the amount of a population of cells (e.g., NK cells) needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

In some embodiments, the cells are derived from iPSCs. In some embodiments, the cells are expanded in culture prior to administration to a subject in need thereof.

In some embodiments, a composition is provided comprising a plurality of Natural Killer cells obtained by or derived by the methods described herein. The composition (e.g., a cell composition) may be prepared as a pharmaceutical composition (e.g., comprising a pharmaceutically acceptable carrier or excipient). A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition and can be determined by standard clinical techniques.

Modes of administration include but are not limited to injection and infusion. In some embodiments, injection includes, without limitation, intravenous, intrathecal, intraperitoneal, intraspinal, intracerebrospinal, and intrasternal infusion. In some embodiments, the route is intravenous. In some embodiments, cells described herein are administered as a bolus or by continuous infusion (e.g., intravenous infusion) over a period of time. In some embodiments, cells described herein are administered in several doses over a period of time (e.g., several infusions over a period of time). The cells described herein can be administered in a single dose or in 2, 3, 4, 5, 6 or more doses (or infusions). In some embodiments, the subject being treated is dosed (e.g., with an infusion) about every 1, 2, 3, 4, 5, 6, 7 or 8 weeks. In some embodiments, the subject being treated is dosed (e.g., with an infusion) every 2-4 weeks (e.g., every 2 weeks, 3 weeks or 4 weeks).

In some embodiments, cells (e.g., NK cells) are administered systemically, which refers to the administration of a population of cells other than directly into a target site, tissue, or organ, such that it enters, instead, the subject's circulatory system and, thus, is subject to metabolism and other like processes. In some embodiments, hematopoietic stem and progenitor cells are administered systemically.

The efficacy of a treatment comprising a composition for the treatment of a medical condition can be determined by the skilled clinician. A treatment is considered "effective treatment," if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Definitions

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In some embodiments, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

The term "aggregate" or "cell aggregates", as used herein, refers to a group of at least two cells being in physical contact with one another and forming a two- or three-dimensional cluster. In some embodiments, a cell aggregate has a spherical shape. In some embodiments, the cell aggregate is a sphere. In some embodiments, the cell aggregate is a spheroid. The spheroid may also be referred to as a clump. In some embodiments, the cell aggregate is formed by suspension culturing.

As used herein, the term "induced pluripotent stem cells" or, iPSCs, means that the stem cells are produced from differentiated adult, neonatal or fetal cells that have been induced or changed, i.e., reprogrammed into cells capable of differentiating into tissues of all three germ or dermal layers: mesoderm, endoderm, and ectoderm. The iPSCs produced do not refer to cells as they are found in nature.

The term "hematopoietic stem and progenitor cells," "hematopoietic stem cells," "hematopoietic progenitor cells," or "hematopoietic precursor cells" refers to cells which are committed to a hematopoietic lineage but are capable of further hematopoietic differentiation and include, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). The term "definitive hematopoietic stem cell" as used herein, refers to CD34+ hematopoietic cells capable of giving rise to both mature myeloid and lymphoid cell types including T cells, NK cells and B cells. Hematopoietic cells also include various subsets of primitive hematopoietic cells that give rise to primitive erythrocytes, megakarocytes and macrophages.

As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3- and CD56$^+$, expressing at least one of NKG2C and CD57, and optionally, CD16, but lack expression of one or more of the following: PLZF, SYK, FceRy, and EAT-2. In some embodiments, isolated subpopulations of CD56$^+$ NK cells comprise expression of CD16, NKG2C, CD57, NKG2D, NCR ligands, NKp30, NKp40, NKp46, activating and inhibitory KIRs, NKG2A and/or DNAM-1.

As used herein, the terms "disruption," "genetic modification" or "gene-edit" generally refer to a genetic modification wherein a site or region of genomic DNA is altered, e.g., by a deletion or insertion, by any molecular biology method, e.g., methods described herein, e.g., by delivering to a site of genomic DNA an endonuclease and at least one gRNA. Exemplary genetic modifications include insertions, deletions, duplications, inversions, and translocations, and combinations thereof. In some embodiments, a genetic modification is a deletion. In some embodiments, a genetic modification is an insertion. In other embodiments, a genetic modification is an insertion-deletion mutation (or indel), such that the reading frame of the target gene is shifted leading to an altered gene product or no gene product.

As used herein, the term "engineered cell" generally refers to a genetically modified cell that is less susceptible to allogeneic rejection during a cellular transplant and/or demonstrates increased survival after transplantation, relative to an unmodified cell. In some embodiments, a genetically modified cell as described herein is an engineered cell. In some embodiments, the engineered cell has increased immune evasion and/or cell survival compared to an unmodified cell. In some embodiments, the engineered cell has increased cell survival compared to an unmodified cell. In some embodiments, the engineered cell has (i) improved persistency, (ii) improved immune evasiveness, (iii) improved cytotoxic activity, (iv) improved ADCC activity, and/or (v) improved anti-tumor activity compared to an unmodified cell. In some embodiments, an engineered cell may be a stem cell. In some embodiments, an engineered cell may be an embryonic stem cell (ESC), an adult stem cell (ASC), an induced pluripotent stem cell (iPSC), or a hematopoietic stem or progenitor cell (HSPC). In some embodiments, an engineered cell may be a differentiated cell. In some embodiments, an engineered cell may be a somatic cell (e.g., immune system cells). In some embodiments, an engineered cell is administered to a subject. In some embodiments, an engineered cell is administered to a subject who has, is suspected of having, or is at risk for a disease. In some embodiments, the engineered cell is capable of being differentiated into lineage-restricted progenitor cells or fully differentiated somatic cells. In some embodiments, the lineage-restricted progenitor cells are pancreatic endoderm progenitors, pancreatic endocrine progenitors, mesenchymal progenitor cells, muscle progenitor cells, blast cells, or neural progenitor cells. In some embodiments, the fully differentiated somatic cells are endocrine secretory cells such as pancreatic beta cells, epithelial cells, endodermal cells, macrophages, hepatocytes, adipocytes, kidney cells, blood cells, or immune system cells.

As used herein, the term "deletion" which may be used interchangeably with the terms "genetic deletion", "knockout", or "KO", generally refers to a genetic modification wherein a site or region of genomic DNA is removed by any molecular biology method, e.g., methods described herein, e.g., by delivering to a site of genomic DNA an endonuclease and at least one gRNA. Any number of nucleotides can be deleted. In some embodiments, a deletion involves the removal of at least one, at least two, at least three, at least four, at least five, at least ten, at least fifteen, at least twenty, or at least 25 nucleotides. In some embodiments, a deletion involves the removal of 10-50, 25-75, 50-100, 50-200, or more than 100 nucleotides. In some embodiments, a deletion involves the removal of an entire target gene. In some embodiments, a deletion involves the removal of part of a target gene. In some embodiments, a deletion involves the removal of a transcriptional regulator, e.g., a promoter region, of a target gene. In some embodiments, a deletion involves the removal of all or part of a coding region such that the product normally expressed by the coding region is no longer expressed, is expressed as a truncated form, or expressed at a reduced level. In some embodiments, a deletion leads to a decrease in expression of a gene relative to an unmodified cell.

As used herein, the term "endonuclease" generally refers to an enzyme that cleaves phosphodiester bonds within a polynucleotide. In some embodiments, an endonuclease specifically cleaves phosphodiester bonds within a DNA polynucleotide. In some embodiments, an endonuclease is a zinc finger nuclease (ZFN), transcription activator like effector nuclease (TALEN), homing endonuclease (HE), meganuclease, MegaTAL, or a CRISPR-associated endonuclease. In some embodiments, an endonuclease is a RNA-guided endonuclease. In some embodiments, the RNA-guided endonuclease is a CRISPR nuclease, e.g., a Type II CRISPR Cas9 endonuclease or a Type V CRISPR Cpf1 endonuclease. In some embodiments, an endonuclease is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease, or a homolog thereof, a recombination of the naturally occurring molecule thereof, a codon-optimized version thereof, or a modified version thereof, or combinations thereof. In some embodiments, an endonuclease may introduce one or more single-stranded breaks (SSBs) and/or one or more double-stranded breaks (DSBs).

As used herein, the term "guide RNA" or "gRNA" generally refers to short ribonucleic acid that can interact with, e.g., bind to, to an endonuclease and bind, or hybridize to a target genomic site or region. In some embodiments, a gRNA is a single-molecule guide RNA (sgRNA). In some embodiments, a gRNA may comprise a spacer extension region. In some embodiments, a gRNA may comprise a tracrRNA extension region. In some embodiments, a gRNA is single-stranded. In some embodiments, a gRNA comprises naturally occurring nucleotides. In some embodiments, a gRNA is a chemically modified gRNA. In some embodiments, a chemically modified gRNA is a gRNA that comprises at least one nucleotide with a chemical modification, e.g., a 2'-O-methyl sugar modification. In some embodiments, a chemically modified gRNA comprises a modified nucleic acid backbone. In some embodiments, a chemically modified gRNA comprises a 2'-O-methyl-phosphorothioate residue. In some embodiments, a gRNA may be pre-complexed with a DNA endonuclease.

As used herein, the term "insertion" which may be used interchangeably with the terms "genetic insertion" or "knock-in", generally refers to a genetic modification wherein a polynucleotide is introduced or added into a site or region of genomic DNA by any molecular biological method, e.g., methods described herein, e.g., by delivering to a site of genomic DNA an endonuclease and at least one gRNA. In some embodiments, an insertion may occur within or near a site of genomic DNA that has been the site of a prior genetic modification, e.g., a deletion or insertion-deletion mutation. In some embodiments, an insertion occurs at a site of genomic DNA that partially overlaps, completely overlaps, or is contained within a site of a prior genetic modification, e.g., a deletion or insertion-deletion mutation. In some embodiments, an insertion involves the introduction of a polynucleotide that encodes a protein of interest. In some embodiments, an insertion involves the introduction of an exogenous promoter, e.g., a constitutive promoter, e.g., a CAG promoter. In some embodiments, an insertion involves the introduction of a polynucleotide that encodes a noncoding gene. In general, a polynucleotide to be inserted is flanked by sequences (e.g., homology arms) having substantial sequence homology with genomic DNA at or near the site of insertion.

The term "cell culture medium" as used herein refers to a solution containing nutrients needed for culturing a cell. The term "cell culture medium" as used herein may be used interchangeably with the term "culture medium," "medium," or "growth medium." The medium includes a commercialized or prepared medium used in culturing the cell.

As used herein, the term "subject" refers to a mammal. In some embodiments, a subject is non-human primate or rodent. In some embodiments, a subject is a human. In some embodiments, a subject has, is suspected of having, or is at risk for, a disease or disorder. In some embodiments, a subject has one or more symptoms of a disease or disorder.

The term "suspension culture" or "suspension agitation", as used herein, refers to the culture of cells, dispersed in a liquid nutrient medium. Due to this culture technique, the cells do not adhere to the solid support or the culture vessel. In some embodiments, in suspension culture the culture vessel is constantly moving or agitated. It is readily understood that suspension cultures comprise cells in various stages of aggregation. A range of aggregate sizes are encountered in the suspensions with sizes ranging from tens of microns in diameter (single cells or couple of hundred aggregated cells) to aggregates hundreds of microns in diameter, consisting of many thousands of cells.

As used herein the term "time sufficient to generate" a specific cell type (e.g., NK cells) may be understood as a time frame sufficient to observe at least one differentiated cell (e.g., an NK cell) among the cell population. In some aspects, the "time sufficient to generate NK cells" includes time to achieve a plurality of NK cells in the cell population (e.g., more than one NK cell). In some aspects, the "time sufficient to generate NK cells" includes time to achieve a majority of NK cells in the cell population (e.g., time to achieve a cell population having more than 50%, more than 60%, more than 70%, more than 80% or more than 90% of NK cells).

Specific Methods of the Disclosure

Accordingly, the present disclosure relates in particular to the following non-limiting compositions and methods.

In a first method, Method 1, the present disclosure provides a method for generating Natural Killer (NK) cells from stem cells, the method comprising: (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; and (g) culturing the cell population in a seventh medium comprising IL-7, FLT3L, IL-15 and SCF for a time sufficient to generate NK cells.

In a second method, Method 2, the present disclosure provides a method for generating Natural Killer (NK) cells from stem cells, the method comprising: (a) culturing a population of stem cells in a first medium comprising a ROCK inhibitor under conditions sufficient to form aggregates; (b) culturing the aggregates in a second medium comprising BMP-4; (c) culturing the aggregates in a third medium comprising BMP-4, FGF2, a WNT pathway activator, and Activin A; (d) culturing the aggregates in a fourth medium comprising FGF2, VEGF, TPO, SCF, IL-3, FLT3L, WNT C-59 and an activin/nodal inhibitor to form a cell population comprising hematopoietic stem and progenitor cells (HSPCs); (e) culturing the cell population in a fifth medium comprising FGF2, VEGF, TPO, SCF, IL-3 and FLT3L; (f) culturing the cell population in a sixth medium comprising IL-3, IL-7, FLT3L, IL-15 and SCF; (g) culturing the cell population in a seventh medium comprising IL-7, FLT3L, IL-15 and SCF; and (h) culturing the cell population in an eighth medium comprising IL-7, FLT3L, IL-15, SCF, and, optionally, nicotinamide for a time sufficient to generate NK cells.

In another method, Method 3, the present disclosure provides a method as provided in any one of Methods 1 or 2, wherein culturing the cell population in the fifth medium in step (e) results in the cell population comprising at least about 25% of HSPCs, optionally comprising about 25% to about 55% of HSPCs.

In another method, Method 4, the present disclosure provides a method as provided in any one of Methods 1 to 3, wherein culturing the cell population in the fifth medium in step (e) results in the cell population comprising about 29% to about 50% of HSPCs.

In another method, Method 5, the present disclosure provides a method as provided in any one of Methods 3 or 4, wherein culturing the cell population in the fifth medium in step (e) results in the cell population comprising about 36% of HSPCs or about 50% of HSPCs.

In another method, Method 6, the present disclosure provides a method as provided in any one of Methods 1 to 5, wherein culturing the cell population in the sixth medium in step (f) results in the formation of progenitor cell population comprising common lymphoid progenitor (CLP) cells.

In another method, Method 7, the present disclosure provides a method as provided in Method 6, wherein the progenitor cell population comprises at least about 15% of CLP cells, optionally wherein the CLP cells express CD7 and CD45.

In another method, Method 8, the present disclosure provides a method as provided in any one of Methods 6 or 7, wherein the progenitor cell population comprises about 15% to about 50% of CLP cells, optionally about 19% to about 45%.

In another method, Method 9, the present disclosure provides a method as provided in any one of Methods 6 to 8, wherein the progenitor cell population comprises about 35% of CLP cells.

In another method, Method 10, the present disclosure provides a method as provided in any one of Methods 1 to 9, wherein culturing the cell population in the seventh medium in step (g) or the eighth medium in step (h) results in the cell population comprising at least about 70% of NK cells.

In another method, Method 11, the present disclosure provides a method as provided in Method 10, wherein culturing the cell population in the seventh medium in step (g) or the eighth medium in step (h) results in the cell population comprising at least about 95% of NK cells.

In another method, Method 12, the present disclosure provides a method as provided in any one of Methods 1 to 11, wherein the second medium further comprises a ROCK inhibitor.

In another method, Method 13, the present disclosure provides a method as provided in any one of Methods 1 to 12, wherein the ROCK inhibitor is thiazovivin or Y27632.

In another method, Method 14, the present disclosure provides a method as provided in any one of Methods 1 to 13, wherein the WNT pathway activator is CHIR-99021.

In another method, Method 15, the present disclosure provides a method as provided in any one of Methods 1 to 14, wherein the activin/nodal inhibitor is SB-431542.

In another method, Method 16, the present disclosure provides a method as provided in any one of Methods 1 to 15, wherein (a) comprises culturing for 12-48 hours.

In another method, Method 17, the present disclosure provides a method as provided in any one of Methods 1 to 16, wherein (b) comprises culturing for up to 24 hours.

In another method, Method 18, the present disclosure provides a method as provided in any one of Methods 1 to 17, wherein (c) comprises culturing for 1-3 days.

In another method, Method 19, the present disclosure provides a method as provided in any one of Methods 1 to 18, wherein (d) comprises culturing for 1-3 days.

In another method, Method 20, the present disclosure provides a method as provided in any one of Methods 1 to 19, wherein (e) comprises culturing for 1-3 days.

In another method, Method 21, the present disclosure provides a method as provided in any one of Methods 1 to 20, wherein (f) comprises culturing for at least 6 days and up to 8 days.

In another method, Method 22, the present disclosure provides a method as provided in any one of Methods 1 to 21, wherein (g) comprises culturing for at least 6 days and up to 21-28 days total.

In another method, Method 23, the present disclosure provides a method as provided in any one of Methods 2 to 22, wherein (g) comprises culturing for up to 6 days.

In another method, Method 24, the present disclosure provides a method as provided in any one of Methods 2 to 23, wherein (h) comprises culturing for at least 6 days and up to 10-16 days total.

In another method, Method 25, the present disclosure provides a method as provided in any one of Methods 1 to 23, wherein: (a) comprises culturing for 16-20 hours; (b) comprises culturing for 6-10 hours; (c) comprises culturing for 2 days; (d) comprises culturing for 2 days; (e) comprises culturing for 2 days; (f) comprises culturing for 6-8 days; and (g) comprises culturing for 6-28 days.

In another method, Method 26, the present disclosure provides a method as provided in any one of Methods 2 to 24, wherein: (a) comprises culturing for 16-20 hours; (b) comprises culturing for 6-10 hours; (c) comprises culturing for 2 days; (d) comprises culturing for 2 days; (e) comprises culturing for 2 days; (f) comprises culturing for 6-8 days; (g) comprises culturing for 6 days; and (h) comprises culturing for 8-16 days.

In another method, Method 27, the present disclosure provides a method as provided in any one of Methods 1 to 26, wherein steps (a)-(g) or steps (a)-(h) occurs between 20-42 days or steps (a)-(h) occur between 23 and 40 days.

In another method, Method 28, the present disclosure provides a method as provided in any one of Methods 1 to 26, wherein steps (a)-(g) or steps (a)-(h) occurs in less than 20 days or steps (a)-(h) occur in less than 30 days.

In another method, Method 29, the present disclosure provides a method as provided in any one of Methods 1 to 28, wherein NK cells are generated in about 20 days or wherein NK cells are generated in about 23 to 30 days.

In another method, Method 30, the present disclosure provides a method as provided in Method 29, wherein steps (a)-(g) occurs in about 20 days and culturing the cell population in the seventh medium in step (g) results in the cell population comprising at least about 70% NK cells or 95% NK cells or steps (a)-(h) occurs in about 28 days and culturing the cell population in the eighth medium in step (h) results in the cell population comprising at least about 70% NK cells or 95% NK cells or steps (a)-(h) occurs in about 30 days and culturing the cell population in the eighth medium in step (h) results in the cell population comprising at least about 70% NK cells or 95% NK cells.

In another method, Method 31, the present disclosure provides a method as provided in any one of Methods 1 to 30, wherein the method is carried out under suspension agitation.

In another method, Method 32, the present disclosure provides a method as provided in Method 31, wherein suspension agitation comprises rotation, optionally wherein the rotation speed is at least about 35 RPM to about 100 RPM.

In another method, Method 33, the present disclosure provides a method as provided in any one of Methods 1 to 31, wherein the first and second media comprises StemFlex or StemBrew medium. In another method, Method 33B, the present disclosure provides a method as provided in any one of Methods 1 to 31, wherein the first media comprises StemFlex or StemBrew medium.

In another method, Method 34, the present disclosure provides a method as provided in any one of Methods 1 to 32, wherein the third, fourth and fifth media comprise APEL medium. In another method, Method 34B, the present disclosure provides a method as provided in any one of Methods 1 to 32, wherein the second, third, fourth and fifth media comprise APEL medium.

In another method, Method 35, the present disclosure provides a method as provided in any one of Methods 1 to 33, wherein the sixth and seventh media comprise DMEM/F12 medium, or optionally DMEM (high glucose)/F12 medium.

In another method, Method 36, the present disclosure provides a method as provided in any one of Methods 1 to 34, wherein the sixth and seventh media comprise human serum, zinc sulfate, ethanolamine, β-mercaptoethanol, glucose, or any combination thereof.

In another method, Method 37, the present disclosure provides a method as provided in any one of Methods 1 to 35, wherein the concentration of human serum is about 5%-40%, the concentration of zinc sulfate is about 1.7-40 mM, the concentration of ethanolamine is about 20-60 mM, the concentration of β-mercaptoethanol is about 0-45 mM, and the concentration of glucose is about 2-40 mM, or any combination thereof.

In another method, Method 38, the present disclosure provides a method as provided in Method 36, wherein the concentration of β-mercaptoethanol is about 1 mM.

In another method, Method 39, the present disclosure provides a method as provided in Method 37, wherein the sixth and seventh medium do not comprise β-mercaptoethanol.

In another method, Method 40, the present disclosure provides a method as provided in Method 36, wherein: (a) the concentration of human serum is about 15%, the concentration of zinc sulfate is about 37 mM, the concentration of ethanolamine is about 50 mM, the concentration of β-mercaptoethanol is about 1 mM, and the concentration of glucose is about 27 mM; or (b) the concentration of human serum is about 20%, the concentration of zinc sulfate is about 36.2 mM, the concentration of ethanolamine is about 50 mM, and the concentration of glucose is about 20 mM.

In another method, Method 41, the present disclosure provides a method as provided in Method 37, wherein the sixth and seventh media comprises DMEM/F12 medium, or optionally DMEM (high glucose)/F12 medium, and a supplement of human serum, zinc sulfate, ethanolamine, β-mercaptoethanol, glucose, or any combination thereof.

In another method, Method 42, the present disclosure provides a method as provided in any one of Methods 1 to 40, wherein the supplement provides an additional concentration of human serum of about 5%-40%, an additional concentration of zinc sulfate of about 1.7-40 mM, an additional concentration of ethanolamine of about 20-60 mM, an additional concentration of β-mercaptoethanol of about 0.5-45 mM, an additional concentration of glucose of about 2-40 mM or any combination thereof.

In another method, Method 43, the present disclosure provides a method as provided in Method 41, wherein (a) the additional concentration of human serum is about 15%, the additional concentration of zinc sulfate is about 37 mM, the additional concentration of ethanolamine is about 50 mM, the additional concentration of β-mercaptoethanol is about 1 mM, and the additional concentration of glucose is about 10.25 mM; or (b) the additional concentration of human serum is about 20%, the additional concentration of zinc sulfate is about 36.2 mM, the additional concentration of ethanolamine is about 50 mM, and the additional concentration of glucose is about 4.66 mM.

In another method, Method 44, the present disclosure provides a method as provided in Method 42, wherein the supplement does not comprise β-mercaptoethanol.

In another method, Method 45, the present disclosure provides a method as provided in any one of Methods 41 to 43, wherein the eight medium comprises DMEM/F12 medium, or optionally DMEM (high glucose)/F12 medium.

In another method, Method 46, the present disclosure provides a method as provided in any one of Methods 2 to 44, wherein the eight medium comprises human serum, zinc sulfate, ethanolamine, glucose, or any combination thereof.

In another method, Method 47, the present disclosure provides a method as provided in Method 46, wherein the concentration of human serum is about 5%-40%, the concentration of zinc sulfate is about 1.7-40 mM, the concentration of ethanolamine is about 20-60 mM, and the concentration of glucose is about 2-40 mM, or any combination thereof.

In another method, Method 48, the present disclosure provides a method as provided in Method 47, wherein: (a) the concentration of human serum is about 10%, the concentration of zinc sulfate is about 37 mM, the concentration of ethanolamine is about 50 mM, and the concentration of glucose is about 20 mM.

In another method, Method 49, the present disclosure provides a method as provided in any one of Methods 2 to 48, wherein the eighth media comprises DMEM/F12 medium, or optionally DMEM (high glucose)/F12 medium and a supplement of human serum, zinc sulfate, ethanolamine, glucose, or any combination thereof.

In another method, Method 50, the present disclosure provides a method as provided in Method 49, wherein the supplement provides an additional concentration of human serum of about 5%-40%, an additional concentration of zinc sulfate of about 1.7-40 mM, an additional concentration of ethanolamine of about 20-60 mM, an additional concentration of glucose of about 2-40 mM or any combination thereof.

In another method, Method 51, the present disclosure provides a method as provided in Method 50, wherein (a) the additional concentration of human serum is about 15%, the additional concentration of zinc sulfate is about 37 mM, the additional concentration of ethanolamine is about 50 mM, and the additional concentration of glucose is about 2.3 mM.

In another method, Method 52, the present disclosure provides a method as provided in any one of Methods 1 to 51, wherein the first medium comprises 10 μM of the ROCK inhibitor.

In another method, Method 53, the present disclosure provides a method as provided in any one of Methods 1 to 52, wherein the second medium comprises 30 ng/mL BMP-4 and, optionally, 10 μM of a ROCK inhibitor.

In another method, Method 54, the present disclosure provides a method as provided in any one of Methods 1 to 53, wherein the third medium comprises 30 ng/mL BMP-4, 100 ng/mL FGF2, 3-10 μM CHIR-99021, 6 μM or 7 μM CHIR-99021, and 2.5-5.0 ng/mL Activin A.

In another method, Method 55, the present disclosure provides a method as provided in Method 54, wherein the third medium is added to the second medium at a 1:1 ratio.

In another method, Method 56, the present disclosure provides a method as provided in any one of Methods 1 to 55, wherein the fourth and fifth media comprise 20 ng/mL FGF, 20 ng/mL VEGF, 20 ng/mL TPO, 100 ng/mL SCF, 40 ng/mL IL-3, and 10-20 ng/mL FLT3L.

In another method, Method 57, the present disclosure provides a method as provided in any one of Methods 1 to 56, wherein the fourth medium further comprises 5 μM SB-431542.

In another method, Method 58, the present disclosure provides a method as provided in any one of Methods 1 to 57, In another method, Method 59, the present disclosure provides a method as provided in any one of Methods 1 to 58, wherein the sixth and seventh media comprises 20 ng/mL IL-7, 10-20 ng/mL FLT3L, 10-20 ng/mL IL-15, and 20 ng/mL SCF.

In another method, Method 60, the present disclosure provides a method as provided in any one of Methods 1 to 59, wherein the sixth medium comprises 5 ng/mL IL-3.

In another method, Method 61, the present disclosure provides a method as provided in any one of Methods 2 to 60, wherein the eighth medium comprises 10-20 ng/mL IL-7, 5-20 ng/mL FLT3L, 10-30 ng/mL IL-15, 20-40 ng/mL SCF and, optionally, 6.5 mM nicotinamide.

In another method, Method 62, the present disclosure provides a method as provided in Method 61, wherein the eighth medium comprises: 10 ng/mL IL-7, 7.5 ng/mL FLT3L, 15 ng/mL IL-15, 20 ng/mL SCF and, optionally, 6.5 mM nicotinamide.

In another method, Method 63, the present disclosure provides a method as provided in any one of Methods 1 to 62, wherein the HSPCs of (d) express CD34 and/or CD45.

In another method, Method 64, the present disclosure provides a method as provided in any one of Methods 1 to 63, wherein the NK cells express CD56 and/or CD45.

In another method, Method 65, the present disclosure provides a method as provided in any one of Methods 1 to 64, wherein the NK cells express at least one activating receptor.

In another method, Method 66, the present disclosure provides a method as provided in Method 65, wherein the at least one activating receptor is selected from the group of NKp44, NKp46, NKG2D, CD16, KIR2DL4, NKp30, and any combination thereof.

In another method, Method 67, the present disclosure provides a method as provided in any one of Methods 1 to 66, wherein the NK cells express at least one inhibitory receptor.

In another method, Method 68, the present disclosure provides a method as provided in Method 67, wherein the at least one inhibitory receptor is selected from the group of NKG2A, KIR3DL2, and any combination thereof.

In another method, Method 69, the present disclosure provides a method as provided in any one of Methods 1 to 68, wherein the NK cells express at least one co-receptor.

In another method, Method 70, the present disclosure provides a method as provided in Method 69, wherein the at least one co-receptor is CD94.

In another method, Method 71, the present disclosure provides a method as provided in any one of Methods 1 to 70, wherein the NK cells comprise at least one function associated with endogenous NK cells.

In another method, Method 72, the present disclosure provides a method as provided in Method 71, wherein the at least one function comprises the ability to induce cell lysis and cell death of a target cell.

In another method, Method 73, the present disclosure provides a method as provided in any one of Methods 71 or 72, wherein the at least one function comprises degranulation.

In another method, Method 74, the present disclosure provides a method as provided in Method 73, wherein degranulation comprises release of perforin and granzyme B.

In another method, Method 75, the present disclosure provides a method as provided in any one of Methods 73 or 74, wherein degranulation comprises expression of CD107a on the cell surface of an NK cell.

In another method, Method 76, the present disclosure provides a method as provided in any one of Methods 1 to 75, wherein the NK cells are generated without sorting $CD34^+$ cells from the cell population.

In another method, Method 77, the present disclosure provides a method as provided in any one of Methods 1 to 76, wherein the population of stem cells is a population of engineered cells.

In another method, Method 78, the present disclosure provides a method as provided in Method 77, wherein the stem cells are genetically modified by an RNA-guided endonuclease system.

In another method, Method 79, the present disclosure provides a method as provided in Method 78, wherein the RNA-guided endonuclease system is a CRISPR system comprising a CRISPR nuclease and a guide RNA.

In another method, Method 80, the present disclosure provides a method as provided in any one of Methods 1 to 79, wherein the stem cells are induced pluripotent stem cells (iPSC), pluripotent stem cells (PSC), embryonic stem cells (ESC), or adult stem cells (ASC).

In another method, Method 81, the present disclosure provides a method as provided in any one of Methods 1 to 80, wherein the stem cell is a mammalian cell, optionally wherein the cell is a human cell.

The present disclosure also provides a population of stem cells, Population 82, obtained during or differentiated during any of the methods as provided in Methods 1 to 81.

In another Population, Population 83, the present disclosure provides a population as provided in Population 82, wherein the population comprises hematopoietic stem and progenitor cells.

The present disclosure also provides a composition, Composition 84, comprising the population of hematopoietic stem and progenitor cells according to Population 83, for use as a medicament.

In another Population, Population 85, the present disclosure provides a Population of hematopoietic stem and progenitor cells obtained during or differentiated during any of the methods as provided in Methods 1 to 81 for use in treating cancer.

In another Population, Population 86, the present disclosure provides a Population of hematopoietic stem and progenitor cells obtained during or differentiated during any of the methods as provided in Methods 1 to 81 for use in treating an infectious disease or an autoimmune disease.

The present disclosure also provides a plurality of natural killer (NK) cells, Plurality 87, obtained by or derived from any of the methods as provided in Methods 1 to 81.

The present disclosure also provides a composition, Composition 88, comprising the plurality of NK cells according to Plurality 87, for use as a medicament.

In another Plurality, Plurality 89, the present disclosure provides a Population of Natural Killer (NK) cells obtained by or derived from any of the methods as provided in Methods 1 to 81 for use in treating cancer.

In another Plurality, Plurality 90, the present disclosure provides a Population of Natural Killer (NK) cells obtained by or derived from any of the methods as provided in Methods 1 to 81 for use in treating an infectious disease or an autoimmune disease.

In another method, Method 91, the present disclosure provides a method comprising administering to a subject the plurality of NK cells according to Plurality 87.

In another method, Method 92, the present disclosure provides a method according to Method 91 wherein the plurality of NK cells is administered to the subject as a pharmaceutical composition.

In another method, Method 93, the present disclosure provides a method comprising administering to a subject the population of stem cells according to Population 82 or Population 83.

In another method, Method 94, the present disclosure provides a method according to Method 93 wherein the population of stem cells is administered to the subject as a pharmaceutical composition.

In another method, Method 95, the present disclosure the present disclosure provides a method according to any one of Methods 91 to 94, wherein the subject is a human who has, is suspected of having, or is at risk for a cancer.

In another method, Method 96, the present disclosure the present disclosure provides a method according any one of Methods 91 to 94, wherein the subject is a human who has, is suspected of having, or is at risk for an infectious disease or an autoimmune disease.

EXAMPLES

Example 1: Cell Maintenance and Expansion

Maintenance of hiPSCs. Cells of human induced pluripotent stem cell (hiPSC) lines were maintained in STEM-FLEX™ Complete media (Life Technologies, A3349401) with single cell passaging using ACCUTASE® (Stemcell Technologies 07920 or equivalent) on BIOLAMININ 521 LN (LN521), BIOLAMININ 511 In (Qn511), or Recombinant Laminin iMatrix-511 E8 (AMSBIO, AMS.892 011). For passaging, 2 µM Thiazovivin was added. Optionally, 1% REVITACELL™ Supplement was added for passaging.

Example 2: Differentiating Stem Cells into Natural Killer Cells—Protocol 1

Published differentiation protocols that take 5-6 weeks to generate iNK cells (NK cells differentiated from iPSC) typically utilize spin aggregation, adherent differentiation with feeder layers, and cell sorting (see FIG. 1). As disclosed herein, a modified protocol (i.e., Protocol 1, also called Aligned Process 1.0 or AP1.0) was developed that is more amenable to scale-up, utilizes spontaneous aggregation, does not require feeder layers or cell sorting, and a shorter timeline, e.g., about 14-28 days to generate iNK cells (see FIG. 1). Protocol 1 was utilized to differentiate stem cells, such as wild-type and/or edited induced pluripotent stem (iPS) cells, into hematopoietic stem and progenitor cells (HSPCs) and then into natural killer (NK) cells. Prior to differentiation, frozen iPS cells were thawed and re-suspended in MED-A medium (Table 1). Flasks pre-coated with laminin-521 were used for cell culturing. Medium was changed daily using MED-B (Table 2) medium until cells were used for differentiation.

NK Cell Differentiation. iPS cells were differentiated using the following steps:

1. Day −1 (afternoon), iPSC aggregation: MED-B medium was aspirated from flasks containing iPSC and the cells were washed with DPBS (no calcium, no magnesium) (Thermo Fisher Scientific, 14190250). DPBS was aspirated and 2 mL ACCUTASE® (Innovative Cell Technologies, AT-104) was added per T25 flask (or 80 µL of ACCUTASE® per 1 $cm^2$). Cells were incubated at 37° C. for 3-5 min or until all the colonies detached. Accutase digested cells were diluted with MED-B medium to a ratio of at least 3:1 (MED-B:ACCUTASE®). Cells were gently resuspended and transferred to a conical tube. Optionally, enough MED-B medium was added to cells to dilute the ACCUTASE© to a ratio of 4:1 (MED-B:ACCUTASE®). Cells were pelleted and re-suspended in 10 mL of MED-C medium (Table 3). Cells were counted and the cell concentration was diluted to $1\times10^6$/mL. $6\times10^6$ cells were transferred to another tube and resuspended in a total of 6 mL of MED-C medium. The cells were transferred to 1 well of ultra-low adhesion 6-well plate (Corning, 3471) and the plate was placed on a platform shaker and rotated at 98 RPM for 18+/−2 hours (overnight).

2. At day 0, morning, at 18+/−2 hours after iPSC aggregation: The plate was rotated in a circular motion to move aggregates towards center of the well and aggregates were collected in a conical tube. Alternatively, all the aggregate solution mix was collected. Aggregates were allowed to settle for 15+/−5 minutes. Cells were resuspended in MED-D medium (Table 4). The cell number in aggregates was counted. The seeding density was adjusted as needed to resuspend $3\times10^5$ cells in aggregates in 2 mL MED-D medium and plated in one well of a 6-well low adhesion plate. Alternatively, for scale up, an appropriate number of cells was resuspended and transferred to a PBS spinner vessel (PBS Biotech). Seeding density tested for PBS seeding vessel was approximately $1-1.2\times10^5$ cells per mL per final media volume (day 0+8 hrs). The plate was placed on a platform shaker and rotated at 98 RPM for 8 hours or the PBS spinner vessel were placed on a PBS base (PBS-MINI MagDrive Base Unit; PBS Biotech), in $CO_2$ incubator with a rotation speed of RPM 38 to 39.

3. At day 0, afternoon, at 8 hours after MED-D medium addition: 2 mL per well of MED-E medium (Table 5) was added or scaled up for PBS spinner vessels. The plate was returned to platform shaker or PBS spinner vessel to its base in the CO2 incubator and left undisturbed until day 2. MED-E medium components were 2× of their final concentration, therefore it was added to cells in MED-D at a 1:1 volume ratio.

4. At day 2: MED-E medium was replaced with MED-F medium (Table 6).

5. At day 4: MED-F medium was replaced with MED-G medium (Table 7).

6. At day 6: Starting at day 6, medium with all aggregates and single cells was transferred into an appropriate volume centrifuge conical tube. Cells were centrifuged and resuspended in MED-H medium (Table 8) and placed back into original wells and onto platform shaker, or into original vessels and onto base, and returned for continued culture.

7. At day 10: Half or full media change was made with MED-H medium.

8. At day 14: Full media change was made with MED-I medium (Table 9).

9. From day 17 onwards: Starting at day 17 (and/or at day 20, and every 2 to 3 days from day 20 onwards), single cell density was estimated from cell culture. If cell density exceeded $3\times10^6$, cells were diluted to $1-2\times10^6$ either by topping up cultures with fresh MED-I medium or by a complete medium change if medium color has completely turned yellow.

TABLE 1

Medium composition for MED-A

| Component | Working Conc. | Volume[1] | Stock Conc. |
|---|---|---|---|
| STEMFLEX ™ Basal (Thermo Fisher, A3349401) | 90% | 900 mL | 100% |
| STEMFLEX ™ Supplement (Thermo Fisher, A3349401) | 1X | 100 mL | 10X |
| Thiazovivin (Biological Industry, 1226056-71-8) | 2 μM | 200 μL | 10 mM |

[1]Volumes are approximate to get the desired concentration.

TABLE 2

Medium composition for MED-B

| Component | Working Conc. | Volume[1] | Stock Conc. |
|---|---|---|---|
| STEMFLEX ™ Basal (Thermo Fisher, A3349401) | 90% | 900 mL | 100% |
| STEMFLEX ™ Supplement (Thermo Fisher, A3349401) | 1X | 100 mL | 10X |

[1]Volumes are approximate to get the desired concentration.

TABLE 3

Medium composition for MED-C

| Component | Working Conc. | Volume[1] | Stock Conc. |
|---|---|---|---|
| STEMFLEX ™ Basal (Thermo Fisher, A3349401) | 90% | 899 mL | 100% |
| STEMFLEX ™ Supplement (Thermo Fisher, A3349401) | 1X | 100 mL | 10X |
| Thiazovivin (Biological Industry, 1226056-71-8) | 10 μM | 1000 μL | 10 mM |

[1]Volumes are approximate to get the desired concentration.

TABLE 4

Medium composition for MED-D

| Component | Working Conc. | Volume[1] | Stock Conc. |
|---|---|---|---|
| STEMdiff APEL 2 Medium (STEMCELL Technologies, 05275) | 100% | 999 mL | 100% |
| rh BMP-4 (Peprotech, 120-05ET) | 30 ng/mL | 300 μL | 100 μg/mL |
| Thiazovivin (Biological Industry, 1226056-71-8) | 10 μM | 1000 μL | 10 mM |

[1]Volumes are approximate to get the desired concentration

TABLE 5

Medium composition for MED-E

| Component | Working Conc. | Volume[1] | Stock Conc. |
|---|---|---|---|
| STEMdiff APEL 2 Medium (STEMCELL Technologies, 05275) | 100% | 998 mL | 100% |
| rh BMP-4 (Peprotech, 120-05ET) | 30 ng/mL | 300 μL | 100 μg/mL |
| rh FGF2 (Peprotech, 100-18C-1MG) | 100 ng/mL | 1000 μL | 100 μg/mL |
| CHIR-99021 (Selleckchem, S1263) | 6 μM | 600 μL | 10 mM |
| Activin-A (R&D Systems, 338-AC-01M/CF) | 5 ng/mL | 100 μL | 50 μg/mL |

[1]Volumes are approximate to get the desired concentration.

TABLE 6

Medium composition for MED-F

| Component | Working Conc. | Volume[1] | Stock Conc. |
|---|---|---|---|
| STEMdiff APEL 2 Medium (STEMCELL Technologies, 05275) | 100% | 997 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |
| WNT C-59 (Selleckchem, S7037) | 2 μM | 200 μL | 10 mM |
| SB431542 (Selleckchem, S1067) | 5 μM | 500 μL | 10 mM |

[1]Volumes are approximate to get the desired concentration.

TABLE 7

Medium composition for MED-G

| Component | Working Conc. | Volume[1] | Stock Conc. |
|---|---|---|---|
| STEMdiff APEL 2 Medium (STEMCELL Technologies, 05275) | 100% | 998 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |

[1]Volumes are approximate to get the desired concentration.

TABLE 8

Medium composition for MED-H

| Component | Working Conc. | Volume[1] | Stock Conc. |
|---|---|---|---|
| DMEM (high glucose, GlutaMAX) (Thermo Fisher, 10566016) | 55.47% | 555 mL | 100% |
| F-12 with GlutaMAX (Thermo Fisher, 31765035) | 27.74% | 277 mL | 100% |

TABLE 8-continued

Medium composition for MED-H

| Component | Working Conc. | Volume[1] | Stock Conc. |
|---|---|---|---|
| GlutaMAX (Thermo Fisher, 35050079) | 1X | 10 mL | 100X |
| Glucose* | 10.25 mM | 4.1 mL | 2500 mM |
| Human AB serum (Valley Biomedical Inc, HP1022) | 15% | 150 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6 M |
| Ascorbic acid (Fisher Scientific, NC0762606) | 20 μg/mL | 2000 μL | 10 mg/mL |
| Sodium selenite (Millipore Sigma, S9133-1MG) | 5 ng/mL | 50 μL | 100 μg/mL |
| β-mercaptoethanol (Thermo Fisher, 21985-023) | 1 μM | 18 μL | 55 mM |
| rh IL-3 (Peprotech, 200-03-100UG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 27 mM (accounting for glucose in DMEM (high glucose) medium, F12 supplement and added glucose provided here).
[1]Volumes are approximate to get the desired concentration.

TABLE 9

Medium composition for MED-I

| Component | Working Conc. | Volume[1] | Stock Conc. |
|---|---|---|---|
| DMEM (high glucose, GlutaMAX) (Thermo Fisher, 10566016) | 55.47% | 555 mL | 100% |
| F-12 with GlutaMAX (Thermo Fisher, 31765035) | 27.74% | 277 mL | 100% |
| GlutaMAX (Thermo Fisher, 35050079) | 1X | 10 mL | 100X |
| Glucose* | 10.25 mM | 4.1 mL | 2500 mM |
| Human AB serum (Valley Biomedical Inc, HP1022) | 15% | 150 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6 M |
| Ascorbic acid (Fisher Scientific, NC0762606) | 20 μg/mL | 2000 μL | 10 mg/mL |
| Sodium selenite (Millipore Sigma, S9133-1MG) | 5 ng/mL | 50 μL | 100 μg/mL |
| β-mercaptoethanol (Thermo Fisher, 21985-023) | 1 μM | 18 μL | 55 mM |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | /mL |

*Total glucose concentration in medium is 27 mM (accounting for glucose in DMEM (high glucose) medium, F12 supplement and added glucose provided here).
[1]Volumes are approximate to get the desired concentration.

Representative culture samples were harvested at various days for FACS and TruSeq analysis to monitor differentiation of the cells as well as to determine the morphology of the cells (see FIG. 2A). For flow cytometry analysis, live cells were collected, washed with 100 BSA in PBS or a commercial cell staining buffer (e.g. Biolegend Cat no 420201), and incubated with appropriate antibody cocktails in 500 BSA in PBS or a commercial cell staining buffer (e.g. Biolegend Cat no 420201) for at least 20 min on ice. The cells were washed and resuspended in 1% BSA in PBS or a commercial cell staining buffer (e.g. Biolegend Cat no 420201) containing 1:1000 SyTOX Blue Dead Cell dye followed by loading the plate on the Flow cytometer for analysis (see Table 11 for antibodies used). For truseq analysis, RNA was extracted from flash frozen cell pellets using the Qiagen RNeasy 96 kit (Cat #74182, Qiagen) with on-column DNase treatment (Cat #79256, Qiagen) according to the manufacturer's instructions, and eluted in a 50 uL volume. QC and quantification of the eluted RNA was performed using the Qiagen QIAxcel RNA QC kit v2.0 (Cat #929104, Qiagen) according to the manufacturer's instructions. The library was prepared using the Illumina TruSeq Targeted RNA Custom Panel Kit, according to the manufacturer's instructions, using 32 amplification cycles. QC and quantification of the DNA libraries was performed on the QIAxcel using the Qiagen QIAxcel DNA High Resolution Kit (Cat #929002, Qiagen) according to the manufacturer's instructions. The DNA libraries were normalized, pooled, and sequenced on the Illumina Miseq instrument. Analysis was performed and the summed read counts were normalized to GAPDH. Gene expression levels were expressed as fold change vs. Day 0.

FIG. 2A shows the stage-wise differentiation of iPSC to iNK cells and various markers that are characteristic of the different stages during NK differentiation. Single cells emerge at days 6-10 and iNK cells emerge between day 10 to day 20. Cells at day 10 of the differentiated process were analyzed by flow cytometry to determine expression of HSC biomarkers CD45 and CD34 and cells at day 14 were analyzed by flow cytometry to determine expression of CLP biomarkers CD7 and CD45 (FIG. 2B). The gene expression profiles indicated that NK cells develop on day 20 with the loss of iPSC and HSPC marker expression. As shown in FIG. 2B, HSC cells were present at day 10 of differentiation and CLP cells were present at day 14 of differentiation consistent with the notion that iNK cells are differentiated via HSPC and CLP stages. Cells at day 6 of the differentiated process were also analyzed by flow cytometry to determine expression of HSC biomarkers CD45 and CD34.

The differentiation process was repeated numerous times where at day 6, at least about 38-55% of the population of cells were CD34$^+$ cells, while at least about 29% to 49% of the population of cells were CD34$^+$CD45$^+$ cells. At day 14, at least about 19-45% of the population of cells were CD7$^+$CD45$^+$ cells. At day 20, at least about 70% of the population of cells were CD56$^+$CD45$^+$ cells.

Figure 3A:
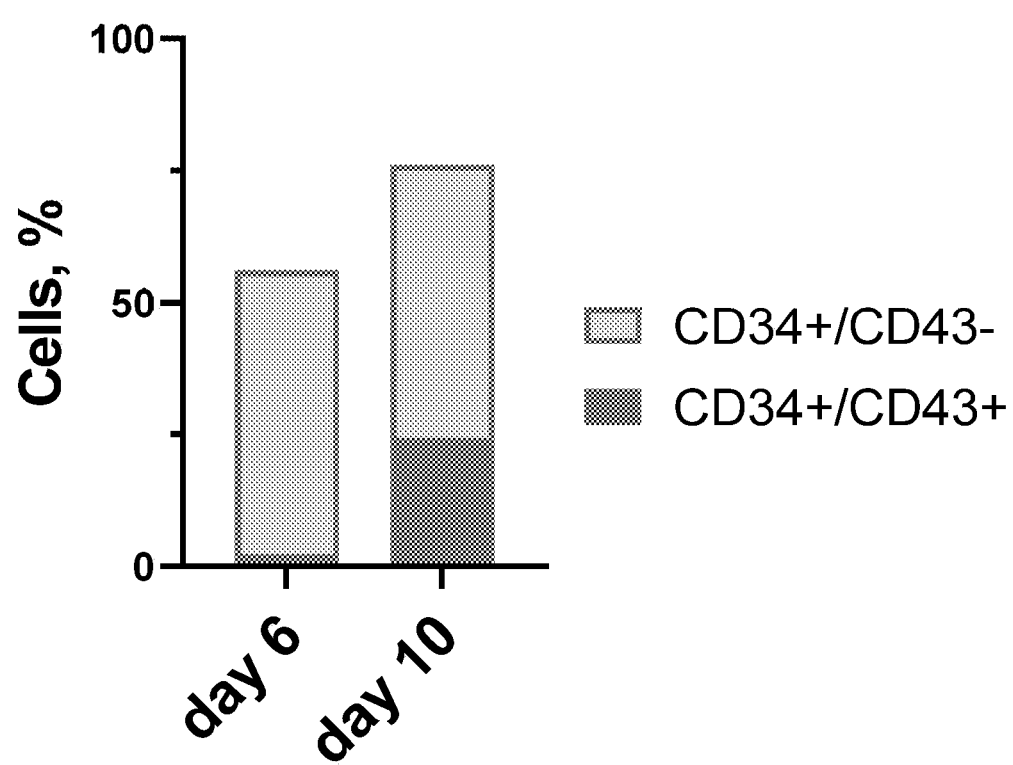
FIG. 3A provides a graph demonstrating the percentages of cells with $CD34^+CD43^-$ and $CD34^+/CD43^+$ expression at days 6 and 10.
Figure 3B:
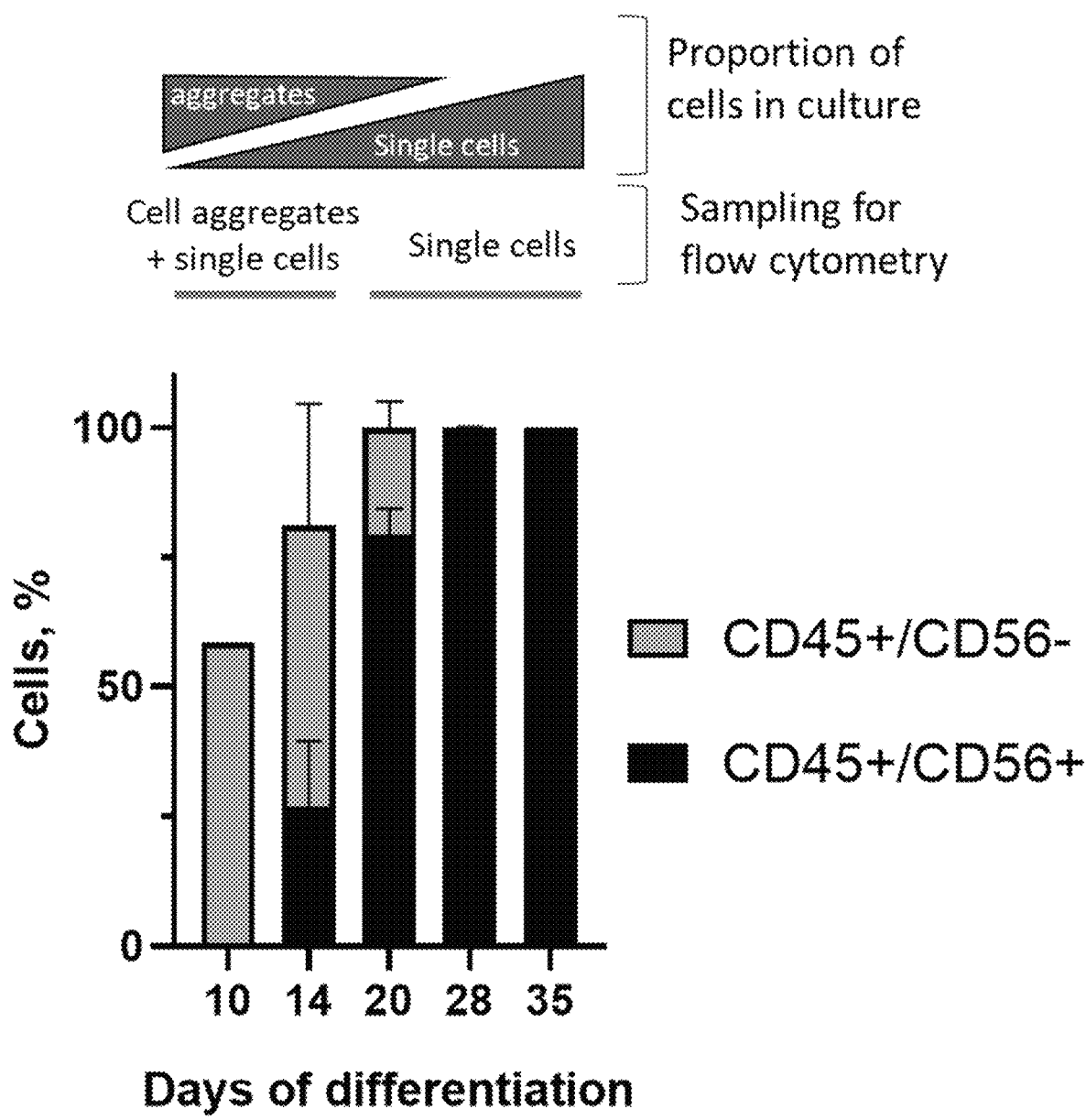
FIG. 3B provides a graph demonstrating the percentages of cells with $CD45^+/CD56^-$ expression and $CD45^+/CD56^+$ expression at days 10, 14, 20, 28, and 35.
Figure 3C:
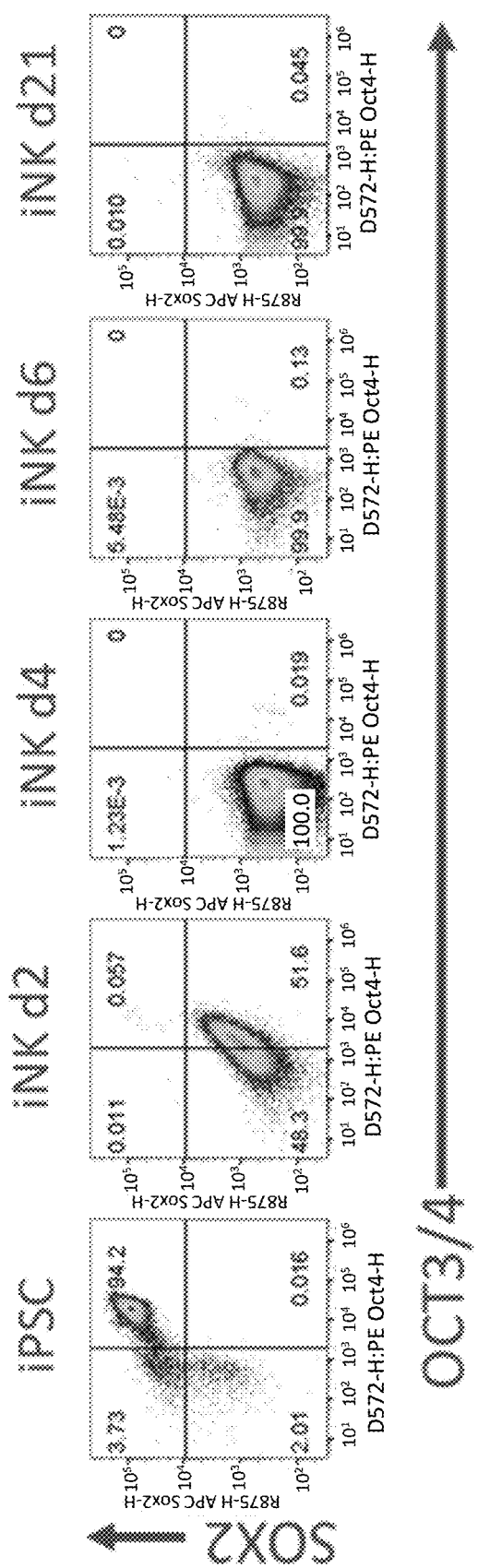
FIG. 3C provides flow cytometry analysis of SOX2 and OCT3/4 expression in iPSC cells, cells at day 2 ("iNK d2"), day 4 ("iNK d4"), day 6 ("iNK d6"), and day 21 ("iNK d21") of differentiation.
Figure 3D:
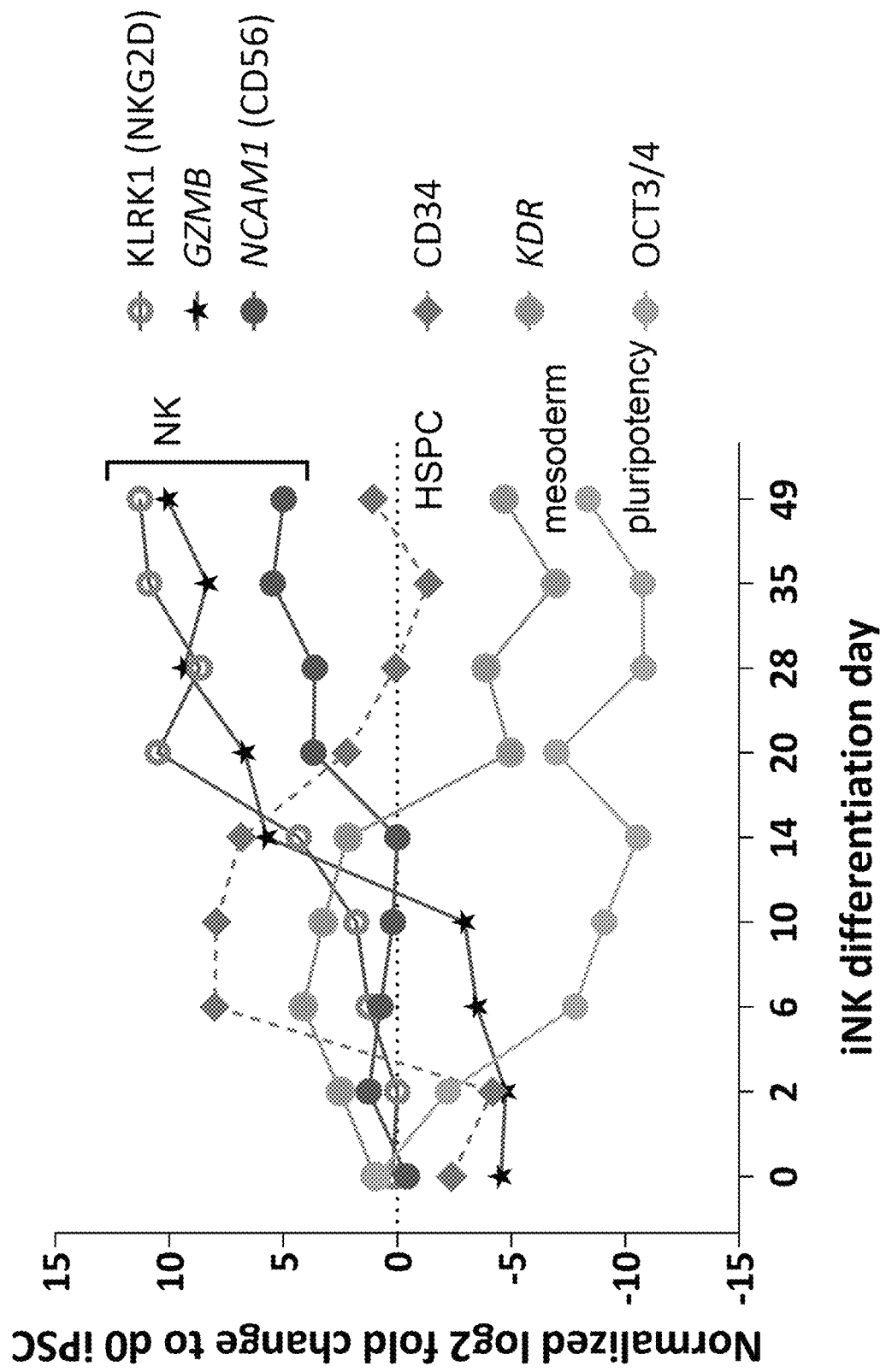
FIG. 3D shows Tru-seq analysis of KLRK1 (NKG2D), G2 MB, NCAM1 (CD56), CD34, KDR, and OCT3/4 expression during iNK differentiation.

At days 6 and 10, early HSPC marker expression (CD34 and CD43) was examined (FIG. 3A). Throughout the differentiation process, cells were analyzed for CD45 and CD56 expression by flow cytometry (FIG. 3B), showing efficient and robust differentiation. Cell aggregates were analyzed at Days 10 and 14 while single cells were analyzed at Days 20, 28, and 35. CD56$^+$ cells first appeared at 2 weeks and constituted the bulk of the population after 3-4 weeks of differentiation. Intracellular pluripotency markers (Oct3/4 and SOX2) flow profiles in iPSC and day 2, 4, 6 and 21 of iNK differentiation showed significant decrease of OCT3/4 starting on day 2 and both markers were eliminated starting on day 4 onward (FIG. 3C). The gene expression profile indicated NIK cell development on day 20 with loss of iPSC and HSPC markers expression (FIG. 3C and FIG. 3D and Table 10).

TABLE 10

Gene expression profile of iNK cells

| Log2 fold change (normalized to Day 0) | Fold Change (normalized to Day 0) | NK cell related markers (Day 20) | NK cell related markers (Day 35) |
|---|---|---|---|
| 2 to 7 | ~10 to 100 fold | EOMES, NFIL3, FCGR3A, KIR2DL1, KIR2DS4, KIR2DL3, KIR3DL1, KIR3DL2, IL15, IL18, IL2RA, KLRF1 (NKP80), SLAMF7 | EOMES, NFIL3, FCGR3A, GZMM, IL15, KLRF1 (NKP80), KLRD1 (CD94) |
| 8 to 10 | 100 fold to 1000 fold | TBX21, NCR1, NCR2, CCR5, CD226 (DNAM-1), GZMM, IL2RB, KLRD1 (CD94) | TBX21, NCR1, NCR2, KIR2DL1, KIR3DL1, KIR3DL2, IL2RA, IL2RB, SLAMF7 |
| >10 | >1000 fold | GZMA, GZMH, GZMK, NCR3, CCL3, CCL4, CCL5, CCR1, IL2RG, KLRB1, KLRC1 (NKG2A), KLRC2 (NKG2C) | GZMA, GZMH, GZMK, NCR3, CCL3, CCL4, CCL5, CCR1, CCR5, CD226 (DNAM-1), IL2RG, KIR2DL1, KIR2DS4, KLRB1, KLRC1 (NKG2A), KLRC2 (NKG2C) |

Figure 3E:
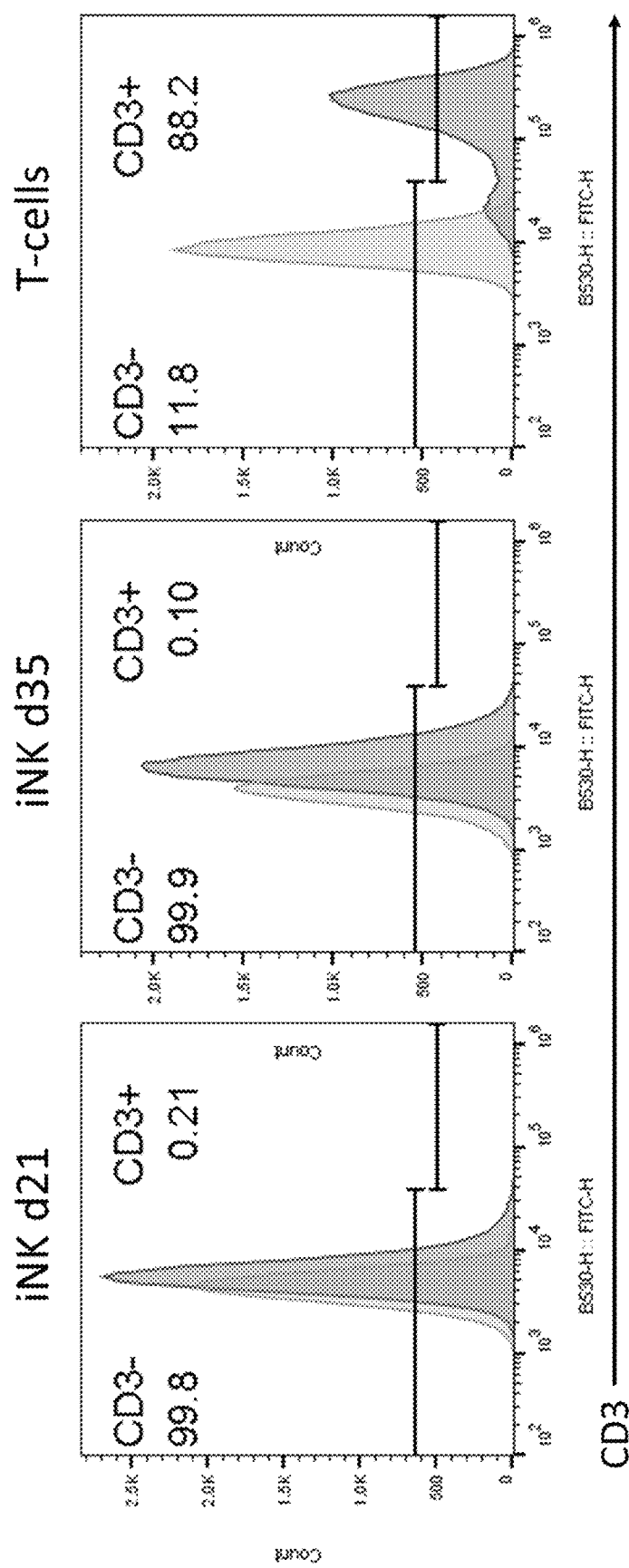
FIG. 3E provides flow cytometry analysis of CD3 expression in cells at day 21 and day 35 of differentiation compared to positive control T-cells.

By day 28, >99% of cells are $CD56^+$ with little to no $CD3^+$ cells (FIG. 3E) thus indicating that there was no significant T-cell contamination found in iNK cultures. The percent (%) of the population expressing CD14 (monocyte), CD19 (B cells), and CD41/CD61 (megakaryocyte/platelet precursors) were also significantly low, indicating minimal or no monocyte, B cell, or megakaryocyte/platelet precursor contamination in iNIK cultures (data not shown).

Figure 3F:
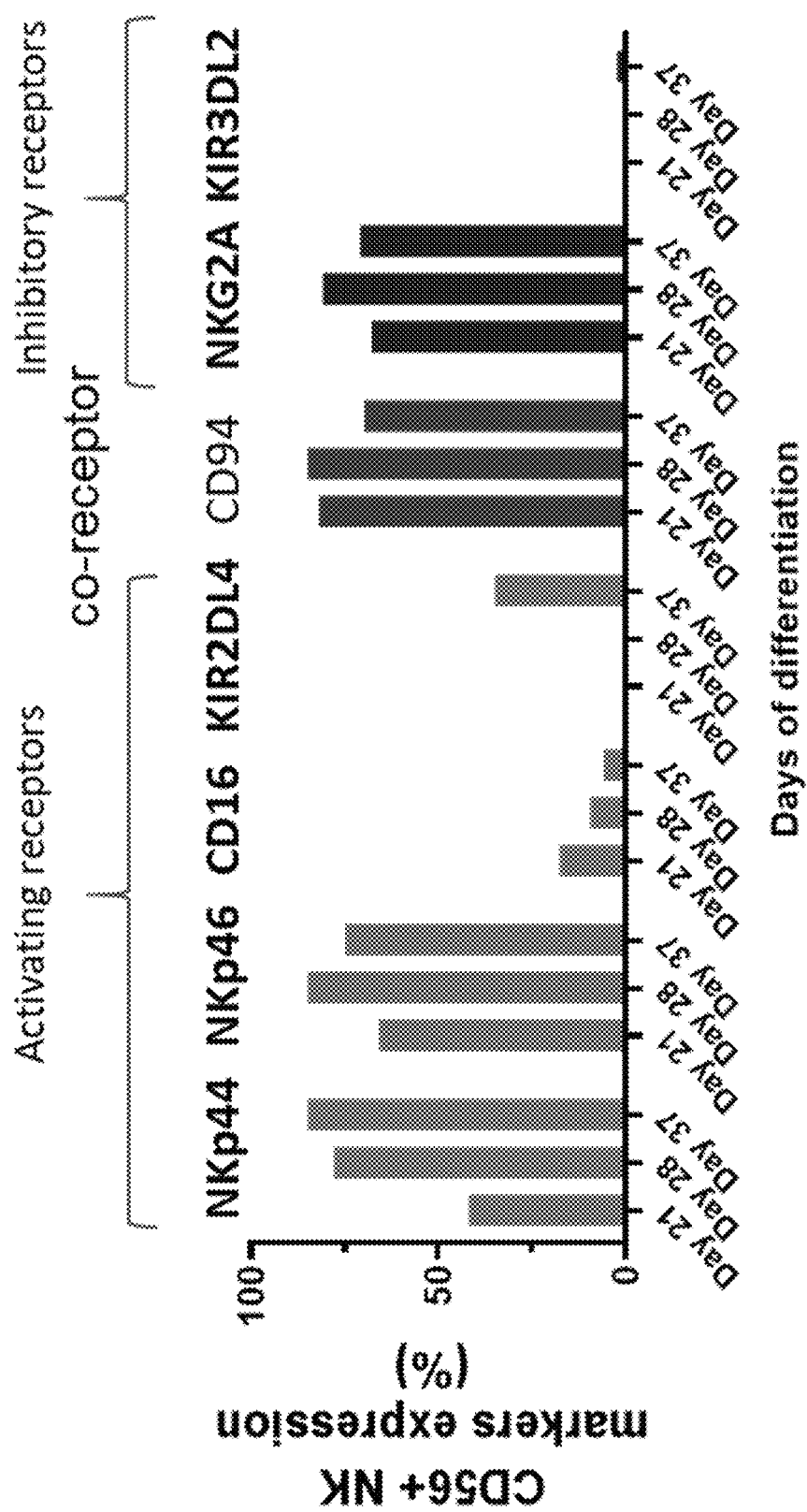
FIG. 3F provides a graph demonstrating expression of differentiation markers in WT at Days 21, 28, and 37 of differentiation from iPSC to iNK cells. Cells were analyzed by flow cytometry for NKp44, NKp46, CD16, KIR2DL4, CD94, NKG2A, and KIR3DL2 expression.

Flow cytometry was performed on filtered single cells on days 21, 28, and 37 to examine NK maturation marker expression levels (activating receptors: NKp44, NKp46, CD16, and KIR2DL4; co-receptor: CD94; inhibitor receptors: NKG2A, and KIR3DL2) (FIG. 3F). Other markers/receptors that are highly expressed in iNK cells: NKP30, DNAM1, OX40, CD69, NG2D3, and FAS (data not shown). FIG. 3F shows that the differentiated cells expressed a majority of maturation markers similarly detected on PB-NK (peripheral blood-NK) cells.

TABLE 11

Antibodies for marker screening

| antigen | fluorophore | company | catalog # | Dilution |
|---|---|---|---|---|
| CD16 | PE-Cy7 | BioLegend | 360708 | 1:50 |
| CD16 | APC | BD Bioscience | 561248 | 1:40 |
| CD235a/Glycophorin A | APC | BioLegend | 349114 | 1:10 |
| CD34 | FITC | Miltenyi | 130-113-178 | 1:25 |
| CD34 | PE | BD | 555822 | 1:10 |
| CD38 | PE-cy7 | eBioscience | 25-0389-42 | 1:25 |
| CD43 | BB515 | BD | 564542 | 1:500 |
| CD45 | PE-Cy7 | BD | 557748 | 1:100 |
| CD45 | BB515 | BD | 564585 | 1:100 |
| CD56 | PE | Miltenyi | 130-113-307 | 1:500 |
| CD56 | BB515 | BD | 564488 | 1:25 |
| CD56/NCAM1 | APC | BD | 555518 | 1:10 |
| CD57 | PE-Cy7 | BioLegend | 359624 | 1:10 |
| CD7 | FITC | BD | 561604 | 1:10 |
| CD94/KLRD1 | APC | Miltenyi | 130-098-976 | 1:5 |
| CD95/Fas1 | FITC | BD | 555673 | 1:10 |
| IL-15 | APC | Invitrogen | MA5-23627 | 1:10 |
| IL-15 | PE | Invitrogen | MA5-23561 | 1:10 |
| IL-15 | FITC | Invitrogen | MA5-23664 | 1:10 |
| KIR2DL4/CD158d | APC | Miltenyi | 130-112-466 | 1:25 |

TABLE 11-continued

Antibodies for marker screening

| antigen | fluorophore | company | catalog # | Dilution |
|---|---|---|---|---|
| KIR3DL2/CD158e/k | PE-Vio770 | Miltenyi | 130-116-180 | 1:100 |
| NKG2A/CD159a | APC | Miltenyi | 130-113-563 | 1:5 |
| NKG2D | BB515 | BD | 564566 | 1:2.5 |
| NKp44/CD336 | PE | BD | 558563 | 1:5 |
| NKp46/CD335 | PE-Cy7 | BD | 562101 | 1:5 |
| Oct3/4 | PE | BD Bioscience | 560186 | 1:10 |
| SOX2 | Alexa 647 | BD Bioscience | 562139 | 1:10 |

Figure 4:
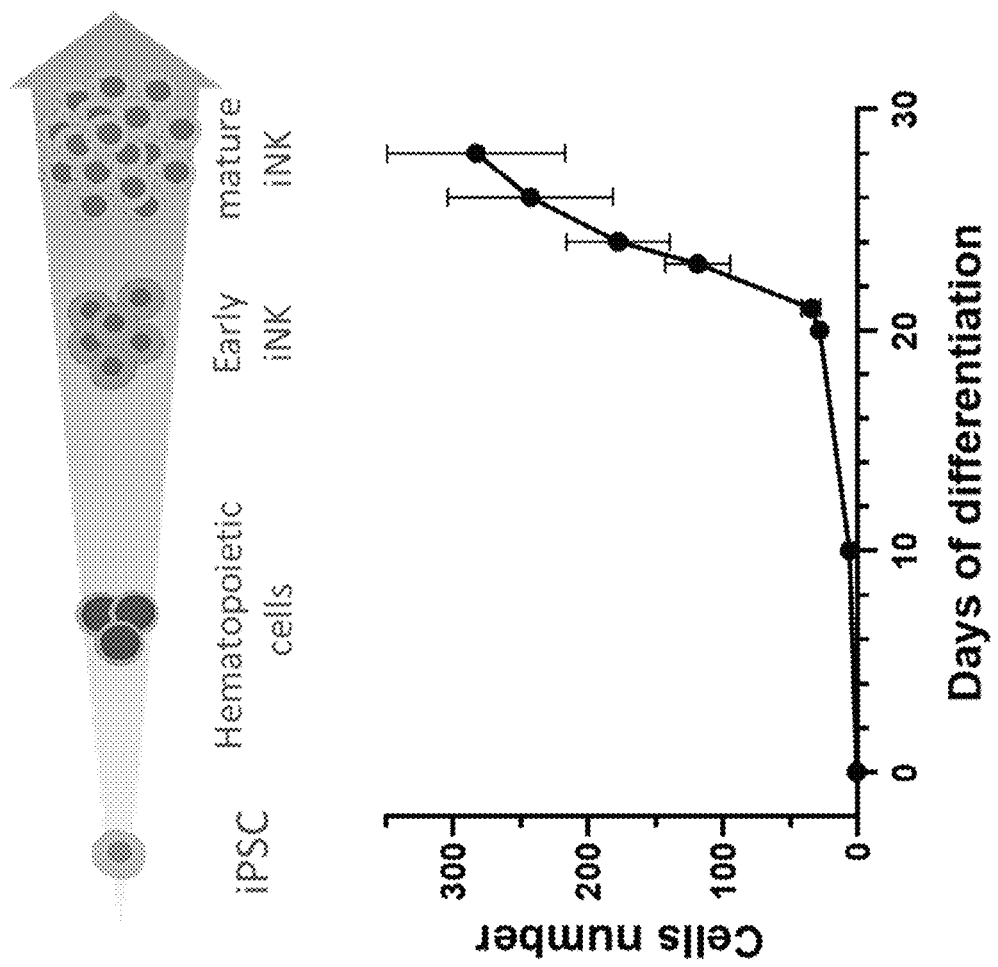
FIG. 4 shows iNK expansion by the protocol described herein (feeder-free) and that one iPSC generated about 200-340 iNK in 28 days.

FIG. 4 shows that the iNIK persisted and expanded in the absence of feeder cells. One IPS cell could generate ~200 to 340 iNK in 28 days. The majority of the expansion happened between days 20-28

Figure 5:
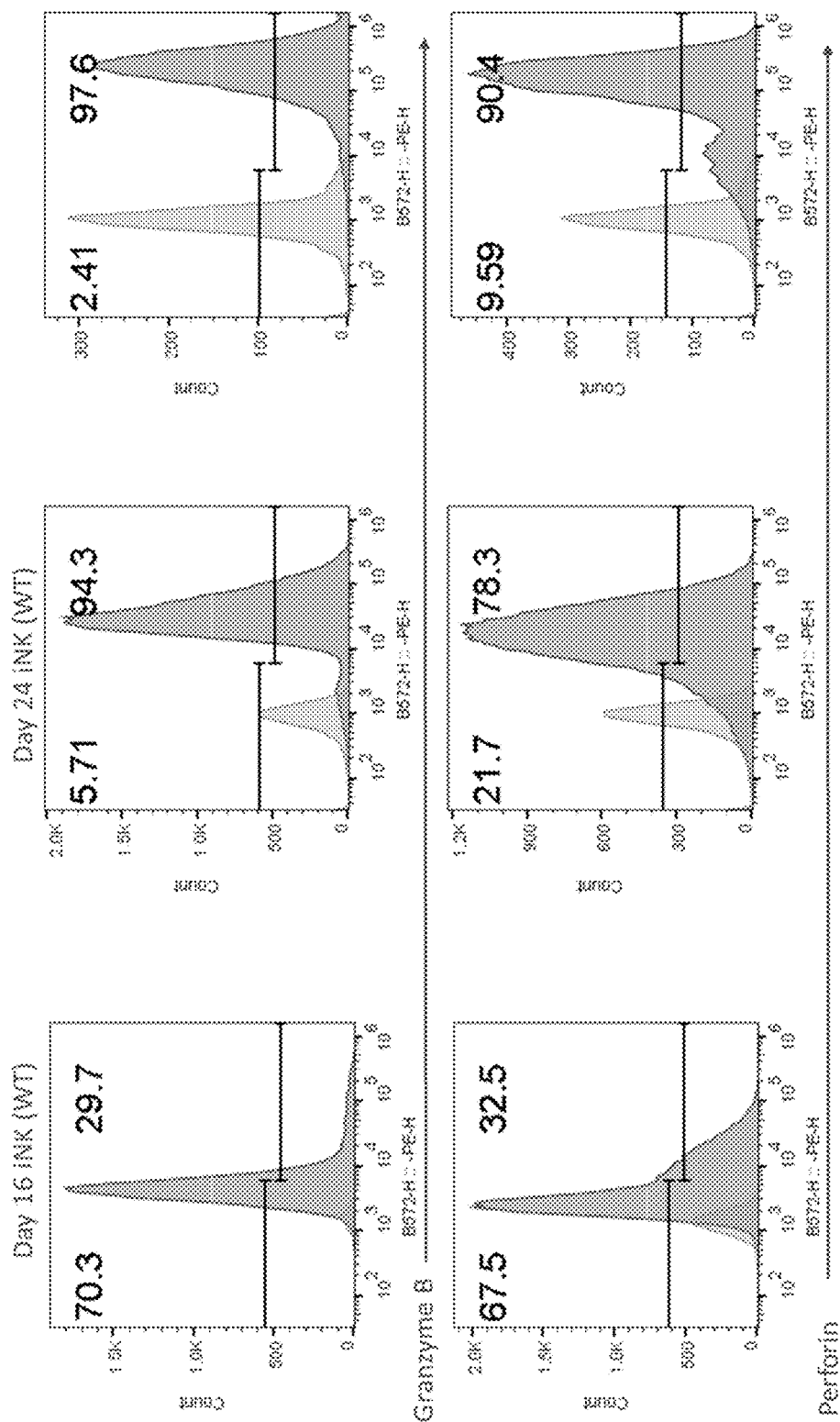
FIG. 5 provides flow cytometry analysis of Granzyme B and Perforin expressing cells at Day 16 and Day 24 of differentiation and cells at Day 38 of differentiation co-incubated with K562 cells.
Figure 20:
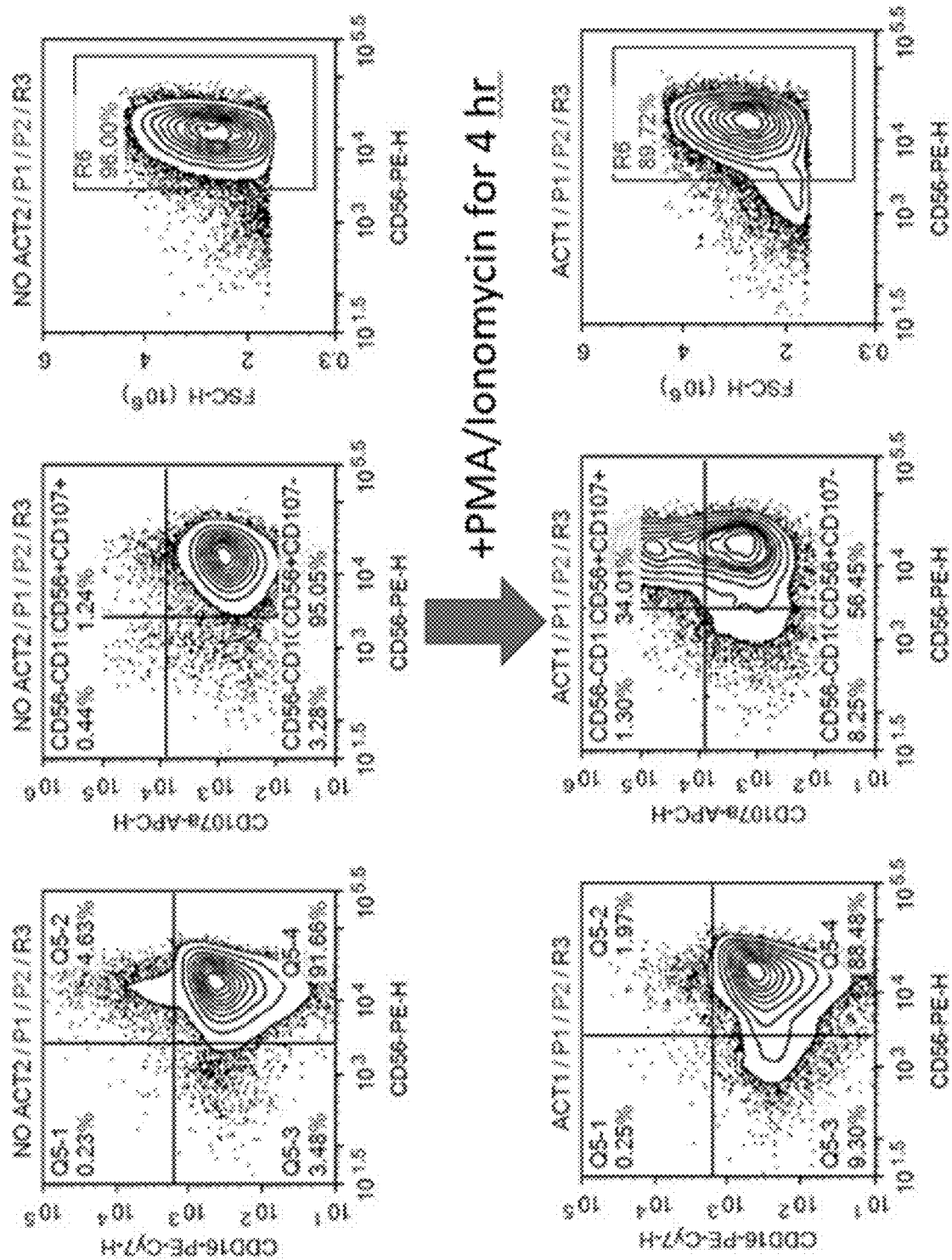
FIG. 20 shows NK cell activation assay (measuring CD16, CD56, and CD107a) with or without PMA (propidium monoazide)/Ionomycin.

Perforin and granzyme-B expression in cells were measured by flow cytometry at day 16 and 24, as well as day 38 differentiated cells that were co-incubated with K562 cells, using commercially available antibodies. FIG. 5 shows that WT cells at day 16 of differentiation had low expression of perforin or granzyme-B but had higher expression at day 24. When cells were co-incubated with K562 target cells for 10 days ("Day 38 iNK"), the intensity of perforin or granzyme-B staining was even higher. This suggests iNK were capable of continuously replenishing intracellular lytic granules content in the presence of target cells.

iNK cells were treated with Propidium Monoazide (PMA)/Ionomycin for 4 hours in an NIK cell activation assay. As shown in FIG. 20, after 4 hours of treatment, there is a loss of $CD16^+$ cells, an emergence of $CD56^-$ cells, and emergence of $CD56^+CD107a^+$ cells.

The cytotoxicity of day 29 derived iNIK cells towards K562 cells and RPMI cells was determined using a 24-hour killing assay. K562-GFP or RPMI-GFP cells (50,000 cells per vial) were incubated with iNK effector cell lines at different ratios as indicated for 24 hours. After incubation, the cells were spun, and resuspended in 175 μl media containing SyTox Blue at a 1:1000 concentration. 25 μL of countbright beads per well were added. The plate was read using the Flow cytometer and 100 μL volume per well was collected for analysis. GFP-positive, SyTox Blue—negative target cells (live cancer cells) and countbright beads were selected and measured absolute events count. Total live cells were calculated as follows:

[Total Cells=((No of live GFP-positive cells)/(Bead count for that sample))/(Bead count per 50 µL/2).

Figure 6A:
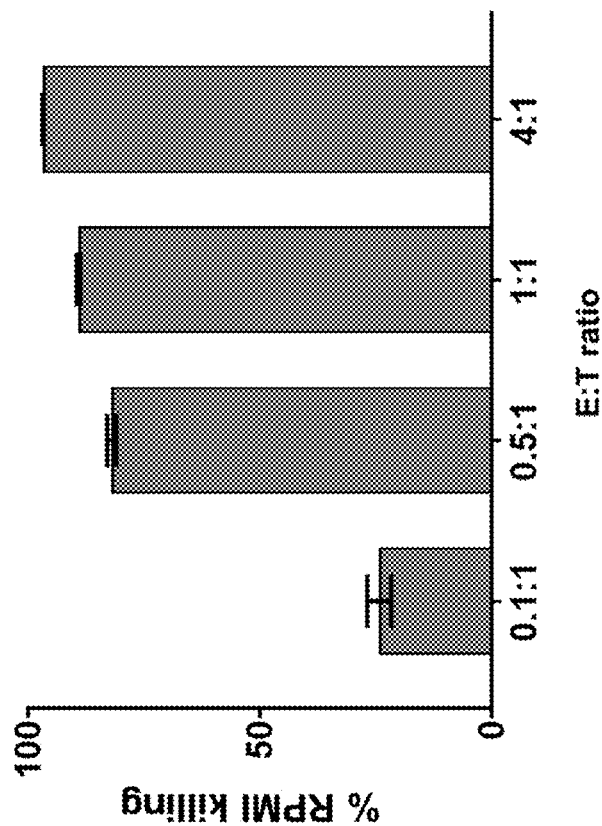
FIGS. 6A-6B provide graphs measuring K562 (FIG. 6A) and RPMI (FIG. 6B) cell killing by iNK cells. Differentiated iNK cells were cultured at different E:T ratios with K562 or RPMI cells for 24 hours.
Figure 6B:
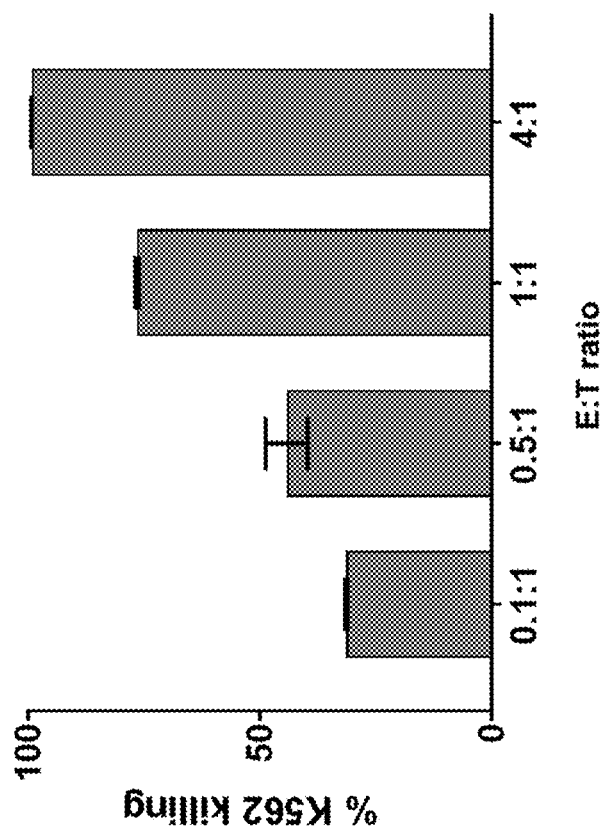

The % of cell lysis was calculated using following formula:

% Cell lysis=(1−((Total Number of target Cells in Test Sample)/(Total Number of Target Cells in Control Sample))×100. The WT iNK cells displayed effective cytotoxicity against K562 (FIG. 6A) and RPMI cancer cell line (FIG. 6B).

Figure 7C:
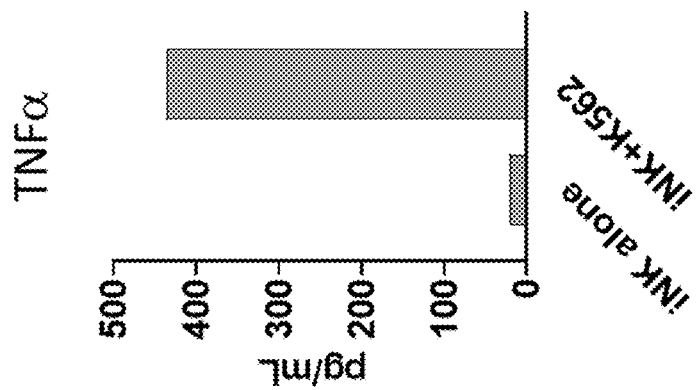
FIGS. 7A-7C provides graphs measuring Granzyme B (FIG. 7A), IFNγ (FIG. 7B) and TNFα (FIG. 7C) levels in WT differentiated cells co-cultured with RPMI cells at 1:1 ratio.
Figure 7B:
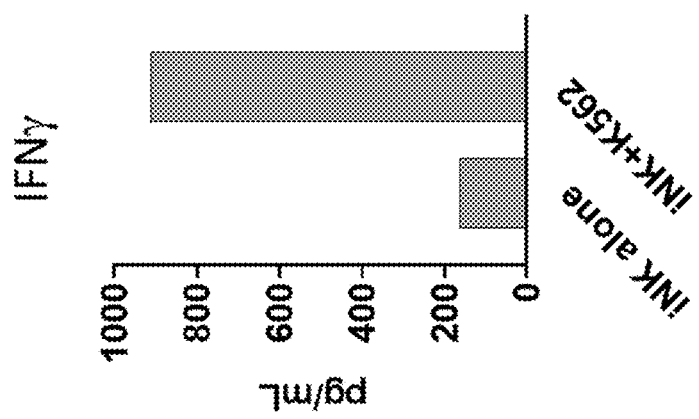
Figure 7A:
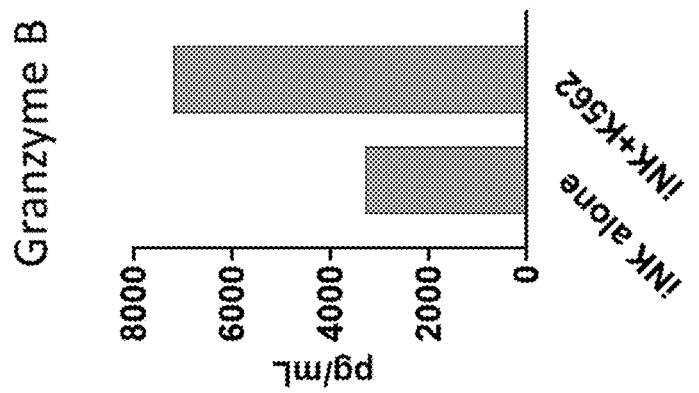

Cytokines (IFNg, TNFα) and Granzyme B secretion by iNK cells were measured with or without adding cancer cells K562 as a target to activate iNK for 24 hours. ProteinSimple Ella system was used for measurements, according to the manufacturer's instructions, with the software version v.3.5.2.20 of the Simple Plex Runner software, and Simple Plex Explorer software. Custom 8-plex Ella cartridges (32×8 Multiplex) were provided by ProteinSimple, along with dilution buffer which was used to dilute each sample at a 1:2 ratio prior to loading 40 µL sample per channel. As shown in FIGS. 7A-7C, the granzyme B, IFNγ, and TNFα levels in media increased in the presence of target cells during 24 hours of incubation, suggesting effective activation and cytotoxic activity of iNK cells in response to cancer target.

Example 3: Effect of CHIR and Activin on CD34+ HSPC

Figure 8:
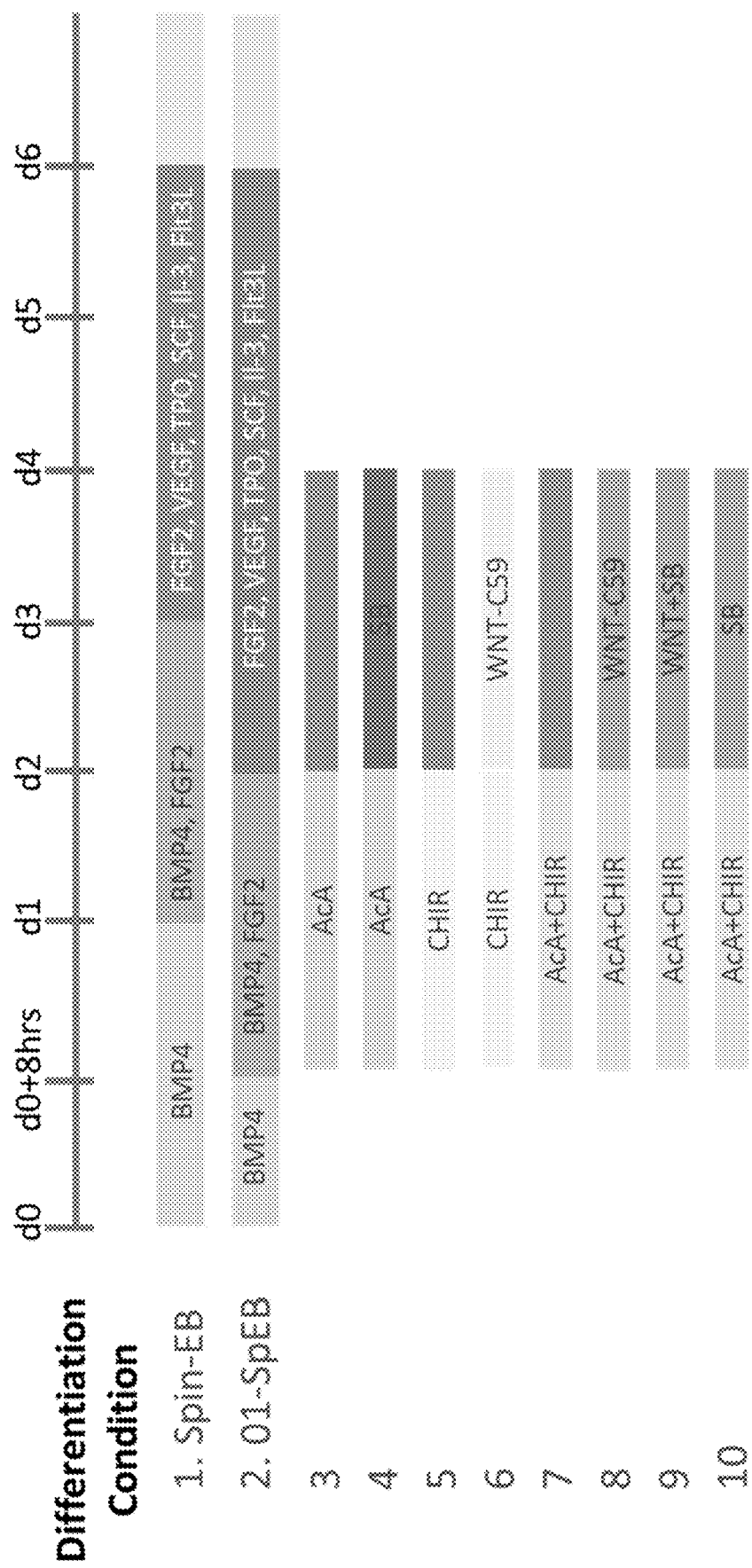
FIG. 8 shows a schematic of the Spin EB and modified Spin EB protocols along with the different components added at Day 0, Day 2, and Day 3.

This Example reports the investigation of WNT signaling pathway molecules, such as CHIR-99021 and Activin A, to increase yields of CD34+ cells as well as CD56+ cells during the later stages of iNK differentiation. FIG. 8 shows a schematic of the Spin EB and modified Spin EB protocols along with the different components added at Day 0 and Day 2 of differentiation.

Figure 9:
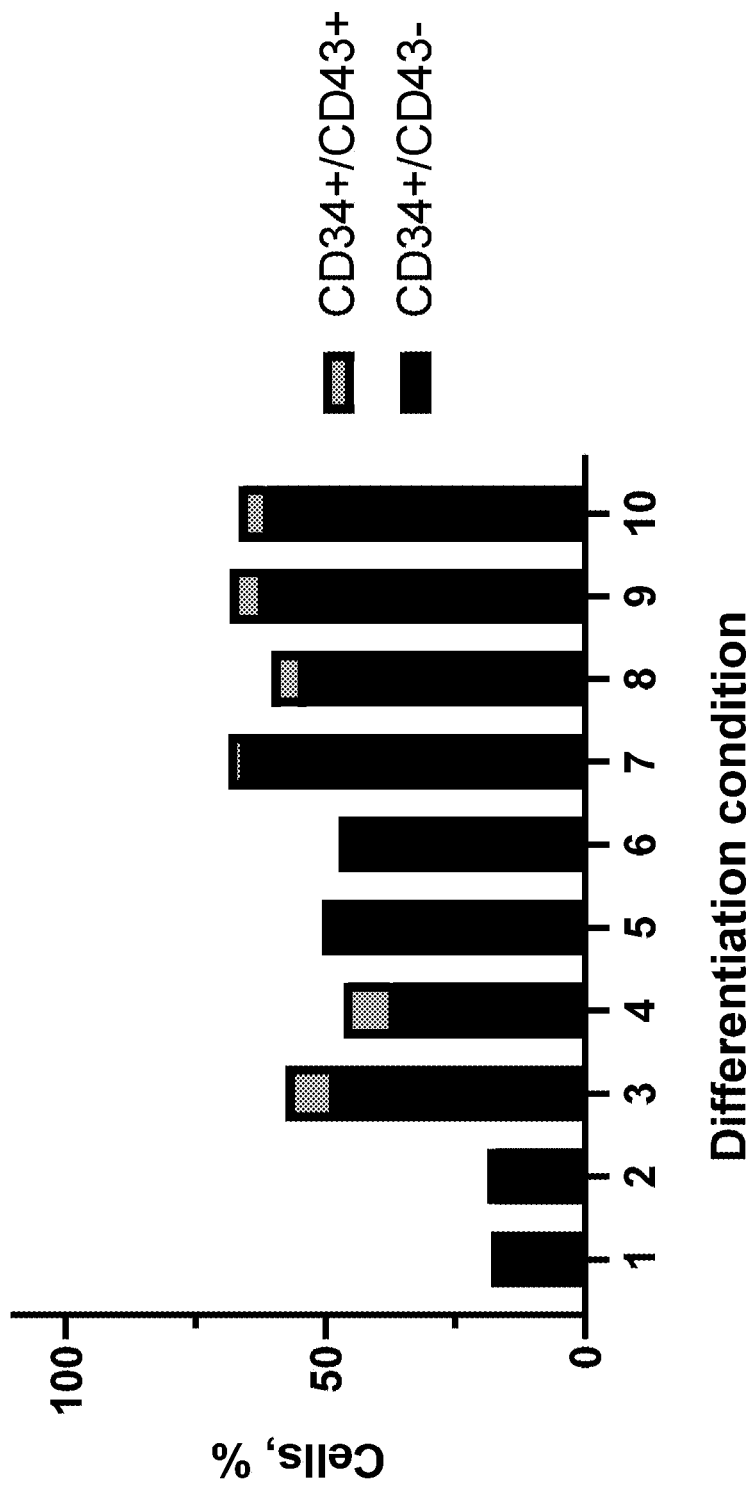
FIG. 9 shows CD34 expression in cells differentiated with the components listed in FIG. 8.

FIG. 9 shows temporal modulation of WNT signaling with small molecules promotes CD34+ cell induction in Day 6 aggregates. All conditions with adding Activin A, CHIR-99021 or their combinations followed by their inhibitors (conditions 3 to 10) yielded 2-3 times higher percentage of CD34+ cells compared to basic SpinEB protocol condition without adding Activin A or CHIR-99021 (conditions 1 and 2). The highest expression of CD34+ cells was observed in Activin A and CHIR combination conditions (conditions 7-10 on the graph).

Figure 10:
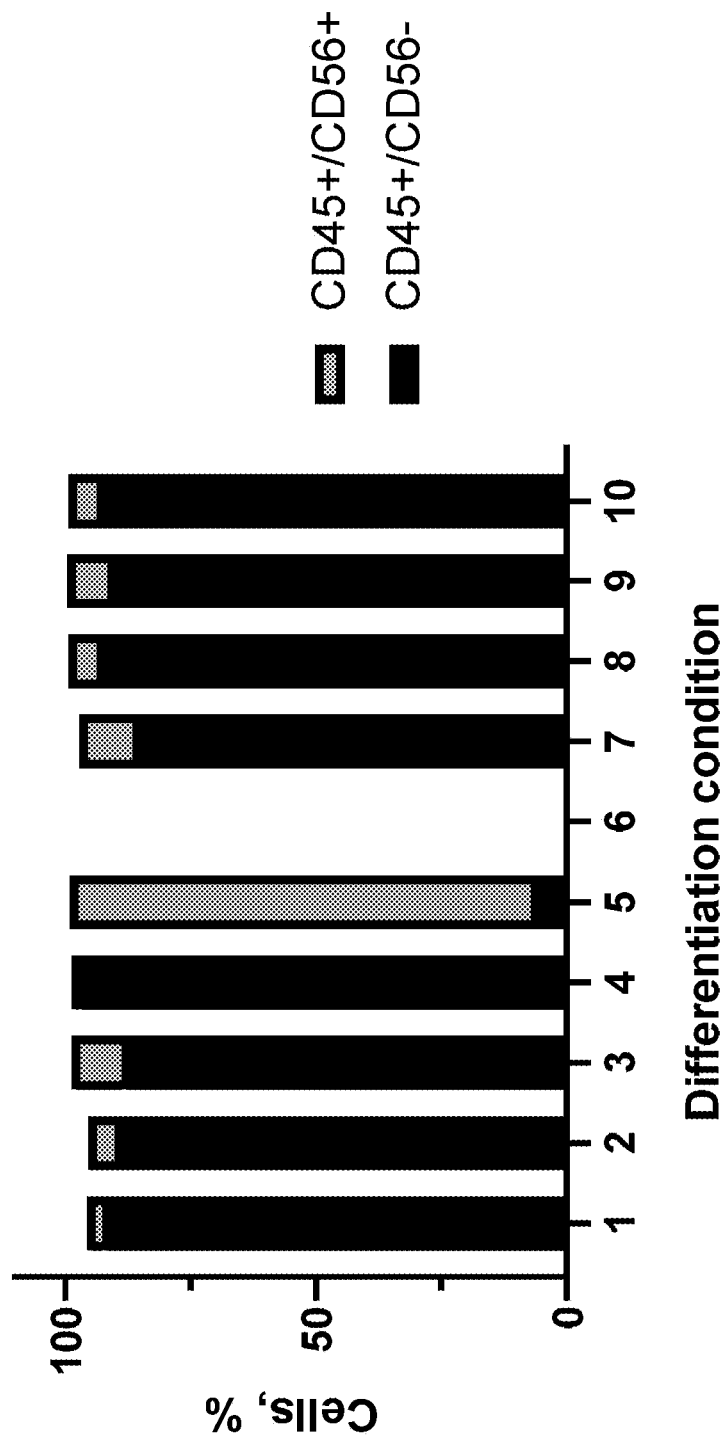
FIG. 10 shows CD45 and CD56 expression in cells differentiated with the components listed in FIG. 8.

For iPSC-HSPC differentiation optimization, CD45/CD56 expression on day 28 was measured (FIG. 10). The HSPC cells on day 6 were further differentiated to iNK in the StemPro-34-based differentiation media Table 12) in the presence of IL7, IL15, SCF, Flt3L, (IL3 was added for days 6-14 only). FIG. 10 shows that early modulation of WNT signaling with small molecule affected the later stage iNK induction. The highest CD56+ percentage was observed with adding CHIR-99021 alone (condition #5). However, it was not an optimal condition as the single cells production and expansion was lower than in conditions in the presence of Activin A molecule (data not shown). Due to low CD56+ cells formation on day 28, the HSPC to iNK differentiation conditions was optimized.

TABLE 12

StemPro media composition

| Stem Pro-34 - based media | Company | Catalog # | Stock | Add, mL |
|---|---|---|---|---|
| Stem Pro-34 SFM | Gibco | 10640-019 | | 500 |
| StemPRO-34 Nutrient Supplement | Gibco | 10641-025 | | 13 (all) |
| NEAA | Gibco | 11140-050 | 100x | 5 |
| L-GLUTAMINE | Gibco | 2503008 | 100x | 5 |
| β-MERCAPTOETHANOL | Gibco | 21985-023 | | 0.5 |
| Ascorbic Acid | Sigma | A8960 | 1% | 2.5 |

Example 4: APEL Medium Formulation Testing

Figure 11:
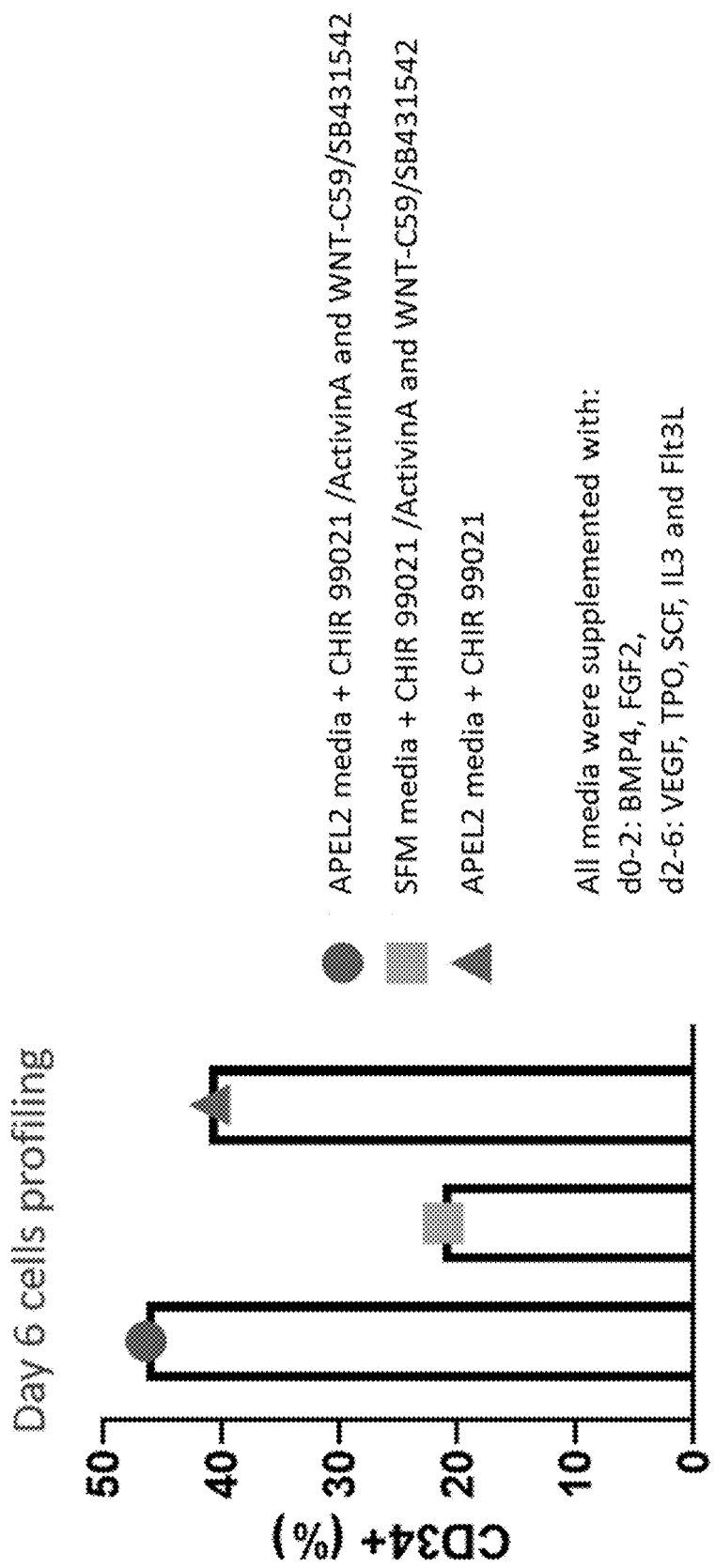
FIG. 11 shows percent of CD34+ expression in cells after Day 6 of differentiation cultured in APEL media or Stemflex media (SFM) with CHIR and/or Activin A (AA).

This Example examines the use of an APEL medium formulation (components listed in Table 13) instead of a commercially available modified APEL2, (Stem Cell Technologies) media with CHIR and/or Activin A. Day 6 cells were profiled for CD34 expression (FIG. 11). In this example commercially available APEL2 media in combination with Activin A, CHIR-99021 followed by WNT-C59 and SB431542 showed the highest yield of CD34+ cells on day 6 (FIG. 11) as well as single cells on day 14 onward (data not shown). This proves APEL2 as an effective media for HSPC formation. The APEL medium formulated in Table 12 promoted formation of CD34+ cells although less efficiently compared to APEL2, which indicated that the recipe could be further optimized.

TABLE 13

APEL medium formulation

| Component | Media |
|---|---|
| IMDM | 50% |
| Ham's F12 (Gibco) | 50% |
| Chemically Defined Lipid Concentrate | 1% |
| ITS-X (Gibco) | 1% |
| GlutaMAX (Gibco) | 2 mM |
| 1-thioglycerol (Sigma-Aldrich) | 450 µM |
| Ascorbic acid (Sigma-Aldrich) | 50 µg/mL |
| Human albumin (CSL Behring) | 0.5% |
| Polyvinyl alcohol (PVA) | 0.05% |

Example 5: Stempro34 vs DMEM/F12 Medium

This Example investigates the use of various alternative base media that can be used for Stage II differentiation. A modified HSPC generation protocol based on APEL medium supplemented with cytokines and added Activin A, CHIR-99021, WNT-C59 and SB431542 showed to be very efficient for CD34+ HSPC formation, however further iNK differentiation efficiency was extremely low. The HSPC to iNK differentiation from day 6 further on was done in StemPro-34-based media (Table 12). Hence, the HSPC to iNK media was optimized. In this Example, the HSPC were differentiated to HSPS until day 6 as described in Example 2 (i.e., steps 1-5). On day 6 to day 21, the cells were transferred to various basal media with supplements as indicated in Table 14. Each media was supplemented with 20 ng/mL IL7, 20 ng/mL IL15, 20 ng/mL SCF, 20 ng/mL Flt3L and 5 ng/mL of IL-3 for days 6-14 and 20 ng/mL IL7, 20 ng/mL IL15, 20 ng/mL SCF, 20 ng/mL Flt3L for days 14-21 of differentiation. On day 6, the cells were transferred to various basal media with supplements as indicated in Table 14.

Figure 12:
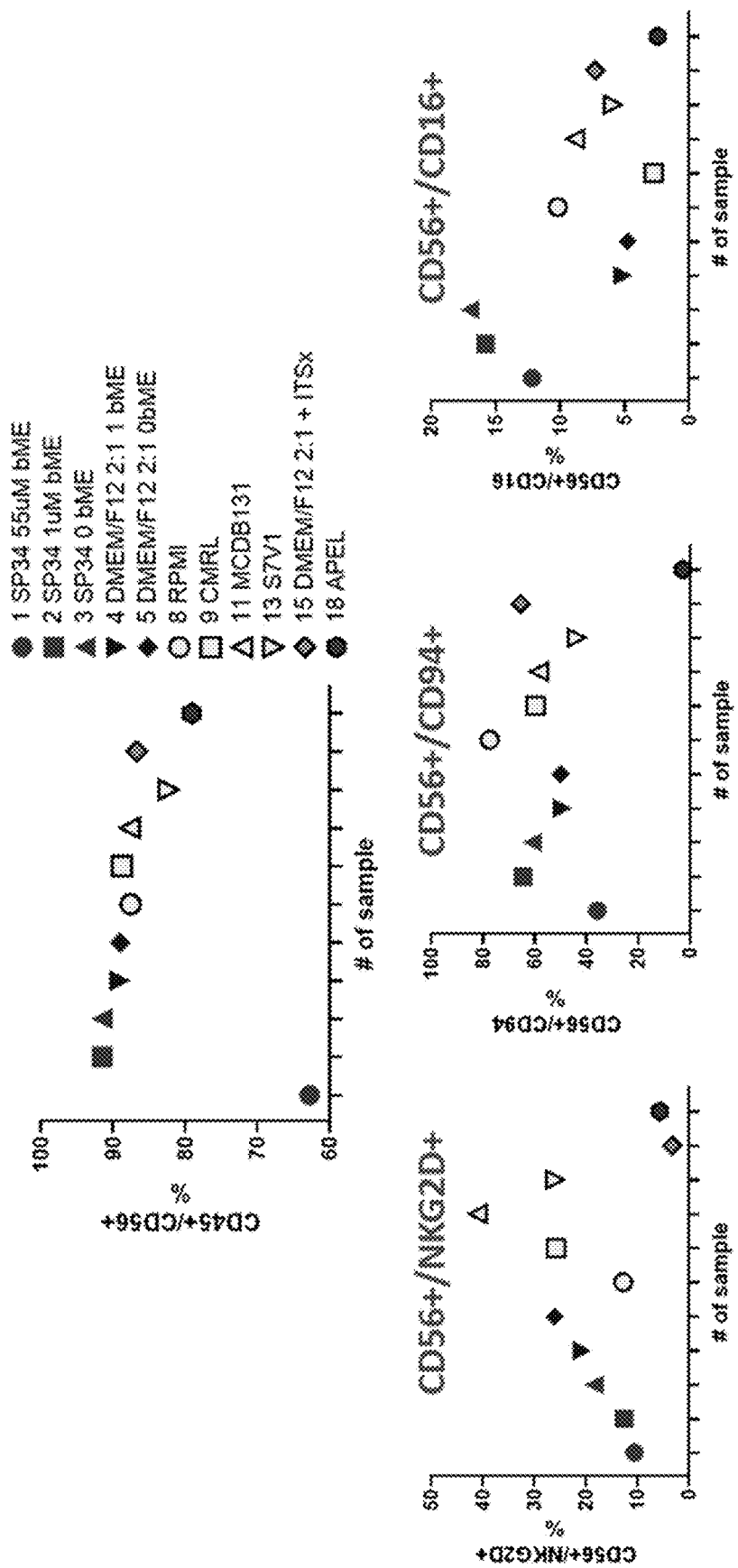
FIG. 12 shows expression of $CD45^+/CD56^+$, $CD56^+/NKG2D^+$, $CD56^+/CD94^+$, and $CD56^+/CD16^+$ cells in different mediums during Stage II of differentiation (HSPCs to NK cells).

Day 21 single cells were profiled for CD45⁺/CD56⁺, CD56⁺/NKG2D⁺, CD56⁺/CD94⁺, and CD56⁺/CD16⁺ expression (FIG. 12). This data showed β-Mercaptoethanol in StemPro-based media prevented iNK differentiation (CD45⁺/CD56⁺ cells increased from around 60% to 90%—samples #1, #2 and #3). The other basal media were comparable in the efficiency of iNK induction on day 21. The DMEM/F12 2:1 basal media was chosen due to its price and higher availability for scale up production.

TABLE 14

Media compositions

| No of sample (FIG. 12) | Basal media | Supplements (L-glucose (L-glu), ascorbic acid (AcsAc), β-Mercaptoethanol (bME), Sodium Selenate (NaSe), ethanolamine (EthAmine), human serum (H. Serum)) |
|---|---|---|
| 1 | StemPro34 | L-glu, AcsAc, NEAA, bME 55 μM |
| 2 | StemPro34 | L-glu, AcsAc, NEAA, bME 1 μM |
| 3 | StemPro34 | L-glu, AcsAc, NEAA, bME 0 μM |
| 4 | DMEM/F12 2:1 | H. Serum, L-glu, AcsAc, NaSe, EthAmine, bME 1 μM |
| 5 | DMEM/F12 2:1 | H. Serum, L-glu, AcsAc, NaSe, EthAmine, bME 0 μM |
| 8 | RPMI | H. Serum, L-glu, AcsAc, NaSe, EthAmine, bME 0 μM |
| 9 | CMRL | H. Serum, L-glu, AcsAc, NaSe, EthAmine, bME 0 μM |
| 11 | MCDB131 | H. Serum, L-glu, AcsAc, NaSe, EthAmine, bME 0 μM |
| 13 | S7V1 | H. Serum, L-glu, AcsAc, NaSe, EthAmine, bME 0 μM |
| 15 | DMEM/F12 2:1 | H. Serum, AcsAc, ITS-x |
| 18 | APEL-2 | |

Example 6: Design of Experiment (DoE) I

This Example reports the identification of optimized concentrations for certain components in the base media. A design of Experiment (DoE) study was performed to determine the concentrations of zinc sulfate, P3-mercaptoethanol, human serum, and glucose that would provide the most differentiation and increased number of cells at differentiation day 20. These factors were selected based on known chemical/biological effects of them in affect general cell proliferation and differentiation. Potential positive/negative involvement of 0-mercaptoethanol, zinc ion, human serum, and glucose in NIK cell or lymphocyte cell proliferation, killer cell receptor function, and cytotoxicity have been previously reported. There were no known studies conducted on testing optimal range of these factors in NK cell induction from HSPC.

Figure 13:
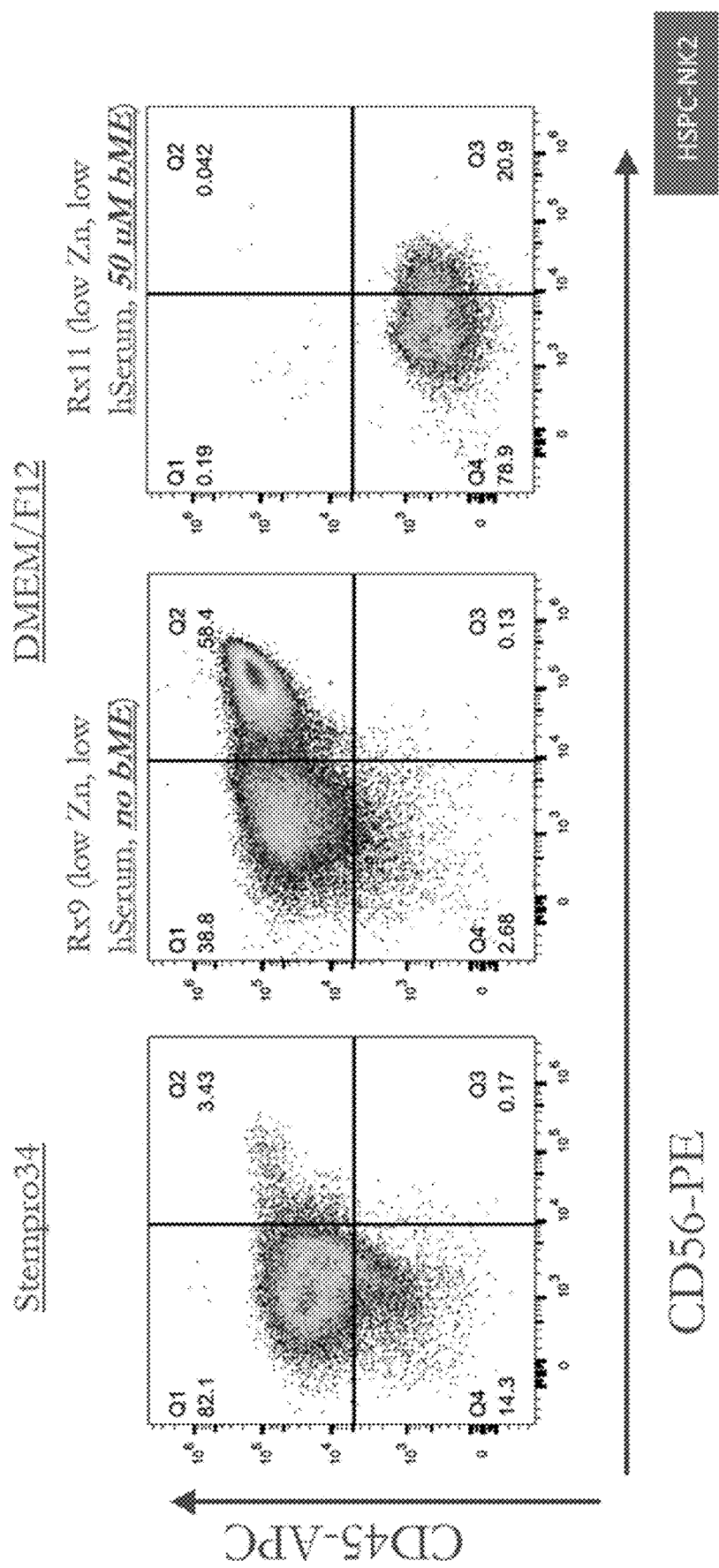
FIG. 13 shows expression of CD45 and CD56 in differentiating cells cultured with or without 50 μM β-mercaptoethanol (bME) on iNK cell induction.

To determine the effects of β-mercaptoethanol on differentiation, CD45⁺ and CD56+ expression was measured in cells cultured in Stempro34 media, DMEM/F12 media with low zinc, low human serum, and no β-mercaptoethanol (bME), or DMEM/F12 media with low zinc, low human serum, and 50 μM β-mercaptoethanol. FIG. 13 shows the negative effect of 3-mercaptoethanol on iNK cell induction.

Figure 14:
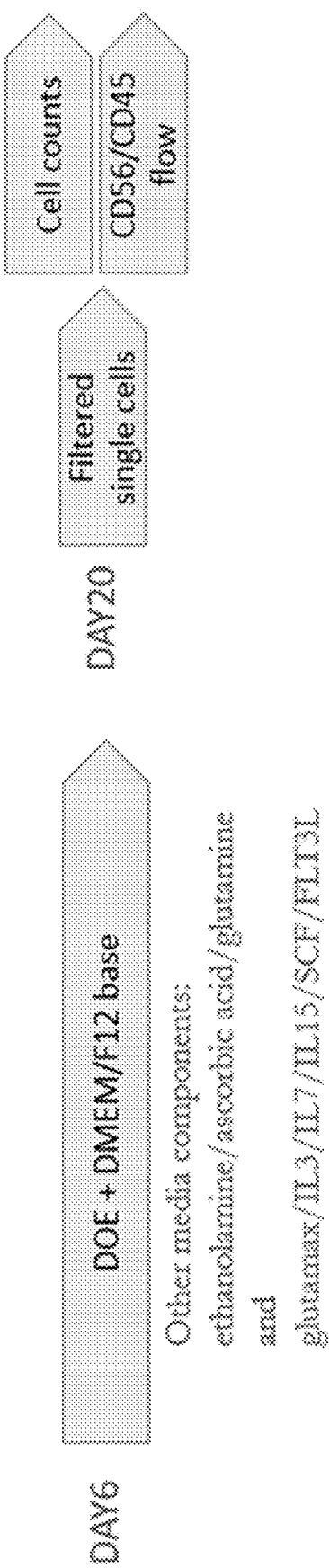
FIG. 14 shows DoE (Design of Experiment) I design. DoE experiments were carried out from day 6 to day 20.

FIG. 14 shows an example of the steps of the DoE experiments and Table 15 lists the variables tested in the DoE and the previous reported concentrations. FIG. 15 shows the conditions and yields.

TABLE 15

Dose concentrations for media compositions

| | Range of variability | |
|---|---|---|
| Variable | Low range | High range |
| Zinc sulfate | 1.7 μM | 20 μM |
| β-mercaptoethanol | 0 | 50 μM |
| Human serum | 2% | 20% |
| Glucose | 8 mM | 20 mM |

Example 7: DoE II

Figure 17:
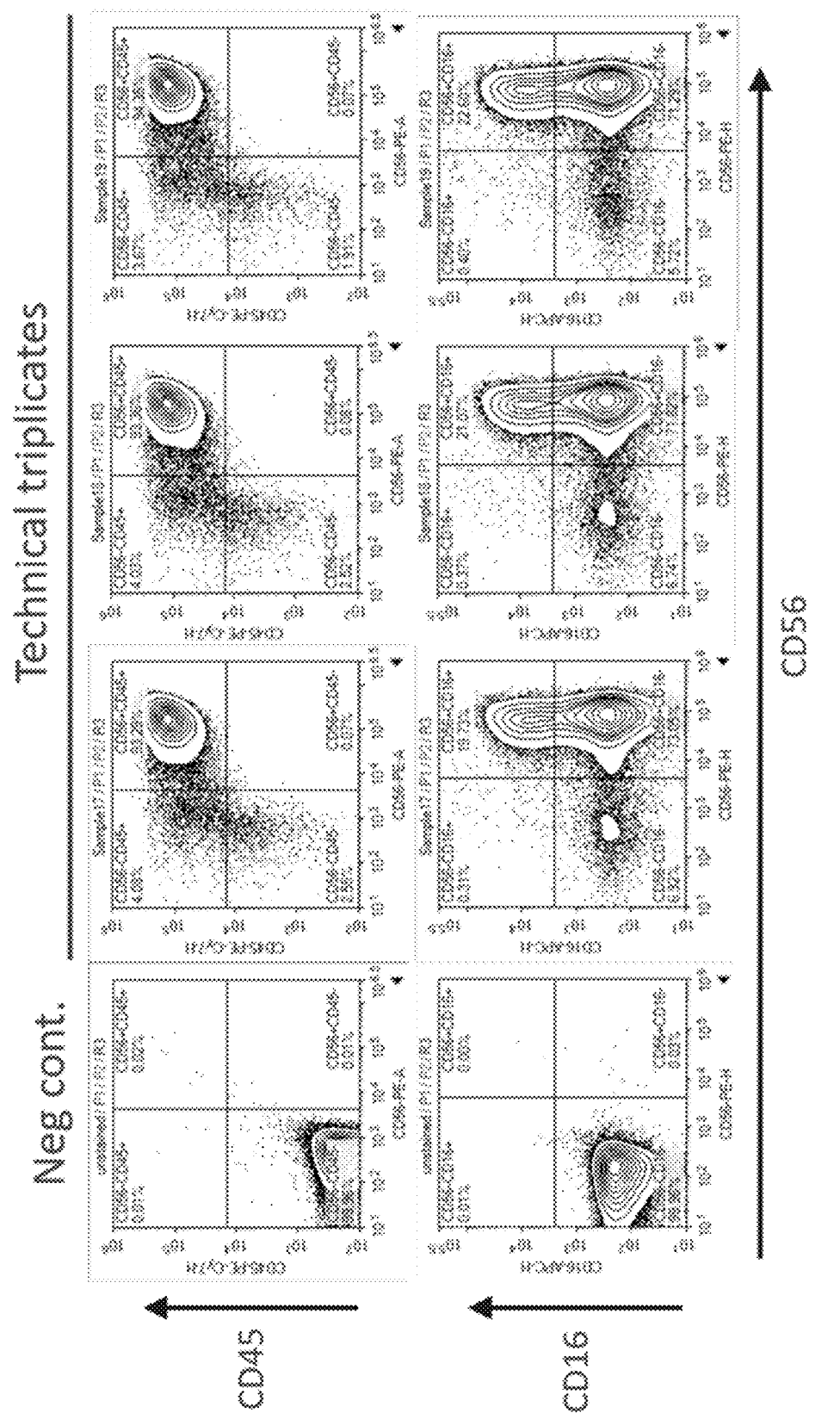
FIG. 17 shows day 20 flow cytometry analysis of CD45, CD56, and CD16 expression of the DoE II experiments 17-19 from FIG. 16.

The results from DoE I indicated the direction of effects of the different variables with zinc sulfate, human serum, and glucose having a positive effect whereas β-mercaptoethanol having a negative effect. A second DoE experiment (DoE II) was subsequently performed to further optimize the concentrations of zinc, β-mercaptoethanol, human serum albumin, and glucose. Table 16 lists the testing range of the variables and the resulting optimal conditions that meet all three criteria of maximizing CD56⁺/CD45⁺, CD45⁺, and CD56⁺/CD16⁺ expressing cell yields from DoE II. FIG. 16 shows the individual conditions and cell yields. FIG. 17 shows CD45, CD16, and CD56 expression of day 20 cells conducted in replicates using conditions at center points as listed in FIG. 17. By day 20, >99% of the population are CD45⁺ blood cells and >90% of the population are CD56⁺ CD45⁺ iNKs.

TABLE 16

Dose concentrations for media compositions

| | Testing Range | | Optimal conditions | Previously reported conditions |
|---|---|---|---|---|
| Variable | Lower Limit | Upper Limit | | |
| Glucose | 25 mM | 40 mM | 27.1 mM | 12.5 mM or >17 mM |
| Zinc sulfate | 25 μM | 40 μM | 37.9 μM | ~1.7 μM |
| Human serum | 20% | 40% | 31.4% | 15% |
| β-mercaptoethanol | 0 | 7.5 μM | 1 μM | 1-24 μM |

Example 8: Marker Expression Comparing 15% (AP1.0) vs 31% (DOE Optimized) Human Serum Concentration This example reports the profiling of surface markers of Day 30 iNK cells differentiated using DoE optimized protocol. The profiling was performed using the surface marker kit Human Cell Surface Marker Screening Panel (Cat no 560747, BD bioscience). As shown in Table 17, Day 30 iNIK cells differentiated using DoE optimized protocol expressed iNK markers CD16, CD45, CD56, CD94, NKP46 and NK P44 at levels comparable to Day 28-35 iNK differentiated using aligned protocol as seen in FIGS. 3B and 3F).

TABLE 17 iNK markers in DOE optimized cells

| CD surface marker | Day 30 DOE optimized surface marker % |
|---|---|
| 16 | 5.42 |
| 45 | 99.93 |
| 56 | 97.75 |
| 94 | 41.86 |
| 335 (NCR1, NKP46) | 83.78 |
| 336 (NKP44) | 66.06 |

Figure 18:
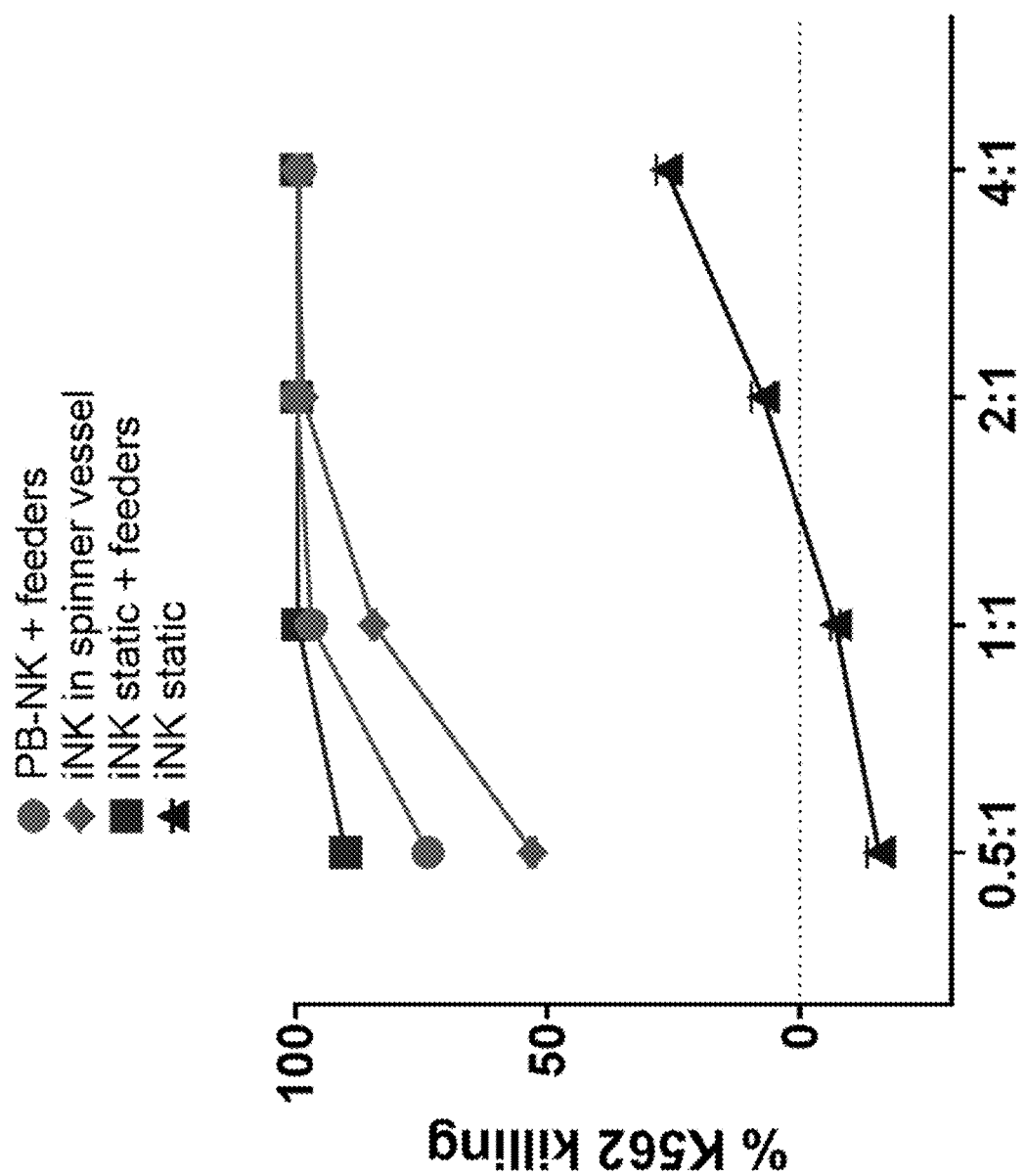
FIG. 18 shows a comparison of iNK cell cytotoxicity against K562 cells generated in rotating spinner vessels versus static conditions and compared to NK cells derived from peripheral blood (PB-NK).

Example 9: Feeder Vs Feeder-Free Culture (Rotating Spinner Vessel Vs Static Conditions This Example reports the comparison of utilizing rotating spinner vessels to generate suspension cells versus static conditions to generate aggregates. iNK cells were generated in rotating spinner vessels and compared to PB-NK cultured on feeder cells and iNK cells derived from cells grown under static conditions and expanded with or without feeder cells. Day 29 iNK cells were collected for killing assay (FIG. 18). For this, K562-GFP were incubated with iNK or PB-NK effector at different ratios as indicated for 36 hours. After incubation, the cells were spun, and resuspended in 175 µl media containing SyTox Blue at a 1:1000 concentration. 25 µL of countbright beads per well were added. The plate was read using the Flow cytometer and 100 µL volume per well was collected for analysis. GFP-positive, SyTox Blue—negative target cells (live cancer cells) and countbright beads were selected and measured absolute events count. Total live cells were calculated as follows:

[Total Cells=((No of live GFP-positive cells)/(Bead count for that sample))/(Bead count per 50 µL/2).

The % of cell lysis was calculated using following formula:

% Cell lysis=(1−((Total Number of target Cells in Test Sample)/(Total Number of Target Cells in Control Sample))×100. iNK cells generated under static condition displayed attenuated killing ability. iNK cells expanded on K562 feeders under static condition have the highest killing capacity. iNK cells cultured in spinner vessel without feeders display comparable killing capacity as K562 feeder-expanded iNK and PB-NK. This example illustrates effective differentiation of highly cytotoxic iNK cells without using feeder cells.

Example 10: Factors Affecting Expansion and Maturation: Seeding Cell Density

This Example reports the optimization of seeding cell density to increase iNK cell expansion rates. 3.75, 5 and 10 Million starting cell populations ($0.75 \times 10^6$/mL, $1 \times 10^6$/mL and $2 \times 10^6$/mL as indicated in the FIGS. 20A, 20B, and 20C legends, respectively) each were counted and plated in 5 mL of media comprised of DMEM (Life Technologies), F12 (Life Technologies), human AB serum (Valley Biomedical), Glutamax, ascorbic acid, sodium selenite and ethanolamine supplemented with 20 ng/mL of each: IL7, IL15, SCF, Flt3L with 0, 1×, or 2× media addition. Initial starting populations seeded at $1 \times 10^6$/mL and $2 \times 10^6$/mL each expanded ~5 times over 6 days. FIG. 19A shows no refreshing media, FIG. 19B shows media added 1 time (indicated by arrow), and FIG. 19C shows media added 2 times (indicated by two arrows).

Figure 19C:
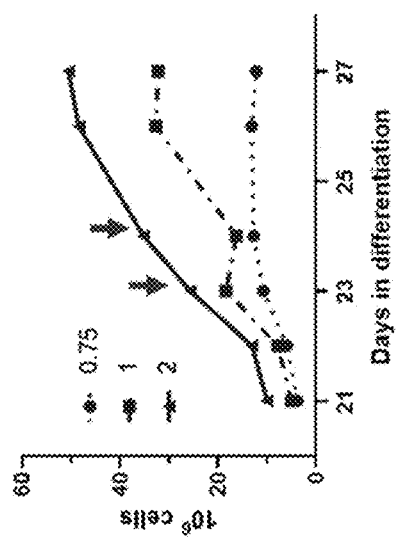
FIGS. 19A-19C show cell density and medium change schedule modulate NK cell expansion rate. 0.75, 1, and 2 represent number of millions of cells plated starting on Day 21, with no media change (FIG. 19A), one change (FIG. 19B), or two media changes (FIG. 19C). Arrows indicate when media was changed.
Figure 19B:
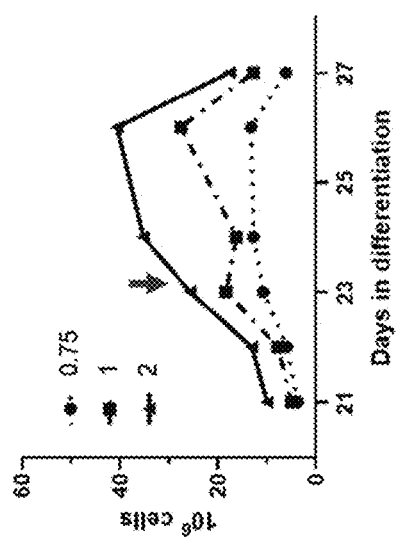
Figure 19A:
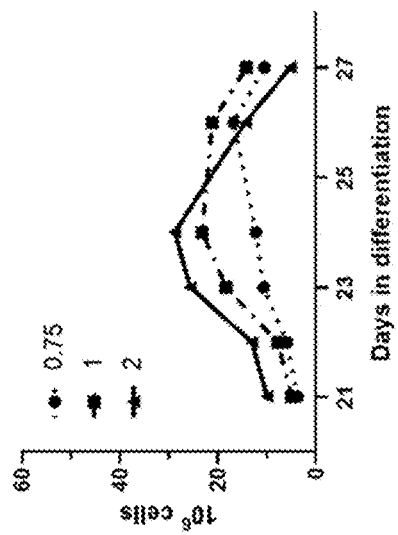

As shown in FIGS. 19A-19C, cell density modulates NK cell expansion rate. iNK cells exhausted media and slowed division at densities over $3 \times 10^6$ cells/mL. iNK cells at low cell density of ~0.75 M cells/mL did not expand as efficiently, and cell number collapsed quickly. The optimal cell concentration for continuous cells expansion was $1-2 \times 10^6$ cells/mL.

Example 11: Differentiating Stem Cells into Natural Killer Cells—Protocol 2

Figure 21:
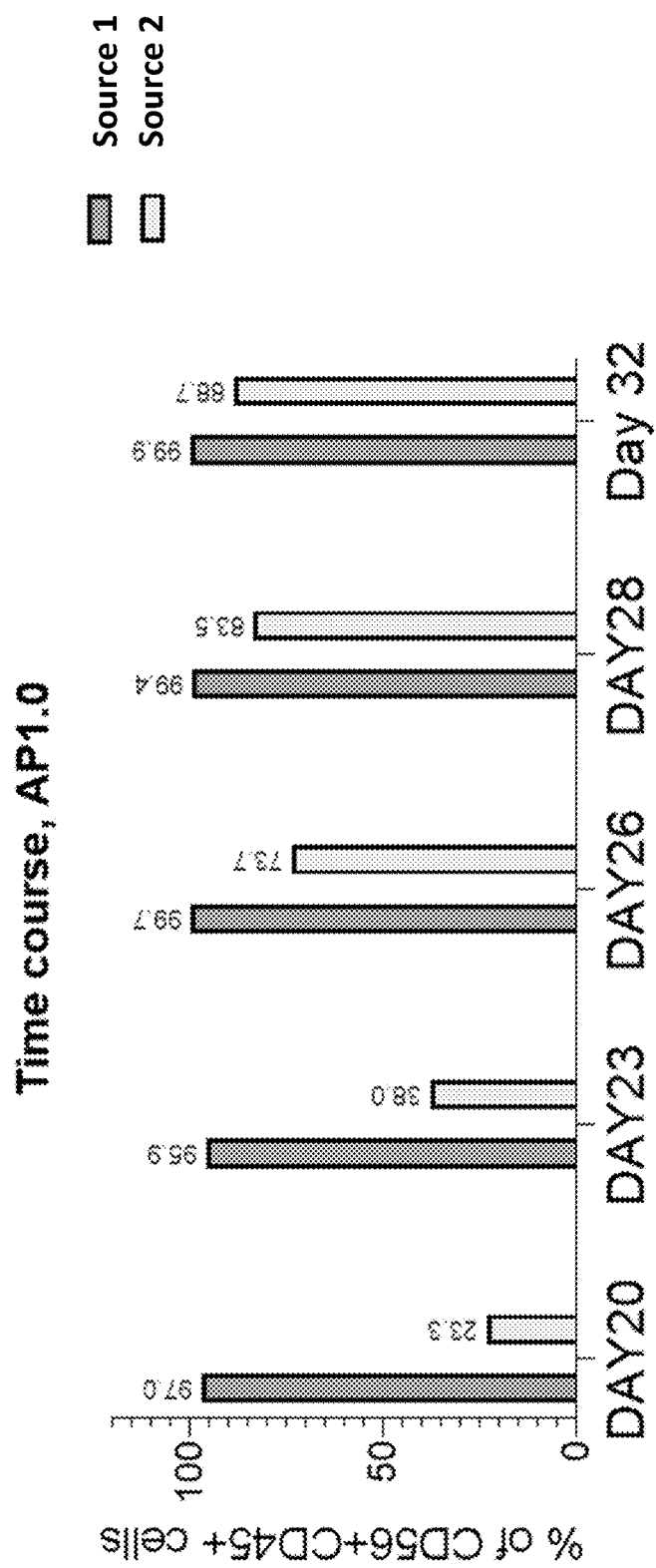
FIG. 21 shows purity of NK cells differentiated from two different sources of iPSC cells using AP.1.0, as measured at differentiation day 20, 23, 26, and 28 using flow cytometry to detect $CD56^+CD45^+$ NK cells.

It was discovered that some induced pluripotent stem (iPS) cells did not differentiate efficiently with Protocol 1 (FIG. 21). As shown in this figure, iPSC cells from two different sources were differentiated using AP.1.0 and single cells were harvested at differentiation day 20, 23, 26, and 28 for flow cytometry of $CD56^+CD45^+$ NK cells. The purity of NK cells derived from Source 2 progressively increased across time points but appeared to plateau at around day 28. Thus, Protocol 2 (also called Aligned Process 2.0 or AP2.0) was developed to differentiate these iPS cells into hematopoietic stem and progenitor cells (HSPCs) and then into natural killer (NK) cells. Prior to differentiation, frozen iPS cells were thawed and re-suspended in NK-MED-001 medium (Table 26). Flasks pre-coated with laminin-521 were used for cell culturing. Medium was changed daily using NK-MED-002 (Table 27) medium until cells were used for differentiation. As described below, in some instances NK-MED-001 and NK-MED-002 were prepared using StemFlex medium instead of StemBrew medium.

NK Cell Differentiation. iPS cells were differentiated using the following steps:

1. Day −1 (afternoon), iPSC aggregation: NK-MED-002 medium was aspirated from flasks containing iPSC and the cells were washed with DPBS (no calcium, no magnesium) (Thermo Fisher Scientific, 14190250). DPBS was aspirated and 2 mL ACCUTASE® (Innovative Cell Technologies, AT-104) was added per T25 flask (or 80 µL of ACCUTASE® per 1 cm2). Cells were incubated at 37° C. for 3-5 min (not more than 7 minutes). Accutase digested cells were diluted with cold NK-MED-002 medium to a ratio of at least 3:1 (NK-MED-002:ACCUTASE®). Cells were gently resuspended and transferred to a conical tube. Optionally, enough NK-MED-002 medium was added to cells to dilute the ACCUTASE® to a ratio of at least 1:1 and up to 4:1 (NK-MED-002:ACCUTASE®). Cells were pelleted by spinning at 20-300 g for 4 to 5 minutes and re-suspended in 10 mL of NK-MED-003 medium (Table 28). Cells were counted and the cell concentration was diluted to $1 \times 10^6$/mL. $6 \times 10^6$ cells were transferred to another tube and resuspended in a total of 6 mL of NK-MED-003 medium. The cells were transferred to 1 well of ultra-low adhesion 6-well plate (Corning, 3471) and the plate was placed on a platform shaker and rotated at 98 RPM for 18+/−2 hours (overnight).

2. At day 0, morning, at 18+/−2 hours after iPSC aggregation: The plate was rotated in a circular motion to move aggregates towards center of the well and aggregates were collected in a conical tube. Alternatively, all the aggregate solution mix was collected. Aggregates were allowed to settle for 15+/−5 minutes. Cells were resuspended in NK-MED-004 medium (Table 29). The cell number in aggregates was counted. The seeding density was adjusted as needed to resuspend $3 \times 10^5$ cells in aggregates in 2 mL NK-MED-004 medium and plated in one well of a 6-well low adhesion plate. Alternatively, for scale up, an appropriate number of cells was resuspended and transferred to a PBS spinner vessel (PBS Biotech). Seeding density tested for PBS seeding vessel was approximately 1×10⁵ cells per mL per final media volume (day 0+8 hrs). The plate was placed on a platform shaker and rotated at 98 RPM for 8 hours or the PBS spinner vessel were placed on a PBS base (PBS-MINI MagDrive Base Unit; PBS Biotech), in CO2 incubator with a rotation speed of RPM 38 to 39.

3. At day 0, afternoon, at 8 hours after NK-MED-004 medium addition: 50 mL or 250 mL per well or spinner vessel, respectively, of NK-MED-005c medium (Table 30) was added. The plate was returned to platform shaker or PBS spinner vessel to its base in the CO2 incubator and left undisturbed until day 2. NK-MED-005c medium components were 2× of their final concentration, therefore it was added to cells in NK-MED-004 at a 1:1 volume ratio.

4. At day 2: NK-MED-005c medium was replaced with NK-MED-006 medium (Table 31).

5. At day 4: NK-MED-006 medium was replaced with NK-MED-007 medium (Table 32).

6. At day 6: NK-MED-007 medium was replaced with NK-MED-008b medium (Table 33), or alternatively: starting at day 6, medium with all aggregates and single cells was transferred into an appropriate volume centrifuge conical tube. Cells were centrifuged and resuspended in NK-MED-008b medium and placed back into original wells and onto platform shaker, or into original vessels and onto base, and returned for continued culture.

7. At day 10: Half or full media change was made with NK-MED-008b medium.

8. At day 14: Full media change was made with NK-MED-009b medium (Table 34).

9. At day 17: One-third media change was made NK-MED-009b medium and then a full media change was made with NK-LED-009b medium.

From day 20 onwards: Starting at day 20, single cell density was estimated from cell culture. A full media change was made with NIK-MED-010 medium (Table 35) and cell density adjusted to within 0.8 to 1.5×10⁶ cells/mL. A full media change with NK-MED-00 medium and adjustment of cell density to 0.8-1.5×10⁶ cells/mL was performed every 2-3 days from day 20 to 30.

TABLE 26

Medium composition for NK-MED-001

| Component | Working Conc. | Volume[1] | Stock Conc. |
|---|---|---|---|
| StemBrew Basal Media | 90% | 980 mL | 100% |
| StemBrew Supplement | 1X | 20 mL | 50X |
| Thiazovivin (Biological Industry, 1226056-71-8) | 2 µM | 200 µL | 10 mM |

[1]Volumes are approximate to get the desired concentration.

TABLE 27

Medium composition for NK-MED-002

| Component | Working Conc. | Volume[1] | Stock Conc. |
|---|---|---|---|
| StemBrew Basal Media | 90% | 980 mL | 100% |
| StemBrew Supplement | 1X | 20 mL | 50X |

[1]Volumes are approximate to get the desired concentration.

TABLE 28

Medium composition for NK-MED-003

| Component | Working Conc. | Volume[1] | Stock Conc. |
|---|---|---|---|
| StemBrew Basal | 90% | 979 mL | 100% |
| StemBrew Supplement | 1X | 20 mL | 50X |
| Thiazovivin (Biological Industry, 1226056-71-8) | 10 µM | 1000 µL | 10 mM |

[1]Volumes are approximate to get the desired concentration.

TABLE 29

Medium composition for NK-MED-004

| Component | Working Conc. | Volume[1] | Stock Conc. |
|---|---|---|---|
| STEMdiff APEL 2 Medium (STEMCELL Technologies, 05275) | 100% | 999 mL | 100% |
| rh BMP-4 (Peprotech, 120-05ET) | 30 ng/mL | 300 µL | 100 µg/mL |
| Thiazovivin (Biological Industry, 1226056-71-8) | 10 µM | 1000 µL | 10 mM |

[1]Volumes are approximate to get the desired concentration.

TABLE 30

Medium composition for NK-MED-005c

| Component | Working Conc. | Volume[1] | Stock Conc. |
|---|---|---|---|
| STEMdiff APEL 2 Medium (STEMCELL Technologies, 05275) | 100% | 998 mL | 100% |
| rh BMP-4 (Peprotech, 120-05ET) | 30 ng/mL | 300 µL | 100 µg/mL |
| rh FGF2 (Peprotech, 100-18C-1MG) | 100 ng/mL | 1000 µL | 100 µg/mL |
| CHIR-99021 (Selleckchem, S1263) | 7 µM | 700 µL | 10 mM |
| Activin-A (R&D Systems, 338-AC-01M/CF | 5 ng/mL | 100 µL | 50 µg/mL |

[1]Volumes are approximate to get the desired concentration.

TABLE 31

Medium composition for NK-MED-006b

| Component | Working Conc. | Volume[1] | Stock Conc. |
|---|---|---|---|
| STEMdiff APEL 2 Medium (STEMCELL Technologies, 05275) | 100% | 997 mL | 100% |
| rh FGF2 (Peprotech, 100-18C-1MG) | 20 ng/mL | 200 µL | 100 µg/mL |
| rh VEGF165 (Peprotech, 100-20-1MG) | 20 ng/mL | 200 µL | 100 µg/mL |
| rh TPO (Peprotech, 300-18) | 20 ng/mL | 200 µL | 100 µg/mL |
| rh SCF (Peprotech, 300-07) | 100 ng/mL | 1000 µL | 100 µg/mL |
| rh IL-3 (Peprotech, 200-03-100UG) | 40 ng/mL | 400 µL | 100 µg/mL |

TABLE 31-continued

Medium composition for NK-MED-006b

| Component | Working Conc. | Volume[1] | Stock Conc. |
|---|---|---|---|
| rh Flt3L (Peprotech, 300-19) | 20 ng/mL | 200 μL | 100 μg/mL |
| SB431542 (Selleckchem, S1067) | 5 μM | 500 μL | 10 mM |

[1]Volumes are approximate to get the desired concentration.

TABLE 32

Medium composition for NK-MED-007

| Component | Working Conc. | Volume[1] | Stock Conc. |
|---|---|---|---|
| STEMdiff APEL 2 Medium (STEMCELL Technologies, 05275) | 100% | 998 mL | 100% |
| rh FGF2 (Peprotech, 100-18C-1MG) | 20 ng/mL | 200 μL | 100 μg/mL |
| rh VEGF165 (Peprotech, 100-20-1MG) | 20 ng/mL | 200 μL | 100 μg/mL |
| rh TPO (Peprotech, 300-18) | 20 ng/mL | 200 μL | 100 μg/mL |
| rh SCF (Peprotech, 300-07) | 100 ng/mL | 1000 μL | 100 μg/mL |
| rh IL-3 (Peprotech, 200-03-100UG) | 40 ng/mL | 400 μL | 100 μg/mL |
| rh Flt3L (Peprotech, 300-19) | 20 ng/mL | 200 μL | 100 μg/mL |

[1]Volumes are approximate to get the desired concentration.

TABLE 33

Medium composition for NK-MED-008b

| Component | Working Conc. | Volume[1] | Stock Conc. |
|---|---|---|---|
| DMEM (high glucose, GlutaMAX) (Thermo Fisher, 10566016) | 50.3% | 503 mL | 100% |
| F-12 with GlutaMAX (Thermo Fisher, 31765035) | 28% | 280 mL | 100% |
| GlutaMAX (Thermo Fisher, 35050079) | 1X | 10 mL | 100X |
| Glucose* | 4.66 mM | 4.2 mL | 1110 mM |
| Human AB serum (Valley Biomedical Inc, HP1022) | 20% | 20 mL | 100% |
| Zinc sulfate (Millipore Sigma, Z0251) | 36.2 μM | 978 μL | 37 mM |
| Ethanolamine (Millipore Sigma, E0135) | 50 μM | 3 μL | 16.6M |
| Ascorbic acid (Fisher Scientific, NC0762606) | 15 μg/mL | 15 μL | 10 mg/mL |
| Sodium selenite (Millipore Sigma, S9133-1MG) | 5 ng/mL | 50 μL | 100 μg/mL |
| rh IL-3 (Peprotech, 200-03-100UG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 20 mM (accounting for glucose in DMEM (high glucose) medium, F12 supplement and added glucose provided here).
[1]Volumes are approximate to get the desired concentration.

TABLE 34

Medium composition for NK-MED-009b

| Component | Working Conc. | Volume[1] | Stock Conc. |
|---|---|---|---|
| DMEM (high glucose, GlutaMAX) (Thermo Fisher, 10566016) | 50.3% | 503 mL | 100% |
| F-12 with GlutaMAX (Thermo Fisher, 31765035) | 28% | 280 mL | 100% |
| GlutaMAX (Thermo Fisher, 35050079) | 1X | 10 mL | 100X |
| Glucose* | 4.66 mM | 4.2 mL | 1110 mM |
| Human AB serum (Valley Biomedical Inc, HP1022) | 20% | 20 mL | 100% |
| Zinc sulfate (Millipore Sigma, Z0251) | 37 μM | 978 μL | 37 mM |
| Ethanolamine (Millipore Sigma, E0135) | 50 μM | 3 μL | 16.6M |
| Ascorbic acid (Fisher Scientific, NC0762606) | 15 μg/mL | 1500 μL | 10 mg/mL |
| Sodium selenite (Millipore Sigma, S9133-1MG) | 5 ng/mL | 50 μL | 100 μg/mL |
| rh IL-7 (Peprotech, 200-07) | 20 ng/mL | 200 μL | 100 μg/mL |
| rh Flt3L (Peprotech, 300-19) | 15 ng/mL | 150 μL | 100 μg/mL |
| rh IL-15 (Peprotech, 200-15) | 15 ng/mL | 150 μL | 100 μg/mL |
| rh SCF (Peprotech, 300-07) | 20 ng/mL | 200 μL | 100 μg/mL |

*Total glucose concentration in medium is 20 mM (accounting for glucose in DMEM (high glucose) medium, F12 supplement and added glucose provided here).
[1]Volumes are approximate to get the desired concentration.

TABLE 35

Medium composition for NK-MED-010

| Component | Working Conc. | Volume[1] | Stock Conc. |
|---|---|---|---|
| DMEM (high glucose, GlutaMAX) | 60.5% | 605 mL | 100% |
| F-12 with GlutaMAX | 28% | 280 mL | 100% |
| GlutaMAX | 1X | 10 mL | 100X |
| Glucose* | 2.33 mM | 2.1 mL | 1110 mM |
| Human AB serum | 10% | 100 mL | 100% |
| Zinc sulfate | 37 μM | 978 μL | 37 mM |
| Ethanolamine | 50 μM | 3 μL | 16.6 M |
| Ascorbic acid | 15 μg/mL | 1500 μL | 10 mg/mL |
| Sodium selenite | 5 ng/mL | 50 μL | 100 μg/mL |
| Nicotinamide | 6.5 mM | 6.5 mL | 1000 mM |
| rh IL-7 | 10 ng/mL | 100 μL | 100 μg/mL |
| rh Flt3L | 7.5 ng/mL | 75 μL | 100 μg/mL |
| rh IL-15 | 15 ng/mL | 150 μL | 100 μg/mL |
| rh SCF | 20 ng/mL | 200 μL | 100 μg/mL |

*Total glucose concentration in medium is 20 mM (accounting for glucose in DMEM (high glucose) medium, F12 supplement and added glucose provided here).
[1]Volumes are approximate to get the desired concentration.

Example 12: DOE IV—Optimizing Stage 2 of AP2.0

This Example reports the identification of optimized concentrations for certain components in the media used in Stage 2 of the AP2.0 differentiation protocol. A design of Experiment (DoE) study was performed to determine the concentrations ascorbic acid, 2-mercaptoethanol, human serum and glucose that would provide the most differentiation and increased number of cells at differentiation day 21.

Differentiation day 6 iPSC cells (Source 2) derived from AP.1.0 were seeded into 6-well plates and differentiated until day 21 with various combinations and concentrations of DoE test variables including ascorbic acid, 2-mercaptoethanol, human serum and glucose, as indicated in FIG. 22. Data on cell yield, iNK purity and CD16+ iNK % were collected. Basic information on cell line and differentiation conditions for DoE IV are provided in Table 36 below. Recommended concentrations used in stage 2 iNK differentiation partially adopted in AP2.0 are provided in Table 37. Human serum concentration was up-adjusted to 20% in finalized NK-MED-008b and NK-MED-009b media used in AP2.0.

TABLE 36

| Cell Line | Source 2 |
|---|---|
| Stage to optimize | 2 |
| Differentiation day | 6 to 20 |
| Readout | Day 21 |
| Media | NK-MED-008 and 009 |

TABLE 37

| | Recommended usage |
|---|---|
| bME, μM | 0 |
| Ascorbic acid, ng/mL | 15 |
| Glucose, mM | 20 |
| Human serum, % | 15 |

Example 13: DOE V— Optimizing Stage 3 of Protocol 2 (AP2.0

This Example reports the identification of optimized concentrations for certain components in the media used in Stage 3 of the AP2.0 differentiation protocol. A design of Experiment (DoE) study was performed to determine the concentrations of beta-mercaptoethanol (B-Me), nicotinamide (NAM), glucose and human serum on iNK cell yield, purity (CD56+CD45+), and various activating receptor (TRAIL), exhaustion receptor (PD1), and framework KIR receptor expression as measured at day 30.

As shown in FIG. 23, Day 20 iNK cells derived from AP1.0 were harvested and reseeded in 6-well plates to test the effect of different combination and concentrations of beta-mercaptoethanol (B-Me), nicotinamide (NAM), glucose and human serum on iNK cell yield, purity (CD56+CD45+), and various activating receptor (TRAIL), exhaustion receptor (PD1), and framework KIR receptor expression. Table 38, below, summarizes the basic information for DoE V set up. Table 39 provides recommended concentrations for each of the variables tested in DoE V. These concentrations were used to modify NK-MED-009 medium to generate NK-MED-010 medium that is being used in AP2.0

TABLE 38

| Cell Line | Source 1 |
|---|---|
| Stage to optimize | 3 |
| Differentiation day | 20 to 30 |
| Readout | Day 30 |
| Media | NK-MED-009 |

TABLE 39

| | Recommended usage |
|---|---|
| bME, μM | 0 |
| NAM, mM | 6.5 |
| Glucose, mM | 20 |
| Human Serum, % | 10 |

Figure 24A:
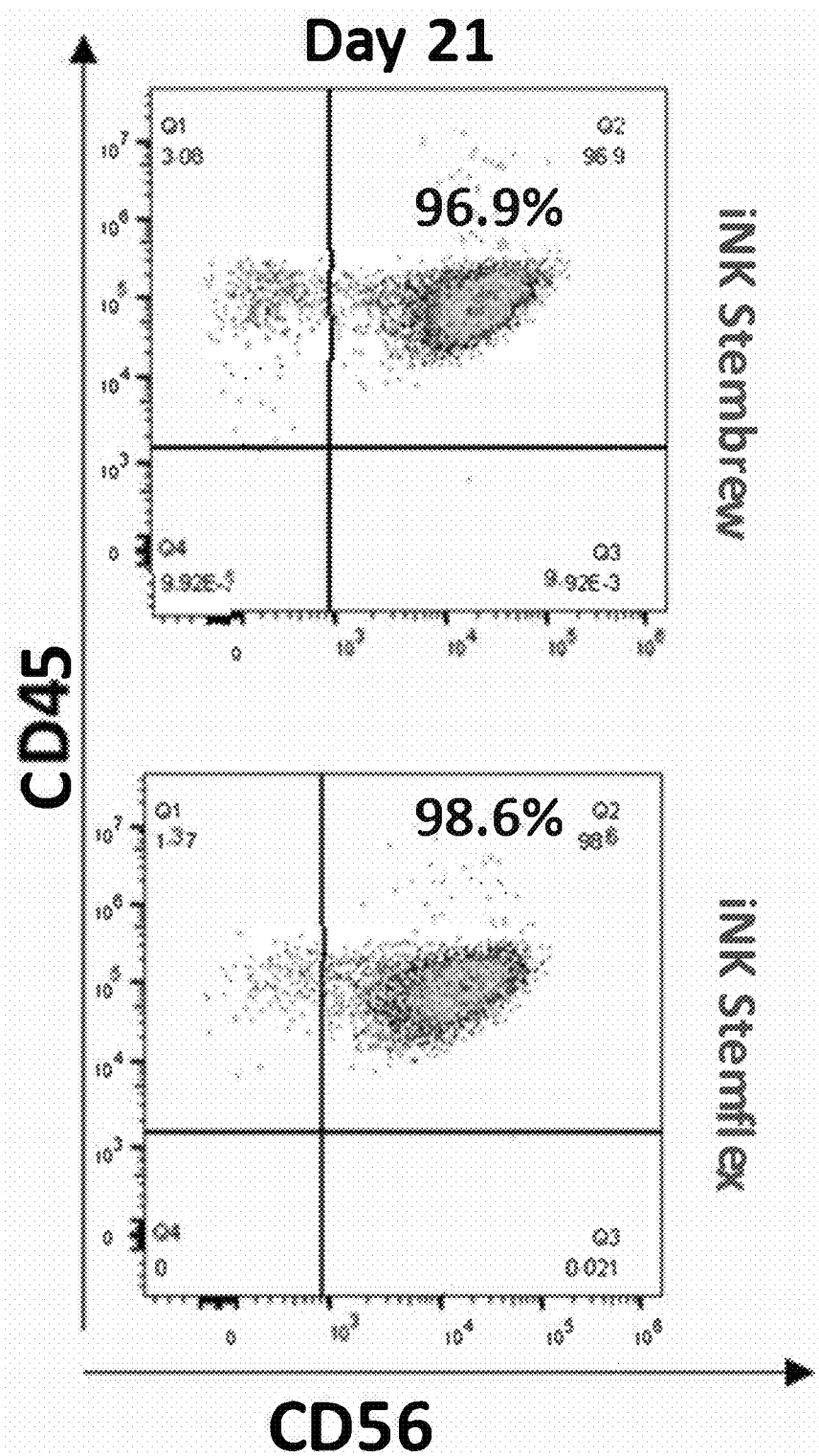
FIG. 24A shows day 21 flow cytometry analysis of CD45 and CD56 expression in differentiated cells after culturing in Stembrew or StemFlex media.
Figure 24B:
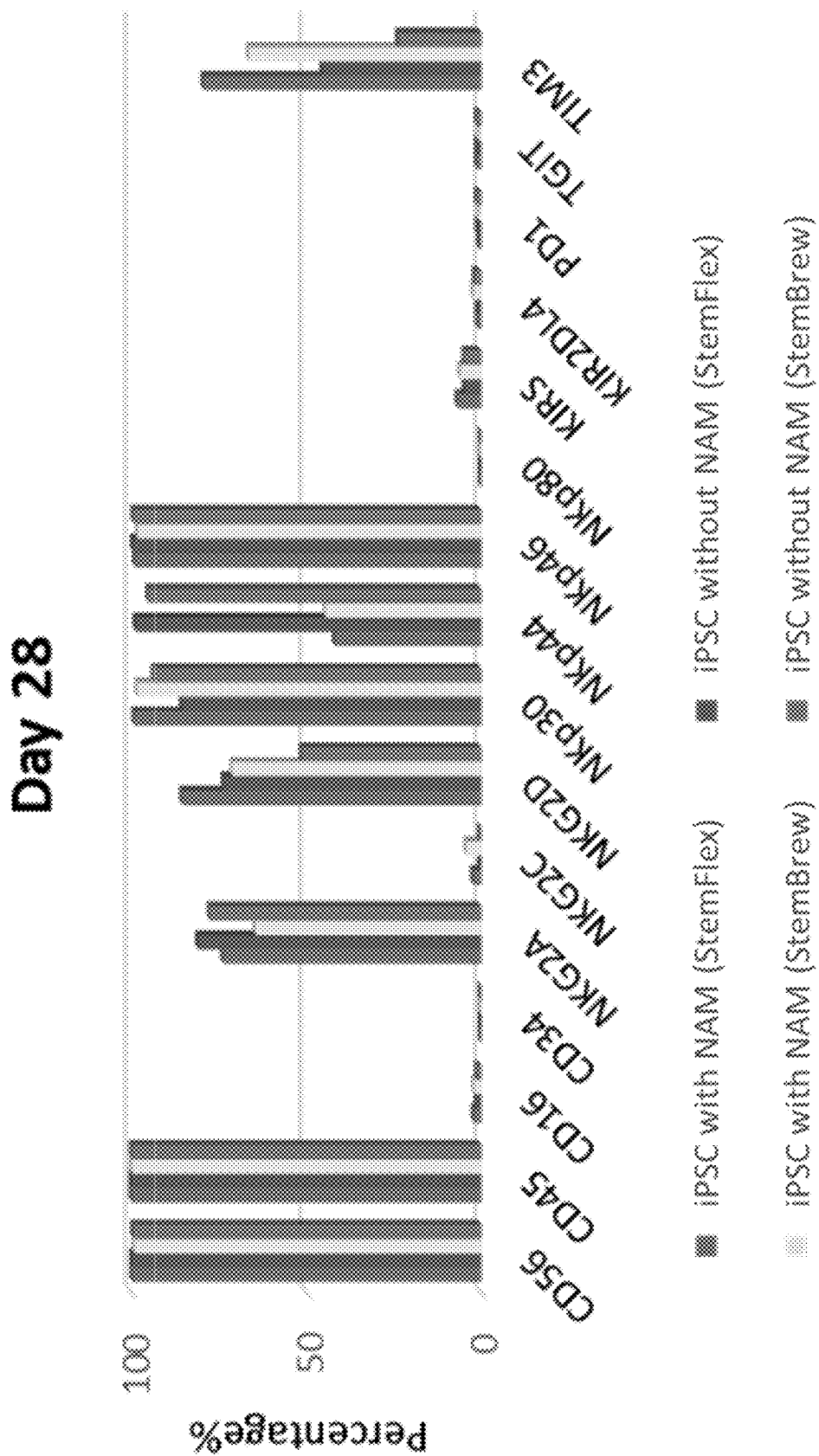
FIG. 24B shows percent of cells positive for the indicated cell markers at day 28 after differentiation in StemFlex or StemBrew media with or without nicotinamide (NAM).
Figure 24C:
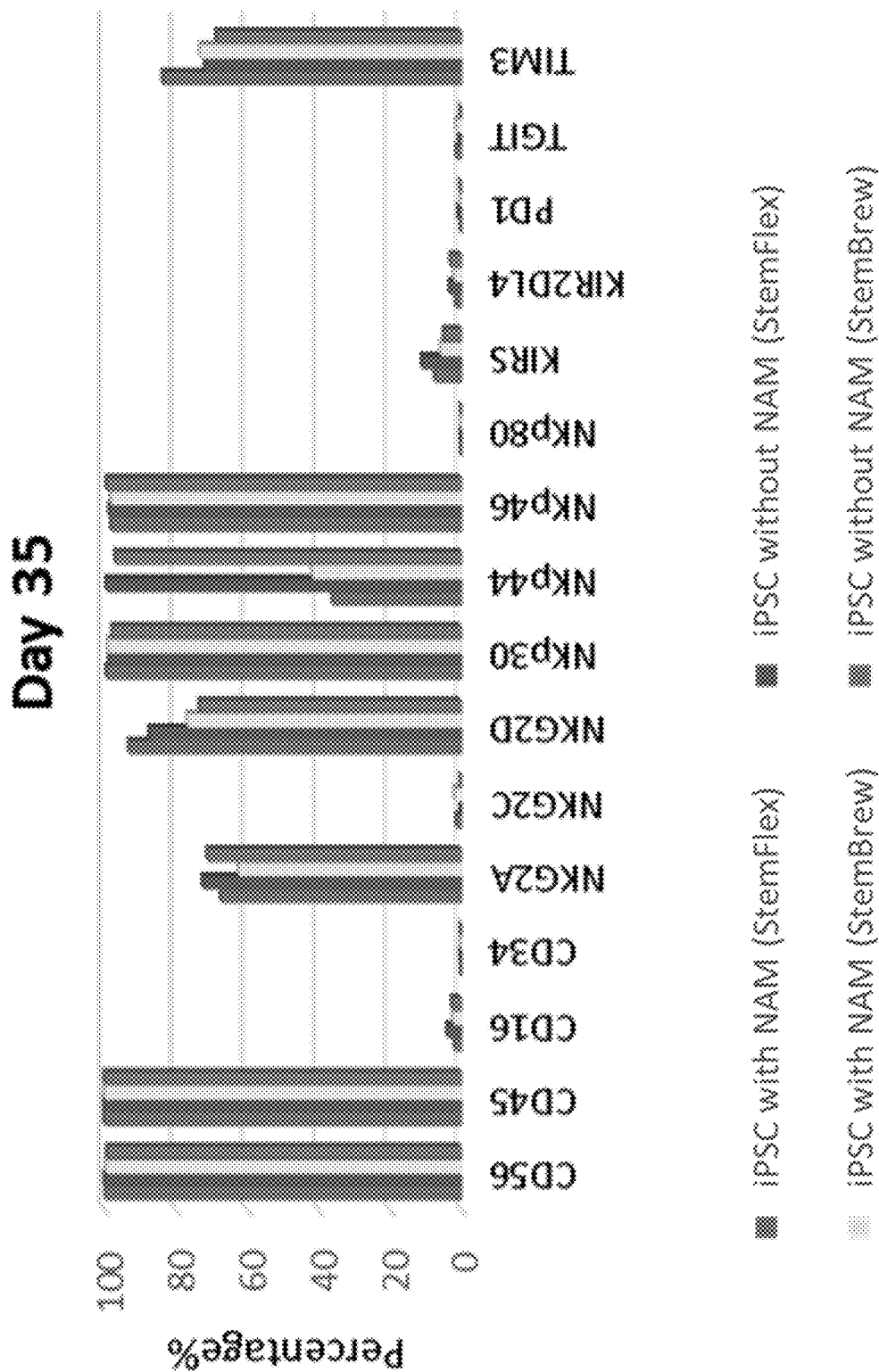
FIG. 24C shows percent of cells positive for the indicated cell markers at day 35 after differentiation in StemFlex or StemBrew media with or without nicotinamide (NAM).

Example 14: Characterization and Cytotoxicity of iNK Differentiated with Protocol 2 (AP2.0 iPSC cells were expanded in either StemFlex (Thermo Scientific) or StemMACS iPS-Brew XF, human, medium (Miltenyi) (e.g., in NK-MED-001 and NK-MED-002) and then differentiated using Protocol 2. Single cells from iNK cultures at differentiation day 21 (FIG. 24A), 28 (FIG. 24B), and 35 (FIG. 24C) were harvested for flow cytometry for the indicated markers. Inclusion and exclusion of nicotinamide (at 6.5 mM), a component in NK-MED-010 medium, was also tested for influence on iNK purity, exhaustion, and receptor expression.

Figure 25A:
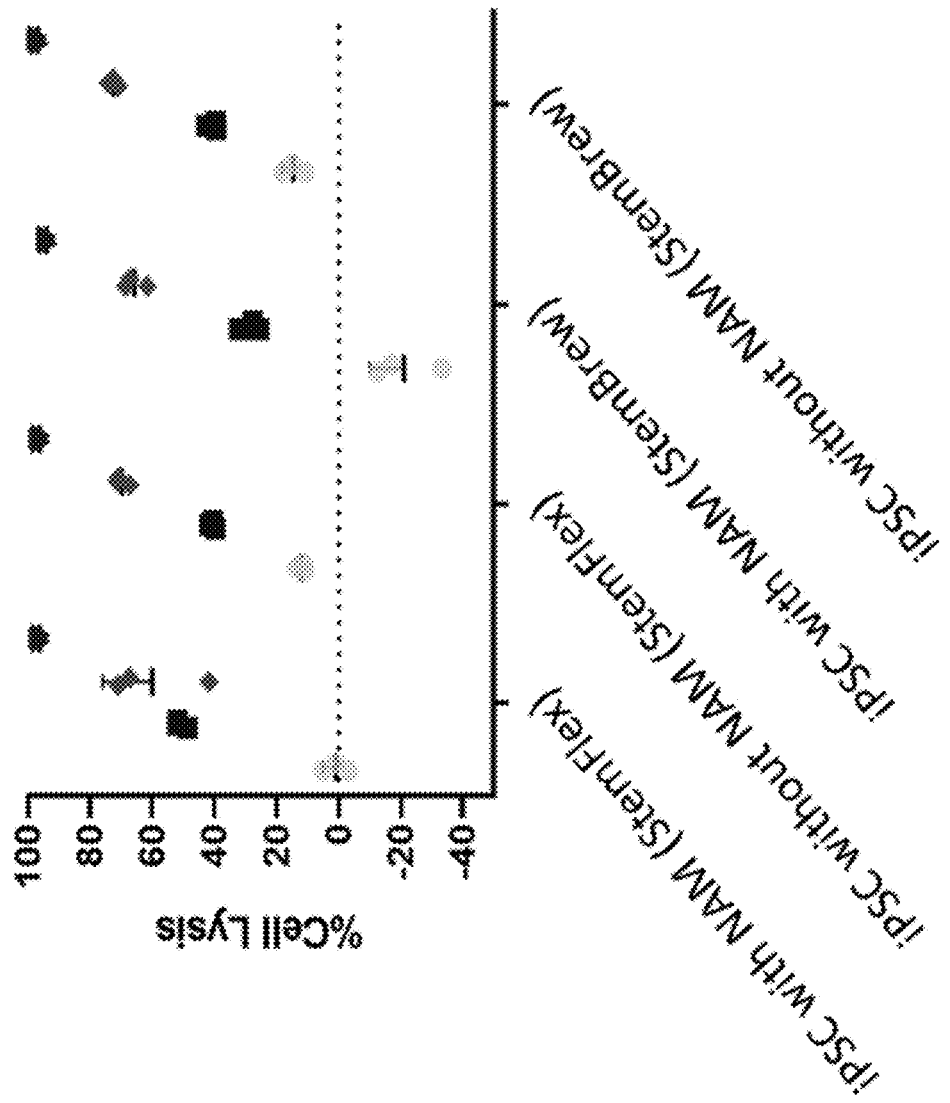
FIG. 25A shows K562 cell toxicity and FIG. 25B shows L428 cell cytotoxicity achieved in the presence of cells differentiated using StemFlex or StemBrew media with or without nicotinamide.
Figure 25B:
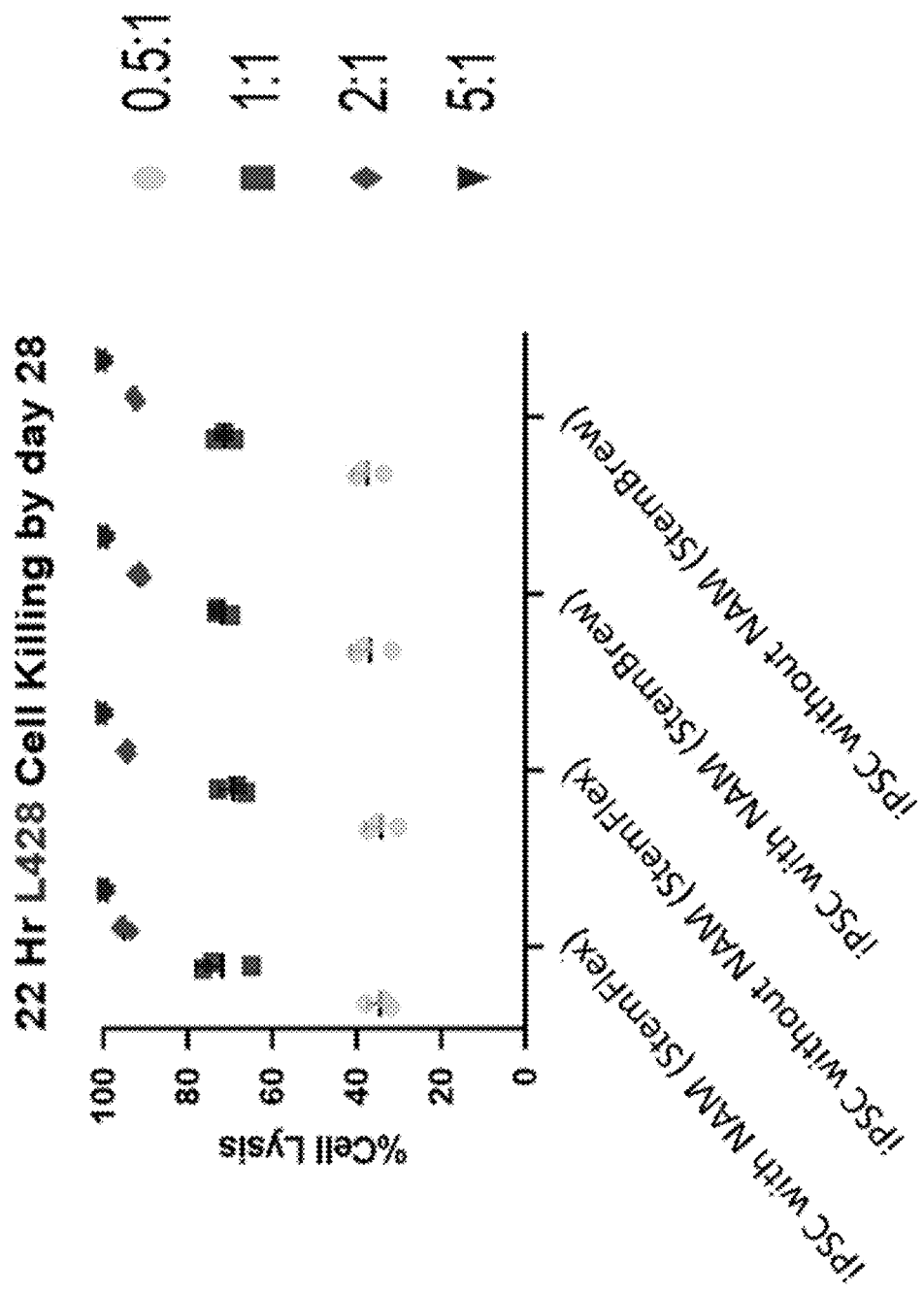

The cytotoxicity of day 28 iNK cells differentiated with AP2.0 and derived from IPSC cells expanded in StemFlex or StemMACS towards K562 cells or L428 cells was determined using a 24-hour killing assay. K562-GFP or L428GFP cells (50,000 cells per well) were incubated with iNK effector cell lines at different ratios as indicated for 22 hours before analysis by flow cytometry on FSC/SCC, FITC (GFP) and pacific blue (cell viability) channels. Inclusion and exclusion of nicotinamide (at 6.5 mM), a component in NK-MED-010 medium, was also tested for influence on iNK cytotoxicity for these cancer cell lines. iNK cells differentiated using Protocol 2 (AP2.0) displayed effective cytotoxicity against K562 (FIG. 25A) and L428 cancer cell line (FIG. 25B). Further, expansion of the precursor cells in StemFlex or StemBrew did not affect the cytotoxic potential of the derived cells.

Figure 26A:
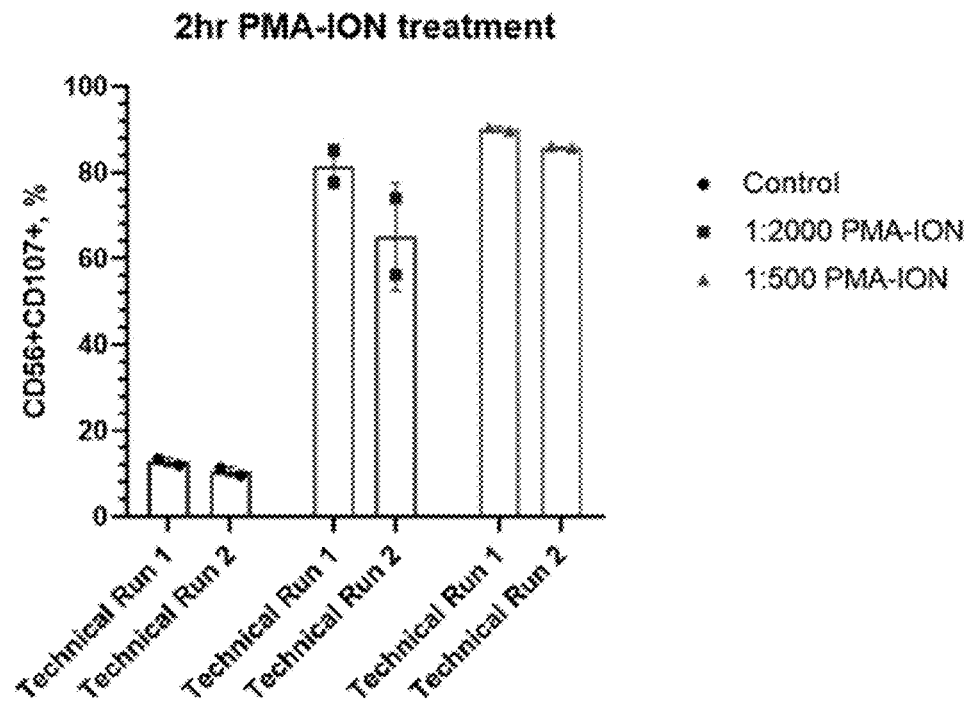
FIG. 26A shows CD107a expression dynamics and FIG. 26B shows Perforin expression dynamics upon PMA/ION stimulation of iNK derived from AP2.0.
Figure 26B:
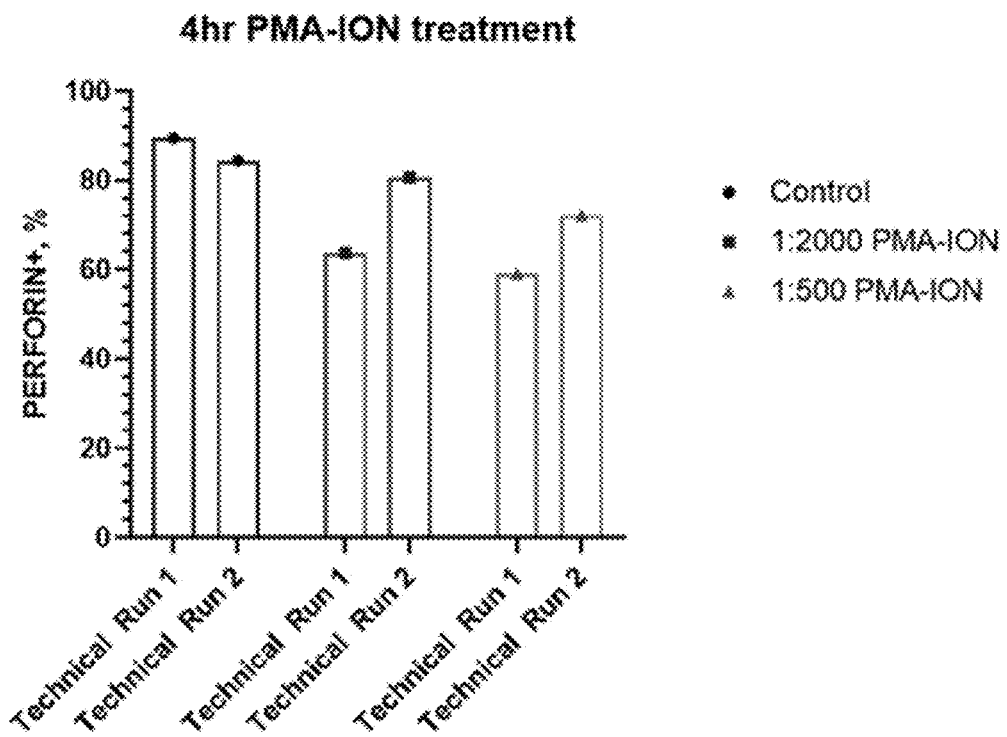

Day 28 iNK cultures were treated with propidium monoazide (PMA)/ionomycin (ION) for 2 or 4 hours at 37° C., 5% $CO_2$. The cultures were then profiled for degranulation marker CD107a (FIG. 26A) and Perforin (FIG. 26B). Induction mimics stimulation event (e.g., increase in CD107a expression and decrease in Perforin levels).

Figure 27:
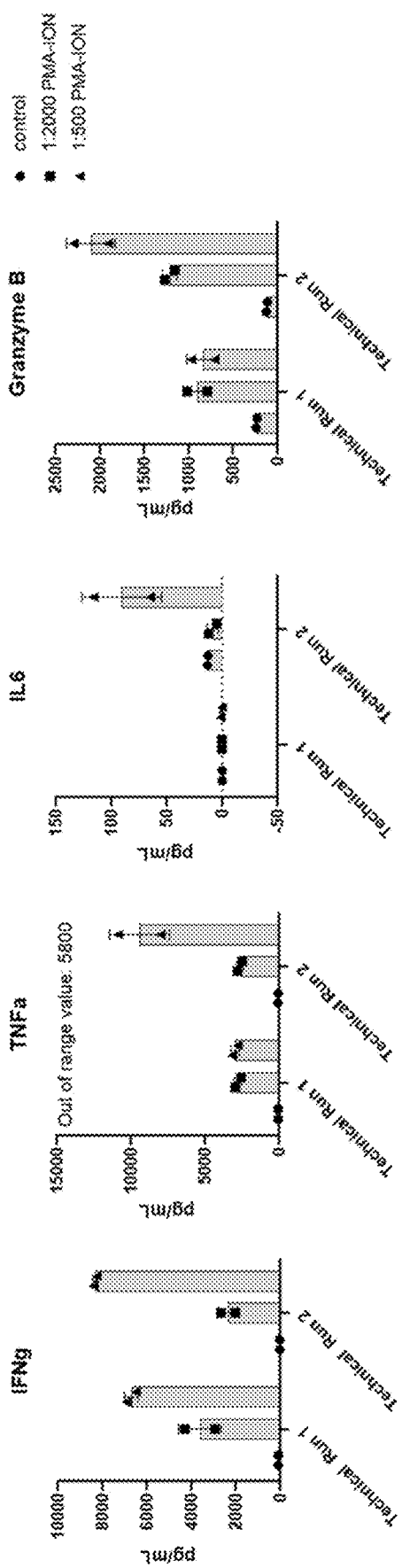
FIG. 27 presents cytokine and granzyme secretion measurements upon PMA/ION stimulation of iNK derived from AP2.0.

Day 28 iNK cultures were treated with different concentrations of PMA and ionomycin for 24 hours at 37° C., 5% $CO_2$. Cytokine and granzyme secretion into the conditioned medium from each treatment were measured using Ella multianalyte assays. Cytokine secretion of IFNg and TNFa, and the secretion of cytotoxic granzyme B were associated with the presence of PMA and ionomycin (FIG. 27).

Example 15: Aligned Process 2.0 (AP2.0) Promoted iNK Derivation Efficiency in Spinner Vessel Format iPSC cells were differentiated with AP2.0 using a spinner vessel format. Single cells were harvested at differentiation day 28 for flow cytometry for CD34, CD45, CD56, or CD16. The percentage of CD45+ cells was about 99.4% and the percentage of CD45+/CD56+ cells was about 82.6% (the percentages of CD34+CD45+ cells and CD56+CD16+ cells was about 2% or less). Data from four independent experiments.

Figure 28:
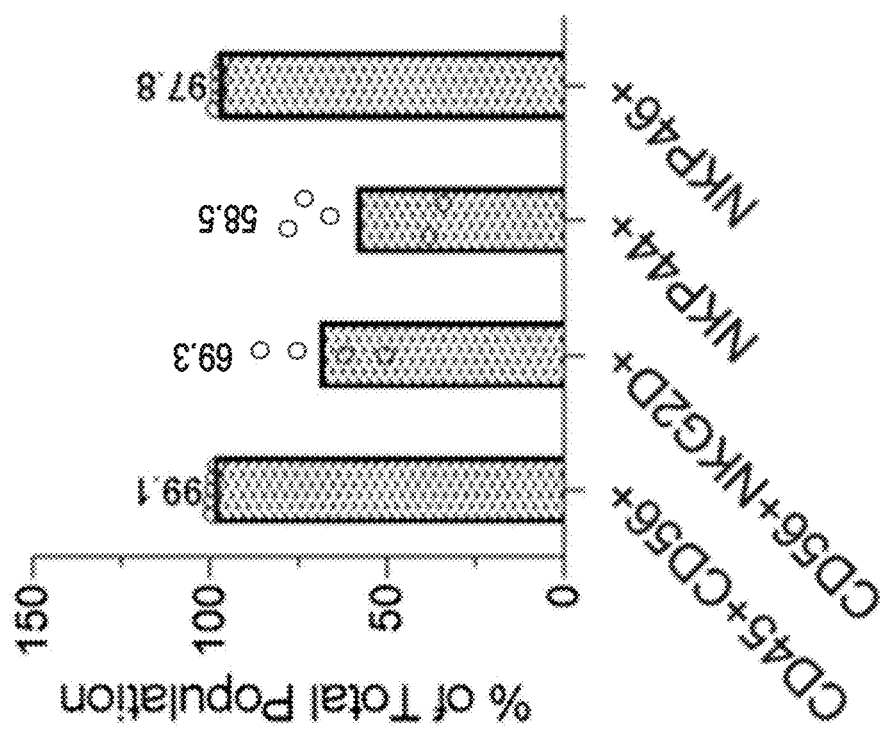
FIG. 28 presents the percentage of iNK cells expressing the indicated markers.

The iNK cultures approached purity at day 28 and expressed high level of NK specific activating receptors NKG2D, NKP44 and NKP46 (FIG. 28). Data from three independent experiments.

Figure 29A:
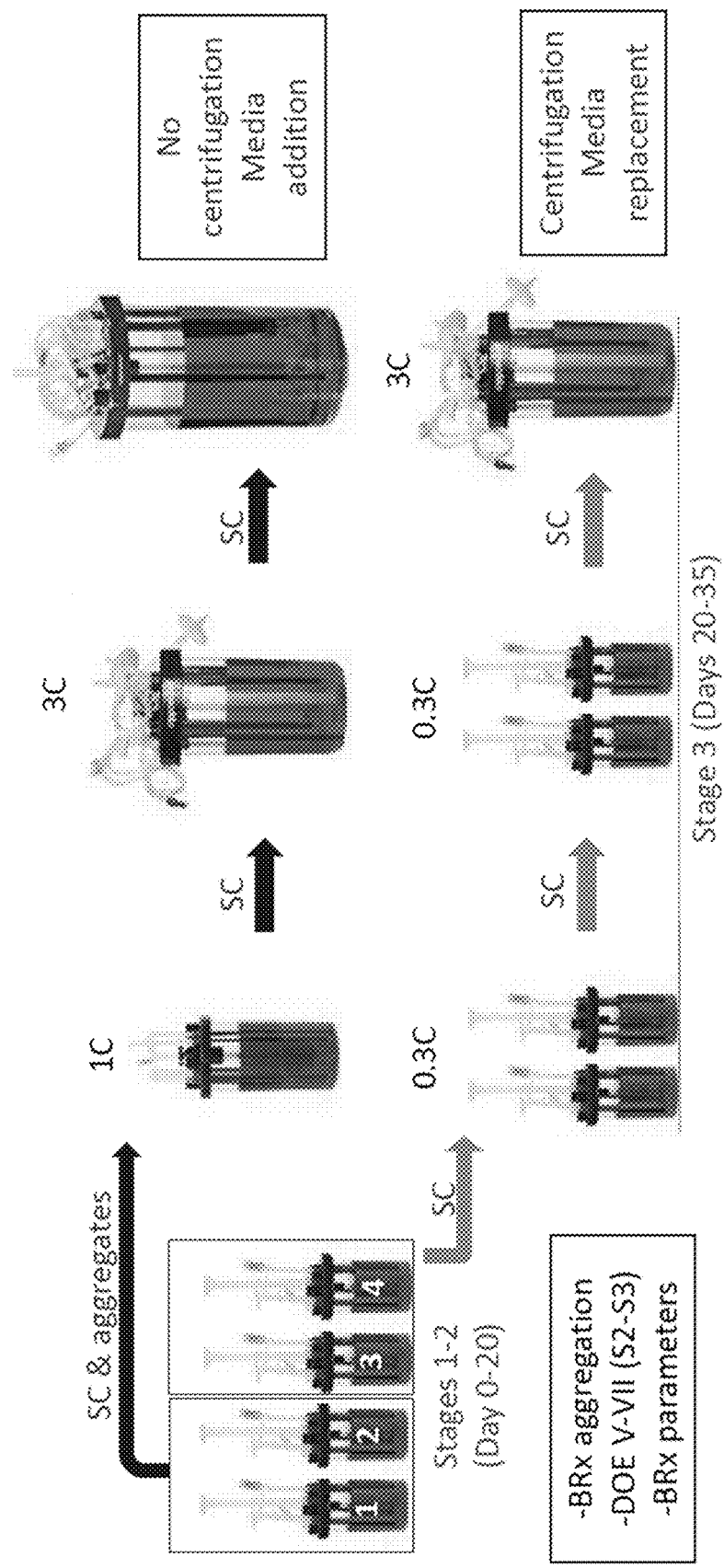
FIG. 29A shows a diagram of a cell differentiation process (using Aligned Process 2) in a bioreactor setting.
Figure 29B:
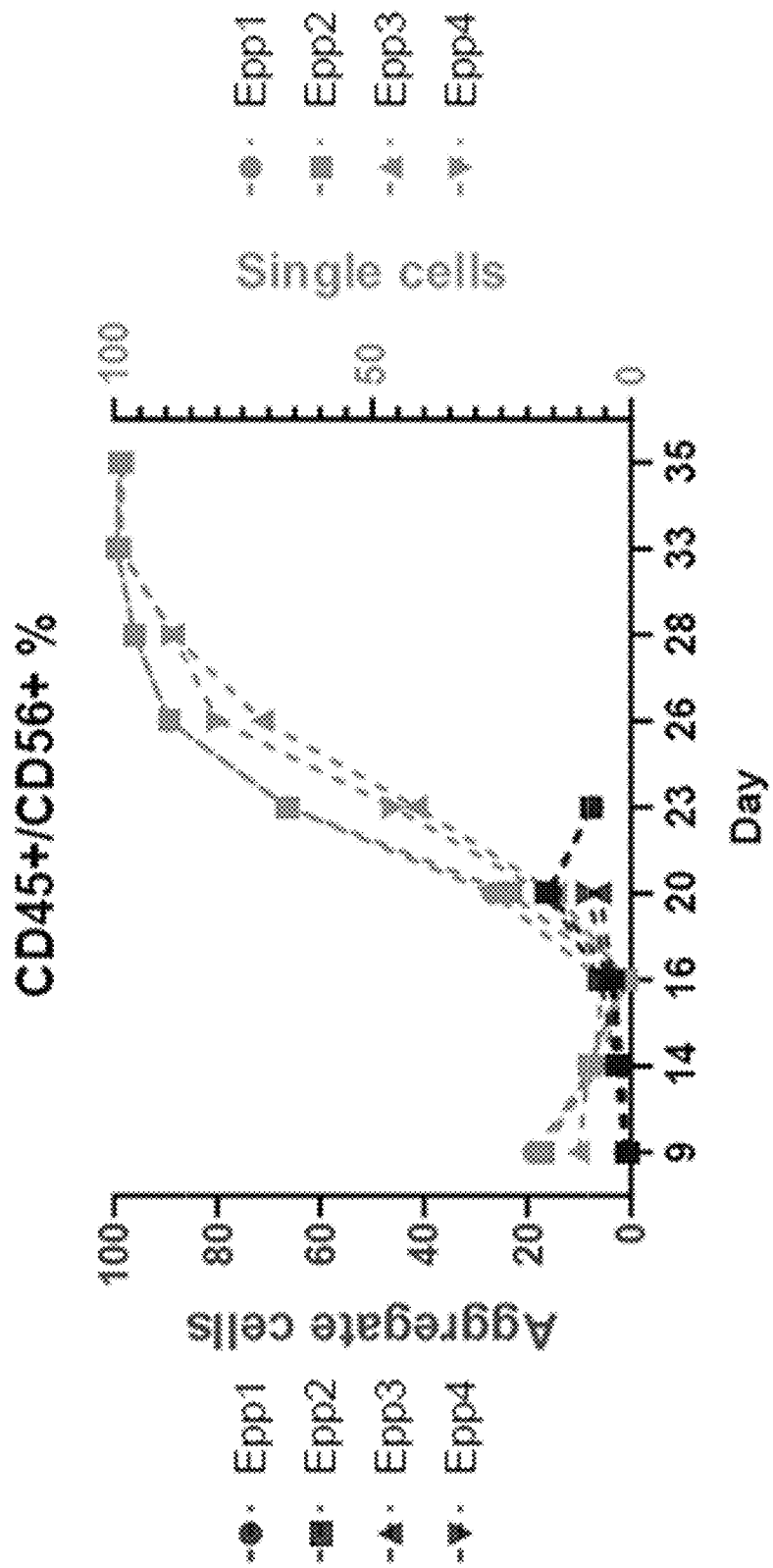
FIG. 29B shows levels of $CD45^+/CD56^+$ single cells or aggregate cells detected at different time points during the Aligned Process 2 in bioreactors.
Figure 29C:
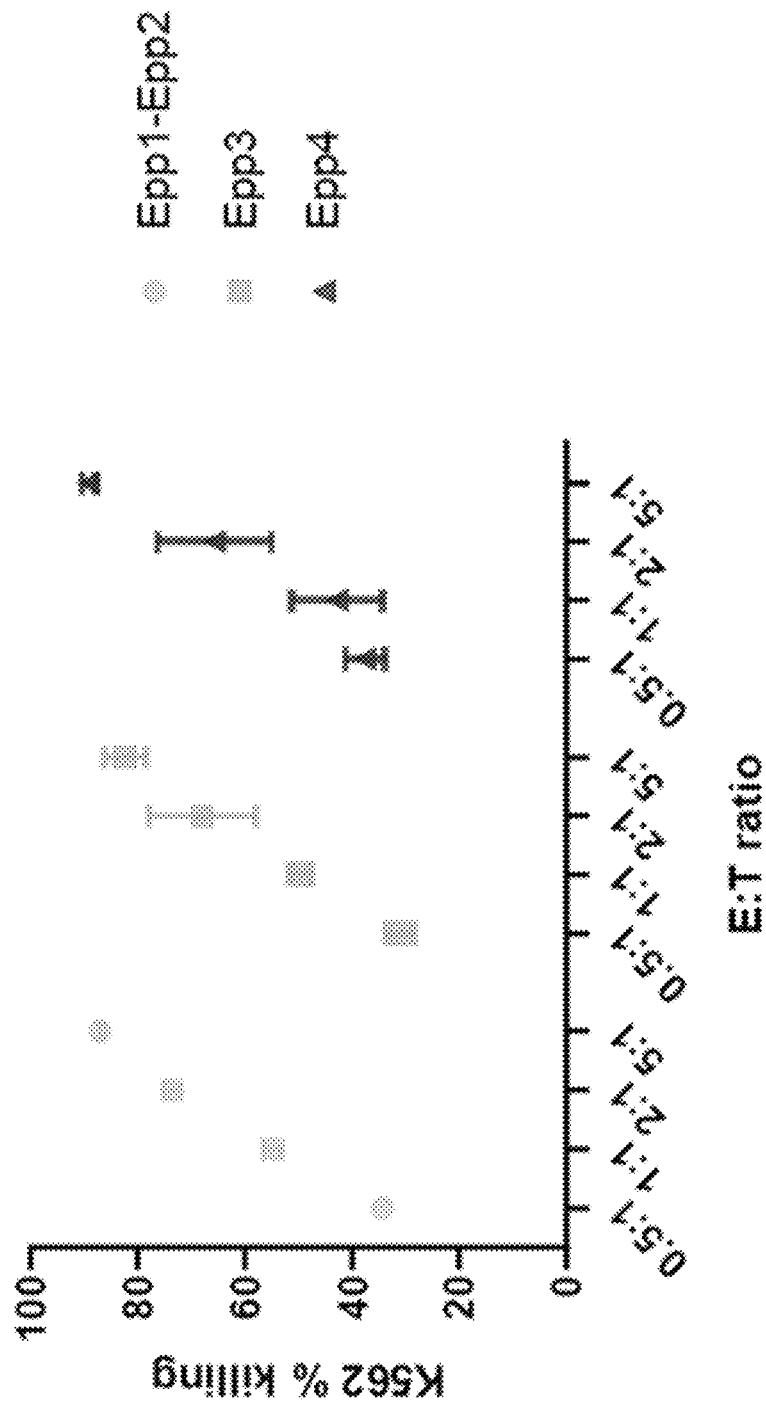
FIG. 29C shows cytotoxic effect of bioreactor differentiated cells (differentiated using Aligned Process 2) against K562 cells.

Example 16: Aligned Process 2.0 (AP2.0) Generated Highly Pure and Cytotoxic NK Population in a Bioreactor Setting iPSC cells were differentiated with AP2.0 using a BioFlo 320 Eppendorf system (FIG. 29A). Four reactions were set up to investigate the effect of the initial aggregate sizes (75 µm-Epp1/2 vs 250 µm-Epp3/4) and of propeller direction (upflow-Epp1/3 vs downflow-Epp2/4). Cultures from reactions Epp1 and 2, and Epp3 and 4 were combined after day 20. Aggregates and single cells were harvested at the indicated differentiation days to detect $CD45^+CD56^+$ cells by flow cytometry (FIG. 29B). 4-hour kill assay was performed on day 28 iNK cells derived from bioreactor using K562 cancer cell lines. A dose dependent cytotoxic effect of the bioreactor derived iNK cells was observed (FIG. 29C).

Figure 30:
FIG. 30 shows levels of $CD45^+CD56^+$ cells detected following differentiation in different concentrations of CHIR-99021.

Example 17: Effect of Various Concentrations of CHIR-99021 in NK-MED-005 Medium on iNK Induction To determine the optimal concentration of CHIR-99021, different concentrations (2.5 µM, 3.5 µM or 4.5 µM) were added to the NK-MED-005c medium (Table 30) to test their effect on iNK induction. Differentiation proceeded according to Protocol 2 (AP2.0) as described in Example 11. Cells were collected and analyzed using flow cytometry to detect $CD45^+CD56^+$ cells at differentiation day 20. FIG. 30 shows that the highest proportion of $CD45^+CD56^+$ cells were collected using a moderate amount of CHIR-99021.

Example 18: Effect of WNT-C59 in NK-MED-006 Medium on iNK Induction

Figure 31A:
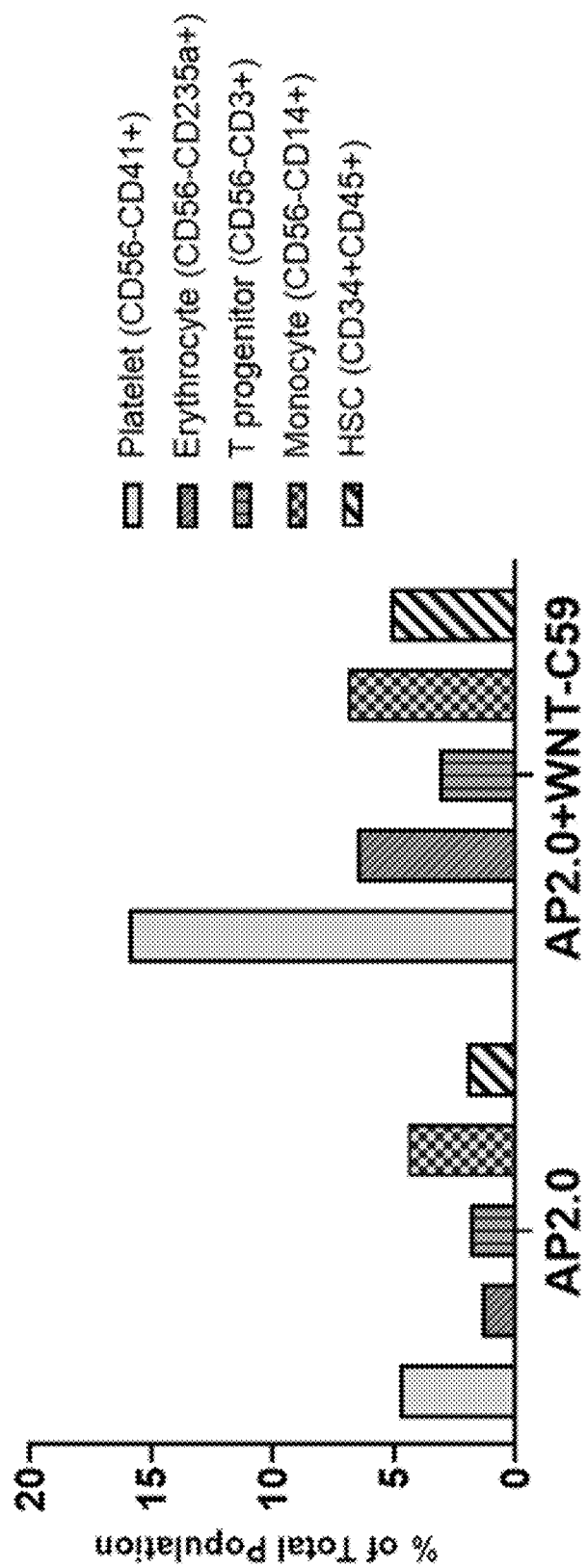
FIG. 31A shows blood marker expression and FIG. 31B shows myeloid progenitor marker CD33 expression in differentiation day 20 cultures derived using AP2.0 with or without addition of WNT-059 in NK-MED-006 medium.
Figure 31B:
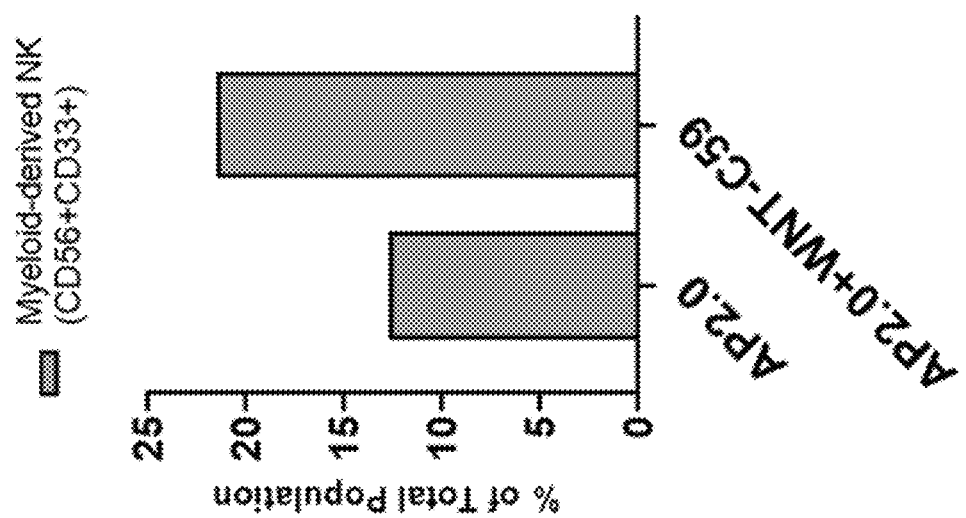

The effect of including WNT-C59 (2 µM) in NK-MED-006 medium during iNK induction using the AP2.0 protocol was examined. FIG. 31A shows blood lineage marker expression in day 20 cultures derived using AP2.0 with or without addition of WNT-C59 in NK-MED-006 medium. The addition of WNT-C59 increased proportion of cells expressing non-NK lineage markers. FIG. 31B shows that addition of WNT-C50 also altered the proportion of iNK that expressed the myeloid progenitor marker CD33, which were known to display limited cytotoxic and cytokine secreting activities.

Example 19: Alternatives to Differentiating Stem Cells into Natural Killer Cells—Protocol 2.5

The differentiation protocol according to Example 11 was repeated with the following alterations, alone or in combination:

1. During the NK Cell differentiation stage, iPS cells were cultured and aggregated using a "scaled up" approach. Specifically, the NK cell differentiation, Step 1 (Day −1 (afternoon), iPSC aggregation) step was performed as follows. iPSCs were grown in T175, T225, 1-cells stack or 2-cell stack and digested with Accutase as previously described. Accutase digested cells were diluted 1:1 with cold NK-MED-002 medium. Cells were gently resuspended and transferred to a conical tube. Cells were pelleted by spinning at 20-300 g for 4 to 5 minutes and re-suspended in 10 mL of NK-MED-003 medium. Cells were counted and the cell concentration was diluted to $1\times10^6$/mL. 60-100×$10^6$ cells were transferred to PBS100 and resuspended in a total of 60-100 mL of NK-MED-003 medium correspondingly. PBS vessels were placed onto PBS base and rotated overnight at 45 RPM.

2. ROCK Inhibitor: The ROCK inhibitor used in NK-MED-003 in the previous step, was Y-27652 (10 µM) instead of thiazovivin.

3. Nicotinamide: Nicotinamide was omitted from NK-MED-010 (used at day 20 onwards).

Cells were differentiated and characterized as described in previous examples.

The invention claimed is:

1. A method for generating Natural Killer (NK) cells from pluripotent stem cells, the method comprising:
   (a) culturing a population of pluripotent stem cells in a first medium comprising a ROCK inhibitor under conditions sufficient to form aggregates;
   (b) culturing the aggregates in a second medium comprising BMP-4;
   (c) culturing the aggregates in a third medium comprising BMP-4, FGF2, a WNT pathway activator, and Activin A;
   (d) culturing the aggregates in a fourth medium comprising FGF2, VEGF, TPO, SCF, IL-3, FLT3L, and an activin/nodal inhibitor to form a cell population comprising hematopoietic stem and progenitor cells (HSPCs);
   (e) culturing the cell population in a fifth medium comprising FGF2, VEGF, TPO, SCF, IL-3 and FLT3L;
   (f) culturing the cell population in a sixth medium comprising IL-3, IL-7, FLT3L, IL-15 and SCF;
   (g) culturing the cell population in a seventh medium comprising IL-7, FLT3L, IL-15 and SCF; and
   (h) culturing the cell population in an eighth medium comprising IL-7, FLT3L, IL-15, and SCF for a time sufficient to generate NK cells.

2. The method of claim 1, wherein culturing the cell population in the sixth medium in step (f) results in the formation of progenitor cell population comprising common lymphoid progenitor (CLP) cells.

3. The method of claim 2, wherein the progenitor cell population comprises at least about 15% of CLP cells and/or wherein the CLP cells express CD7 and CD45.

4. The method of claim 1, wherein the ROCK inhibitor is thiazovivin or Y27632; the WNT pathway activator is CHIR-99021 and/or the activin/nodal inhibitor is SB-431542.

5. The method of claim 1, wherein the second medium further comprises a ROCK inhibitor and/or the eighth medium further comprises nicotinamide.

6. The method of claim 1, wherein (a) comprises culturing for 12-48 hours; (b) comprises culturing for up to 24 hours; (c) comprises culturing for 1-3 days; (d) comprises culturing for 1-3 days; (e) comprises culturing for 1-3 days; (f) comprises culturing for at least 6 days and up to 8 days; (g) comprises culturing for up to 6 days; (h) comprises culturing for at least 6 days and up to 10-16 days total; or any combination of (a), (b), (c), (d), (e), (f), (g), or (h).

7. The method of claim 6, wherein: (a) comprises culturing for 16-20 hours; (b) comprises culturing for 6-10 hours; (c) comprises culturing for 2 days; (d) comprises culturing for 2 days; (e) comprises culturing for 2 days; (f) comprises culturing for 6-8 days; (g) comprises culturing for 6 days; and (h) comprises culturing for 8-16 days.

8. The method of claim 1, wherein the method is carried out under suspension agitation.

9. The method of claim 1, wherein the sixth, seventh and eighth media comprise human serum, zinc sulfate, ethanolamine, glucose, or any combination thereof, and/or the sixth, seventh and eighth media comprise DMEM (high glucose)/F12 medium, and a supplement of human serum, zinc sulfate, ethanolamine, glucose or any combination thereof.

10. The method of claim 1, wherein the third medium is added to the second medium at a 1:1 ratio.

11. The method of claim 1, wherein the fourth media comprises 20 ng/mL FGF, 20 ng/mL VEGF, 20 ng/mL TPO, 100 ng/mL SCF, 40 ng/mL IL-3, 10-20 ng/mL FLT3L, and 5 µM SB-431542.

12. The method of claim 1, wherein the fifth medium comprises 20 ng/mL FGF, 20 ng/mL VEGF, 20 ng/mL TPO, 100 ng/mL SCF, 40 ng/mL IL-3, and 10-20 ng/mL FLT3L.

13. The method of claim 1, wherein the sixth media comprises 20 ng/mL IL-7, 10-20 ng/mL FLT3L, 10-20 ng/mL IL-15, 20 ng/mL SCF, and 5 ng/mL IL-3.

14. The method of claim 1, wherein the seventh medium comprises 20 ng/mL TL-7, 10-20 ng/mL FLT3L, 10-20 ng/mL IL-15, and 20 ng/mL SCF.

15. The method of claim 1, wherein the eighth medium comprises 10-20 ng/mL IL-7, 5-20 ng/mL FLT3L, 10-30 ng/mL IL-15, and 20-40 ng/mL SCF.

16. The method of claim 15, wherein the eighth medium further comprises 6.5 mM nicotinamide.

17. The method of claim 1, wherein the NK cells express (a) at least one of CD56 or CD45 and/or (b) at least one of: an activating receptor, an inhibitory receptor or a co-receptor.

18. The method of claim 17, wherein the at least one activating receptor is selected from the group of NKp44, NKp46, NKG2D, CD16, KIR2DL4, NKp30, and any combination thereof, the at least one inhibitory receptor is selected from the group of NKG2A, KIR3DL2, and any combination thereof, and/or the at least one co-receptor is CD94.

19. The method of claim 1, wherein the NK cells comprise at least one function associated with endogenous NK cells.

20. The method of claim 19, wherein the at least one function comprises (a) the ability to induce cell lysis and cell death of a target cell; (b) degranulation; or (c) a combination thereof.

21. The method of claim 20, wherein degranulation comprises (a) release of perforin and granzyme B; (b) expression of CD107a on the cell surface of an NK cell; or (c) a combination thereof.

22. The method of claim 1, wherein the NK cells are generated without sorting $CD34^+$ cells from the cell population.

23. The method of claim 1, wherein the population of pluripotent stem cells is a population of engineered cells.

24. The method of claim 23, wherein the stem cells are genetically modified by an RNA-guided endonuclease system.

25. The method of claim 24, wherein the RNA-guided endonuclease system is a CRISPR system comprising a CRISPR nuclease and a guide RNA.

26. The method of claim 1, wherein the pluripotent stem cells are induced pluripotent stem cells (iPSC), embryonic stem cells (ESC), or adult stem cells (ASC).

27. The method of claim 26, wherein the pluripotent stem cells are mammalian cells.

28. The method of claim 27, wherein the mammalian cells are human cells.

29. A method comprising administering to a subject a plurality of NK cells generated by the method of claim 1.

* * * * *